(12) United States Patent
Tsuzuki et al.

(10) Patent No.: US 8,987,445 B2
(45) Date of Patent: Mar. 24, 2015

(54) SULFONAMIDE COMPOUNDS HAVING TRPM8 ANTAGONISTIC ACTIVITY

(75) Inventors: Yasuyuki Tsuzuki, Osaka (JP); Daisuke Sawamoto, Osaka (JP); Toshiaki Sakamoto, Osaka (JP); Taku Kato, Osaka (JP); Yasuki Niwa, Osaka (JP); Nobumasa Awai, Osaka (JP)

(73) Assignee: Mitsubishi Tanabe Pharma Corporation, Osaka-shi (JP)

( * ) Notice: Subject to any disclaimer, the term of this patent is extended or adjusted under 35 U.S.C. 154(b) by 0 days.

(21) Appl. No.: 14/004,911

(22) PCT Filed: Mar. 15, 2012

(86) PCT No.: PCT/JP2012/057412
§ 371 (c)(1),
(2), (4) Date: Sep. 13, 2013

(87) PCT Pub. No.: WO2012/124825
PCT Pub. Date: Sep. 20, 2012

(65) Prior Publication Data
US 2014/0005393 A1    Jan. 2, 2014

Related U.S. Application Data

(60) Provisional application No. 61/453,396, filed on Mar. 16, 2011.

(51) Int. Cl.
| | | |
|---|---|---|
| *C07D 487/04* | (2006.01) | |
| *C07D 405/12* | (2006.01) | |
| *C07D 401/12* | (2006.01) | |
| *C07D 409/12* | (2006.01) | |
| *C07D 471/04* | (2006.01) | |
| *C07D 417/12* | (2006.01) | |
| *C07D 413/12* | (2006.01) | |
| *C07D 217/22* | (2006.01) | |

(52) U.S. Cl.
CPC ............ *C07D 487/04* (2013.01); *C07D 217/22* (2013.01); *C07D 401/12* (2013.01); *C07D 405/12* (2013.01); *C07D 409/12* (2013.01); *C07D 413/12* (2013.01); *C07D 417/12* (2013.01); *C07D 471/04* (2013.01)
USPC ............................ 544/333; 546/113; 546/143

(58) Field of Classification Search
CPC .. C07D 487/04; C07D 405/12; C07D 401/12; C07D 409/12; C07D 471/04; C07D 417/12; C07D 413/12
USPC .................. 544/333; 546/113, 143
See application file for complete search history.

(56) References Cited

FOREIGN PATENT DOCUMENTS

| | | |
|---|---|---|
| WO | WO 2009/012430 A1 | 1/2009 |
| WO | WO 2010/010435 | 1/2010 |
| WO | WO 2010/125831 A1 | 11/2010 |
| WO | WO 2010/144680 A1 | 12/2010 |

OTHER PUBLICATIONS

Wolff, Manfred E., Burger's Medicinal Chemistry and Drug Discovery, Fifth Ed., vol. 1: Principles and Practice, John Wiley & Sons, 1995, 975.*
Banker, Gilbert S. et al., Modem Pharmaceutics, Marcel Dekker, New York, 1996.*
Srimali, S., et al.,Proton-catalyzed rearrangement of sulfonamides to sulfones. I. Conversion of substituted arylquinolylamine sulfonamide into the isomeric substituted diarylsulfone, Revue Roumaine de Chimie, 23(4), 613-16 (1978).*
Abe, J. et al., "$Ca^{2+}$-dependent PKC Activation Mediates Menthol-induced Desensitization of Transient Receptor Potential M8," Neuroscience Letters, vol. 397, pp. 140-144 (2006).
Gauchan, P. et al., "Involvement of Increased Expression of Transient Receptor Potential Melastatin 8 in Oxaliplatin-induced Cold Allodynia in Mice," Neuroscience Letters, vol. 458, pp. 93-95 (2009).
McKemy, D. et al., "Identification of a Cold Receptor Reveals a General Role for TRP Channels in Thermosensation," Nature, vol. 416, pp. 52-58 (2002).

(Continued)

*Primary Examiner* — Erich A Leeser
(74) *Attorney, Agent, or Firm* — Finnegan, Henderson, Farabow, Garrett & Dunner LLP

(57) ABSTRACT

Sulfonamide compounds having TRPM8 antagonistic activity are provided. A sulfonamide compound of formula (I) or a pharmaceutically acceptable salt thereof, or a prodrug thereof: (I) wherein Ring A is bicyclic aromatic heterocycle comprised of (a) pyridine is condensed with benzene; or (b) pyridine is condensed with monocyclic aromatic heterocycle, and Ring A binds to a sulfonylamino moiety on a carbon atom adjacent to a nitrogen atom of the pyridine ring constituting Ring A, Ring B is (a) monocyclic or bicyclic aromatic hydrocarbon; (b) monocyclic or bicyclic alicyclic hydrocarbon; (c) monocyclic or bicyclic aromatic heterocycle; or (d) monocyclic or bicyclic non-aromatic heterocycle, Ring C is (a) benzene; or (b) monocyclic aromatic heterocycle, and other symbols are the same as defined in the specification.

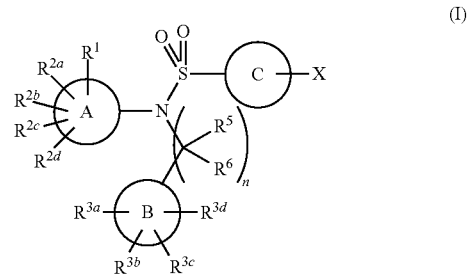

25 Claims, No Drawings

(56) References Cited

OTHER PUBLICATIONS

Premkumar, L. et al., "Downregulation of Transient Receptor Potential Melastatin 8 by Protein Kinase C-Mediated Dephosphorylation," The Journal of Neuroscience, vol. 25, No. 49, pp. 11322-11329 (2005).

Xing, H. et al., "TRPM8 Mechanism of Cold Allodynia after Chronic Nerve Injury," The Journal of Neuroscience, vol. 27, No. 50, pp. 13680-13690 (2007).

International Preliminary Report of Patentability for International Application No. PCT/JP2012/057412, mailed Sep. 26, 2013, from the International Bureau of WIPO.

* cited by examiner

US 8,987,445 B2

SULFONAMIDE COMPOUNDS HAVING TRPM8 ANTAGONISTIC ACTIVITY

CROSS REFERENCE TO RELATED APPLICATIONS

This application is a national phase application based on PCT/JP2012/057412, filed Mar. 15, 2012, and claims the benefit of U.S. Provisional Application No. 61/453,396, filed Mar. 16, 2011, the contents of both of which are incorporated herein by reference.

TECHNICAL FIELD

The present invention relates to novel sulfonamide compounds having TRPM8 antagonistic activity which are useful as a medicament.

BACKGROUND ART

Transient receptor potential (TRP) channels are non-selective cation channels that are activated by a variety of physical (e.g., temperature, osmolarity, mechanical) and chemical stimuli. A subset of the TRP channel superfamily is thermo-responsive, each channel being activated over a discrete temperature range, cumulatively spanning from noxious cold to noxious heat. TRP melastatin 8 (TRPM8) belongs to the melastatin subgroup of the TRP channel superfamily. TRPM8 is sensitive to cold temperature and menthol, and therefore also called as cold menthol receptor-1 (CMR-1) (e.g., Nonpatent Document 1). TRPM8 is known to be stimulated by cool to cold temperatures (8 to 28° C.) as well as by chemical substances such as menthol and icilin.

TRPM8 is located on primary nociceptive neurons (A-δ and C-fibers) and is also modulated by inflammation-mediated second messenger signals (e.g., Nonpatent Document 2 and 3). The location of TRPM8 on both A-δ and C-fibers may provide a basis for abnormal cold sensitivity in pathologic conditions wherein these neurons are altered, resulting in pain, often of a burning nature. TRPM8 immunostaining in primary afferents was increased in rats with chronic constriction injury (CCI), a neuropathic pain model manifesting cold allodynia in hindlimbs (e.g., Nonpatent Document 4). The expression of TRPM8 in primary afferents was increased in oxaliplatin-induced cold allodynia model in mice (e.g., Nonpatent Document 5).

Cold intolerance and paradoxical burning sensations induced by chemical substances or thermal cooling closely parallel symptoms seen in a wide range of clinical disorders and thus provide a strong rationale for the development on TRPM8 modulators as novel antihyperalgesic or antiallodynic agents. TRPM8 is also known to be expressed in the brain, lung, bladder, gastrointestinal tract, blood vessels, prostate and immune cells, thereby providing the possibility for therapeutic modulation in a wide range of maladies.

N-Benzothipheneylsulfonamide compounds (e.g., Patent Document 1), N-benzimidazolylsulfonamide compounds (e.g., Patent Document 2), N-phenylsulfonamide compounds, N-pyridylsulfonamide compounds (e.g., Patent Document 3), etc. have been known as a TRPM8 modulator. However, it has never been reported that a compound wherein the compound has a bicyclic aromatic heterocycle comprised of pyridine condensed with benzene or of pyridine condensed with monocyclic aromatic heterocycle and the bicyclic aromatic heterocyle binds to a sulfonylamino moiety has TRPM8 antagonistic activity.

[Patent document 1] WO 2009/012430 pamphlet
[Patent document 2] WO 2010/144680 pamphlet
[Patent document 3] WO 2010/125831 pamphlet
[Nonpatent document 1] D. D. McKemy, and other two persons, "Identification of a cold receptor reveals a general role for TRP channels in thermosensation", Nature, 2002, Vol. 416, No. 6876, p. 52-58
[Nonpatent document 2] J. Abe, and other four persons, "$Ca^{2+}$-dependent PKC activation mediates menthol-induced desensitization of transient receptor potential M8", Neuroscience Letters, 2006, Vol. 397, No. 1-2, p. 140-144
[Nonpatent document 3] L. S. Premkumar, and other four persons, "Downregulation of Transient Receptor Potential Melastatin 8 by Protein Kinase C-Mediated Dephosphorylation", The Journal of Neuroscience, 2005, Vol. 25, No. 49, p. 11322-11329
[Nonpatent document 4] H. Xing, and other four persons, "TRPM8 Mechanism of Cold Allodynia after Chronic Nerve Injury", The Journal of Neuroscience, 2007, Vol. 27, No. 50, p. 13680-13690
[Nonpatent document 5] P. Gauchan, and other three persons, "Involvement of increased expression of transient receptor potential melastatin 8 in oxaliplatin-induced cold allodynia in mice", Neuroscience Letters, 2009, Vol. 458, No. 2, p. 93-95

SUMMARY OF INVENTION

Problems to be Solved by the Invention

The purpose of the present invention is to provide novel sulfonamide compounds having TRPM8 antagonistic activity which are useful as a medicament.

Means of Solving the Problems

The present invention is directed to a compound of formula (I):

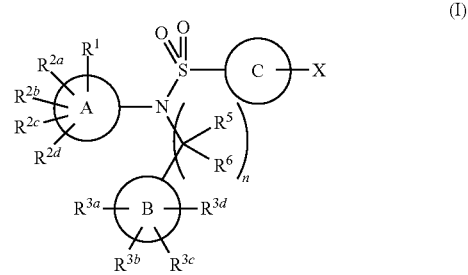

wherein Ring A is bicyclic aromatic heterocycle comprised of (a) pyridine condensed with benzene; or (b) pyridine condensed with monocyclic aromatic heterocycle, and Ring A binds to a sulfonylamino moiety on a carbon atom adjacent to a nitrogen atom of the pyridine ring constituting Ring A, Ring B is (a) monocyclic or bicyclic aromatic hydrocarbon; (b) monocyclic or bicyclic alicyclic hydrocarbon; (c) monocyclic or bicyclic aromatic heterocycle; or (d) monocyclic or bicyclic non-aromatic heterocycle, Ring C is (a) benzene; or (b) monocyclic aromatic heterocycle, $R^1$ is (a) hydrogen; (b) optionally substituted alkyl; (c) optionally substituted cycloalkyl; (d) optionally substituted alkoxy; (e) optionally substituted phenyl; (f) halogen; or (g) nitrile, $R^{2a}$, $R^{2b}$, $R^{2c}$ and $R^{2d}$ are each independently (a) hydrogen; (b) optionally substituted alkyl; (c) optionally substituted cycloalkyl; (d) optionally substituted alkoxy; (e) optionally substituted phenyl; (f) optionally substituted monocyclic aromatic heterocyclic group; (g) optionally substituted monocyclic non-aromatic heterocyclic group; (h) halogen; or (i) nitrile, $R^{3a}$, $R^{3b}$, $R^{3c}$ and $R^{3d}$ are each independently (a) hydrogen; (b) optionally substituted alkyl; (c) optionally substituted cycloalkyl; (d) optionally substituted alkoxy; (e) optionally substituted cycloalkoxy; (f) optionally substituted phenyl; (g) optionally substituted monocyclic aromatic heterocyclic group; (h) optionally substituted monocyclic non-aromatic heterocyclic group; (i) optionally substituted phenoxy; (j) halogen; or (k) hydroxy, or two substituent groups selected from $R^{3a}$, $R^{3b}$, $R^{3c}$ and $R^{3d}$ combine each other to form oxo, $R^5$ and $R^6$ are each independently (a) hydrogen; (b) alkyl; (c) halogenoalkyl; (d) cycloalkyl; or (e) halogenocycloalkyl, or $R^5$ and $R^6$ combine each other at their terminals together with the adjacent carbon atom to form monocyclic alicyclic hydrocarbon, n is 0, 1 or 2, X is carboxy, alkoxycarbonyl, hydroxyalkyl, optionally substituted aminocarbonyl, or optionally substituted alkanoyl; or a pharmaceutically acceptable salt thereof, or a prodrug thereof.

Effect of the Invention

A compound of formula (I) shows excellent inhibitory effects on behavior induced by TRPM8 agonists as well as excellent TRPM8 antagonistic activity. Accordingly, a compound of formula (I) is useful as a medicament for prevention and treatment of various diseases involving TRPM8 (e.g., chronic pain such as neuropathic pain (preferably, neuropathic pain caused by cold allodynia or diabetic neuropathy)).

DESCRIPTION OF EMBODIMENTS

Each definition of each term used herein is as follows.

The term "alkyl" refers to straight or branched-chain saturated hydrocarbon chain with 1 to 6 carbons, and includes methyl, ethyl, propyl, isopropyl, butyl, t-butyl, isobutyl, and various branched-chain isomers thereof, preferably straight or branched-chain saturated hydrocarbon chain with 1 to 4 carbons.

The term "alkenyl" refers to straight or branched-chain unsaturated hydrocarbon chain with 2 to 6 carbons containing one carbon-carbon double bond, and includes vinyl, propenyl, butenyl, and various branched-chain isomers thereof, preferably straight or branched-chain unsaturated hydrocarbon chain with 2 to 4 carbons.

The term "cycloalkyl" refers to alicyclic saturated hydrocarbon with 3 to 7 carbons, and includes cyclopropyl, cyclobutyl, cyclopentyl or cyclohexyl, preferably alicyclic saturated hydrocarbon with 3 to 6 carbons.

The term "cycloalkenyl" refers to alicyclic unsaturated hydrocarbon with 3 to 7 carbons containing one carbon-carbon double bond, and includes cyclopropenyl, cyclobutenyl, cyclopentenyl or cyclohexenyl, preferably alicyclic unsaturated hydrocarbon with 3 to 6 carbons.

The term "halogen" or "halogeno" refers to fluorine, chlorine, bromine and iodine, preferably chlorine and fluorine.

The term "alkoxy" refers to a group wherein oxygen atom binds to the straight or branched-chain alkyl with 1 to 6 carbons, and includes methoxy, ethoxy, propoxy, isopropoxy, butoxy, t-butoxy, isobutoxy, and various branched-chain isomers thereof, preferably a group wherein oxygen atom binds to straight or branched-chain saturated hydrocarbon with 1 to 4 carbons.

The term "cycloalkoxy" refers to a group wherein oxygen atom binds to the cycloalkyl with 3 to 7 carbons, and includes cyclopropoxy, cyclobutoxy, cyclopentoxy or cyclohexoxy, preferably a group wherein oxygen atom binds to alicyclic saturated hydrocarbon with 3 to 6 carbons.

The term "alkanoyl" refers to a group wherein the alkyl binds to carbonyl, and includes acetyl, propanoyl, butyryl, pentanoyl and various branched-chain isomers thereof, preferably a group wherein straight or branched-chain saturated hydrocarbon chain with 1 to 4 carbons binds to carbonyl.

The terms "halogenoalkyl", "halogenoalkoxy" and "halogenocycloalkyl" refer to the alkyl, alkoxy and cycloalkyl which are substituted by 1 to 7 halogen atoms, respectively.

The term "monocyclic or bicyclic aromatic hydrocarbon" refers to monocyclic or bicyclic aromatic hydrocarbon with 6 to 11 carbons as a ring atom, and includes monocyclic aromatic hydrocarbon such as benzene; and bicyclic aromatic hydrocarbon with 9 to 11 carbons as a ring atom such as naphthalene, tetrahydronaphthalene, indene, indane or azulene.

The term "monocyclic alicyclic hydrocarbon" refers to monocyclic alicyclic hydrocarbon with 3 to 7 carbons as a ring atom, and includes cyclopropane, cyclobutane, cyclopentane, cyclopentene, cyclohexane or cyclohexene, preferably monocyclic alicyclic hydrocarbon with 3 to 6 carbons as a ring atom.

The term "monocyclic or bicyclic alicyclic hydrocarbon" refers to monocyclic or bicyclic alicyclic hydrocarbon with 3 to 12 carbons as a ring atom, and includes monocyclic alicyclic hydrocarbon with 3 to 7 carbons as a ring atom such as cyclopropane, cyclobutane, cyclopentane, cyclopentene, cyclohexane or cyclohexene; bicyclic alicyclic hydrocarbon with 8 to 12 carbons as a ring atom such as bicyclooctane, bicyclononane, bicyclononene, bicyclodecane, bicyclodecene, spiro-octane, spiro-nonane, spiro-decane or spiro-undecane.

The term "monocyclic aromatic heterocycle" refers to 5 to 6-membered monocyclic aromatic heterocycle containing carbon atoms and 1 to 4 heteroatoms selected from oxygen atom, sulfur atom and nitrogen atom, and includes pyrrole, furan, thiophene, pyrazole, imidazole, oxazole, isooxazole, thiazole, isothiazole, thiadiazole, pyridine, pyrimidine or pyridazine.

The term "monocyclic or bicyclic aromatic heterocycle" refers to 5 to 11-membered monocyclic or bicyclic aromatic heterocycle containing carbon atoms and 1 to 4 heteroatoms selected from oxygen atom, sulfur atom and nitrogen atom, and includes 5 to 6-membered monocyclic aromatic heterocycle such as pyrrole, furan, thiophene, pyrazole, imidazole, oxazole, isooxazole, thiazole, isothiazole, thiadiazole, pyridine, pyrimidine or pyridazine; 8 to 11-membered bicyclic aromatic heterocycle such as indole, indoline, isoindoline, indazole, benzofuran, dihydrobenzofuran, dihydroisobenzofuran, benzothiophene, dihydrobenzothiophene, dihydroisobenzothiophene, benzooxazole, dihydrobenzooxazole, benzothiazole, dihydrobenzothiazole, quinoline, tetrahydroquinoline, isoquinoline, tetrahydroisoquinoline, naphthyridine, tetrahydronaphthyridine, quinoxaline, tetrahydroquinoxaline or quinazoline.

The term "monocyclic or bicyclic non-aromatic heterocycle" refers to 4 to 12-membered monocyclic or bicyclic non-aromatic heterocycle containing carbon atoms and 1 to 4 heteroatoms selected from oxygen atom, sulfur atom and nitrogen atom, and includes 4 to 7-membered monocyclic non-aromatic heterocycle such as pyrrolidine, piperidine, tetrahydrofuran, tetrahydrothiophene, dihydroisooxazole and morpholine; 8 to 12-membered bicyclic non-aromatic heterocycle such as octahydroindoline, octahydrobenzofuran, octahydrobenzothiophene, decahydroquinoline, decahydroisoquinoline, oxaaza-spiro-nonene, oxaaza-spiro-decene, oxaaza-spiro-undecene.

The term "monocyclic aromatic heterocyclic group" refers to 5 to 6-membered monocyclic aromatic heterocyclic group containing carbon atoms and 1 to 4 heteroatoms selected from oxygen atom, sulfur atom and nitrogen atom, and includes pyrrolyl, furyl, thienyl, pyrazolyl, imidazolyl, oxazolyl, isooxazolyl, thiazolyl, isothiazolyl, thiadiazolyl, pyridyl, pyrimidyl or pyridazyl.

The term "monocyclic non-aromatic heterocyclic group" refers to 4 to 7-membered monocyclic non-aromatic heterocyclic group containing carbon atoms and 1 to 4 heteroatoms selected from oxygen atom, sulfur atom and nitrogen atom, and includes pyrrolidinyl, piperidinyl, tetrahydrofuranyl, tetrahydrothienyl, dihydroisooxazolyl and morpholyl.

Each definition of each symbol in a compound of formula (I) is explained in detail as follows.

The monocyclic aromatic heterocycle in the "bicyclic aromatic heterocycle comprised of pyridine condensed with monocyclic aromatic heterocycle" of Ring A is preferably pyrrole, thiophene or pyridine.

Ring A is preferably bicyclic aromatic heterocycle comprised of (a) pyridine condensed with benzene; (b) pyridine condensed with pyrrole; (c) pyridine condensed with thiophene; or (d) pyridine condensed with pyridine, particularly bicyclic aromatic heterocycle comprised of pyridine condensed with benzene, specifically quinoline (particularly, quinolin-2-yl) or isoquinoline (particularly, isoquinolin-3-yl).

The "monocyclic or bicyclic aromatic hydrocarbon" of Ring B is preferably benzene, naphthalene, tetrahydronaphthalene, or indane.

The "monocyclic or bicyclic alicyclic hydrocarbon" of Ring B is preferably cyclopentane or cyclohexane.

The "monocyclic or bicyclic aromatic heterocycle" of Ring B is preferably thiophene, pyridine, pyrimidine, indole, indazole, dihydrobenzofuran, dihydroisobenzofuran, benzothiophene, benzooxazole, benzothiazole, quinoline or isoquinoline.

The "monocyclic or bicyclic non-aromatic heterocycle" of Ring B is preferably piperidine or oxaaza-spiro-decene.

Ring B is preferably (a) monocyclic or bicyclic aromatic hydrocarbon; or (b) monocyclic or bicyclic aromatic heterocycle, specifically benzene, naphthalene, tetrahydronaphthalene, indane, thiophene, pyridine, pyrimidine, indole, indazole, dihydrobenzofuran, dihydroisobenzofuran, benzothiophene, benzooxazole, benzothiazole, quinoline or isoquinoline, more preferably benzene, naphthalene, tetrahydronaphthalene, indane, thiophene, pyridine, indole or benzothiophene, particularly benzene, naphthalene (particularly, naphthalen-2-yl), tetrahydronaphthalene (particularly, 1,2,3,4-tetrahydronaphthalen-6-yl), indane (particularly, indan-1-yl or indan-5-yl), pyridine (particularly, pyridin-2-yl) or benzothiophene (particularly, benzothiophen-2-yl).

The "monocyclic aromatic heterocycle" of Ring C is preferably thiophene or pyridine.

Ring C is preferably benzene, thiophene or pyridine, particularly benzene.

The number of the substituents in the "optionally substituted alkyl" of $R^1$ may be one or more (for example, 1 to 7), and the substituents may be the same or different. As for such substituents, cycloalkyl, alkoxy, halogen, oxo and hydroxy can be mentioned for example.

The number of the substituents in the "optionally substituted cycloalkyl" of $R^1$ may be one or more (for example, 1 to 7), and the substituents may be the same or different. As for such substituents, alkyl, alkoxy and halogen can be mentioned for example.

The number of the substituents in the "optionally substituted alkoxy" of $R^1$ may be one or more (for example, 1 to 7), and the substituents may be the same or different. As for such substituents, cycloalkyl, alkoxy, halogen and hydroxy can be mentioned for example.

The number of the substituents in the "optionally substituted phenyl" of $R^1$ may be one or more (for example, 1 to 3), and the substituents may be the same or different. As for such substituents, alkyl, halogenoalkyl, cycloalkyl, halogenocycloalkyl, alkoxy, halogenoalkoxy and halogen can be mentioned for example.

$R^1$ is preferably (a) hydrogen; (b) optionally substituted alkyl; (c) optionally substituted cycloalkyl; (d) optionally substituted alkoxy; or (e) halogen. More preferable one is (a) hydrogen; (b) $C_1$-$C_6$ alkyl which may be optionally substituted by 1 to 7 groups selected from halogen, oxo and hydroxy; (c) $C_3$-$C_7$ cycloalkyl; (d) $C_1$-$C_6$ alkoxy; or (e) halogen, and specifically, hydrogen, methyl, trifluoromethyl, ethyl, oxoethyl, hydroxyethyl, isopropyl, cyclopropyl, methoxy, chloro or bromo is preferable. Particularly, (a) $C_1$-$C_6$ alkyl which may be optionally substituted by 1 to 7 halogens; (b) $C_3$-$C_7$ cycloalkyl; (c) $C_1$-$C_6$ alkoxy; or (d) halogen is preferable, and specifically, methyl, trifluoromethyl, isopropyl, cyclopropyl or methoxy is preferable. More preferable one is methyl, trifluoromethyl or cyclopropyl.

The number of the substituents in the "optionally substituted alkyl" of $R^{2a}$, $R^{2b}$, $R^{2c}$ or $R^{2d}$ may be each one or more (for example, 1 to 7), and the substituents may be the same or different. As for such substituents, alkoxy, cycloalkyl, halogen, oxo and hydroxy can be mentioned for example.

The number of the substituents in the "optionally substituted cycloalkyl" of $R^{2a}$, $R^{2b}$, $R^{2c}$ or $R^{2d}$ may be each one or more (for example, 1 to 7), and the substituents may be the same or different. As for such substituents, alkyl, alkoxy and halogen can be mentioned for example.

The number of the substituents in the "optionally substituted alkoxy" of $R^{2a}$, $R^{2b}$, $R^{2c}$ or $R^{2d}$ may be each one or more (for example, 1 to 7), and the substituents may be the same or different. As for such substituents, alkoxy, cycloalkyl and halogen can be mentioned for example.

The number of the substituents in the "optionally substituted phenyl" of $R^{2a}$, $R^{2d}$ may be each one or more (for example, 1 to 3), and the substituents may be the same or different. As for such substituents, alkyl, halogenoalkyl, cycloalkyl, halogenocycloalkyl, alkoxy, halogenoalkoxy and halogen can be mentioned for example.

The number of the substituents in the "optionally substituted monocyclic aromatic heterocyclic group" of $R^{2a}$, $R^{2b}$, $R^{2c}$ or $R^{2d}$ may be each one or more (for example, 1 to 3), and the substituents may be the same or different. As for such substituents, alkyl, halogenoalkyl, cycloalkyl, halogenocycloalkyl, alkoxy, halogenoalkoxy and halogen can be mentioned for example.

The number of the substituents in the "optionally substituted monocyclic non-aromatic heterocyclic group" of $R^{2a}$, $R^{2b}$, $R^{2c}$ or $R^{2d}$ may be each one or more (for example, 1 to 3), and the substituents may be the same or different. As for such substituents, alkyl, halogenoalkyl, cycloalkyl, halogenocycloalkyl, alkoxy, halogenoalkoxy and halogen can be mentioned for example.

$R^{2a}$, $R^{2b}$ and $R^{2c}$ are each independently and preferably (a) hydrogen; (b) optionally substituted alkyl; (c) optionally substituted cycloalkyl; or (d) halogen. More preferable one is (a) hydrogen; (b) $C_1$-$C_6$ alkyl; (c) $C_3$-$C_7$ cycloalkyl; or (d) halogen, and specifically, hydrogen, methyl, cyclopropyl or chlorine is preferable. Particularly, hydrogen is preferable.

$R^{2d}$ is preferably (a) hydrogen; (b) optionally substituted alkyl; (c) optionally substituted cycloalkyl; (d) optionally substituted alkoxy; (e) optionally substituted phenyl; (f) optionally substituted monocyclic aromatic heterocyclic group; (g) optionally substituted monocyclic non-aromatic heterocyclic group; or (h) halogen. More preferable one is (a) hydrogen; (b) $C_1$-$C_6$ alkyl which may be optionally substituted by 1 to 7 groups selected from $C_1$-$C_6$ alkoxy, halogen and hydroxy; (c) $C_3$-$C_7$ cycloalkyl; (d) $C_1$-$C_6$ alkoxy; (e) phenyl; (f) 5 to 6-membered monocyclic aromatic heterocyclic group; (g) monocyclic non-aromatic heterocyclic group; or (h) halogen, and specifically, hydrogen, methyl, trifluoromethyl, methoxymethyl, ethyl, hydroxyethyl, propyl, isopropyl, cyclopropyl, cyclopentyl, methoxy, ethoxy, isopropoxy, phenyl, pyridyl, pyrrolidyl, fluorine, chlorine or bromine is preferable. Particularly, (a) hydrogen; (b) $C_1$-$C_6$ alkyl; (c) $C_3$-$C_7$ cycloalkyl; or (d) $C_1$-$C_6$ alkoxy is preferable, and specifically, hydrogen, methyl, ethyl, isopropyl, cyclopropyl, cyclopentyl, methoxy or ethoxy is preferable. More preferable one is hydrogen, isopropyl or cyclopropyl.

The number of the substituents in the "optionally substituted alkyl" of $R^{3a}$, $R^{3b}$, $R^{3c}$ or $R^{3d}$ may be each one or more (for example, 1 to 7), and the substituents may be the same or different. As for such substituents, cycloalkyl, halogenocycloalkyl (in which the cycloalkyl and halogenocycloalkyl may be each independently and optionally substituted by 1 to 3 groups selected from alkyl and halogenoalkyl), alkoxy, halogenoalkoxy, phenyl, monocyclic aromatic heterocyclic group, monocyclic non-aromatic heterocyclic group (in which the phenyl, aromatic heterocyclic group and non-aromatic heterocyclic group may be each independently and optionally substituted by 1 to 3 groups selected from alkyl, halogenoalkyl, cycloalkyl, halogenocycloalkyl, alkoxy, halogenoalkoxy and halogen), halogen, oxo and hydroxy can be mentioned for example.

The number of the substituents in the "optionally substituted cycloalkyl" of $R^{3a}$, $R^{3b}$, $R^{3c}$ or $R^{3d}$ may be each one or more (for example, 1 to 7), and the substituents may be the same or different. As for such substituents, alkyl, halogenoalkyl, alkoxy, halogenoalkoxy, halogen and hydroxy can be mentioned for example.

The number of the substituents in the "optionally substituted alkoxy" of $R^{3a}$, $R^{3b}$, $R^{3c}$ or $R^{3d}$ may be each one or more (for example, 1 to 7), and the substituents may be the same or different. As for such substituents, cycloalkyl, halogenocycloalkyl (in which the cycloalkyl and halogenocycloalkyl may be each independently and optionally substituted by 1 to 3 groups selected from alkyl and halogenoalkyl), alkoxy, halogenoalkoxy, phenyl, monocyclic aromatic heterocyclic group, monocyclic non-aromatic heterocyclic group (in which the phenyl, aromatic heterocyclic group and non-aromatic heterocyclic group may be each independently and optionally substituted by 1 to 3 groups selected from alkyl, halogenoalkyl, cycloalkyl, halogenocycloalkyl, alkoxy, halogenoalkoxy and halogen), halogen and hydroxy can be mentioned for example.

The number of the substituents in the "optionally substituted cycloalkoxy" of $R^{3a}$, $R^{3b}$, $R^{3c}$ or $R^{3d}$ may be each one or more (for example, 1 to 7), and the substituents may be the same or different. As for such substituents, alkyl, halogenoalkyl, alkoxy, halogenoalkoxy, halogen and hydroxy can be mentioned for example.

The number of the substituents in the "optionally substituted phenyl" of $R^{3a}$, $R^{3b}$, $R^{3c}$ or $R^{3d}$ may be each one or more (for example, 1 to 3), and the substituents may be the same or different. As for such substituents, alkyl, halogenoalkyl, cycloalkyl, halogenocycloalkyl, alkoxy, halogenoalkoxy and halogen can be mentioned for example.

The number of the substituents in the "optionally substituted monocyclic aromatic heterocyclic group" of $R^{3a}$, $R^{3b}$, $R^{3c}$ or $R^{3d}$ may be each one or more (for example, 1 to 3), and the substituents may be the same or different. As for such substituents, alkyl, halogenoalkyl, cycloalkyl, halogenocycloalkyl, alkoxy, halogenoalkoxy and halogen can be mentioned for example.

The number of the substituents in the "optionally substituted monocyclic non-aromatic heterocyclic group" of $R^{3a}$, $R^{3b}$, $R^{3c}$ or $R^{3d}$ may be each one or more (for example, 1 to 3), and the substituents may be the same or different. As for such substituents, alkyl, halogenoalkyl, cycloalkyl, halogenocycloalkyl, alkoxy, halogenoalkoxy and halogen can be mentioned for example.

The number of the substituents in the "optionally substituted phenoxy" of $R^{3a}$, $R^{3b}$, $R^{3c}$ or $R^{3d}$ may be each one or more (for example, 1 to 3), and the substituents may be the same or different. As for such substituents, alkyl, halogenoalkyl, cycloalkyl, halogenocycloalkyl, alkoxy, halogenoalkoxy and halogen can be mentioned for example.

$R^{3a}$, $R^{3b}$, $R^{3c}$ and $R^{3d}$ are each independently and preferably (a) hydrogen; (b) optionally substituted alkyl; (c) optionally substituted cycloalkyl; (d) optionally substituted alkoxy; (e) optionally substituted cycloalkoxy; (f) optionally substituted phenyl; (g) optionally substituted monocyclic aromatic heterocyclic group; (h) optionally substituted phenoxy; (i) halogen; or (j) hydroxy. More preferable one is (a) hydrogen; (b) $C_1$-$C_6$ alkyl which may be optionally substituted by 1 to 7 groups selected from $C_3$-$C_7$ cycloalkyl (in which the cycloalkyl may be optionally substituted by 1 to 3 groups selected from $C_1$-$C_6$ alkyl and $C_1$-$C_6$ halogenoalkyl), $C_1$-$C_6$ alkoxy, $C_1$-$C_6$ halogenoalkoxy, halogen and hydroxy; (c) $C_3$-$C_7$ cycloalkyl which may be optionally substituted by 1 to 7 groups selected from $C_1$-$C_6$ alkyl, $C_1$-$C_6$ halogenoalkyl and halogen; (d) $C_1$-$C_6$ alkoxy which may be optionally substituted by 1 to 7 groups selected from $C_3$-$C_7$ cycloalkyl, $C_1$-$C_6$ alkoxy, $C_1$-$C_6$ halogenoalkoxy and halogen; (e) $C_3$-$C_7$ cycloalkoxy; (f) phenyl which may be optionally substituted by 1 to 3 halogens; (g) 5 to 6-membered monocyclic aromatic heterocyclic group; (h) phenoxy; (i) halogen; or (j) hydroxy, and particularly, (a) hydrogen; (b) $C_1$-$C_6$ alkyl which may be optionally substituted by 1 to 7 groups selected from $C_3$-$C_7$ cycloalkyl (in which the cycloalkyl may be optionally substituted by 1 to 3 groups selected from $C_1$-$C_6$ alkyl and $C_1$-$C_6$ halogenoalkyl), $C_1$-$C_6$ alkoxy, $C_1$-$C_6$ halogenoalkoxy and halogen; (c) $C_3$-$C_7$ cycloalkyl which may be optionally substituted by 1 to 7 groups selected from $C_1$-$C_6$ alkyl, $C_1$-$C_6$ halogenoalkyl and halogen; (d) $C_1$-$C_6$ alkoxy which may be optionally substituted by 1 to 7 groups selected from $C_3$-$C_7$ cycloalkyl, $C_1$-$C_6$ alkoxy, $C_1$-$C_6$ halogenoalkoxy and halogen; or (e) halogen is preferable.

$R^5$ and $R^6$ are each independently and preferably hydrogen or alkyl, particularly hydrogen.

n is preferably 0 or 1.

The number of the substituent in the "optionally substituted aminocarbonyl" of X may be one. As for such substituent, alkyl, alkoxy and nitrile can be mentioned for example.

The number of the substituents in the "optionally substituted alkanoyl" of X may be one or more (for example, 1 to 3), and the substituents may be the same or different. As for such substituents, halogen can be mentioned for example.

X is preferably (a) carboxy; (b) $C_1$-$C_6$ alkoxycarbonyl; (c) hydroxy-$C_1$-$C_6$ alkyl; (d) aminocarbonyl wherein a nitrogen atom may be optionally substituted by one group selected from $C_1$-$C_6$ alkyl, $C_1$-$C_6$ alkoxy and nitrile; (e) $C_2$-$C_7$ alkanoyl which may be optionally substituted by 1 to 3 halogens. Particularly (a) carboxy or (b) aminocarbonyl wherein a nitrogen atom may be optionally substituted by one group selected from $C_1$-$C_6$ alkyl, $C_1$-$C_6$ alkoxy and nitrile is preferable, and specifically carboxy is preferable.

The pharmaceutically acceptable salt of a compound of formula (I) includes an alkali metal salt of lithium, sodium, potassium, etc.; a group-II metal salt of calcium, magnesium, etc.; a salt with zinc or aluminum; a salt with amine such as ammonia, choline, diethanolamine, lysine, ethylenediamine, t-butylamine, t-octylamine, tris(hydroxymethyl)aminomethane, N-methyl-glucosamine, triethanolamine, dehydroabietylamine; a salt with inorganic acid such as hydrochloric acid, hydrobromic acid, hydroiodic acid, sulfuric acid, nitric acid, phosphoric acid; a salt with organic acid such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, benzenesulfonic acid; or a salt with acidic amino acid such as aspartic acid, glutamic acid.

The pharmaceutically acceptable salt of a compound of formula (I) includes an intramolecular salt, a hydrate, and a solvate thereof.

The term "prodrug" refers to a compound which is converted in the body into an activated form having pharmacological effects, for example by hydrolysis in the blood. Examples of the pharmaceutically acceptable prodrug are described in the literatures [T. Higuchi and V. Stella, Prodrugs as Novel Drug Delivery Systems, "Bioreversible Carriers in Drug Design", edited by Edward B. Roche, American Pharmaceutical Association and Pergamon Press, A. C. S. Symposium Series, Vol. 14, (1987); and D. Fleisher, R. Bong and B. H. Stewart, "Improved oral drug delivery: Solubility limitations overcome by the use of prodrugs", Advanced Drug Delivery Reviews (1996) 19(2): 115-130]. The prodrug wherein a compound of formula (I) is carboxylic acid compound includes an ester such as methyl ester, ethyl ester, a double ester.

The compound of the present invention may optionally have one or more asymmetric carbon atoms which are contained in any one of substituent groups. A compound of formula (I) may exist in the form of enantiomer or diastereomer or a mixture thereof. The compound of the present invention encompasses a mixture of stereoisomers, or pure or substantially pure isomers. A compound of formula (I) which is obtained in the form of diastereomer or enantiomer may be separated by a conventional method known in the art, for example chromatography or fractional crystallization.

In a preferable embodiment of the present invention, $R^1$ is (a) hydrogen; (b) $C_1$-$C_6$ alkyl which may be optionally substituted by 1 to 7 groups selected from $C_3$-$C_7$ cycloalkyl, $C_1$-$C_6$ alkoxy, halogen, oxo and hydroxy; (c) $C_3$-$C_7$ cycloalkyl which may be optionally substituted by 1 to 7 groups selected from $C_1$-$C_6$ alkyl, $C_1$-$C_6$ alkoxy and halogen; (d) $C_1$-$C_6$ alkoxy which may be optionally substituted by 1 to 7 groups selected from $C_3$-$C_7$ cycloalkyl, $C_1$-$C_6$ alkoxy, halogen and hydroxy; (e) phenyl which may be optionally substituted by 1 to 3 groups selected from $C_1$-$C_6$ alkyl, $C_1$-$C_6$ halogenoalkyl, $C_3$-$C_7$ cycloalkyl, $C_3$-$C_7$ halogenocycloalkyl, $C_1$-$C_6$ alkoxy, $C_1$-$C_6$ halogenoalkoxy and halogen; (f) halogen; or (g) nitrile, $R^{2a}$, $R^{2b}$, $R^{2c}$ and $R^{2d}$ are each independently (a) hydrogen; (b) $C_1$-$C_6$ alkyl which may be optionally substituted by 1 to 7 groups selected from $C_1$-$C_6$ alkoxy, $C_3$-$C_7$ cycloalkyl, halogen, oxo and hydroxy; (c) $C_3$-$C_7$ cycloalkyl which may be optionally substituted by 1 to 7 groups selected from $C_1$-$C_6$ alkyl, $C_1$-$C_6$ alkoxy and halogen; (d) $C_1$-$C_6$ alkoxy which may be optionally substituted by 1 to 7 groups selected from $C_1$-$C_6$ alkoxy, $C_3$-$C_7$ cycloalkyl and halogen; (e) phenyl which may be optionally substituted by 1 to 3 groups selected from $C_1$-$C_6$ alkyl, $C_1$-$C_6$ halogenoalkyl, $C_3$-$C_7$ cycloalkyl, $C_3$-$C_7$ halogenocycloalkyl, $C_1$-$C_6$ alkoxy, $C_1$-$C_6$ halogenoalkoxy and halogen; (f) 5 to 6-membered monocyclic aromatic heterocyclic group which may be optionally substituted by 1 to 3 groups selected from $C_1$-$C_6$ alkyl, $C_1$-$C_6$ halogenoalkyl, $C_3$-$C_7$ cycloalkyl, $C_3$-$C_7$ halogenocycloalkyl, $C_1$-$C_6$ alkoxy, $C_1$-$C_6$ halogenoalkoxy and halogen; (g) 4 to 7-membered monocyclic non-aromatic heterocyclic group which may be optionally substituted by 1 to 3 groups selected from $C_1$-$C_6$ alkyl, $C_1$-$C_6$ halogenoalkyl, $C_3$-$C_7$ cycloalkyl, $C_3$-$C_7$ halogenocycloalkyl, $C_1$-$C_6$ alkoxy, $C_1$-$C_6$ halogenoalkoxy and halogen; (h) halogen; or (i) nitrile, $R^{3a}$, $R^{3b}$, $R^{3c}$ and $R^{3d}$ are each independently (a) hydrogen; (b) $C_1$-$C_6$ alkyl which may be optionally substituted by 1 to 7 groups selected from $C_3$-$C_7$ cycloalkyl, $C_3$-$C_7$ halogenocycloalkyl (in which the cycloalkyl and halogenocycloalkyl may be each independently and optionally substituted by 1 to 3 groups selected from $C_1$-$C_6$ alkyl and $C_1$-$C_6$ halogenoalkyl), $C_1$-$C_6$ alkoxy, $C_1$-$C_6$ halogenoalkoxy, phenyl, 5 to 6-membered monocyclic aromatic heterocyclic group, 4 to 7-membered monocyclic non-aromatic heterocyclic group (in which the phenyl, aromatic heterocyclic group and non-aromatic heterocyclic group may be each independently and optionally substituted by 1 to 3 groups selected from $C_1$-$C_6$ alkyl, $C_1$-$C_6$ halogenoalkyl, $C_3$-$C_7$ cycloalkyl, $C_3$-$C_7$ halogenocycloalkyl, $C_1$-$C_6$alkoxy, $C_1$-$C_6$ halogenoalkoxy and halogen), halogen, oxo and hydroxy; (c) $C_3$-$C_7$ cycloalkyl which may be optionally substituted by 1 to 7 groups selected from $C_1$-$C_6$ alkyl, $C_1$-$C_6$ halogenoalkyl, $C_1$-$C_6$ alkoxy, $C_1$-$C_6$ halogenoalkoxy, halogen and hydroxy; (d) $C_1$-$C_6$ alkoxy which may be optionally substituted by 1 to 7 groups selected from $C_3$-$C_7$ cycloalkyl, $C_3$-$C_7$ halogenocycloalkyl (in which the cycloalkyl and halogenocycloalkyl may be each independently and optionally substituted by 1 to 3 groups selected from $C_1$-$C_6$ alkyl and $C_1$-$C_6$ halogenoalkyl), $C_1$-$C_6$ alkoxy, $C_1$-$C_6$ halogenoalkoxy, phenyl, 5 to 6-membered monocyclic aromatic heterocyclic group, 4 to 7-membered monocyclic non-aromatic heterocyclic group (in which the phenyl, aromatic heterocyclic group and non-aromatic heterocyclic group may be each independently and optionally substituted by 1 to 3 groups selected from $C_1$-$C_6$ alkyl, $C_1$-$C_6$ halogenoalkyl, $C_3$-$C_7$ cycloalkyl, $C_3$-$C_7$ halogenocycloalkyl, $C_1$-$C_6$ alkoxy, $C_1$-$C_6$ halogenoalkoxy and halogen), halogen and hydroxy; (e) $C_3$-$C_7$ cycloalkoxy which may be optionally substituted by 1 to 7 groups selected from $C_1$-$C_6$ alkyl, $C_1$-$C_6$ halogenoalkyl, $C_1$-$C_6$ alkoxy, $C_1$-$C_6$ halogenoalkoxy, halogen and hydroxy; (f) phenyl which may be optionally substituted by 1 to 3 groups selected from $C_1$-$C_6$ alkyl, $C_1$-$C_6$ halogenoalkyl, $C_3$-$C_7$ cycloalkyl, $C_3$-$C_7$ halogenocycloalkyl, $C_1$-$C_6$ alkoxy, $C_1$-$C_6$ halogenoalkoxy and halogen; (g) 5 to 6-membered monocyclic aromatic heterocyclic group which may be optionally substituted by 1 to 3 groups selected from $C_1$-$C_6$ alkyl, $C_1$-$C_6$ halogenoalkyl, $C_3$-$C_7$ cycloalkyl, $C_3$-$C_7$ halogenocycloalkyl, $C_1$-$C_6$ alkoxy, $C_1$-$C_6$ halogenoalkoxy and halogen; (h) 4 to 7-membered monocyclic non-aromatic heterocyclic group which may be optionally substituted by 1 to 3 groups selected from $C_1$-$C_6$ alkyl, $C_1$-$C_6$ halogenoalkyl, $C_3$-$C_7$ cycloalkyl, $C_3$-$C_7$ halogenocycloalkyl, $C_1$-$C_6$ alkoxy, $C_1$-$C_6$ halogenoalkoxy and halogen; (i) phenoxy which may be optionally substituted by 1 to 3 groups selected from $C_1$-$C_6$ alkyl, $C_1$-$C_6$ halogenoalkyl, $C_3$-$C_7$ cycloalkyl, $C_3$-$C_7$ halogenocycloalkyl, $C_1$-$C_6$ alkoxy, $C_1$-$C_6$ halogenoalkoxy and halogen; (j) halogen; or (k) hydroxy, or two substituent groups selected from $R^{3a}$, $R^{3b}$, $R^{3c}$ and $R^{3d}$ combine each other to form oxo, $R^5$ and $R^6$ are each independently (a) hydrogen; (b) $C_1$-$C_6$ alkyl; (c) $C_1$-$C_6$ halogenoalkyl; (d) $C_3$-$C_7$ cycloalkyl; or (e) $C_3$-$C_7$ halogenocycloalkyl, or $R^5$ and $R^6$ combine each other at their terminals together with the adjacent carbon atom to form 3 to 7-membered alicyclic monocyclic hydrocarbon, X is (a) carboxy; (b) $C_1$-$C_6$ alkoxycarbonyl; (c) hydroxy-$C_1$-$C_6$ alkyl; (d) aminocarbonyl wherein a nitrogen atom may be optionally substituted by one group selected from $C_1$-$C_6$ alkyl, $C_1$-$C_6$ alkoxy and nitrile; or (e) $C_2$-$C_7$ alkanoyl which may be optionally substituted by 1 to 3 halogens.

In another preferable embodiment of the present invention, Ring A is quinoline, isoquinoline or pyrrolopyridine.

In another further preferable embodiment of the present invention, the compound of the present invention is represented by the following formula (I-A):

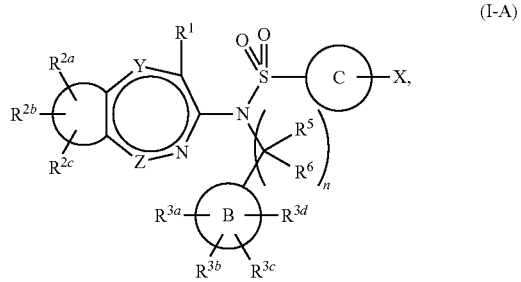

(I-A)

wherein a group of formula:

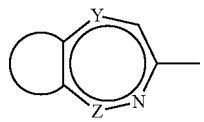

is bicyclic aromatic heterocycle comprised of pyridine fused with (a) benzene or (b) monocyclic aromatic heterocycle (wherein one of Y and Z is $CR^{2d}$, and the other is a chemical bond), and other symbols are the same as defined above. In this embodiment, a group of formula:

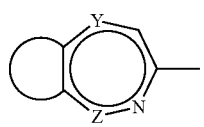

is preferably a group of formula:

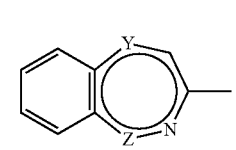

wherein the symbols are the same as defined above.

In another preferable embodiment of the present invention, Ring C is benzene, and X is carboxy and binds to Ring C at 4-position to the aminosulfonyl moiety.

In another preferable embodiment of the present invention, the compound of the present invention is represented by the following formula (I-B):

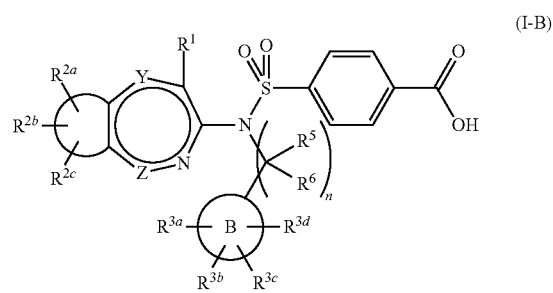

(I-B)

wherein symbols are the same as defined above.

In another preferable embodiment of the present invention, Ring A, $R^1$, $R^{2a}$, $R^{2b}$, $R^{2c}$ and $R^{2d}$ are represented by the following formula:

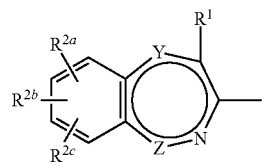

wherein symbols are the same as defined above.

In another preferable embodiment of the present invention, Ring B is (a) monocyclic or bicyclic aromatic hydrocarbon; or (b) monocyclic or bicyclic aromatic heterocycle, and n is 0 or 1. More preferably, Ring B is benzene, naphthalene, tetrahydronaphthalene, indane, pyridine, indole, dihydrobenzofuran, dihydroisobenzofuran, or benzothiophene, particularly benzene, naphthalene (particularly, naphthalen-2-yl), tetrahydronaphthalene (particularly, 1,2,3,4-tetrahydronaphthalen-6-yl), indane (particularly, indan-1-yl or indan-5-yl), pyridine (particularly, pyridin-2-yl) or benzothiophene (particularly, benzothiophen-2-yl).

In this embodiment, a preferable partial structure of formula:

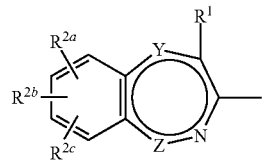

is a group of formula (A):

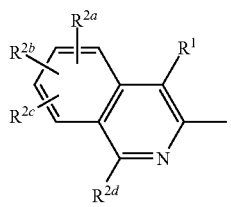

(A)

wherein symbols are the same as defined above.

In another preferable embodiment, a partial structure of formula:

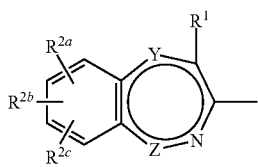

is a group of formula (B):

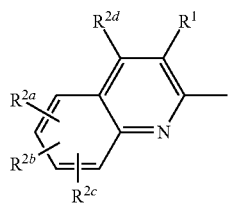

(B)

wherein symbols are the same as defined above.

In another preferable embodiment of the present invention, $R^1$ is (a) $C_1$-$C_6$ alkyl which may be optionally substituted by 1 to 7 halogens; (b) $C_3$-$C_7$ cycloalkyl; (c) $C_1$-$C_6$ alkoxy or (d) halogen, $R^{2a}$, $R^{2b}$ and $R^{2c}$ are hydrogen, $R^{2d}$ is (a) hydrogen; (b) $C_1$-$C_6$ alkyl which may be optionally substituted by 1 to 7 halogens; (c) $C_3$-$C_7$ cycloalkyl; or (d) $C_1$-$C_6$ alkoxy, $R^{3a}$ and $R^{3b}$ are each independently (a) hydrogen; (b) $C_1$-$C_6$ alkyl which may be optionally substituted by 1 to 7 groups selected from $C_3$-$C_7$ cycloalkyl (in which the cycloalkyl may be optionally substituted by 1 to 3 groups selected from $C_1$-$C_6$ alkyl and $C_1$-$C_6$ halogenoalkyl), $C_1$-$C_6$ alkoxy, $C_1$-$C_6$ halogenoalkoxy, and halogen; (c) $C_3$-$C_7$ cycloalkyl which may be optionally substituted by 1 to 7 groups selected from $C_1$-$C_6$ alkyl, $C_1$-$C_6$ halogenoalkyl, and halogen; (d) $C_1$-$C_6$ alkoxy which may be optionally substituted by 1 to 7 groups selected from $C_3$-$C_7$ cycloalkyl, $C_1$-$C_6$ alkoxy, $C_1$-$C_6$ halogenoalkoxy, and halogen; or (e) halogen, $R^{3c}$ and $R^{3d}$ are hydrogen, $R^5$ and $R^6$ are hydrogen, n is 1.

In another preferable embodiment of the present invention, a partial structure of formula:

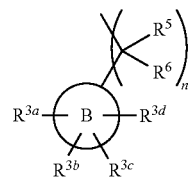

is a group of formula (C):

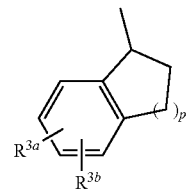

(C)

wherein p is 1 or 2, and other symbols are the same as defined above, $R^1$ is (a) $C_1$-$C_6$ alkyl which may be optionally substituted by 1 to 7 halogens; (b) $C_3$-$C_7$ cycloalkyl; (c) $C_1$-$C_6$ alkoxy; or (d) halogen, $R^{2a}$ and $R^{2b}$ are hydrogen, $R^{2d}$ is (a) hydrogen; (b) $C_1$-$C_6$ alkyl which may be optionally substituted by 1 to 7 halogens; (c) $C_3$-$C_7$ cycloalkyl; or (d) $C_1$-$C_6$ alkoxy, $R^{3a}$ and $R^{3b}$ are each independently (a) hydrogen; (b) $C_1$-$C_6$ alkyl which may be optionally substituted by 1 to 7 groups selected from $C_3$-$C_7$ cycloalkyl (in which the cycloalkyl may be optionally substituted by 1 to 3 groups selected from $C_1$-$C_6$ alkyl and $C_1$-$C_6$ halogenoalkyl), $C_1$-$C_6$ alkoxy, $C_1$-$C_6$ halogenoalkoxy, and halogen; (c) $C_3$-$C_7$ cycloalkyl which may be optionally substituted by 1 to 7 groups selected from $C_1$-$C_6$ alkyl, $C_1$-$C_6$ halogenoalkyl, and halogen; (d) $C_1$-$C_6$ alkoxy which may be optionally substituted by 1 to 7 groups selected from $C_3$-$C_7$ cycloalkyl, $C_1$-$C_6$ alkoxy, $C_1$-$C_6$ halogenoalkoxy, and halogen; or (e) halogen.

In another preferable embodiment of the present invention, a partial structure of formula (A):

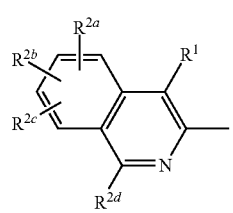

(A)

is the following partial structure of formula (A-I):

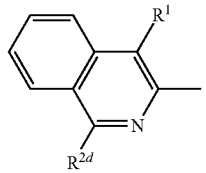

(A-I)

wherein the symbols are the same as defined above,

Ring B is benzene or pyridine (particularly, pyridin-2-yl), $R^1$ is methyl, trifluoromethyl, isopropyl, cyclopropyl, or methoxy, $R^{2d}$ is (a) hydrogen; (b) $C_1$-$C_6$ alkyl which may be optionally substituted by 1 to 7 halogens; (c) $C_3$-$C_7$ cycloalkyl; or (d) $C_1$-$C_6$ alkoxy, $R^{3a}$ and $R^{3b}$ are each independently (a) hydrogen; (b) $C_1$-$C_6$ alkyl which may be optionally substituted by 1 to 7 groups selected from $C_3$-$C_7$ cycloalkyl (in which the cycloalkyl may be optionally substituted by 1 to 3 groups selected from $C_1$-$C_6$ alkyl and $C_1$-$C_6$ halogenoalkyl), $C_1$-$C_6$ alkoxy, $C_1$-$C_6$ halogenoalkoxy, and halogen; (c) $C_3$-$C_7$ cycloalkyl; (d) $C_1$-$C_6$ alkoxy which may be optionally substituted by 1 to 7 halogens; or (e) halogen, $R^{3c}$ and $R^{3d}$ are hydrogen, $R^5$ and $R^6$ are hydrogen, n is 1.

In this embodiment, a preferable partial structure of formula (A):

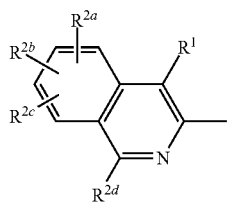

(A)

is the following partial structure of formula (A-II):

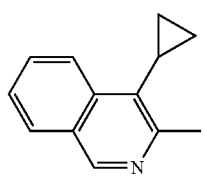

(A-II)

Ring B is benzene or pyridine (particularly, pyridin-2-yl), $R^{3a}$ and $R^{3b}$ are each independently (a) hydrogen; (b) $C_1$-$C_6$ alkyl which may be optionally substituted by 1 to 7 groups selected from $C_3$-$C_7$ cycloalkyl (in which the cycloalkyl may be optionally substituted by 1 to 3 groups selected from $C_1$-$C_6$ alkyl and $C_1$-$C_6$ halogenoalkyl), $C_1$-$C_6$ alkoxy, $C_1$-$C_6$ halogenoalkoxy, and halogen; (c) $C_3$-$C_7$ cycloalkyl; (d) $C_1$-$C_6$ alkoxy which may be optionally substituted by 1 to 7 halogens; or (e) halogen, $R^{3c}$ and $R^{3d}$ are hydrogen, $R^5$ and $R^6$ are hydrogen, n is 1.

In this embodiment, more preferably, $R^{3a}$ and $R^{3b}$ are each independently (a) hydrogen; (b) $C_1$-$C_6$ alkyl which may be optionally substituted by 1 to 7 groups selected from $C_3$-$C_7$ cycloalkyl and halogen; (c) $C_1$-$C_6$ alkoxy which may be optionally substituted by 1 to 7 halogens; or (e) halogen.

In another preferable embodiment of the present invention, a preferable partial structure of formula (A):

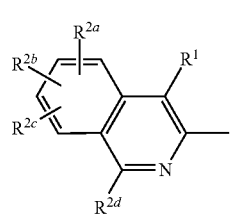

(A)

is the following partial structure of formula (A-III):

(A-III)

Ring B is benzene, $R^{3a}$ and $R^{3b}$ are each independently (a) hydrogen; (b) $C_1$-$C_6$ alkyl which may be optionally substituted by 1 to 7 groups selected from $C_3$-$C_7$ cycloalkyl (in which the cycloalkyl may be optionally substituted by 1 to 3 groups selected from $C_1$-$C_6$ alkyl and $C_1$-$C_6$ halogenoalkyl), $C_1$-$C_6$ alkoxy, $C_1$-$C_6$ halogenoalkoxy, and halogen; (c) $C_3$-$C_7$ cycloalkyl; (d) $C_1$-$C_6$ alkoxy which may be optionally substituted by 1 to 7 halogens; or (e) halogen, $R^{3c}$ and $R^{3d}$ are hydrogen, $R^5$ and $R^6$ are hydrogen, n is 1.

In this embodiment, more preferably, $R^{3a}$ and $R^{3b}$ are each independently (a) hydrogen; (b) $C_1$-$C_6$ alkyl which may be optionally substituted by 1 to 7 groups selected from $C_3$-$C_7$ cycloalkyl and halogen; (c) $C_1$-$C_6$ alkoxy which may be optionally substituted by 1 to 7 halogens; or (e) halogen.

In another preferable embodiment of the present invention, a preferable partial structure of formula (A):

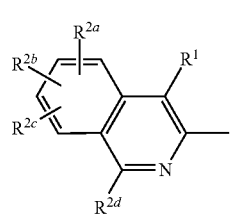

(A)

is the following partial structure of formula (A-IV):

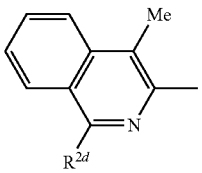

(A-IV)

wherein Me is methyl, and the other symbol is the same as defined above,

Ring B is benzene, $R^{2d}$ is (a) hydrogen; (b) $C_1$-$C_6$ alkyl which may be optionally substituted by 1 to 7 halogens; or (c) $C_3$-$C_7$ cycloalkyl, $R^{3a}$ and $R^{3b}$ are each independently (a) hydrogen; (b) $C_1$-$C_6$ alkyl which may be optionally substituted by 1 to 7 groups selected from $C_3$-$C_7$ cycloalkyl (in which the cycloalkyl may be optionally substituted by 1 to 3 groups selected from $C_1$-$C_6$ alkyl and $C_1$-$C_6$ halogenoalkyl), $C_1$-$C_6$ alkoxy, $C_1$-$C_6$ halogenoalkoxy, and halogen; (c) $C_3$-$C_7$ cycloalkyl; (d) $C_1$-$C_6$ alkoxy which may be optionally substituted by 1 to 7 halogens; or (e) halogen, $R^{3c}$ and $R^{3d}$ are hydrogen, $R^5$ and $R^6$ are hydrogen, n is 1.

In this embodiment, more preferably, $R^{2d}$ is hydrogen, isopropyl or cyclopropyl, $R^{3a}$ and $R^{3b}$ are each independently (a) hydrogen; (b) $C_1$-$C_6$ alkyl which may be optionally substituted by 1 to 7 groups selected from $C_3$-$C_7$ cycloalkyl and halogen; (c) $C_1$-$C_6$ alkoxy which may be optionally substituted by 1 to 7 halogens; or (e) halogen.

In another preferable embodiment of the present invention, a preferable partial structure of formula (A):

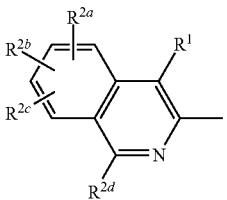

(A)

is the following partial structure of formula (A-V):

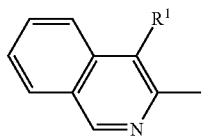

(A-V)

wherein the symbol is the same as defined above,

Ring B is benzene, $R^1$ is isopropyl or methoxy, $R^{3a}$ and $R^{3b}$ are each independently (a) hydrogen; (b) $C_1$-$C_6$ alkyl which may be optionally substituted by 1 to 7 groups selected from $C_3$-$C_7$ cycloalkyl (in which the cycloalkyl may be optionally substituted by 1 to 3 groups selected from $C_1$-$C_6$ alkyl and $C_1$-$C_6$ halogenoalkyl), $C_1$-$C_6$ alkoxy, $C_1$-$C_6$ halogenoalkoxy, and halogen; (c) $C_3$-$C_7$ cycloalkyl; (d) $C_1$-$C_6$ alkoxy which may be optionally substituted by 1 to 7 halogens; or (e) halogen, $R^{3a}$ and $R^{3d}$ are hydrogen, $R^5$ and $R^6$ are hydrogen, n is 1.

In this embodiment, more preferably, $R^{3a}$ and $R^{3b}$ are each independently (a) hydrogen; (b) $C_1$-$C_6$ alkyl which may be optionally substituted by 1 to 7 groups selected from $C_3$-$C_7$ cycloalkyl and halogen; (c) $C_1$-$C_6$ alkoxy which may be optionally substituted by 1 to 7 halogens; or (e) halogen.

In another preferable embodiment of the present invention, a preferable partial structure of formula:

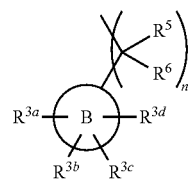

is a group of formula (D):

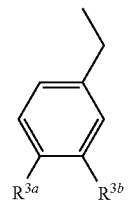

(D)

wherein the symbols are the same as defined above, $R^{3a}$ and $R^{3b}$ are each independently (a) hydrogen; (b) $C_1$-$C_6$ alkyl which may be optionally substituted by 1 to 7 groups selected from $C_3$-$C_7$ cycloalkyl and halogen; (c) $C_1$-$C_6$ alkoxy which may be optionally substituted by 1 to 7 halogens; or (e) halogen.

A preferable compound of the present invention is selected from the group consisting of:

4-({(4-methylisoquinolin-3-yl)[4-(trifluoromethoxy)benzyl]amino}sulfonyl)benzoic acid;

4-{[[3-fluoro-4-(trifluoromethoxy)benzyl](4-methylisoquinolin-3-yl)amino]sulfonyl}benzoic acid;

4-({1-cyclopropyl-4-methylisoquinolin-3-yl)[4-(trifluoromethoxy)benzyl]amino}sulfonyl)-benzoic acid;

4-{[[4-(1-ethoxy-2,2,2-trifluoro-1-methylethyl)benzyl](4-methylisoquinolin-3-yl)amino]-sulfonyl}benzoic acid;

4-({(3-methylquinolin-2-yl)[4-(trifluoromethoxy)benzyl]amino}sulfonyl)benzoic acid;

4-{[[4-fluoro-3-(trifluoromethyl)benzyl] (3-methylquinolin-2-yl)amino]sulfonyl}benzoic acid;

4-{[(4-t-butylbenzyl)(4-methylisoquinolin-3-yl)amino] sulfonyl}benzoic acid;

4-{[[4-(cyclopropylmethyl)benzyl](4-methylisoquinolin-3-yl)-amino]sulfonyl}benzoic acid;

4-{[[4-fluoro-3-(trifluoromethyl)benzyl] (4-methylisoquinolin-3-yl)amino]sulfonyl}benzoic acid;

4-{[(4-methylisoquinolin-3-yl)(2-naphthylmethyl)amino] sulfonyl}benzoic acid;

4-({(1-methoxy-4-methylisoquinolin-3-yl)[4-(trifluoromethoxy)benzyl]amino}sulfonyl)-benzoic acid;

4-({(4-chloroisoquinolin-3-yl)[4-(trifluoromethoxy)benzyl]amino}sulfonyl)benzoic acid;

4-{[(4-methylisoquinolin-3-yl)(5,6,7,8-tetrahydronaphthalen-2-ylmethyl)amino]sulfonyl}-benzoic acid;

4-{[(2,3-dihydro-1H-inden-5-ylmethyl)(4-methylisoquinolin-3-yl)amino]sulfonyl}benzoic acid;

4-{[[(1,1-dimethyl-2,3-dihydro-1H-inden-5-yl)methyl](4-methylisoquinolin-3-yl)amino]-sulfonyl}benzoic acid;

4-{[[(2,2-dimethyl-2,3-dihydro-1H-inden-5-yl)methyl](4-methylisoquinolin-3-yl)amino]-sulfonyl}benzoic acid;

4-{[[(3,3-dimethyl-2,3-dihydro-1-benzofuran-6-yl)methyl](4-methylisoquinolin-3-yl)amino]-sulfonyl}benzoic acid;

4-{[[(1-benzothiophen-2-yl)methyl](4-methylisoquinolin-3-yl)amino]sulfonyl}benzoic acid;

4-({(1,4-dimethylisoquinolin-3-yl)[4-(trifluoromethoxy)benzyl]amino}sulfonyl)benzoic acid; and 4-({(4-methylisoquinolin-3-yl)[4-(2,2,2-trifluoro-1-methoxy-1-methylethyl)benzyl]amino}-sulfonyl)benzoic acid; or a pharmaceutically acceptable salt thereof, or a prodrug thereof.

Another preferable compound of the present invention is selected from the group consisting of:

4-({(1-cyclopropyl-4-methylisoquinolin-3-yl)[4-(trifluoromethoxy)benzyl]amino}sulfonyl)-benzoic acid;

4-({(1-methoxy-4-methylisoquinolin-3-yl)[4-(trifluoromethoxy)benzyl]amino}sulfonyl)-benzoic acid;

4-({(1-isopropyl-4-methylisoquinolin-3-yl)[4-(trifluoromethoxy)benzyl]amino}sulfonyl)-benzoic acid;

4-{[{3-chloro-4-[cyclopropyl(difluoro)methyl]benzyl}(4-methylisoquinolin-3-yl)amino]-sulfonyl}benzoic acid;

4-({(4-cyclopropylisoquinolin-3-yl) [4-(trifluoromethoxy)benzyl]amino}sulfonyl)benzoic acid;

4-{[{3-chloro-4-[cyclopropyl (difluoro)methyl]benzyl}(1-cyclopropyl-4-methylisoquinolin-3-yl)amino] sulfonyl}benzoic acid;

4-{[{4-[cyclopropyl(difluoro)methyl]-3-fluorobenzyl}(4-methylisoquinolin-3-yl)amino]-sulfonyl}benzoic acid;

4-({[4-(trifluoromethoxy)benzyl][4-(trifluoromethyl)isoquinolin-3-yl]amino}sulfonyl)benzoic acid;

4-[((4-cyclopropylisoquinolin-3-yl){[5-(trifluoromethyl)pyridin-2-yl]methyl}amino) sulfonyl]-benzoic acid;

4-{[{3-chloro-4-[cyclopropyl(difluoro)methyl]benzyl}(4-cyclopropylisoquinolin-3-yl)amino]-sulfonyl}benzoic acid;

4-{[{4-[cyclopropyl(difluoro)methyl]-3-fluorobenzyl}(4-cyclopropylisoquinolin-3-yl)amino]-sulfonyl}benzoic acid;

4-({(4-cyclopropylisoquinolin-3-yl)[5-(trifluoromethoxy)-2,3-dihydro-1H-inden-1-yl]amino}-sulfonyl)benzoic acid;

4-({{3-chloro-4-[cyclopropyl(difluoro)methyl]benzyl}[4-(trifluoromethyl)isoquinolin-3-yl]-amino}sulfonyl)benzoic acid; and 4-({{4-[cyclopropyl(difluoro)methyl]-3-fluorobenzyl}[4-(trifluoromethyl)isoquinolin-3-yl]-amino}sulfonyl)benzoic acid; or a pharmaceutically acceptable salt thereof, or a prodrug thereof.

The compound of the present invention has a novel structure wherein bicyclic aromatic heterocycle in which pyridine is condensed with benzene or pyridine is condensed with monocyclic aromatic heterocycle binds to a sulfonylamino moiety, and shows excellent TRPM8 antagonistic activity in the menthol-induced calcium influx inhibiting test. The compound of the present invention also shows excellent inhibitory effects on Wet Dog Shakes induced by TRPM8 agonist (e.g., menthol or icilin) in rat, for example.

Accordingly, the compound of the present invention is useful for the prevention and treatment of (a) chronic pain: such as neuropathic pain (for example cold allodynia, diabetic neuropathy, postherpetic neuralgia, complex regional pain syndrome, chemotherapy-induced peripheral neuropathy, trigeminal neuralgia, post stroke pain, spinal cord injury pain, neuralgia, or nerve injury-induced neuropathic pain), nociceptive pain (for example rheumatoid arthritis, osteoarthritis, postoperative pain, or myofascial pain), or mixed pain (for example cancer pain, fibromyalgia syndrome, or chronic low back pain);

(b) cephalalgia: such as migraine, or cluster or tension headache;

(c) urologic disease: such as detrusor overactivity, overactive bladder, urinary incontinence, neurogenic bladder, detrusor hyperreflexia, idiopathic detrusor overactivity, detrusor instability, interstitial cystitis, benign prostatic hyperplasia, chronic prostatitis, or lower urinary tract symptom;

(d) carcinoma: such as prostate cancer, or breast cancer;

(e) respiratory disease: such as asthma, COPD (chronic obstructive pulmonary disease), or pulmonary hypertension;

(f) gastrointestinal disease: such as irritable bowel syndrome;

(g) psychiatric disease: such as mood disorder (for example depression, or bipolar disorder), or anxiety disorder (for example anxiety);

(h) neurological disease: such as neurodegenerative disease, or stroke; or (i) dermatosis: such as pruritus.

The compound of the present invention is preferably useful for the prevention and treatment of chronic pain or urologic disease, particularly chronic pain.

The compound of the present invention or a pharmaceutically acceptable salt thereof, or a prodrug thereof may be administered orally or parenterally, and may be used in the form of suitable pharmaceutical formulation. The pharmaceutical formulation suitable for oral administration includes a solid formulation such as tablet, granule, capsule, powder, or a liquid formulation, suspension, emulsion. The pharmaceutical formulation suitable for parenteral administration includes suppository; injection or intravenous infusion in which water for injection, physiological saline or aqueous glucose solution is used; and an inhalant formulation.

The pharmaceutical composition herein may comprise about 0.01 mg/kg to about 100 mg/kg (preferably, about 0.01 mg/kg to about 50 mg/kg, more preferably about 0.01 mg/kg to about 30 mg/kg) of the active ingredient per a unit dose, for example per a tablet, capsule, powder, injection, suppository, teaspoon, and may be administered in the dose of about 0.01 mg/kg/day to about 100 mg/kg/day (preferably, about 0.01 mg/kg/day to about 50 mg/kg/day, more preferably about 0.01 mg/kg/day to about 30 mg/kg/day). The pharmaceutical composition comprising any one of compounds defined herein and pharmaceutically acceptable carriers may be used in the method of treating diseases described herein. The dosage form may comprise about 0.01 mg/kg to about 100 mg/kg (preferably, about 0.01 mg/kg to about 50 mg/kg, more preferably about 0.01 mg/kg to about 30 mg/kg) of the active ingredient, and may be formed in any forms suitable for the selected administration mode. The dose may vary according to the administration routes, the needs of subjects, the severities of conditions to be treated and compounds to be used. The pharmaceutical composition may be daily or periodically administered.

Compound (I) of the present invention may be prepared by the methods of the following scheme 1, 2 or 3, but preparation methods of Compound (I) are not limited thereto.

It is required and/or desired that sensitive or reactive groups in the interest molecule may be protected during any preparation processes of the compound of the present invention. The protection may be achieved by conventional protective groups. The protective groups and common uses thereof are described in T. W. Greene, et al., "Protecting Groups in Organic Synthesis", John Wiley & Sons, New York, 2006. The protective group may be removed in the subsequent process by a conventional method.

Scheme 1:

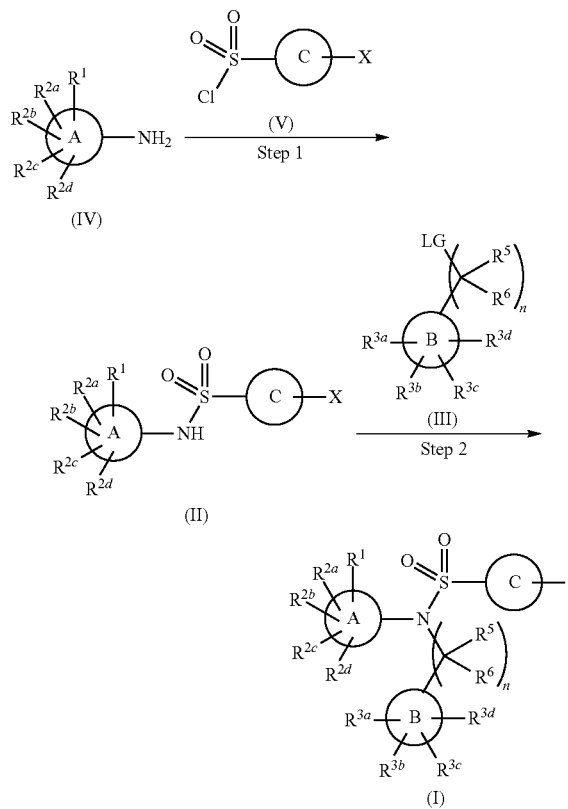

(In the above scheme, LG is a leaving group and includes halogen such as chlorine, bromine, substituted sulfonyloxy such as p-toluenesulfonyloxy, methanesulfonyloxy and trifluoromethylsulfonyloxy, and other symbols are the same as defined above.)

Compound (IV) may be reacted with Compound (V) to give Compound (II). The resulting compound may be reacted with Compound (III) to give Compound (I).

Step 1:

Compound (II) may be prepared by condensing Compound (IV) with Compound (V) in a solvent in the presence of a base.

Any solvents which do not affect the reaction may be preferably used as the solvent in the condensation, and examples of the solvent include ether such as tetrahydrofuran, 1,4-dioxane, 1,2-dimethoxyethane; hydrocarbon such as toluene, hexane, xylene; halogenohydrocarbon such as dichloromethane, chloroform 1,2-dichloroethane; ester such as ethyl acetate, butyl acetate; ketone such as acetone, butanone; amide such as N,N-dimethylformamide, N,N-dimethylacetamide, 1,3-dimethyl-2-imidazolidinone and N-methylpyrrolidone; sulfoxide such as dimethyl sulfoxide, and the following amines may be also used as the solvent. These solvents may be used alone or in combination. A preferable solvent in the reaction is amine such as pyridine; or halogenohydrocarbon such as chloroform.

Any conventional bases may be used as the base, and examples of the base include alkali metal amide such as lithium diisopropylamide, sodium amide, lithium bistrimethylsilylamide; alkali metal carbonate such as sodium carbonate, potassium carbonate, sodium hydrogen carbonate, potassium hydrogen carbonate; alkali metal phosphate such as sodium phosphate, potassium phosphate; amine such as triethylamine, diisopropylethylamine, pyridine, N-methylmorpholine, preferably amine such as pyridine.

The reaction may be carried out at low temperature, room temperature or high temperature, for example at 0° C. to 120° C.

When two equimolar amount of compound of formula (V) are condensed with one equimolar amount of compound of formula (IV) in the condensation reaction and a sulfonimide compound is obtained, the sulfonimide compound may be treated with tetrabutylammonium fluoride to give the corresponding Compound (II).

Step 2:

Compound (I) may be prepared by condensing Compound (II) with Compound (III) in a solvent in the presence of a base.

Any solvents which do not affect the reaction may be preferably used as the solvent in the condensation, and examples of the solvent include ether such as tetrahydrofuran, 1,4-dioxane, 1,2-dimethoxyethane; hydrocarbon such as toluene, hexane, xylene; ester such as ethyl acetate, butyl acetate; ketone such as acetone, butanone; amide such as N,N-dimethylformamide, N,N-dimethylacetamide, 1,3-dimethyl-2-imidazolidinone and N-methylpyrrolidone; sulfoxide such as dimethyl sulfoxide, and the following amines may be also used as the solvent. These solvents may be used alone or in combination. A preferable solvent in the reaction is amide such as N,N-dimethylformamide.

Any conventional bases may be used as the base, and examples of the base include alkali metal amide such as lithium diisopropylamide, sodium amide, lithium bistrimethylsilylamide; alkali metal carbonate such as sodium carbonate, potassium carbonate, cesium carbonate, sodium hydrogen carbonate, potassium hydrogen carbonate; alkali metal phosphate such as sodium phosphate, potassium phosphate; amine such as triethylamine, diisopropylethylamine, pyridine, N-methylmorpholine, preferably alkali metal carbonate such as potassium carbonate.

The reaction may be carried out at low temperature, room temperature or high temperature, for example at −20° C. to 80° C.

Scheme 2:

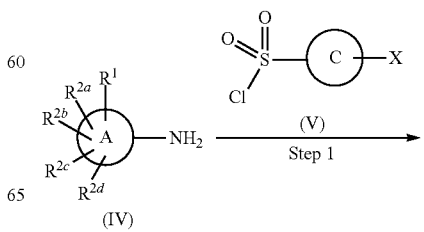

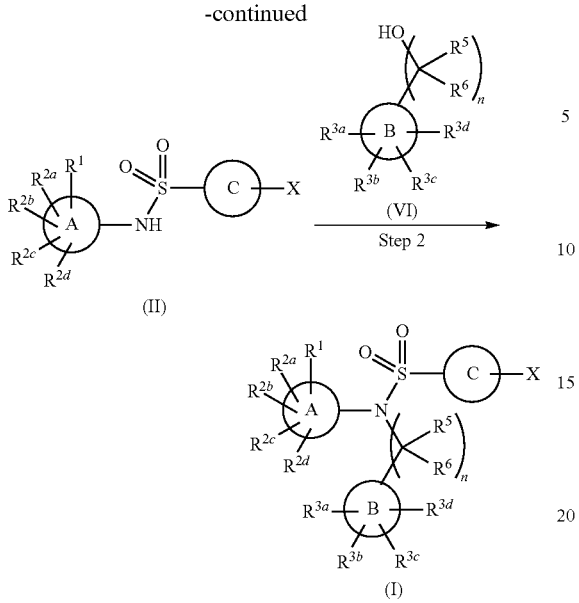

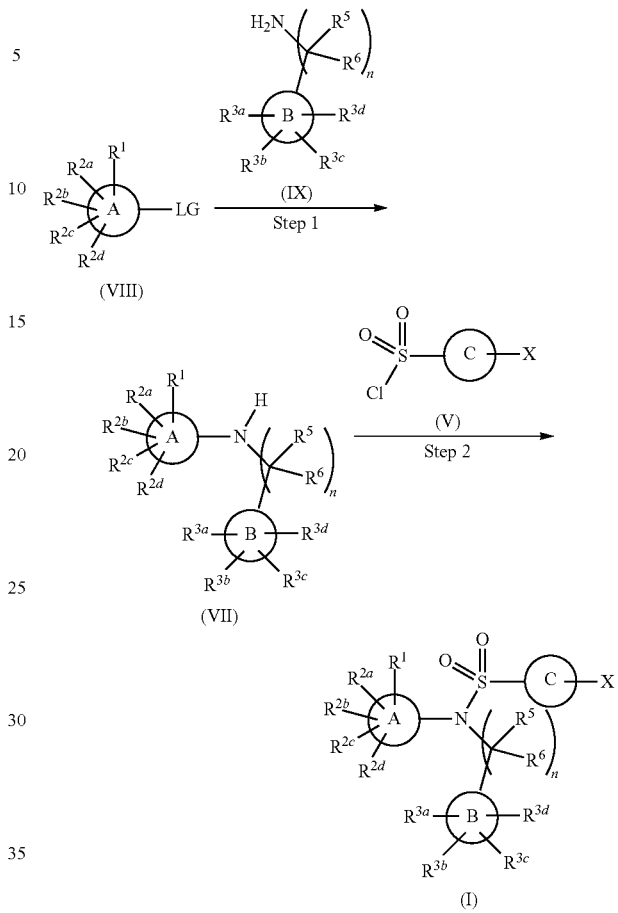

(In the above scheme, symbols are the same as defined above.)

Compound (IV) may be reacted with Compound (V) to give Compound (II). The resulting compound may be reacted with Compound (VI) to give Compound (I).

Step 1:

Compound (II) may be prepared according to the method of Scheme 1, Step 1.

Step 2:

Compound (I) may be prepared by Mitsunobu reaction of Compound (II) with Compound (VI) in a solvent.

Mitsunobu reaction may be carried out in an appropriate solvent in the presence of phosphine and azodicarboxylate compound.

Examples of phosphine include triphenylphosphine, diphenyl (2-pyridyl)phosphine, (4-dimethylaminophenyl) diphenylphosphine, isopropyldiphenylphosphine, diethylphenylphosphine, dicyclohexylphenylphosphine, tributylphosphine, tri-t-butylphosphine, tricyclohexylphosphine. Examples of the azodicarboxylate compound include diethyl azodicarboxylate, diisopropyl azodicarboxylate, dibutyl azodicarboxylate, azodicarbonyl dipiperazine, tetramethyl azodicarboxamide. The reaction may be carried out in the presence of cyanomethylenetributylphosphorane in place of phosphine and azodicarboxylate compound.

Any solvents which do not affect the reaction may be preferably used as the solvent, and examples of the solvent include ether such as tetrahydrofuran, 1,4-dioxane, 1,2-dimethoxyethane; hydrocarbon such as toluene, hexane, xylene; ester such as ethyl acetate, butyl acetate; ketone such as acetone, butanone; amide such as N,N-dimethylformamide, N,N-dimethylacetamide, 1,3-dimethyl-2-imidazolidinone and N-methylpyrrolidone; sulfoxide such as dimethyl sulfoxide. These solvents may be used alone or in combination. A preferable solvent in the reaction is ether such as tetrahydrofuran.

The reaction may be carried out at low temperature, room temperature or high temperature, for example at −20° C. to 80° C.

(In the above scheme, symbols are the same as defined above.)

Compound (VIII) may be reacted with Compound (IX) to give Compound (VII). The resulting compound may be reacted with Compound (V) to give Compound (I).

Step 1:

Compound (VII) may be prepared by condensing Compound (VIII) with Compound (IX) in a solvent or without a solvent in the presence of a base.

Any solvents which do not affect the reaction may be preferably used as the solvent in the condensation, and examples of the solvent include ether such as tetrahydrofuran, 1,4-dioxane, 1,2-dimethoxyethane; hydrocarbon such as toluene, hexane, xylene; ester such as ethyl acetate, butyl acetate; ketone such as acetone, butanone; amide such as N,N-dimethylformamide, N,N-dimethylacetamide, 1,3-dimethyl-2-imidazolidinone and N-methylpyrrolidone; sulfoxide such as dimethyl sulfoxide. These solvents may be used alone or in combination. The absence of solvent is preferable in the reaction.

A conventional bases may be used as the base, and examples of the base include alkali metal amide such as lithium diisopropylamide, sodium amide, lithium bistrimethylsilylamide; alkali metal carbonate such as sodium carbonate, potassium carbonate, sodium hydrogen carbonate, potassium hydrogen carbonate; alkali metal phosphate such as sodium phosphate, potassium phosphate; amine such as triethylamine, diisopropylethylamine, pyridine, N-methylmorpholine. Excess amounts of Compound (IX) may be also used as the base. A preferable base in the reaction is excess amounts of Compound (IX).

The reaction may be carried out at high temperature, for example at 100° C. to 250° C., and may be preferably carried out by microwave irradiation.

Step 2:

Compound (I) may be prepared according to the method of Scheme 1, Step 1.

Further, an interconversion may be carried out by a conventional method for Compound (I) prepared in the above preparation, or for an intermediate compound obtained during the preparation of Compound (I).

Compound (I) wherein Ring B is indole and an intermediate compound thereof may be prepared by oxidizing Compound (I) wherein Ring B is indoline and an intermediate compound thereof, respectively. The oxidation reaction may be carried out in an appropriate solvent in the presence of an oxidizing agent.

The oxidizing agent includes 2,3-dichloro-5,6-dicyano-p-benzoquinone. The solvent may be selected from any solvents which do not affect the reaction, and examples of the solvent include aromatic hydrocarbon such as toluene and xylene; ether such as tetrahydrofuran, 1,2-dimethoxyethane and 1,4-dioxane; halogenohydrocarbon such as dichloromethane, chloroform and 1,2-dichloroethane. These solvents may be used alone or in combination.

Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is optionally substituted phenyl, and an intermediate compound thereof (hereinafter may also be referred to as the compound containing optionally substituted phenyl) may be prepared by coupling Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is halogen (particularly, bromine, iodine), and an intermediate compound thereof (hereinafter may also be referred to as the compound containing halogen), respectively, with $Ar^1B(OH)_2$ or cyclic borate ester thereof, $Ar^1BF_3K$ or $Ar^1Sn(n-Bu)_3$ (wherein $Ar^1$ is optionally substituted phenyl, and n-Bu is butyl), etc.

The coupling reaction may be carried out by a conventional aryl coupling reaction, for example Suzuki coupling (cf., Suzuki et al., Synth. Commun. 11:513 (1981); Suzuki, Pure and Appl. Chem. 57:1749-1758 (1985); Suzuki et al., Chem. Rev. 95:2457-2483 (1995); Shieh et al., J. Org. Chem. 57:379-381 (1992); Martin et al., Acta Chemica Scand inavica 47:221-230 (1993); Wallace et al., Tetrahedron Lett. 43:6987-6990 (2002) and Molander et al., J. Org. Chem. 68:4302-4314 (2003)) and Stille coupling (cf., Stille, Angew. Chem. Int. Ed. Engl. 25:508-524 (1986) and Liebeskind et al., J. Org. Chem. 59:5905-5911 (1994)).

The coupling reaction may be carried out in an appropriate solvent with or without a ligand, base and additive in the presence of Pd catalyst.

Examples of the Pd catalyst include tetrakis(triphenylphosphine)palladium (0), palladium (II) acetate, bis(acetonitrile)dichloropalladium (II), dichlorobis(triphenylphosphine)palladium (II), a complex of [1,1'-bis(diphenylphosphino)ferrocene]dichloropalladium (II) with dichloromethane, tris(dibenzylidene-acetone)dipalladium (0)-chloroform adduct and palladium (II) chloride. Examples of the base include alkali metal carbonate such as cesium carbonate, potassium carbonate, sodium carbonate and sodium hydrogen carbonate; alkali metal phosphate such as tribasic potassium phosphate, sodium phosphate and sodium hydrogen phosphate; amine such as N,N-diisopropylethylamine; alkali metal fluoride such as cesium fluoride and potassium fluoride; alkali metal alkoxide such as sodium-t-butoxide, potassium-t-butoxide. Examples of the ligand include triphenylphosphine, tributylphosphine, tri-t-butylphosphonium tetrafluoroborate, 1,3-bis(diphenylphosphino)propane, 2,2'-bis(diphenylphosphino)-1,1'-binaphthyl, 1,1'-bis(diphenylphosphino)ferrocene, 2-(di-tert-butylphosphino)biphenyl, 2-dicyclohexylphosphino-2'-(N,N-dimethylamino)biphenyl, 2-(dicyclohexylphosphino)biphenyl, di(1-adamantyl)butylphosphine. Examples of the additive include copper (I) iodide.

The solvent may be selected from any solvents which do not affect the coupling reaction, and examples of the solvent include aromatic hydrocarbon such as toluene and xylene; ether such as tetrahydrofuran, 1,2-dimethoxyethane and 1,4-dioxane; amide such as N,N-dimethylformamide, N,N-dimethylacetamide, 1,3-dimethyl-2-imidazolidinone and N-methylpyrrolidone; alcohol such as methanol, ethanol and 2-propanol; water. These solvents may be used alone or in combination.

The coupling reaction may be carried out at room temperature or high temperature, for example at 20° C. to 150° C.

Compound (I) wherein the substituent group $R^{2a}$, $R^{2b}$, $R^{2c}$, $R^{2d}$, $R^{3a}$, $R^{3b}$, $R^{3c}$ or $R^{3d}$ is optionally substituted monocyclic aromatic heterocyclic group or optionally substituted monocyclic non-aromatic heterocyclic group and an intermediate compound thereof may be prepared by coupling Compound (I) wherein the substituent group $R^{2a}$, $R^{2b}$, $R^{2c}$, $R^{2d}$, $R^{3a}$, $R^{3b}$, $R^{3c}$ or $R^{3d}$ is halogen (particularly, bromine, iodine) and an intermediate compound thereof, respectively, with $Ar^2B(OH)_2$, $Ar^2BF_3K$ or $Ar^2Sn(n-Bu)_3$ (wherein $Ar^2$ is optionally substituted monocyclic aromatic heterocyclic group or optionally substituted monocyclic non-aromatic heterocyclic group, and n-Bu is the same as defined above).

This reaction may be carried out according to the method of the coupling reaction as in the above preparation of the compound containing optionally substituted phenyl from the compound containing halogen.

Compound (I) wherein the substituent group $R^{2a}$, $R^{2b}$, $R^{2c}$, $R^{2d}$, $R^{3a}$, $R^{3b}$, $R^{3c}$ or $R^{3d}$ is optionally substituted monocyclic non-aromatic heterocyclic group comprising a nitrogen atom as a ring atom and binds to Ring A or Ring B via the nitrogen atom and an intermediate compound thereof may be prepared by coupling Compound (I) wherein the substituent group $R^{2a}$, $R^{2b}$, $R^{2c}$, $R^{2d}$, $R^{3a}$, $R^{3b}$, $R^{3c}$ or $R^{3d}$ is halogen (particularly, bromine, iodine) and an intermediate compound thereof, respectively, with the corresponding monocyclic non-aromatic heterocyclic group wherein a nitrogen atom is substituted by hydrogen.

This reaction may be carried out by a conventional amination method, for example Buchwald-Hartwig amination method (cf., Yang, B. H.; Buchwald, S. L. J. Organomet. Chem. 576 (1999) 125-146).

Specifically, it may be carried out according to the method of the coupling reaction as in the above preparation of the compound containing optionally substituted phenyl from the compound containing halogen.

Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is optionally substituted alkyl and an intermediate compound thereof may be prepared by alkylating Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is halogen (particularly, bromine, iodine) and an intermediate compound thereof, respectively.

The alkylation reaction may be carried out by treating Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is halogen or an intermediate compound thereof with alkyllithium (e.g., butyllithium), followed by the corresponding halogenoalkyl (e.g., iodoalkyl) in an appropriate solvent (e.g., ether such as tetrahydrofuran).

Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is methyl and an intermediate compound thereof may be prepared by coupling Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is halogen (particularly, bromine, iodine) and an intermediate compound thereof, respectively, with methyl borate or cyclic borate ester thereof, trimethylboroxine or potassium methyltrifluoroborate.

This reaction may be carried out according to the method of the coupling reaction as in the above preparation of the compound containing optionally substituted phenyl from the compound containing halogen.

Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is optionally substituted $C_2$-$C_6$ alkyl and an intermediate compound thereof may be prepared by coupling Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is halogen (particularly, bromine, iodine) and an intermediate compound thereof, respectively, with $R^7B(OH)_2$ or $R^7BF_3K$ (wherein $R^7$ is optionally substituted $C_2$-$C_6$ alkenyl) to give an optionally substituted alkenyl compound, followed by hydrogenation.

The preparation reaction of the optionally substituted alkenyl compound may be carried out according to the method of the coupling reaction as in the above preparation of the compound containing optionally substituted phenyl from the compound containing halogen.

The hydrogenation reaction of the optionally substituted alkenyl compound may be carried out under hydrogen atmosphere in an appropriate solvent in the presence of a catalyst.

Examples of the catalyst include palladium carbon, palladium hydroxide, and platinum oxide.

The solvent may be selected from any solvents which do not affect the reaction, and examples of the solvent include ether such as tetrahydrofuran, 1,2-dimethoxyethane and 1,4-dioxane; alcohol such as methanol, ethanol and 2-propanol; ester such as ethyl acetate; carboxylic acid such as acetic acid. These solvents may be used alone or in combination.

The reaction may be carried out at room temperature or high temperature, for example at 20° C. to 80° C.

Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is cyclopropylmethyl and an intermediate compound thereof may be prepared by coupling Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is halogen (particularly, bromine, iodine) and an intermediate compound thereof, respectively, with allyl tributyl tin, followed by cyclopropylation of double bonds of the resulted allyl.

The preparation reaction of the allyl compound may be carried out according to the method of the coupling reaction as in the above preparation of the compound containing optionally substituted phenyl from the compound containing halogen.

The cyclopropylation reaction may be carried out in an appropriate solvent in the presence of dihalogenomethane and diethylzinc.

Examples of the dihalogenomethane include chloroiodomethane and diiodomethane.

The solvent may be selected from any solvents which do not affect the cyclopropylation reaction, and examples of the solvent include halogenohydrocarbon such as dichloromethane, chloroform and 1,2-dichloroethane. These solvents may be used alone or in combination.

The reaction may be carried out at room temperature or high temperature, for example at 20° C. to 80° C.

Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is oxo-substituted alkyl and an intermediate compound thereof may be prepared by N-methoxy-N-methylamidation of Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is alkyl which is substituted by hydroxy and oxo on the same carbon atom and an intermediate compound thereof, respectively, followed by alkylation or cycloalkylation of the resulting amide with $R^8Li$ or $R^8MgLG^1$ (wherein $R^8$ is the corresponding optionally substituted alkyl or the corresponding optionally substituted cycloalkyl, and $LG^1$ is halogen).

The N-methoxy-N-methylamidation reaction may be carried out in an appropriate solvent (e.g., halogenohydrocarbon such as dichloromethane, chloroform or dichloroethane) with or without N-hydroxybenzotriazole in the presence of amine (e.g., N,O-dimethylhydroxyamine or N,O-dimethylhydroxyamine hydrochloride), a condensing agent (e.g., carbodiimide such as 1-ethyl-3-(3-dimethylaminopropyl)carbodiimide hydrochloride) and base (e.g., amine such as triethylamine).

The alkylation or cycloalkylation reaction may be carried out in an appropriate solvent (e.g., ether such as tetrahydrofuran or hydrocarbon such as hexane, or a mixture thereof).

Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is optionally substituted alkanoyl and an intermediate compound thereof may be prepared by coupling Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is halogen (particularly, bromine, iodine) and an intermediate compound thereof, respectively, with $R^9Sn(n-Bu)_3$ (wherein $R^9$ is 1-alkoxy-1-alken-1-yl, and n-Bu is butyl) to give an alkenyl ether compound, followed by hydrolysis. The preparation reaction of the alkenylether compound may be carried out according to the method of the coupling reaction as in the above preparation of the compound containing optionally substituted phenyl from the compound containing halogen.

The hydrolysis may be carried out in an appropriate solvent (e.g., ether such as tetrahydrofuran; ester such as ethyl acetate; or water, or a mixture thereof) in the presence of acid (e.g., inorganic acid such as hydrogen chloride).

Alternatively, Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is optionally substituted alkanoyl and an intermediate compound thereof may be prepared by alkanoylation of Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is halogen (particularly, bromine, iodine) and an intermediate compound thereof, respectively.

The alkanoylation reaction may be carried out by treating Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is halogen or an intermediate compound thereof with alkyllithium (e.g., butyllithium), followed by the following compound of formula:

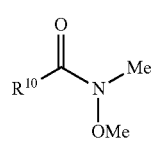

wherein $R^{10}$ is optionally substituted alkyl and Me is methyl, in an appropriate solvent (e.g., ether such as tetrahydrofuran or hydrocarbon such as hexane, or a mixture thereof).

Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is optionally substituted cycloalkyl and an intermediate compound thereof may be prepared by coupling Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is halogen (particularly, bromine, iodine) and an intermediate compound thereof, respectively, with $R^{11}B(OH)_2$ or $R^{11}BF_3K$ (wherein $R^{11}$ is optionally substituted cycloalkyl).

This reaction may be carried out according to the method of the coupling reaction as in the above preparation of the compound containing optionally substituted phenyl from the compound containing halogen.

Alternatively, Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is optionally substituted cycloalkyl and an intermediate compound thereof may be prepared by coupling Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is halogen (particularly, bromine, iodine) and an intermediate compound thereof, respectively, with $R^{12}B(OH)_2$ or $R^{12}BF_3K$ (wherein $R^{12}$ is optionally substituted cycloalkenyl) to give a optionally substituted cycloalkenyl compound, followed by hydrogenation.

The preparation reaction of the optionally substituted cycloalkenyl compound may be carried out according to the method of the coupling reaction as in the above preparation of the compound containing optionally substituted phenyl from the compound containing halogen.

The hydrogenation of the cycloalkenyl compound may be carried out according to the method of the above hydrogenation of the optionally substituted $C_2$-$C_6$ alkenyl compound.

Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is hydrogen and an intermediate compound thereof may be prepared by reducing Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is halogen (particularly, bromine, iodine) and an intermediate compound thereof, respectively.

The reduction reaction may be carried out under hydrogen atmosphere in an appropriate solvent with or without a base in the presence of a catalyst.

Examples of the catalyst include palladium carbon, palladium hydroxide and platinum oxide. Examples of the base include amine such as triethylamine.

The solvent may be selected from any solvents which do not affect the reaction, and examples of the solvent include ether such as tetrahydrofuran, 1,2-dimethoxyethane and 1,4-dioxane; alcohol such as methanol, ethanol and 2-propanol; ester such as ethyl acetate; carboxylic acid such as acetic acid. These solvents may be used alone or in combination.

The reaction may be carried out at room temperature or high temperature, for example at 20° C. to 80° C.

Alternatively, the reduction reaction may be carried out in an appropriate solvent (e.g., secondary alcohol such as 2-propanol) with or without a ligand (e.g., triphenylphosphine) in the presence of Pd catalyst (e.g., palladium (II) acetate) and base (e.g., alkali metal carbonate such as potassium carbonate).

Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is fluoroalkyl and an intermediate compound thereof may be prepared by coupling Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is halogen (particularly, iodine) and an intermediate compound thereof, respectively, with methyl fluorosulfonyldifluoroacetate, potassium fluoroalkyl carboxylate or fluoroalkyl trimethylsilane.

The coupling reaction may be carried out in an appropriate solvent with or without an additive in the presence of Cu complex.

Examples of the Cu complex include copper (I) bromide, copper (I) iodide or copper (I) thiophene-2-carboxylate, preferably copper (I) bromide and copper (I) iodide. The reaction may be also carried out by adding an additive. Examples of the additive include potassium fluoride.

Any solvents which do not affect the reaction may be preferably used, and examples of the solvent include ether such as tetrahydrofuran, 1,4-dioxane, 1,2-dimethoxyethane; amide such as N,N-dimethylformamide, N,N-dimethylacetamide, 1,3-dimethyl-2-imidazolidinone and N-methylpyrrolidone; aprotic polar solvent such as dimethyl sulfoxide, hexamethylphosphoric triamide. These solvents may be used alone or in combination. A preferable solvent in the reaction is a mixture of amide such as N,N-dimethylformamide and aprotic polar solvent such as hexamethylphosphoric triamide.

The reaction may be carried out at room temperature or high temperature, for example at 20° C. to 120° C.

Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is alkyl which is difluorinated on the same carbon atom and an intermediate compound thereof may be prepared by difluorinating Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is oxo-substituted alkyl and an intermediate compound thereof, respectively.

The difluorinating reaction may be carried out in an appropriate solvent (e.g., halogenohydrocarbon such as dichloromethane, chloroform or dichloroethane) or without a solvent with or without a catalyst (e.g., alcohol such as methanol or ethanol) in the presence of a fluorinating agent (e.g., diethylaminosulfur trifluoride or bis(2-methoxyethyl)aminosulfur trifluoride).

The reaction may be preferably carried out at 0° C. to 100° C., particularly at 20° C. to 80° C.

Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is alkoxy-substituted alkyl and an intermediate compound thereof may be prepared by alkylating Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is hydroxy-substituted alkyl and an intermediate compound thereof, respectively, with $R^{13}LG^2$ (wherein $R^{13}$ is alkyl, and $LG^2$ is a leaving group and includes halogen such as bromine, iodine; substituted sulfonyloxy such as p-toluenesulfonyloxy, methanesulfonyloxy, trifluoromethanesulfonyloxy, and alkoxysulfonyloxy).

The alkylating reaction may be carried out in an appropriate solvent in the presence of a base.

Any solvents which do not affect the reaction may be preferably used as the solvent in the alkylation reaction, and examples of the solvent include ether such as tetrahydrofuran, 1,4-dioxane, 1,2-dimethoxyethane; hydrocarbon such as toluene, hexane, xylene; ester such as ethyl acetate, butyl acetate; amide such as N,N-dimethylformamide, N,N-dimethylacetamide, 1,3-dimethyl-2-imidazolidinone and N-methylpyrrolidone. These solvents may be used alone or in combination, preferably amide such as N,N-dimethylformamide.

Examples of the base include alkali metal hydride such as sodium hydride, potassium hydride; alkali metal hydroxide such as sodium hydroxide, potassium hydroxide; alkaline-earth metal hydroxide such as calcium hydroxide, barium hydroxide; alkali metal alkoxide such as sodium methoxide, sodium ethoxide, potassium ethoxide, potassium t-butoxide; alkali metal amide such as lithium diisopropylamide, sodium amide, lithium bistrimethylsilylamide; alkali metal carbonate such as sodium carbonate, potassium carbonate, sodium hydrogen carbonate, potassium hydrogen carbonate, preferably alkali metal hydride such as sodium hydride.

Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is alkyl which is substituted on the same carbon atom by (a) $C_1$-$C_3$ perfluoroalkyl (e.g., trifluoromethyl, pentafluoroethyl or heptafluoropropyl) and (b) hydroxy and an intermediate compound thereof may be prepared by perfluoroalkylating Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is oxo-substituted alkyl and an intermediate compound thereof, respectively, with $R^{14}SiMe_3$ (wherein $R^{14}$ is perfluoroalkyl, and Me is methyl).

The perfluoroalkylating reaction may be carried out in an appropriate solvent (e.g., ether such as tetrahydrofuran) in the presence of a fluoride ion source (e.g., tetrabutylammonium fluoride).

Compound (I) wherein two substituent groups selected from the substituent groups $R^{3a}$, $R^{3b}$, $R^{3c}$ and $R^{3d}$ are (a) $C_1$-$C_3$ perfluoroalkyl (e.g., trifluoromethyl, pentafluoroethyl or heptafluoropropyl) and (b) hydroxy which are on the same carbon atom constituting Ring B and an intermediate compound thereof may be prepared by perfluoroalkylating Compound (I) wherein two substituent groups selected from the corresponding substituent groups $R^{3a}$, $R^{3b}$, $R^{3c}$ and $R^{3d}$ combine each other to form oxo and an intermediate compound thereof, respectively, with $R^{15}SiMe_3$ (wherein $R^{15}$ is perfluoroalkyl, and Me is methyl).

This reaction may be carried out according to the method of the above perfluoroalkylating reaction of oxo-substituted alkyl.

Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is alkyl which is substituted on the same carbon atom by cycloalkyl and hydroxy and an intermediate compound thereof may be prepared by cycloalkylating Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is oxo-substituted alkyl and an intermediate compound thereof, respectively, with $R^{16}L^1$ or $R^{16}MgLG'$ (wherein $R^{16}$ is cycloalkyl, and $LG^1$ is halogen).

The cycloalkylating reaction may be carried out in an appropriate solvent (e.g., ether such as tetrahydrofuran).

Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is hydroxy-substituted alkyl and an intermediate compound thereof may be prepared by reducing Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is oxo-substituted alkyl and an intermediate compound thereof, respectively.

The reduction reaction may be carried out in an appropriate solvent (e.g., alcohol such as methanol, ethanol) in the presence of a reducing agent (e.g., lithium borohydride, sodium borohydride).

Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is alkyl and an intermediate compound thereof may be prepared by silane-reduction of Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is hydroxy-substituted alkyl and an intermediate compound thereof, respectively.

The reduction reaction may be carried out in an appropriate solvent (e.g., halogenohydrocarbon such as chloroform) or without a solvent in the presence of an acid (e.g., carboxylic acid such as trifluoroacetic acid) and a reducing agent (e.g., trialkylsilane such as triethylsilane).

Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is optionally substituted alkyl and attaches at a nitrogen atom constituting Ring A or Ring B and an intermediate compound thereof may be prepared by alkylating Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is hydrogen and an intermediate compound thereof, respectively, with $R^{17}LG^2$ (wherein $R^{17}$ is optionally substituted alkyl, and $LG^2$ is a leaving group and includes halogen such as bromine, iodine; substituted sulfonyloxy such as p-toluenesulfonyloxy, methanesulfonyloxy, trifluoromethanesulfonyloxy, and alkoxysulfonyloxy).

The preparation reaction of this compound may be carried out according to the method of the above alkylating reaction of hydroxy-substituted alkyl, and a preferable base is alkali metal carbonate such as potassium carbonate, or alkali metal hydride such as sodium hydride.

Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is optionally substituted cycloalkyl and attaches at a nitrogen atom constituting Ring A or Ring B and an intermediate compound thereof (hereinafter may also be referred to as the compound containing optionally substituted cycloalkyl) may be prepared by coupling Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is hydrogen and an intermediate compound thereof (hereinafter may also be referred tows the compound containing hydrogen on the nitrogen atom), respectively, with $R^{18}B(OH)_2$ or $R^{18}BF_3K$ (wherein $R^{18}$ is optionally substituted cycloalkyl).

The coupling reaction may be carried out in an appropriate solvent (e.g., halogenohydrocarbon such as 1,2-dichloroethane) with or without a ligand (e.g., diamine such as 2,2'-bipyridyl) in the presence of Cu catalyst (e.g., copper (II) acetate) and a base (e.g., alkali metal carbonate such as sodium carbonate).

Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is optionally substituted alkoxy and an intermediate compound thereof may be prepared by alkoxylating Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is halogen (particularly, bromine or iodine) and an intermediate compound thereof, respectively.

The alkoxylating reaction may be carried out in an appropriate solvent (e.g., ether such as tetrahydrofuran) in the presence of the corresponding alcohol and base (e.g., alkali metal hydride such as sodium hydride).

Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is iodine and an intermediate compound thereof may be prepared by iodinating Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is bromine and an intermediate compound thereof, respectively.

The iodinating reaction may be carried out in an appropriate solvent with or without a ligand in the presence of an iodinating agent and a catalyst.

Examples of the iodinating agent include sodium iodide. Examples of the catalyst include copper (I) iodide. Examples of the ligand include diamine such as N,N'-dimethylethylenediamine, and N,N'-1,2-cyclohexanediamine.

The solvent may be selected from any solvents which do not affect the reaction, and examples of the solvent include ether such as tetrahydrofuran, 1,4-dioxane, 1,2-dimethoxyethane; alkylnitrile such as acetonitrile, propionitrile. These solvents may be used alone or in combination.

The reaction may be carried out at room temperature or high temperature, for example at 20° C. to 120° C.

Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is fluorine and an intermediate compound thereof may be prepared by fluorinating Compound (1) wherein the substituent group $R^1$, $R^{2a}$, $R^{2b}$, $R^{2c}$, $R^{2d}$, $R^{3a}$, $R^{3b}$, $R^{3c}$ or $R^{3d}$ is bromine or iodine and an intermediate compound thereof, respectively.

The fluorinating reaction may be carried out by treating Compound (I) which is bromine or iodine or an intermediate compound thereof in an appropriate solvent (e.g., ether such as tetrahydrofuran or aliphatic hydrocarbon such as hexane, or a mixture thereof) with alkyllithium (e.g., butyllithium), followed by a fluorinating agent (e.g., N-fluorobenzenesulfonimide).

Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is halogen and an intermediate compound thereof may be prepared by halogenating Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is hydrogen and an intermediate compound thereof, respectively.

The halogenating reaction may be carried out in an appropriate solvent (e.g., ether such as tetrahydrofuran, amide such as N,N-dimethylformamide, halogenohydrocarbon such as dichloromethane, or carboxylic acid such as acetic acid, or a mixture thereof) in the presence of a halogenating agent (e.g., N-halogenosuccinimide).

Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is alkyl and an intermediate compound thereof may be prepared by treating Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is oxo-substituted alkyl and an intermediate compound thereof, respectively, with hydrazine, followed by reducing the resulting hydrazone.

The treatment with hydrazine may be carried out in an appropriate solvent (e.g., alcohol such as ethanol) in the presence of hydrazine monohydrate.

The reduction reaction of hydrazone may be carried out in an appropriate solvent (e.g., alcohol such as ethylene glycol) in the presence of a base (e.g., alkali metal hydroxide such as potassium hydroxide).

Alternatively, Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is alkyl and an intermediate compound thereof may be prepared by silane-reduction of Compound (I) wherein the substituent group $R^1$, $R^{2a}$, $R^{2b}$, $R^{2c}$, $R^{2d}$, $R^{3a}$, $R^{3b}$, $R^{3c}$ or $R^{3d}$ is oxo-substituted alkyl and an intermediate compound thereof, respectively. The silane-reduction of the oxo-substituted alkyl may be carried out according to the method of the above silane-reduction of hydroxy-substituted alkyl.

Compound (I) wherein two substituent groups selected from the substituent groups $R^{3a}$, $R^{3b}$, $R^{3c}$ and $R^{3d}$ are two hydrogens on the same carbon atom constituting Ring B and an intermediate compound thereof may be prepared by hydrazone-reduction or silane-reduction of Compound (I) wherein two substituent groups selected from the substituent group $R^{3a}$, $R^{3b}$, $R^{3c}$ and $R^{3d}$ combine each other to form oxo and an intermediate compound thereof, respectively.

The hydrazone-reduction or silane-reduction may be carried out according to the method of the above reduction of the oxo-substituted alkyl.

Compound (I) wherein the substituent group X is carboxy and an intermediate compound thereof may be prepared by hydrolyzing Compound (I) wherein the substituent group X is alkoxycarbonyl and an intermediate compound thereof, respectively, according to a conventional method.

The hydrolysis may be carried out by treating Compound (I) wherein the substituent group X is alkoxycarbonyl or an intermediate compound thereof with a base (e.g., sodium hydroxide, potassium hydroxide, lithium hydroxide, sodium methoxide and sodium ethoxide) in an appropriate inactive solvent (e.g., tetrahydrofuran, 1,4-dioxane, methanol, ethanol and water, or a mixture thereof).

Compound (I) wherein the substituent group X is hydroxyalkyl and an intermediate compound thereof may be prepared by reacting Compound (I) wherein the substituent group X is alkoxycarbonyl or alkanoyl and an intermediate compound thereof, respectively, with lithium aluminum hydride or alkylmagnesium bromide.

Compound (I) wherein the substituent group X is optionally substituted aminocarbonyl and an intermediate compound thereof may be prepared by amidating Compound (I) wherein the substituent group X is carboxy or alkoxycarbonyl and an intermediate compound thereof, respectively, with the corresponding amine according to a conventional method.

[Preparation of Intermediate Compounds]

Compound (IV) may be prepared according to the following Scheme A1.

Scheme A1:

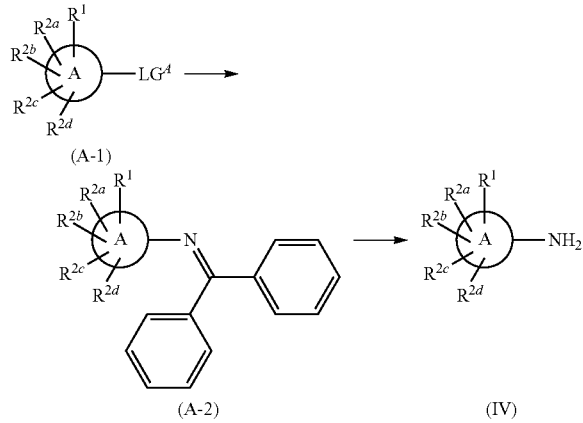

(In the above Scheme, $LG^A$ is a leaving group and includes halogen such as chlorine, bromine; substituted sulfonyloxy such as trifluoromethylsulfonyloxy, and other symbols are the same as defined above.)

Compound (A-1) may be aminated to give Compound (A-2). The resulting compound may be hydrolyzed to give Compound (IV).

The amination of Compound (A-1) may be carried out in an appropriate solvent (e.g., aromatic hydrocarbon such as toluene) with or without a ligand (e.g., phosphine such as 2,2'-bis (diphenylphosphino)-1,1'-binaphthyl) in the presence of benzophenone imine, palladium catalyst (e.g., tris (dibenzylideneacetone)dipalladium) and a base (e.g., alkali metal alkoxide such as sodium-t-butoxide). The reaction may be carried out at high temperature, for example at 80° C. to 140° C.

The hydrolysis of Compound (A-2) may be carried out by treating with an acid (e.g., an inorganic acid such as hydrogen chloride) in an appropriate solvent (e.g., ether such as tetrahydrofuran; water, or a mixture thereof). The reaction may be carried out at low temperature, room temperature or high temperature, for example at 0° C. to 60° C.

Compound (IV-1) among Compound (IV) may be prepared according to the following Scheme A2.

Scheme A2:

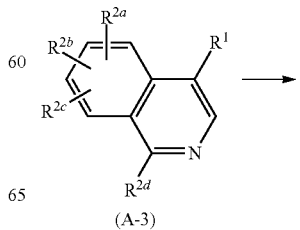

(A-3)

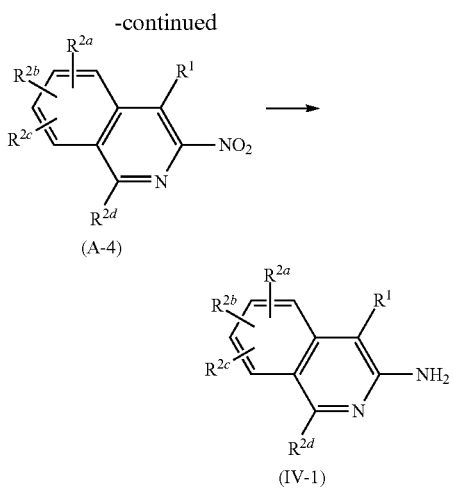

(In the above Scheme, symbols are the same as defined above.)

Compound (A-3) may be nitrated to give Compound (A-4). The resulting compound may be reduced to give Compound (IV-1).

The nitration of Compound (A-3) may be carried out without a solvent in the presence of a nitrating agent (e.g., potassium nitrate) and an acid (e.g., an inorganic acid such as sulfuric acid). The reaction may be carried out at room temperature or high temperature, for example at 20° C. to 100° C.

The reduction of Compound (A-4) may be carried out in an appropriate solvent (e.g., alcohol such as ethanol; carboxylic acid such as acetic acid, or a mixture thereof) in the presence of a reducing agent (e.g., iron (0)). The reaction may be carried out at high temperature, for example at 60° C. to 120° C.

Compound (IV-2) among Compound (IV) may be prepared according to the following Scheme A3.

Scheme A3:

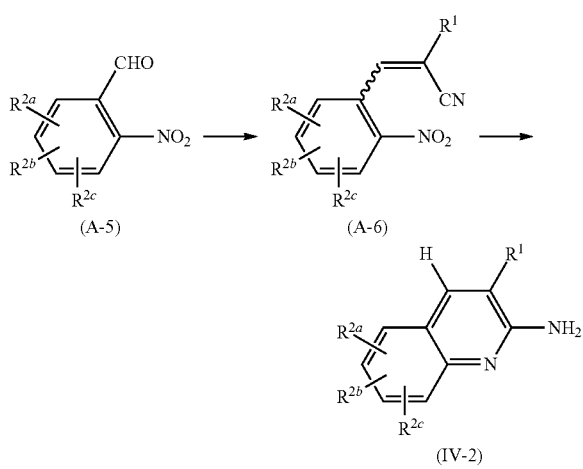

(In the above Scheme, symbols are the same as defined above.)

Compound (A-5) may be alkenylated to give Compound (A-6). The resulting nitro compound may be reduced to convert into an amino compound, followed by cyclization to give Compound (IV-2).

The alkenylation of Compound (A-5) may be carried out in an appropriate solvent (e.g., ether such as tetrahydrofuran) in the presence of the corresponding phosphonic acid ester (e.g., substituted diethyl phosphonate) and a base (e.g., alkali metal alkoxide such as potassium-t-butoxide). The reaction may be carried out at room temperature or high temperature, for example at 20° C. to 100° C.

The reduction of Compound (A-6) may be carried out in an appropriate solvent (e.g., alcohol such as ethanol) in the presence of a reducing agent (e.g., tin (II) chloride). The reaction may be carried out at high temperature, for example at 60° C. to 100° C.

The cyclization of the resulting amino compound may be carried out in an appropriate solvent (e.g., alcohol such as ethanol) in the presence of a base (e.g., alkali metal alkoxide such as sodium ethoxide). The reaction may be carried out at high temperature, for example at 60° C. to 100° C.

Compound (IV-3) among Compound (IV) may be prepared according to the following Scheme A4.

Scheme A4:

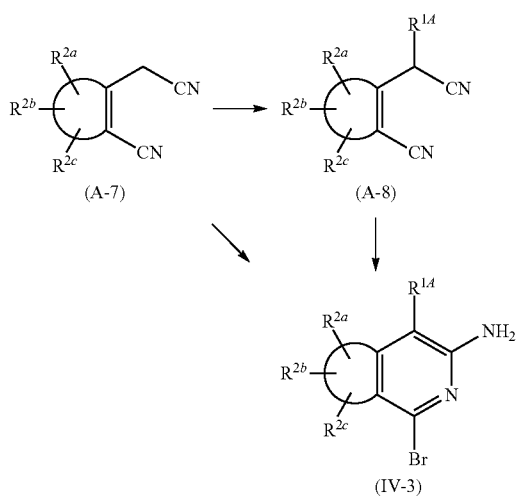

(In the above Scheme, a group:

is benzene or monocyclic aromatic heterocycle; a group:

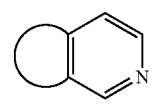

is bicyclic aromatic heterocycle comprised of (a) pyridine condensed with benzene; or (b) pyridine condensed with monocyclic aromatic heterocycle; $R^{1A}$ is hydrogen or optionally substituted alkyl; and other symbols are the same as defined above.)

Compound (A-7) may be alkylated to give Compound (A-8). The resulting compound may be cyclized to give Compound (IV-3) wherein $R^{1A}$ is optionally substituted alkyl.

Compound (A-7) may be cyclized to give Compound (IV-3) wherein $R^{1A}$ is hydrogen.

The alkylation of Compound (A-7) may be carried out in an appropriate solvent (e.g., ether such as tetrahydrofuran; alcohol such as ethanol) in the presence of the corresponding halogenoalkyl (e.g., alkyl iodide or alkyl bromide) and a base (e.g., organic lithium such as butyllithium; or alkali metal alkoxide such as sodium ethoxide). The reaction may be carried out at low temperature or room temperature, for example at −80° C. to 20° C.

The cyclization of Compound (A-7) or (A-8) may be carried out in an appropriate solvent (e.g., carboxylic acid such as acetic acid) in the presence of hydrogen bromide. The reaction may be carried out at low temperature or room temperature, for example at −20° C. to 20° C.

Compound (VIII-1) among Compound (VIII) may be prepared according to the following Scheme A5.

Scheme A5:

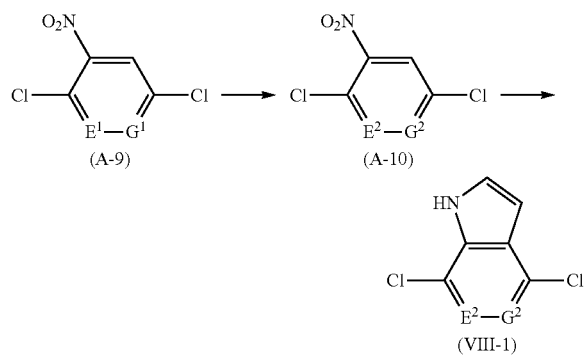

(In the above Scheme, $E^1$, $E^2$, $G^1$ and $G^2$ are CH, CH, $N^+O^-$, and N, respectively, or are $N^+O^-$, N, CH and CH, respectively.)

Compound (A-9) may be reduced to give Compound (A-10). The resulting compound may be converted into pyrrolopyridine to give Compound (VIII-1).

The reduction of Compound (A-9) may be carried out in an appropriate solvent (e.g., halogenohydrocarbon such as chloroform) in the presence of a reducing agent (e.g., phosphorus oxychloride). The reaction may be carried out at high temperature, for example at 40° C. to 100° C.

The conversion of Compound (A-10) into pyrrolopyridine may be carried out in an appropriate solvent (e.g., ether such as tetrahydrofuran) in the presence of a vinylating agent (e.g., vinyl magnesium bromide). The reaction may be carried out at low temperature or room temperature, for example at −40° C. to 20° C.

Compound (VI-1) among Compound (VI) may be prepared according to the following Scheme B1.

Scheme B1:

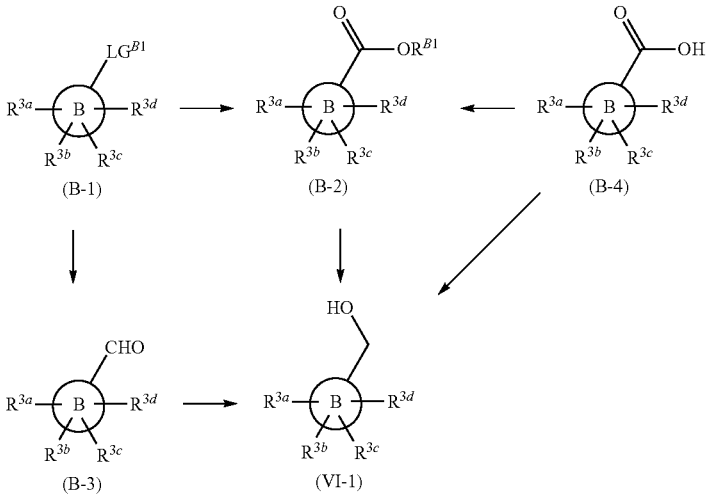

(In the above Scheme, $LG^{B1}$ is halogen (particularly, bromine or iodine), $R^{B1}$ is alkyl, and other symbols are the same as defined above.)

Compound (B-1) may be alkoxycarbonylated to give Compound (B-2). The resulting compound may be reduced to give Compound (VI-1).

Compound (B-1) may be formylated to give Compound (B-3). The resulting compound may be reduced to give Compound (VI-1).

Compound (B-4) may be esterified to give Compound (B-2). The resulting compound may be reduced to give Compound (VI-1).

Compound (B-4) may be also reduced to give Compound (VI-1).

The alkoxycarbonylation of Compound (B-1) may be carried out under carbon monoxide atmosphere in an appropriate solvent (e.g., amide such as N,N-dimethylformamide or N,N-dimethylacetamide) with or without a ligand (e.g., 1,1'-bis(diphenylphosphino)ferrocene) in the presence of the corresponding alcohol ($R^{B1}OH$), a base (e.g., amine such as triethylamine) and a palladium catalyst (e.g., palladium acetate). The reaction may be carried out at high temperature, for example at 60° C. to 120° C.

The reduction of Compound (B-2) may be carried out in an appropriate solvent (e.g., aromatic hydrocarbon such as toluene, xylene; ether such as tetrahydrofuran, diethyl ether; alcohol such as methanol, ethanol, or a mixture thereof) in the presence of a reducing agent (e.g., lithium borohydride, sodium borohydride, lithium aluminum hydride, diisobutylaluminum hydride). The reaction may be carried out at low temperature or room temperature, for example at −80° C. to 20° C.

The formylation of Compound (B-1) may be carried out by treating Compound (B-1) with butyllithium, followed by N,N-dimethylformamide, in an appropriate solvent (e.g., ether such as tetrahydrofuran). The reaction may be carried out at low temperature or room temperature, for example at −80° C. to 20° C.

The reduction of Compound (B-3) may be carried out according to the method of the above reduction of Compound (B-2).

The esterification of Compound (B-4) may be carried out in the presence of thionyl chloride in a solvent of the corresponding alcohol ($R^{B1}$ OH). The reaction may be carried out at low temperature or room temperature, for example at −20° C. to 20° C.

Alternatively, the esterification of Compound (B-4) may be carried out in an appropriate solvent (e.g., amide such as N,N-dimethylformamide) in the presence of the corresponding iodoalkyl ($R^{B1}$I) and a base (e.g., alkali metal carbonate such as potassium carbonate). The reaction may be carried out at room temperature or high temperature, for example at 20° C. to 60° C.

The reduction of Compound (B-4) may be carried out in an appropriate solvent (e.g., ether such as tetrahydrofuran) in the presence of a reducing agent (e.g., borane complex such as borane-tetrahydrofuran complex or borane-dimethylsulfide complex). The reaction may be carried out at low temperature or room temperature, for example at −20° C. to 20° C.

Alternatively, the reduction of Compound (B-4) may be carried out by treating Compound (B-4) with an activating agent (e.g., N,N'-carbodiimidazole), followed by a reducing agent (e.g., sodium borohydride), in an appropriate solvent (e.g., ether such as tetrahydrofuran). The reaction may be carried out at low temperature, room temperature or high temperature, for example at −20° C. to 80° C.

Compound (VI-2) among Compound (VI) may be prepared according to the following Scheme B2.

Scheme B2:

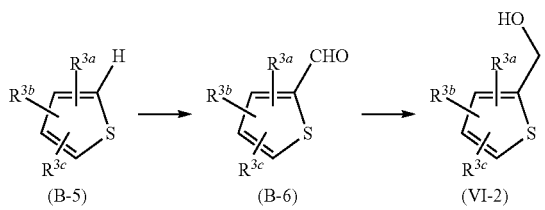

(B-5)   (B-6)   (VI-2)

(In the above Scheme, symbols are the same as defined above.)

Compound (B-5) may be formylated to give Compound (B-6). The resulting compound may be reduced to give Compound (VI-2).

The formylation of Compound (B-5) may be carried out by treating Compound (B-5) with a base (e.g., alkali metal amide such as lithium diisopropylamide), followed by a formylating agent (e.g., N,N-dimethylformamide), in an appropriate solvent (e.g., ether such as tetrahydrofuran). The reaction may be carried out at low temperature or room temperature, for example at −80° C. to 20° C.

The reduction of Compound (B-6) may be carried out according to the method of the above reduction of Compound (B-2).

Compound (VI-3) among Compound (VI) may be prepared according to the following Scheme B3.

Scheme B3:

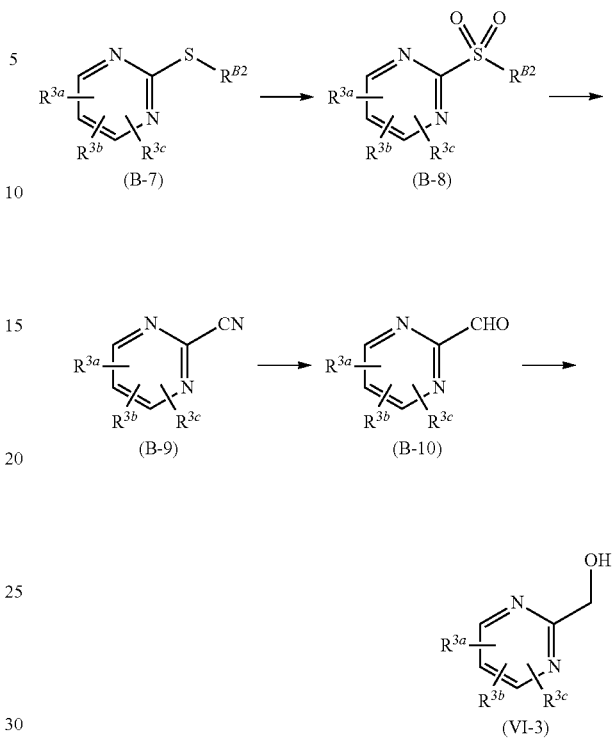

(In the above Scheme, $R^{B2}$ is alkyl, and other symbols are the same as defined above.)

Compound (B-7) may be oxidized to give Compound (B-8). The resulting compound may be cyanated to give Compound (B-9). The resulting compound may be reduced to give Compound (B-10). Further, the resulting compound may be reduced to give Compound (VI-3).

The oxidization of Compound (B-7) may be carried out in an appropriate solvent (e.g., halogenohydrocarbon such as dichloromethane) in the presence of an oxidizing agent (e.g., peroxycarboxylic acid such as metachloroperoxybenzoic acid). The reaction may be carried out at low temperature, room temperature or high temperature, for example at 0° C. to 50° C.

The cyanation of Compound (B-8) may be carried out in an appropriate solvent (e.g., halogenohydrocarbon such as dichloromethane) in the presence of a cyanating agent (e.g., tetrabutylammonium cyanide). The reaction may be carried out at room temperature or high temperature, for example at 20° C. to 50° C.

The reduction of Compound (B-9) may be carried out in an appropriate solvent (e.g., ether such as tetrahydrofuran) in the presence of a reducing agent (e.g., diisobutylaluminum hydride). The reaction may be carried out at low temperature, for example at −80° C. to 0° C.

The reduction of Compound (B-10) may be carried out according to the method of the above reduction of Compound (B-2).

Compound (VI-4) among Compound (VI) may be prepared according to the following Scheme B4.

Scheme B4:

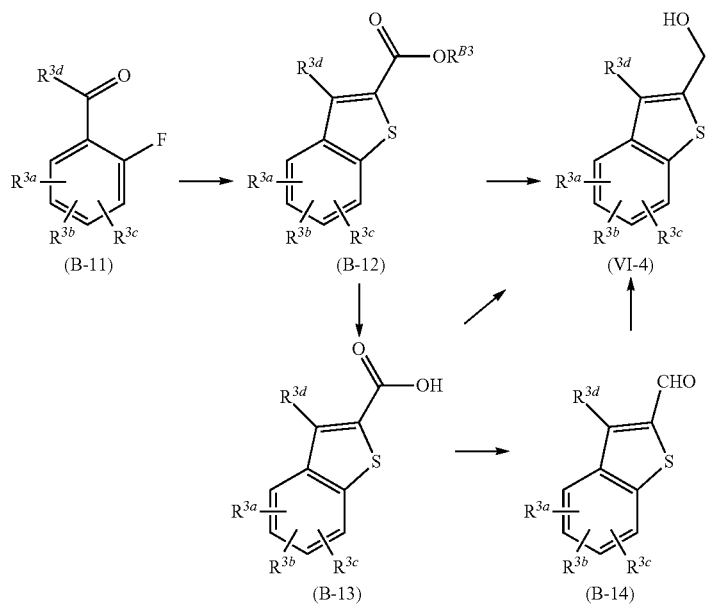

(In the above Scheme, $R^{B3}$ is alkyl, and other symbols are the same as defined above.)

Compound (B-11) may be converted into benzothiophene to give Compound (B-12). The resulting compound may be reduced to give Compound (VI-4).

Compound (B-12) may be hydrolyzed to give Compound (B-13). The carboxyl group of the resulting compound may be converted into N-methoxy-N-methylamide, followed by reduction to give Compound (B-14). The resulting compound may be reduced to give Compound (VI-4).

Compound (B-13) may be reduced to give Compound (VI-4).

The conversion of Compound (B-11) into benzothiophene may be carried out in an appropriate solvent (e.g., amide such as N,N-dimethylformamide) in the presence of the corresponding thioglycolic acid ester and a base (e.g., alkali metal carbonate such as potassium carbonate). The reaction may be carried out at high temperature, for example at 40° C. to 80° C.

The reduction of Compound (B-12) may be carried out according to the method of the above reduction of Compound (B-2).

The hydrolysis of Compound (B-12) may be carried out according to the method of the above conversion of Compound (I) wherein the substituent group X is alkoxycarbonyl and an intermediate compound thereof into Compound (I) wherein the substituent group X is carboxy and an intermediate compound thereof, respectively.

The conversion of Compound (B-13) into N-methoxy-N-methylamide may be carried out in an appropriate solvent (e.g., halogenohydrocarbon such as dichloromethane, chloroform or dichloroethane) in the presence of an amine (e.g., N,O-dimethylhydroxyamine or N,O-dimethylhydroxyamine hydrochloride) and a base (e.g., an organic base such as triethylamine). The subsequent reduction may be carried out according to the method of the above reduction of Compound (B-9).

The reduction of Compound (B-14) may be carried out according to the method of the above reduction of Compound (B-2).

The reduction of Compound (B-13) into Compound (VI-4) may be carried out according to the method of the above reduction of Compound (B-4).

Compound (VI-5) among Compound (VI) may be prepared according to the following Scheme B5.

Scheme B5:

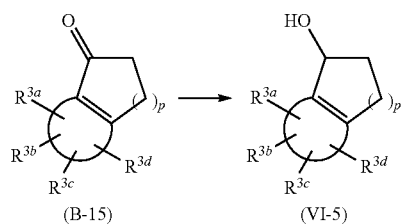

(In the above Scheme, p is 1 or 2; a group:

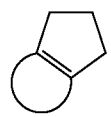

is (a) bicyclic aromatic hydrocarbon comprised of benzene condensed with monocyclic alicyclic hydrocarbon; or (b) bicyclic aromatic heterocycle comprised of monocyclic aromatic heterocycle condensed with monocyclic alicyclic hydrocarbon; and other symbols are the same as defined above.)

Compound (B-15) may be reduced to give Compound (VI-5).

The reduction of Compound (B-15) may be carried out according to the method of the above reduction of Compound (B-2).

Alternatively, the reduction of Compound (B-15) may be carried out in an appropriate solvent (e.g., ether such as tetrahydrofuran) with or without a catalyst (e.g., boron-containing 5-membered ring compound such as (2S)-1-(1,3,2-dioxaborolan-2-yloxy)-3-methyl-1,1-diphenylbutan-2-amine) in the presence of a reducing agent (e.g., borane complex such as borane-tetrahydrofuran complex or borane-dimethylsulfide complex). The reaction may be carried out at low temperature or room temperature, for example at −40° C. to 20° C.

The protection of amino group may be carried out by converting amino group into t-butoxycarbonyl, for example.

The conversion of amino group into t-butoxycarbonyl may be carried out in an appropriate solvent (e.g., halogenohydrocarbon such as dichloromethane) in the presence of di-t-butyl dicarbonate and a catalyst (e.g., N,N-dimethyl-4-aminopyridine).

The removal of t-butylcarbonyl protective group may be carried out by treating with an acid (e.g., hydrogen chloride or trifluoroacetic acid) in an appropriate solvent (e.g., ether such as tetrahydrofuran) or without a solvent.

Alternatively, the removal of t-butylcarbonyl protective group may be carried out in an appropriate solvent (e.g., a mixed solvent of dimethyl sulfoxide and water) at high temperature, for example at 100° C. to 150° C.

The protection of hydroxy may be carried out by converting hydroxy into methoxymethyl, for example.

The conversion of hydroxy into methoxymethyl may be carried out in an appropriate solvent (e.g., halogenohydrocarbon such as dichloromethane) in the presence of chloromethyl methyl ether and a base (e.g., amine such as N,N-diisopropylethylamine).

The removal of methoxymethyl protective group may be carried out by treating with an acid (e.g., hydrogen chloride) in an appropriate solvent (e.g., a mixed solvent of alcohol such as ethanol and water).

Other starting materials may be commercially available, or may be easily prepared according to a conventional method known in the art.

The present invention is illustrated by Examples in more detail as follows, but is not limited thereto.

EXAMPLES

In the following Example section and tables, Me means methyl, Et means ethyl and n-Pr means propyl. And a racemic mixture may be separated by a chiral HPLC to give the optically active compounds.

Example 1

Preparation of ethyl 4-({(4-methylisoquinolin-3-yl)[4-(trifluoromethoxy)benzyl]amino}-sulfonyl)benzoate

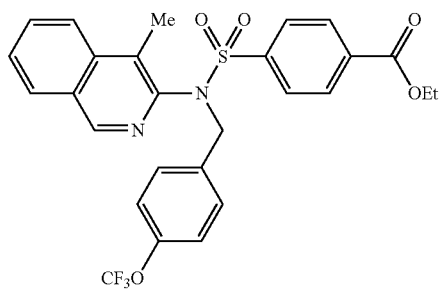

(1) To a solution of 4-methylisoquinoline-3-amine (2.00 g, 12.6 mmol) in pyridine (50.6 ml) was added ethyl 4-chlorosulfonylbenzoate (3.30 g, 13.3 mmol) at room temperature. The mixture was stirred at 80° C. for 3 hours, and then the reaction solution was concentrated under reduced pressure. The resulting residue was diluted with 2 mol/L hydrochloric acid solution and water, and extracted with ethyl acetate twice. The organic layer was combined, washed with water and saturated brine, dried over anhydrous sodium sulfate, and then concentrated under reduced pressure. The resulting residue was purified by silica gel column chromatography (hexane:ethyl acetate=4:1→1:1), and then washed with diisopropyl ether to give ethyl 4-{[(4-methylisoquinolin-3-yl)amino]sulfonyl}benzoate (4.29 g, 92%) as a pale yellow powder.

APCI-MS m/z:371 [M+H]$^+$.

(2) To a solution of the above compound (800 mg, 2.16 mmol) in N,N-dimethylformamide (21.6 ml) were added potassium carbonate (358 mg, 2.59 mmol) and 1-(bromomethyl)-4-(trifluoromethoxy)benzene (427 μl, 2.59 mmol) at room temperature. The mixture was stirred at the same temperature overnight, and then to the reaction solution was added water. The mixture was extracted with ethyl acetate twice. The organic layer was combined, washed with water and saturated brine, dried over anhydrous sodium sulfate, and then concentrated under reduced pressure. The resulting residue was purified by silica gel column chromatography (hexane:ethyl acetate=9:1→3:1) to give ethyl 4-({(4-methylisoquinolin-3-yl)[4-(trifluoromethoxy)benzyl]amino}sulfonyl)benzoate (1.12 g, 95%) as a colorless powder.

APCI-MS m/z:545[M+H]$^+$.

$^1$H-NMR (DMSO-d$_6$) δ 1.37 (3H, t, J=7.3 Hz), 2.44 (3H, s), 4.39 (2H, q, J=7.3 Hz), 4.45-5.30 (2H, m), 7.20 (2H, d, J=8.2 Hz), 7.30 (2H, d, J=8.8 Hz), 7.74 (1H, t, J=7.3 Hz), 7.81-7.88 (3H, m), 8.05 (1H, d, J=8.5 Hz), 8.10-8.18 (3H, m), 9.00 (1H, s).

Example 2

Preparation of sodium 4-({(4-methylisoquinolin-3-yl)[4-(trifluoromethoxy)benzyl]amino}-sulfonyl)benzoate

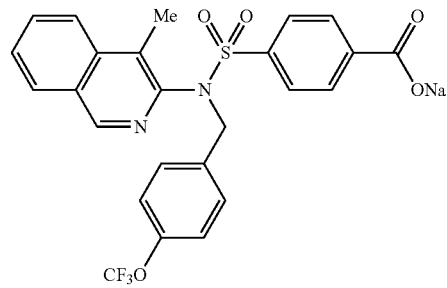

A suspension of ethyl 4-({(4-methylisoquinolin-3-yl)[4-(trifluoromethoxy)benzyl]-amino}sulfonyl)benzoate (1.11 g, 2.04 mmol) prepared in Example 1 and 2 mol/L aqueous sodium hydroxide solution (1.02 ml, 2.04 mmol) in ethanol (20.4 ml) was heated to reflux for 1 hour. The reaction solution was concentrated under reduced pressure, and the resulting residue is washed with diethyl ether and pentane to give sodium 4-({(4-methylisoquinolin-3-yl)[4-(trifluoromethoxy)benzyl]amino}sulfonyl)benzoate (1.07 g, 94%) as a colorless powder.

ESI-MS m/z:515[M−Na]⁻.

¹H-NMR (DMSO-d$_6$) δ 2.46 (3H, s), 4.40-5.20 (2H, m), 7.19 (2H, d, J=8.0 Hz), 7.30 (2H, d, J=8.7 Hz), 7.58 (2H, d, J=8.3 Hz), 7.72 (1H, t, J=7.1 Hz), 7.80-7.85 (1H, m), 7.98 (2H, d, J=8.7 Hz), 8.04 (1H, d, J=8.7 Hz), 8.11 (1H, d, J=8.0 Hz), 9.01 (1H, s).

Example 3

Preparation of ethyl 4-{[[3-fluoro-4-(trifluoromethoxy)benzyl](4-methylisoquinolin-3-yl)-amino]sulfonyl}benzoate

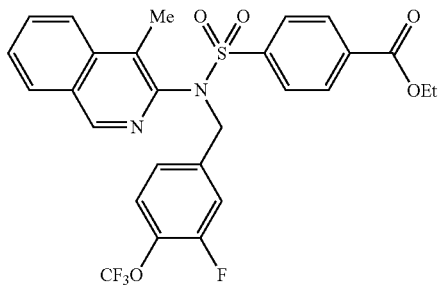

To a solution of ethyl 4-{[(4-methylisoquinolin-3-yl)amino]sulfonyl}benzoate (80 mg, 0.22 mmol) obtained in Example 1-(1) and [3-fluoro-4-(trifluoromethoxy)phenyl]methanol (57 mg, 0.27 mmol) obtained in Reference example 1 in tetrahydrofuran (3 ml) was added triphenylphosphine (85 mg, 0.32 mmol) at room temperature. The above solution was cooled to 0° C., and then thereto was added diisopropyl azodicarboxylate (64 μl, 0.32 mmol). The mixture was slowly warmed to room temperature and stirred at the same temperature overnight. The reaction solution was concentrated under reduced pressure, and the resulting residue was purified by silica gel column chromatography (hexane:ethyl acetate=5:1→2:1) to give ethyl 4-{[[3-fluoro-4-(trifluoromethoxy)benzyl](4-methylisoquinolin-3-yl)amino]sulfonyl}benzoate (51 mg, 42%) as a white solid.

APCI-MS m/z:563[M+H]⁺.

¹H-NMR (DMSO-d$_6$) δ 1.36 (3H, t, J=7.0 Hz), 2.50 (3H, s), 4.39 (2H, q, J=7.2 Hz), 4.68-5.01 (2H, m), 7.18 (1H, d, J=8.5 Hz), 7.33 (1H, dd, J=10.9, 1.8 Hz), 7.43 (1H, dd, J=8.5, 8.5 Hz), 7.75 (1H, m), 7.83-7.88 (3H, m), 8.09 (1H, d, J=8.5 Hz), 8.13-8.15 (3H, m), 9.01 (1H, s).

Example 4

Preparation of sodium 4-{[[3-fluoro-4-(trifluoromethoxy)benzyl](4-methylisoquinolin-3-yl)-amino]sulfonyl}benzoate

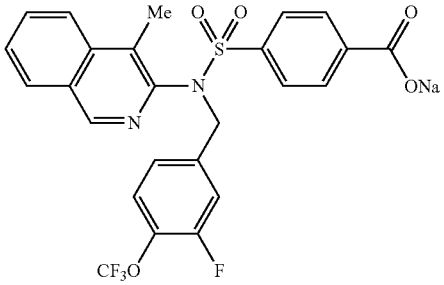

To a suspension of ethyl 4-{[[3-fluoro-4-(trifluoromethoxy)benzyl](4-methylisoquinolin-3-yl)amino]sulfonyl}benzoate (47 mg, 0.084 mmol) prepared in Example 3 in ethanol (1 ml) was added 1 mol/L aqueous sodium hydroxide solution (167 μl, 0.167 mmol), and the mixture was stirred at room temperature overnight. To the reaction solution was added water (2 ml), and then the solution was acidified by 6 mol/L hydrochloric acid solution. The precipitated solid was filtered, washed with water, and then dried at 60° C. under reduced pressure to give a white solid (39.7 mg). The solid was resuspended in ethanol (1 ml), and then thereto was added 1 mol/L aqueous sodium hydroxide solution (73 μl, 0.073 mmol). The mixture was stirred and dissolved, and then the reaction solution was concentrated under reduced pressure and the precipitated solid was dried to give sodium 4-{[[3-fluoro-4-(trifluoromethoxy)benzyl](4-methylisoquinolin-3-yl)amino]sulfonyl}benzoate (42 mg, 89%) as a white solid.

ESI-MS m/z:533[M−Na]⁻.

¹H-NMR (DMSO-d$_6$) δ 2.52 (3H, s), 4.68 (1H, brs), 4.96 (1H, brs), 7.18 (1H, d, J=8.7 Hz), 7.33 (1H, dd, J=11.2, 1.9 Hz), 7.42 (1H, dd, J=8.0, 8.0 Hz), 7.73 (1H, m), 7.56 (2H, m), 7.84 (1H, m), 7.97 (2H, m), 8.07 (1H, d, J=8.7 Hz), 8.12 (1H, d, J=8.0 Hz), 9.11 (1H, s).

Example 5

Preparation of ethyl 4-({(4-chloro-1-methyl-1H-pyrrolo[2,3-c]pyridin-7-yl)[4-(trifluoromethoxy)benzyl]amino}sulfonyl)benzoate

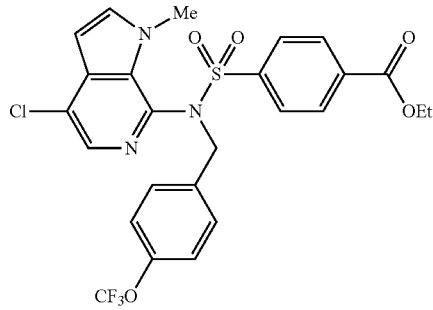

(1) A mixture of 4,7-dichloro-1-methyl-1H-pyrrolo[2,3-c]pyridine (153 mg, 760 μmol) obtained in Reference example 2 and 4-(trifluoromethoxy)benzylamine (1.45 g, 7.60 mmol) was stirred at 200° C. for 6 hours under microwave irradiation. After cooling, to the reaction solution was added 1 mol/L aqueous citric acid solution, and the mixture was extracted with ethyl acetate twice. The organic layer was combined, washed with water, filtered through diatomite column, and then concentrated under reduced pressure. The resulting residue was purified by silica gel column chromatography (hexane:ethyl acetate=19:1→1:1) to give 4-chloro-1-methyl-N-[4-(trifluoromethoxy)benzyl]-1H-pyrrolo[2,3-c]pyridine-7-amine (138 mg, 51%) as a yellow viscous material.

APCI-MS m/z:356/358[M+H]⁺.

(2) To a solution of the above compound (136 mg, 381 μmol) in pyridine (1.91 ml) was added ethyl 4-chlorosulfonylbenzoate (190 mg, 763 μmol) at room temperature, and the mixture was stirred at 80° C. for 6 hours. Then, thereto was added additional ethyl 4-chlorosulfonylbenzoate (379 mg, 1.53 mmol), and the mixture was stirred at 80° C. overnight. After cooling, the reaction solution was diluted with ethyl acetate, washed with 1 mol/L aqueous citric acid solution, water, saturated aqueous sodium hydrogen carbonate solution and saturated brine, dried over anhydrous sodium sulfate, and then concentrated under reduced pressure. The resulting residue was purified by silica gel column chromatography (hexane:ethyl acetate=19:1→4:1) to give ethyl 4-({(4-chloro-1-methyl-1H-pyrrolo[2,3-c]pyridin-7-yl)[4-(trifluoromethoxy)benzyl]amino}sulfonyl)benzoate (51.1 mg, 24%) as a pale yellow viscous material.

APCI-MS m/z:568/570[M+H]$^+$.

$^1$H-NMR (DMSO-d$_6$) δ 1.37 (3H, t, J=7.3 Hz), 3.87 (3H, s), 4.39 (2H, q, J=7.3 Hz), 4.59 (1H, d, J=13.0 Hz), 5.07 (1H, d, J=13.0 Hz), 6.56 (1H, d, J=3.0 Hz), 7.20 (2H, d, J=8.0 Hz), 7.25 (2H, d, J=8.8 Hz), 7.66 (2H, d, J=3.0 Hz), 7.85 (1H, d, J=8.5 Hz), 7.97 (1H, s), 8.16 (2H, d, J=8.5 Hz).

Example 6

Preparation of sodium 4-({(4-chloro-1-methyl-1H-pyrrolo[2,3-c]pyridin-7-yl)[4-(trifluoromethoxy)benzyl]amino}sulfonyl)benzoate

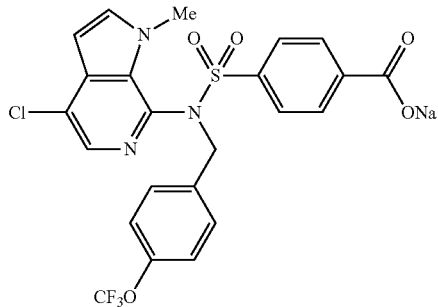

Ethyl 4-({(4-chloro-1-methyl-1H-pyrrolo[2,3-c]pyridin-7-yl)[4-(trifluoromethoxy)-benzyl]amino}sulfonyl)benzoate (50.7 mg, 89.3 μmol) prepared in Example 5 was treated in a similar manner to Example 2 to give sodium 4-({(4-chloro-1-methyl-1H-pyrrolo[2,3-c]pyridin-7-yl)[4-(trifluoromethoxy)benzyl]amino}sulfonyl)benzoate (49.4 mg, 98%) as a colorless powder.

ESI-MS m/z:538/540[M−Na]$^-$.

$^1$H-NMR (DMSO-d$_6$) δ 3.90 (3H, s), 4.58 (1H, d, J=13.2 Hz), 4.99 (1H, d, J=13.2 Hz), 6.54 (1H, d, J=3.2 Hz), 7.20 (2H, d, J=8.0 Hz), 7.25 (2H, d, J=8.7 Hz), 7.53 (2H, d, J=8.3 Hz), 7.64 (1H, d, J=2.9 Hz), 7.96-8.00 (3H, m).

Example 7

Preparation of ethyl 4-{[[(4'-fluorobiphenyl-4-yl)methyl](4-methylisoquinolin-3-yl)amino]-sulfonyl}benzoate

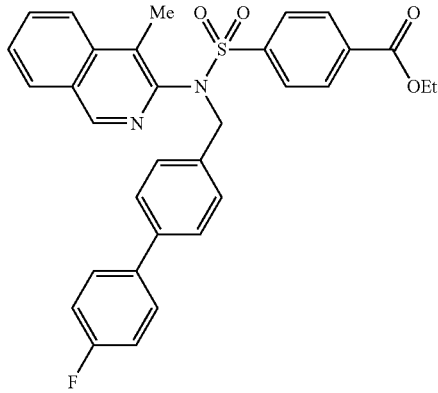 [SMILES: CCOC(=O)c1ccc(S(=O)(=O)N(Cc2ccc(-c3ccc(F)cc3)cc2)c2ncc3ccccc3c2C)cc1]

(1) Ethyl 4-{[(4-methylisoquinolin-3-yl)amino]sulfonyl}benzoate obtained in Example 1-(1) and 1-bromo-4-(bromomethyl)benzene were treated in a similar manner to Example 1-(2) to give ethyl 4-{[(4-bromobenzyl)(4-methylisoquinolin-3-yl)amino]sulfonyl}benzoate (469 mg, 79%) as a colorless powder.

APCI-MS m/z:539[M+H]$^+$.

(2) To a mixed solution of the above compound (110 mg, 0.2 mmol), 4-fluorophenylboric acid (33 mg, 0.22 mmol) and tetrakis(triphenylphosphine)palladium (0) (5 mg, 0.004 mmol) in 1,2-dimethoxyethane (2.0 ml) and water (1.0 ml) was added sodium carbonate (33 mg, 0.3 mmol), and the mixture was heated to reflux for 6 hours. To the reaction solution was added water, and the mixture was extracted with ethyl acetate twice. The organic layer was combined, washed with water and saturated brine, dried over anhydrous sodium sulfate, and then concentrated under reduced pressure. The resulting residue was purified by silica gel column chromatography (hexane:ethyl acetate=9:1→3:1) to give ethyl 4-{[[(4'-fluorobiphenyl-4-yl)methyl](4-methylisoquinolin-3-yl)amino]sulfonyl}benzoate (88.0 mg, 78%) as a colorless powder.

Example 8

Preparation of 4-{[[(4'-fluorobiphenyl-4-yl)methyl](4-methylisoquinolin-3-yl)amino]-sulfonyl}benzoic acid

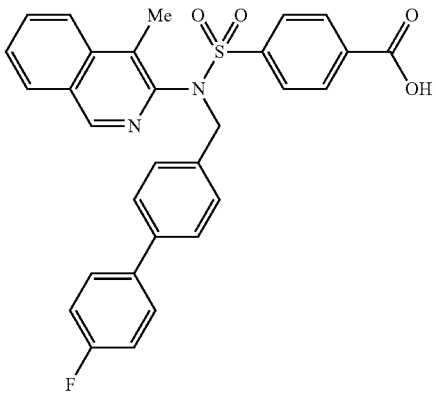 [SMILES: Cc1c(N(Cc2ccc(-c3ccc(F)cc3)cc2)S(=O)(=O)c2ccc(C(=O)O)cc2)ncc2ccccc12]

A suspension of ethyl 4-{[[(4'-fluorobiphenyl-4-yl)methyl](4-methylisoquinolin-3-yl)amino]sulfonyl}benzoate (88.0 mg, 0.16 mmol) prepared in Example 7 and 1 mol/L aqueous sodium hydroxide solution (320 μl, 0.32 mmol) in methanol (1.6 ml) was stirred at room temperature overnight, and then to the reaction solution was added 2 mol/L hydrochloric acid solution (400 μl). The mixture was extracted with chloroform twice. The organic layer was combined, washed with water and saturated brine, dried over anhydrous sodium sulfate, and then concentrated under reduced pressure. The resulting residue was purified by silica gel column chromatography (chloroform:methanol=10:0→9:1) to give 4-{[[(4'-fluorobiphenyl-4-yl)methyl](4-methylisoquinolin-3-yl)amino]sulfonyl}benzoic acid (62.1 mg, 74%) as a colorless powder.

APCI-MS m/z:527[M+H]$^+$.

$^1$H-NMR (DMSO-d$_6$) δ 2.49 (3H, s), 4.50-5.15 (2H, m), 7.19-7.28 (4H, m), 7.50 (2H, d, J=8.4 Hz), 7.58-7.63 (2H, m), 7.70-7.74 (1H, m), 7.80-7.86 (3H, m), 8.03-8.06 (1H, m), 8.11-8.15 (3H, m), 9.01 (1H, s).

Example 9

Preparation of ethyl 4-({(1-cyclopropyl-4-methylisoquinolin-3-yl)[4-(trifluoromethoxy)-benzyl]amino}sulfonyl)benzoate

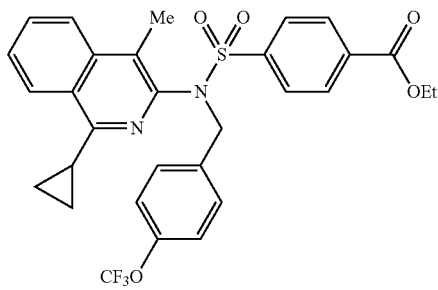

(1) 1-Bromo-4-methylisoquinoline-3-amine, ethyl 4-chlorosulfonylbenzoate and 1-(bromomethyl)-4-(trifluoromethoxy)benzene were treated in a similar manner to Examples 1-(1) and (2) to give ethyl 4-({(1-bromo-4-methylisoquinolin-3-yl)[4-(trifluoromethoxy)-benzyl]amino}sulfonyl)benzoate as a colorless solid.
APCI-MS m/z:623/625 [M+H]$^+$.

(2) A mixture of the above compound (100 mg, 160 μmol), potassium cyclopropyltrifluoroborate (45.9 mg, 321 μmol), palladium acetate (3.7 mg, 16.0 μmol), di(1-adamantyl)butylphosphine (9.1 mg, 24.1 μmol), cesium carbonate (105 mg, 321 μmol), water (80 μl) and toluene (802 μl) was heated to reflux under argon atmosphere for 3 hours. After cooling, the reaction solution was diluted with ethyl acetate, filtered through diatomite column, and then concentrated under reduced pressure. The resulting residue was purified by silica gel column chromatography (hexane:ethyl acetate=19:1→17:3) to give ethyl 4-({(1-cyclopropyl-4-methylisoquinolin-3-yl)[4-(trifluoromethoxy)benzyl]amino}sulfonyl)benzoate (93.0 mg, 99%) as a pale yellow solid.
APCI-MS m/z:585[M+H]$^+$.
$^1$H-NMR (DMSO-d$_6$) δ 0.25-0.95 (4H, m), 1.37 (3H, t, J=7.3 Hz), 2.38 (3H, s), 2.73-2.82 (1H, m), 4.40 (2H, q, J=7.3 Hz), 4.46-5.12 (2H, m), 7.20 (2H, d, J=8.2 Hz), 7.26 (2H, d, J=8.8 Hz), 7.69-7.75 (1H, m), 7.77-7.84 (3H, m), 8.01 (1H, d, J=8.2 Hz), 8.14 (2H, d, J=8.5 Hz), 8.49 (1H, d, J=8.2 Hz).

Example 10

Preparation of sodium 4-({(1-cyclopropyl-4-methylisoquinolin-3-yl)[4-(trifluoromethoxy)-benzyl]amino}sulfonyl)benzoate

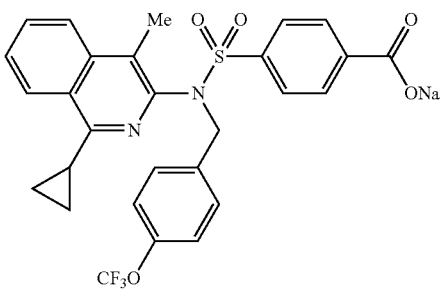

A mixture of ethyl 4-({(1-cyclopropyl-4-methylisoquinolin-3-yl)[4-(trifluoromethoxy)-benzyl]amino}sulfonyl)benzoate (92.0 mg, 157 μmol) prepared in Example 9, 2 mol/L aqueous sodium hydroxide solution (79 μl, 157 μmol) and ethanol (1.57 ml) was heated to reflux for 1 hour. The reaction solution was concentrated under reduced pressure, and the resulting residue was washed with diethyl ether and pentane to give sodium 4-({(1-cyclopropyl-4-methylisoquinolin-3-yl)[4-(trifluoromethoxy)benzyl]amino}sulfonyl)benzoate (86.6 mg, 95%) as a colorless powder.
ESI-MS m/z:555[M−Na]$^-$.
$^1$H-NMR (DMSO-d$_6$) δ 0.45-0.95 (4H, m), 2.41 (3H, s), 2.76-2.83 (1H, m), 4.40-5.10 (2H, m), 7.19 (2H, d, J=8.0 Hz), 7.27 (2H, d, J=8.7 Hz), 7.53 (2H, d, J=8.7 Hz), 7.68-7.73 (1H, m), 7.77-7.82 (1H, m), 7.97-8.02 (3H, m), 8.49 (1H, d, J=8.3 Hz).

Example 11

Preparation of ethyl 4-{[{[5-fluoro-6-(trifluoromethyl)pyridin-2-yl]methyl}(4-methylisoquinolin-3-yl)amino]sulfonyl}benzoate

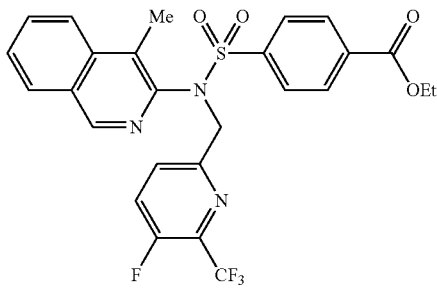 [SMILES: CCOC(=O)c1ccc(S(=O)(=O)N(Cc2ccc(F)c(C(F)(F)F)n2)c2ncc3ccccc3c2C)cc1]

(1) Ethyl 4-{[(4-methylisoquinolin-3-yl)amino]sulfonyl}benzoate obtained in Example 1-(1) and 6-(bromomethyl)-3-fluoro-2-iodopyridine obtained in Reference example 3 were treated in a similar manner to Example 1-(2) to give ethyl 4-{[[(5-fluoro-6-iodopyridin-2-yl)methyl](4-methylisoquinolin-3-yl)amino]sulfonyl}benzoate as a colorless viscous material.
APCI-MS m/z:606[M+H]$^+$.

(2) To a mixed solution of the above compound (68 mg, 0.112 mmol) in N,N-dimethylformamide (0.5 mL) and hexamethylphosphoric triamide (0.5 mL) were added methyl 2,2-difluoro-2-(fluorosulfonyl)acetate (104 μL, 0.82 mmol) and copper (I) iodide (156 mg, 0.82 mmol) at room temperature under argon atmosphere. The reaction solution was stirred at 70° C. overnight, cooled to room temperature, and then to the reaction solution was added water. The mixture was extracted with ethyl acetate twice. The organic layer was combined, washed with water and saturated brine, dried over anhydrous sodium sulfate, and then concentrated under reduced pressure. The resulting residue was purified by silica gel column chromatography (hexane:ethyl acetate=17:3→3:2) to give ethyl 4-{[{[5-fluoro-6-(trifluoromethyl)pyridin-2-yl]methyl}(4-methylisoquinolin-3-yl)-amino]sulfonyl}benzoate (41 mg, 68%) as a colorless powder.
APCI-MS m/z:548[M+H]$^+$.
$^1$H-NMR (CDCl$_3$) δ 1.43 (3H, t, J=7.3 Hz), 2.73 (3H, s), 4.44 (2H, q, J=7.3 Hz), 5.02 (2H, s), 7.44-7.49 (1H, m), 7.63-7.66 (1H, m), 7.73-7.76 (2H, m), 7.78 (2H, d, J=8.5 Hz), 7.93 (1H, d, J=8.3 Hz), 8.03 (1H, d, J=8.3 Hz), 8.16 (2H, d, J=8.5 Hz), 8.82 (1H, s).

Example 12

Preparation of sodium 4-{[{[5-fluoro-6-(trifluoromethyl)pyridin-2-yl]methyl}(4-methylisoquinolin-3-yl)amino]sulfonyl}benzoate

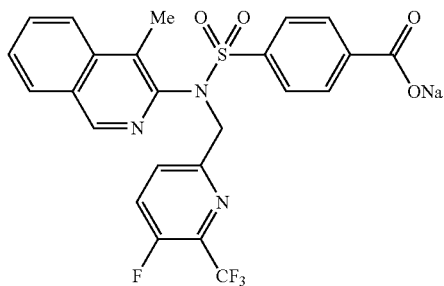

Ethyl 4-{[{[5-fluoro-6-(trifluoromethyl)pyridin-2-yl]methyl}(4-methylisoquinolin-3-yl)amino]sulfonyl}benzoate (38 mg, 0.64 mmol) prepared in Example 11 was treated in a similar manner to Example 2 to give sodium 4-{[{[5-fluoro-6-(trifluoromethyl)pyridin-2-yl]methyl}(4-methylisoquinolin-3-yl)amino]sulfonyl}benzoate (35 mg, 93%) as a colorless powder.

ESI-MS m/z:518[M−Na]−.

$^1$H-NMR (DMSO-d$_6$) δ 2.61 (3H, s), 4.85 (1H, brs), 5.10 (1H, brs), 7.55 (2H, d, J=8.7 Hz), 7.70-7.74 (1H, m), 7.77-7.79 (1H, m), 7.83-7.86 (1H, m), 7.92-7.95 (1H, m), 7.96 (2H, d, J=8.3 Hz), 8.10 (2H, d, J=8.7 Hz), 8.97 (1H, s).

Example 13

Preparation of ethyl 4-{[[4-(1-ethoxy-2,2,2-trifluoro-1-methylethyl)benzyl](4-methylisoquinolin-3-yl)amino]sulfonyl}benzoate

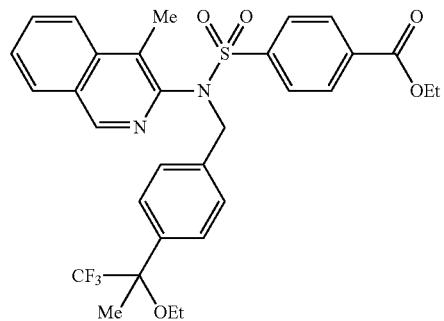 [SMILES: CCOC(=O)c1ccc(S(=O)(=O)N(Cc2ccc(C(C)(OCC)C(F)(F)F)cc2)c2ncc3ccccc3c2C)cc1]

(1) Ethyl 4-{[(4-methylisoquinolin-3-yl)amino]sulfonyl}benzoate obtained in Example 1-(1) and 4-(2,2,2-trifluoro-1-hydroxy-1-methylethyl)benzylalcohol were treated in a similar manner to Example 3 to give ethyl 4-({(4-methylisoquinolin-3-yl)[4-(2,2,2-trifluoro-1-hydroxy-1-methylethyl)benzyl]amino}sulfonyl)benzoate as a colorless viscous material.

APCI-MS m/z:573[M+H]$^+$.

(2) To a solution of the above compound (100 mg, 0.18 mmol) in N,N-dimethylformamide (2 ml) was added sodium hydride (10.5 mg, 0.26 mmol) at 0° C. The mixture was stirred at 0° C. for 30 minutes, and then thereto was added iodoethane (42 μl, 0.52 mmol) at the same temperature. The mixture was stirred at room temperature overnight, and then to the reaction solution was added water. The mixture was extracted with ethyl acetate three times. The organic layer was combined, washed with water twice, dried over anhydrous sodium sulfate, and then concentrated under reduced pressure. The resulting residue was purified by silica gel column chromatography (hexane:ethyl acetate=10:0→7:3) to give ethyl 4-{[[4-(1-ethoxy-2,2,2-trifluoro-1-methylethyl)benzyl](4-methylisoquinolin-3-yl)amino]sulfonyl}benzoate (103 mg, 98%) as a colorless liquid.

APCI-MS m/z:601[M+H]$^+$.

$^1$H-NMR (400 MHz, DMSO-d$_6$) δ 1.00-1.13 (3H, m), 1.37 (3H, t, J=7.0 Hz), 1.66 (3H, s), 2.39 (3H, s), 2.89-3.05 (1H, m), 3.29-3.41 (1H, m), 4.39 (2H, q, J=7.0 Hz), 4.48-5.16 (2H, m), 7.22 (2H, d, J=8.5 Hz), 7.34 (2H, d, J=8.2 Hz), 7.73 (1H, t, J=7.3 Hz), 7.82 (1H, d, J=8.5 Hz), 7.86 (2H, d, J=8.5 Hz), 8.03 (1H, d, J=8.5 Hz), 8.12-8.15 (3H, m), 9.11 (1H, s).

Example 14

Preparation of 4-{[[4-(1-ethoxy-2,2,2-trifluoro-1-methylethyl)benzyl](4-methylisoquinolin-3-yl)amino]sulfonyl}benzoic acid

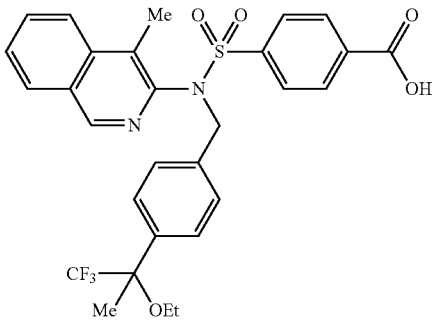 [SMILES: CCOC(C)(c1ccc(CN(c2ncc3ccccc3c2C)S(=O)(=O)c2ccc(C(=O)O)cc2)cc1)C(F)(F)F]

To a mixed solution of ethyl 4-{[[4-(1-ethoxy-2,2,2-trifluoro-1-methylethyl)benzyl](4-methylisoquinolin-3-yl)amino]sulfonyl}benzoate (102 mg, 0.17 mmol) prepared in Example 13 in ethanol (1 mL) and tetrahydrofuran (1 mL) was added 2 mol/L aqueous sodium hydroxide solution (340 μL, 0.68 mmol) at room temperature. The reaction solution was stirred at room temperature overnight, and then to the reaction solution was added 2 mol/L hydrochloric acid solution (1 ml). The mixture was extracted with chloroform three times. The organic layer was combined, dried over anhydrous sodium sulfate, and then concentrated under reduced pressure. The resulting residue was purified by silica gel column chromatography (chloroform:methanol=10:0→10:1) to give 4-{[[4-(1-ethoxy-2,2,2-trifluoro-1-methylethyl)benzyl](4-methylisoquinolin-3-yl)amino]sulfonyl}benzoic acid (82 mg, 85%) as a colorless powder.

APCI-MS m/z:573[M+H]$^+$.

$^1$H-NMR (DMSO-d$_6$) δ 1.00-1.14 (3H, m), 1.66 (3H, s), 2.39 (3H, s), 2.89-3.05 (1H, m), 3.17-3.51 (1H, m), 4.49-5.28 (2H, m), 7.22 (2H, d, J=8.5 Hz), 7.34 (2H, d, J=8.2 Hz), 7.73 (1H, t, J=7.3 Hz), 7.81-7.85 (3H, m), 8.03 (1H, d, J=8.8 Hz), 8.11-8.14 (3H, m), 9.02 (1H, s), 12.71-14.59 (1H, m).

Examples 15 to 37

The corresponding starting compounds were treated in a similar manner to Examples 1, 2 and/or 8 to give the following compounds of Table 1. Interconversions of a carboxylic acid compound and a salt thereof to each other may be carried out by a conventional salt formation and a conventional desalination, respectively.

TABLE 1

| Example | Structure | Physical data |
|---|---|---|
| 15 | 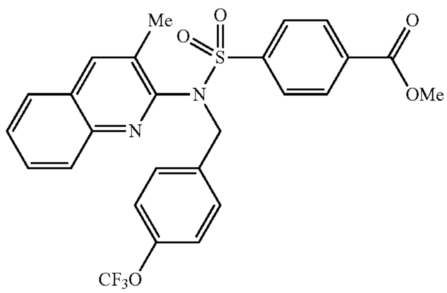 | solid<br>APCI-MS m/z:<br>531[M + H]+ |
| 16 | 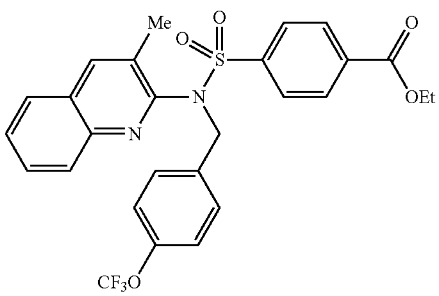 | solid<br>APCI-MS m/z:<br>545[M + H]+ |
| 17 | 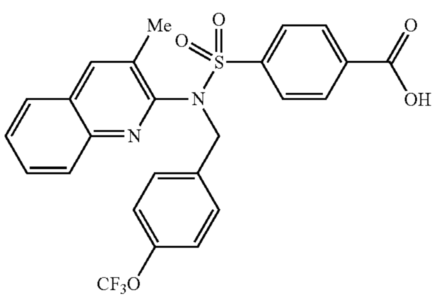 | solid<br>ESI-MS m/z:<br>515[M − H]− |
| 18 | 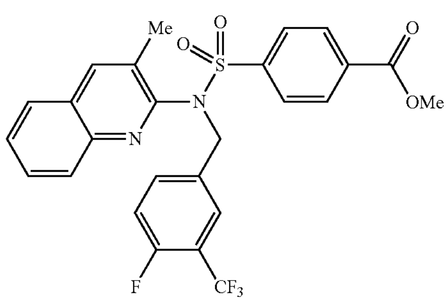 [SMILES: COC(=O)c1ccc(S(=O)(=O)N(Cc2ccc(F)c(C(F)(F)F)c2)c2nc3ccccc3cc2C)cc1] | powder<br>APCI-MS m/z:<br>533[M + H]+ |
| 19 | 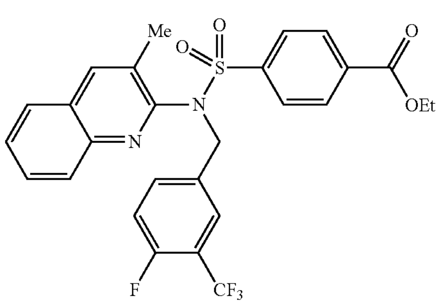 [SMILES: CCOC(=O)c1ccc(S(=O)(=O)N(Cc2ccc(F)c(C(F)(F)F)c2)c2nc3ccccc3cc2C)cc1] | powder<br>APCI-MS m/z:<br>547[M + H]+ |

TABLE 1-continued

| Example | Structure | Physical data |
|---|---|---|
| 20 | 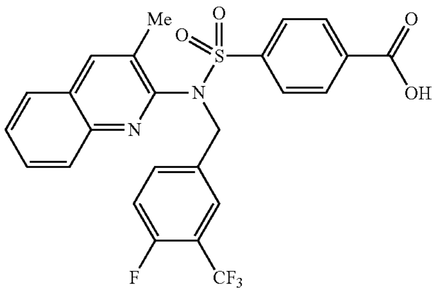 [SMILES: Cc1cc2ccccc2nc1N(Cc1ccc(F)c(C(F)(F)F)c1)S(=O)(=O)c1ccc(C(=O)O)cc1] | powder ESI-MS m/z: 517[M − H]⁻ |
| 21 | 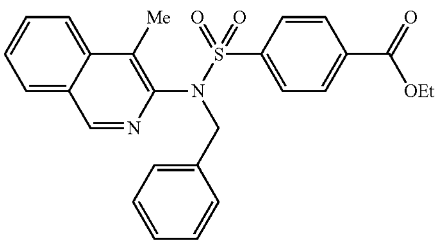 [SMILES: CCOC(=O)c1ccc(S(=O)(=O)N(Cc2ccccc2)c2ncc3ccccc3c2C)cc1] | powder APCI-MS m/z: 461[M + H]⁺ |
| 22 | 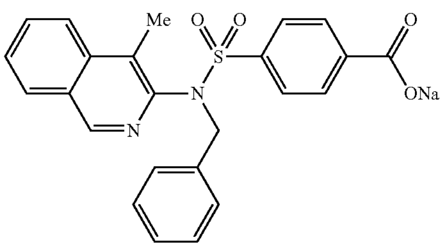 | powder ESI-MS m/z: 431[M − Na]⁻ |
| 23 | 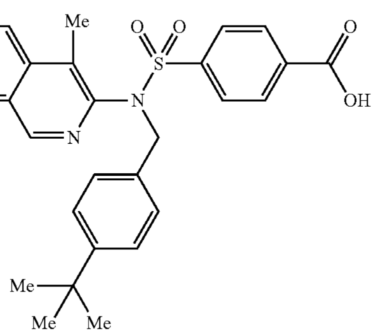 | powder APCI-MS m/z: 489[M + H]⁺ |
| 24 | 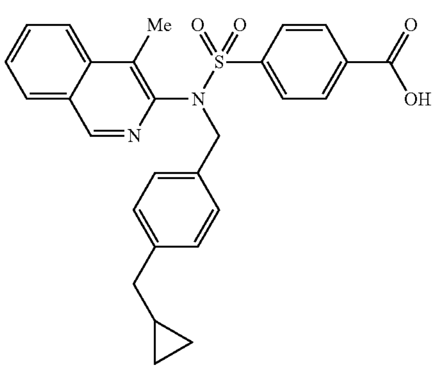 [SMILES: Cc1c(N(Cc2ccc(CC3CC3)cc2)S(=O)(=O)c2ccc(C(=O)O)cc2)ncc2ccccc12] | powder APCI-MS m/z: 487[M + H]⁺ |

TABLE 1-continued

| Example | Structure | Physical data |
|---|---|---|
| 25 | 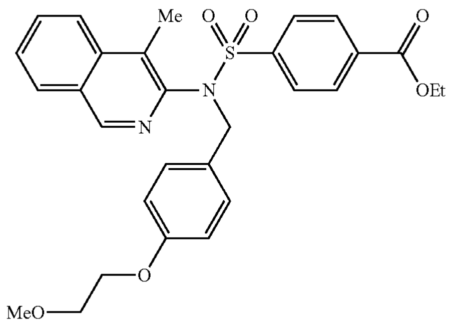 | powder APCI-MS m/z: 535[M + H]$^+$ |
| 26 | 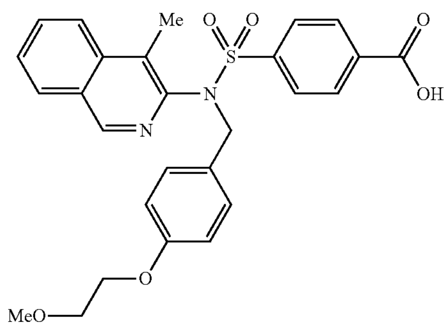 [SMILES: CCOC(=O)c1ccc(S(=O)(=O)N(Cc2ccc(OCCOC)cc2)c2ncc3ccccc3c2C)cc1] | powder APCI-MS m/z: 507[M + H]$^+$ |
| 27 | 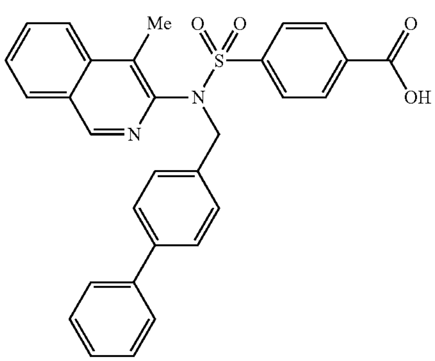 [SMILES: Cc1c(N(Cc2ccc(-c3ccccc3)cc2)S(=O)(=O)c2ccc(C(=O)O)cc2)ncc2ccccc12] | powder APCI-MS m/z: 509[M + H]$^+$ |
| 28 | 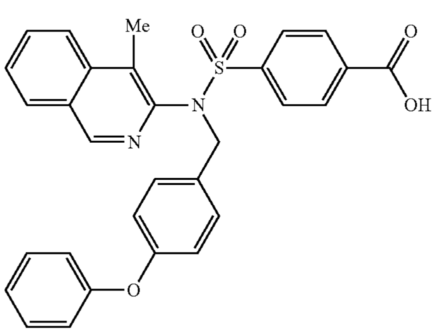 [SMILES: Cc1c(N(Cc2ccc(Oc3ccccc3)cc2)S(=O)(=O)c2ccc(C(=O)O)cc2)ncc2ccccc12] | powder APCI-MS m/z: 525[M + H]$^+$ |

TABLE 1-continued

| Example | Structure | Physical data |
|---|---|---|
| 29 | (4-methylisoquinolin-3-yl)-N-(4-fluoro-3-trifluoromethylbenzyl)-4-(ethoxycarbonyl)benzenesulfonamide | powder<br>APCI-MS m/z:<br>547[M + H]$^+$ |
| 30 | (4-methylisoquinolin-3-yl)-N-(4-fluoro-3-trifluoromethylbenzyl)-4-(sodium carboxylate)benzenesulfonamide | powder<br>ESI-MS m/z:<br>517[M − Na]$^-$ |
| 31 | (4-methylisoquinolin-3-yl)-N-(naphthalen-1-ylmethyl)-4-carboxybenzenesulfonamide | powder<br>APCI-MS m/z:<br>483[M + H]$^+$ |
| 32 | (4-methylisoquinolin-3-yl)-N-(naphthalen-2-ylmethyl)-4-carboxybenzenesulfonamide | powder<br>APCI-MS m/z:<br>483[M + H]$^+$ |
| 33 | (1-methoxy-4-methylisoquinolin-3-yl)-N-(4-trifluoromethoxybenzyl)-4-(ethoxycarbonyl)benzenesulfonamide | powder<br>APCI-MS m/z:<br>575[M + H]$^+$ |

TABLE 1-continued

| Example | Structure | Physical data |
|---------|-----------|---------------|
| 34 | 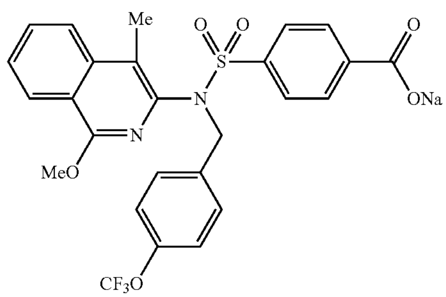 | powder<br>ESI-MS m/z:<br>545[M − Na]− |
| 35 | 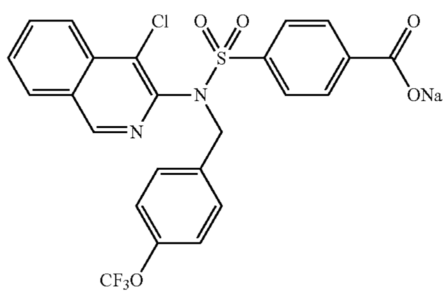 | powder<br>ESI-MS m/z:<br>535/537[M − Na]− |
| 36 | 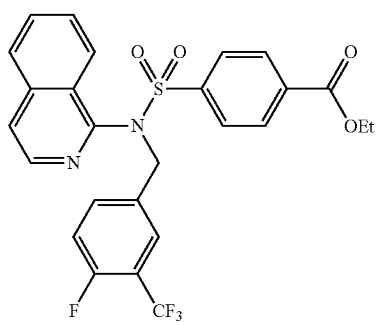 [SMILES: CCOC(=O)c1ccc(S(=O)(=O)N(Cc2ccc(F)c(C(F)(F)F)c2)c2nccc3ccccc23)cc1] | powder<br>APCI-MS m/z:<br>533[M + H]+ |
| 37 | 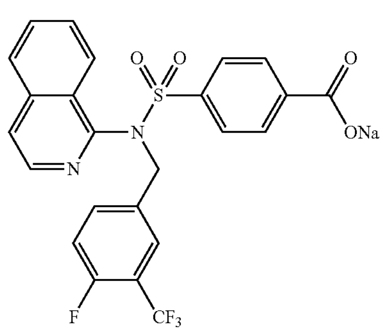 | powder<br>ESI-MS m/z:<br>503[M − Na]− |

Examples 38 to 87

The corresponding starting compounds were treated in a similar manner to Examples 3, 4 and/or 8 to give the following compounds of Table 2. Interconversions of a carboxylic acid compound and a salt thereof to each other may be carried out by a conventional salt formation and a conventional desalination, respectively.

TABLE 2

| Example | Structure | Physical data |
|---|---|---|
| 38 | 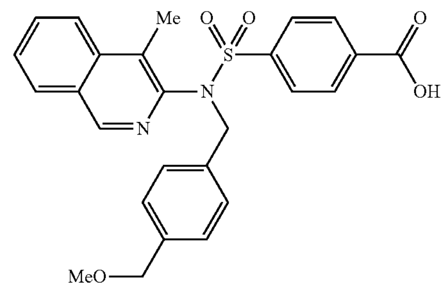 [SMILES: COCc1ccc(CN(c2ncc3ccccc3c2C)S(=O)(=O)c2ccc(C(=O)O)cc2)cc1] | powder APCI-MS m/z: 477[M + H]⁺ |
| 39 | 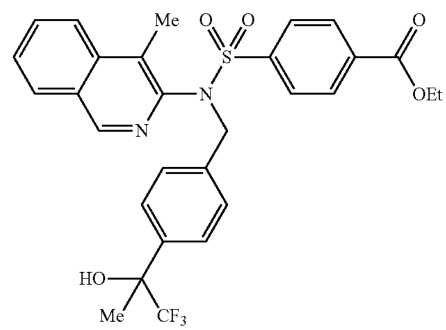 [SMILES: CCOC(=O)c1ccc(S(=O)(=O)N(Cc2ccc(C(C)(O)C(F)(F)F)cc2)c2ncc3ccccc3c2C)cc1] | powder APCI-MS m/z: 573[M + H]⁺ |
| 40 | 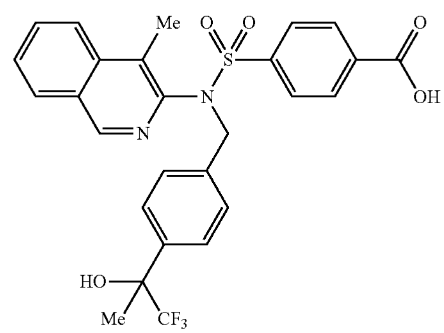 [SMILES: Cc1c(N(Cc2ccc(C(C)(O)C(F)(F)F)cc2)S(=O)(=O)c2ccc(C(=O)O)cc2)ncc2ccccc12] | solid APCI-MS m/z: 545[M + H]⁺ |
| 41 | 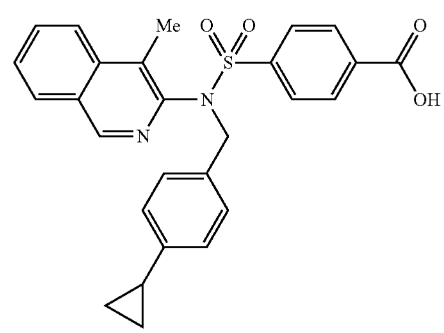 [SMILES: Cc1c(N(Cc2ccc(C3CC3)cc2)S(=O)(=O)c2ccc(C(=O)O)cc2)ncc2ccccc12] | powder APCI-MS m/z: 473[M + H]⁺ |

TABLE 2-continued

| Example | Structure | Physical data |
|---|---|---|
| 42 | 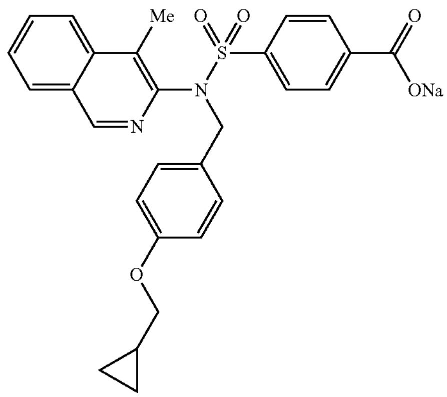 | powder ESI-MS m/z: 501[M − Na]+ |
| 43 | 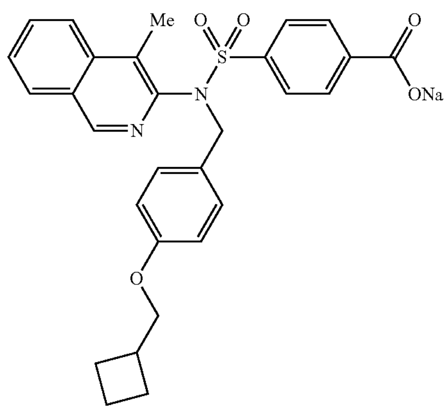 | powder ESI-MS m/z: 515[M − Na]− |
| 44 | 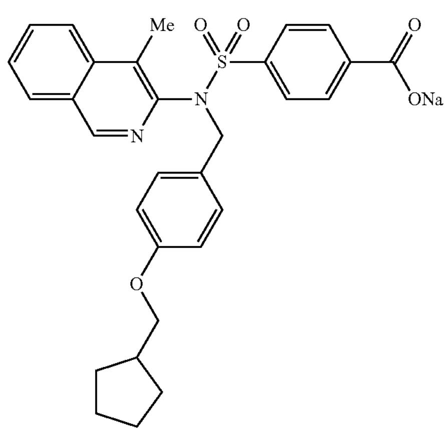 | powder ESI-MS m/z: 529[M − Na]− |

TABLE 2-continued

| Example | Structure | Physical data |
|---|---|---|
| 45 | (structure) | powder<br>APCI-MS m/z:<br>489[M + H]⁺ |
| 46 | (structure) | powder<br>APCI-MS m/z:<br>517[M + H]⁺ |
| 47 | (structure) | powder<br>APCI-MS m/z:<br>510[M + H]⁺ |
| 48 | (structure) | solid<br>APCI-MS m/z:<br>510[M + H]⁺ |

TABLE 2-continued

| Example | Structure | Physical data |
|---|---|---|
| 49 | 4-methylisoquinolin-3-yl, N-(2-phenoxybenzyl), sulfonyl-benzoic acid | powder<br>APCI-MS m/z:<br>525[M + H]$^+$ |
| 50 | 4-methylisoquinolin-3-yl, N-(3-phenoxybenzyl), sulfonyl-benzoic acid | powder<br>APCI-MS m/z:<br>525[M + H]$^+$ |
| 51 | 4-methylisoquinolin-3-yl, N-(4-cyclopropylmethoxy-3-fluorobenzyl), sulfonyl-benzoate sodium | powder<br>ESI-MS m/z:<br>519[M − Na]$^-$ |
| 52 | 4-methylisoquinolin-3-yl, N-(4-cyclopropylmethoxy-3-chlorobenzyl), sulfonyl-benzoate sodium | powder<br>ESI-MS m/z:<br>535/537[M − Na]$^-$ |

TABLE 2-continued
| Example | Structure | Physical data |
|---|---|---|
| 53 | 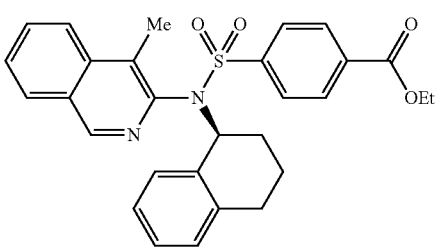 [SMILES: CCOC(=O)c1ccc(S(=O)(=O)N(c2ncc3ccccc3c2C)[C@H]2CCCc3ccccc32)cc1] | solid<br>APCI-MS m/z:<br>501[M + H]$^+$ |
| 54 | 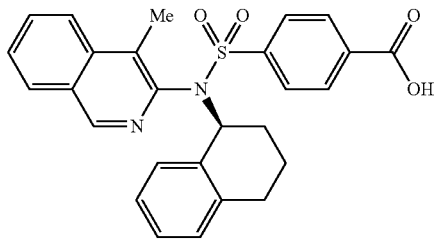 [SMILES: Cc1c(N([C@H]2CCCc3ccccc32)S(=O)(=O)c2ccc(C(=O)O)cc2)ncc2ccccc12] | solid<br>APCI-MS m/z:<br>473[M + H]$^+$ |
| 55 | 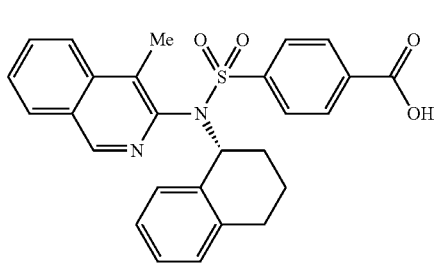 [SMILES: Cc1c(N([C@@H]2CCCc3ccccc32)S(=O)(=O)c2ccc(C(=O)O)cc2)ncc2ccccc12] | solid<br>APCI-MS m/z:<br>473[M + H]$^+$ |
| 56 | 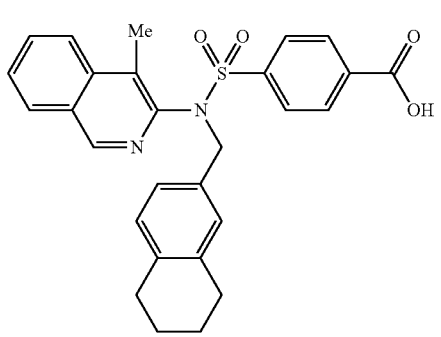 [SMILES: Cc1c(N(Cc2ccc3c(c2)CCCC3)S(=O)(=O)c2ccc(C(=O)O)cc2)ncc2ccccc12] | powder<br>APCI-MS m/z:<br>487[M + H]$^+$ |
| 57 | 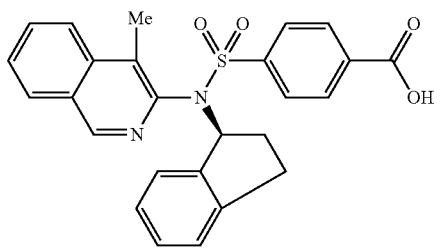 [SMILES: Cc1c(N([C@H]2CCc3ccccc32)S(=O)(=O)c2ccc(C(=O)O)cc2)ncc2ccccc12] | solid<br>APCI-MS m/z:<br>459[M + H]$^+$ |

TABLE 2-continued

| Example | Structure | Physical data |
|---|---|---|
| 58 | 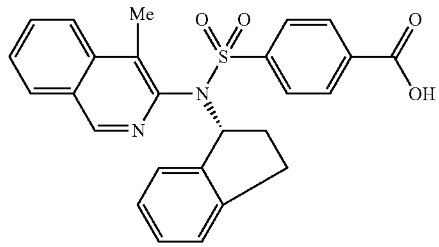 [SMILES: Cc1c(N([C@@H]2CCc3ccccc32)S(=O)(=O)c2ccc(C(=O)O)cc2)ncc2ccccc12] | solid<br>APCI-MS m/z:<br>459[M + H]⁺ |
| 59 | 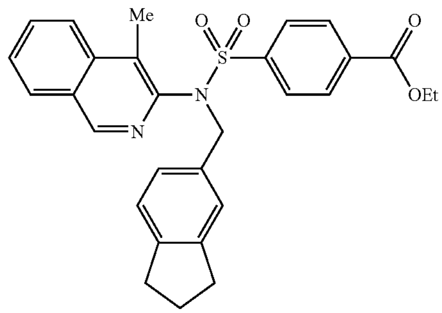 [SMILES: CCOC(=O)c1ccc(S(=O)(=O)N(Cc2ccc3c(c2)CCC3)c2ncc3ccccc3c2C)cc1] | viscous material<br>APCI-MS m/z:<br>501[M + H]⁺ |
| 60 | 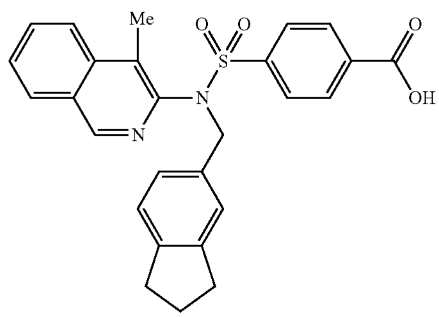 [SMILES: Cc1c(N(Cc2ccc3c(c2)CCC3)S(=O)(=O)c2ccc(C(=O)O)cc2)ncc2ccccc12] | solid<br>APCI-MS m/z:<br>473[M + H]⁺ |
| 61 | 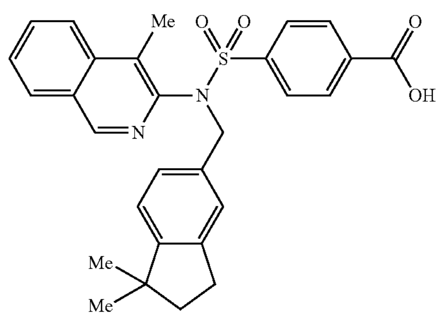 [SMILES: Cc1c(N(Cc2ccc3c(c2)CCC3(C)C)S(=O)(=O)c2ccc(C(=O)O)cc2)ncc2ccccc12] | powder<br>APCI-MS m/z:<br>501[M + H]⁺ |
| 62 | 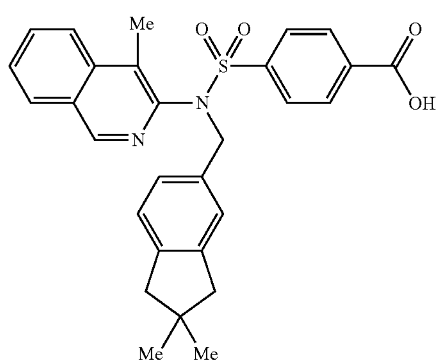 | powder<br>APCI-MS m/z:<br>501[M + H]⁺ |

TABLE 2-continued

| Example | Structure | Physical data |
|---|---|---|
| 63 | 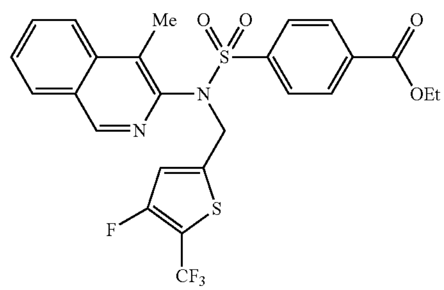 [SMILES: CCOC(=O)c1ccc(S(=O)(=O)N(Cc2cc(F)c(C(F)(F)F)s2)c2ncc3ccccc3c2C)cc1] | powder APCI-MS m/z: 553[M + H]+ |
| 64 | 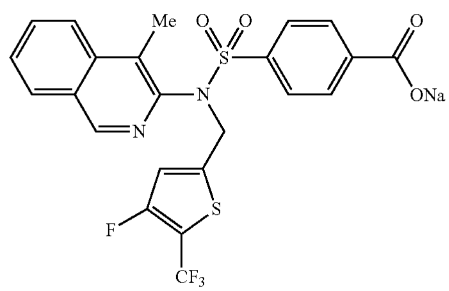 | powder ESI-MS m/z: 523[M − Na]− |
| 65 | 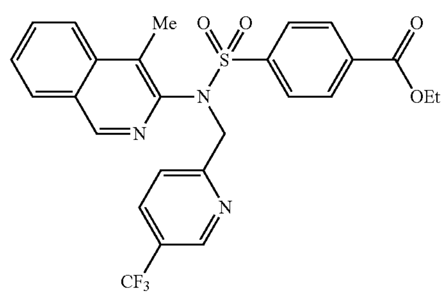 [SMILES: CCOC(=O)c1ccc(S(=O)(=O)N(Cc2ccc(C(F)(F)F)cn2)c2ncc3ccccc3c2C)cc1] | powder APCI-MS m/z: 530[M + H]+ |
| 66 | 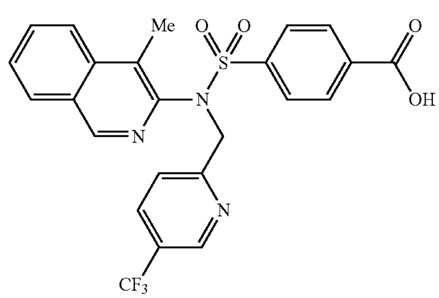 [SMILES: Cc1c(N(Cc2ccc(C(F)(F)F)cn2)S(=O)(=O)c2ccc(C(=O)O)cc2)ncc2ccccc12] | powder APCI-MS m/z: 502[M + H]+ |
| 67 | 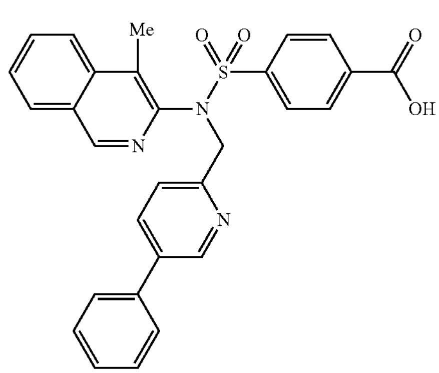 [SMILES: Cc1c(N(Cc2ccc(-c3ccccc3)cn2)S(=O)(=O)c2ccc(C(=O)O)cc2)ncc2ccccc12] | powder APCI-MS m/z: 510[M + H]+ |

TABLE 2-continued

| Example | Structure | Physical data |
|---|---|---|
| 68 | 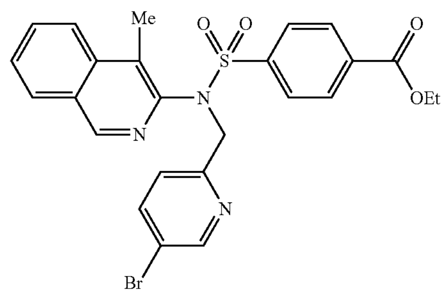 [SMILES: CCOC(=O)c1ccc(S(=O)(=O)N(Cc2ccc(Br)cn2)c2ncc3ccccc3c2C)cc1] | solid<br>APCI-MS m/z:<br>540/542[M + H]⁺ |
| 69 | 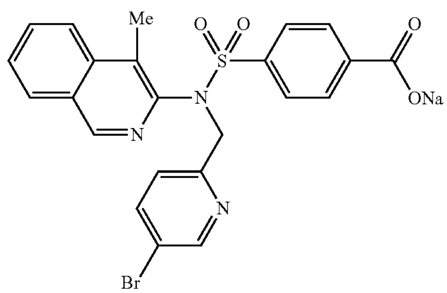 | powder<br>ESI-MS m/z:<br>510/512[M − Na]⁻ |
| 70 | 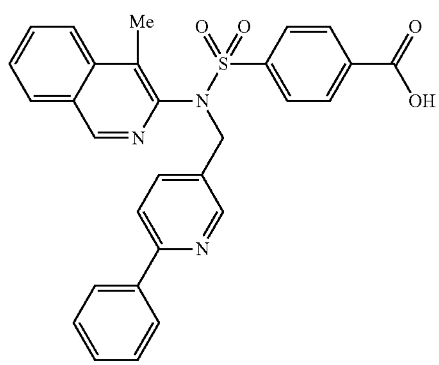 [SMILES: Cc1c(N(Cc2ccc(-c3ccccc3)nc2)S(=O)(=O)c2ccc(C(=O)O)cc2)ncc2ccccc12] | solid<br>APCI-MS m/z:<br>510[M + H]⁺ |
| 71 | 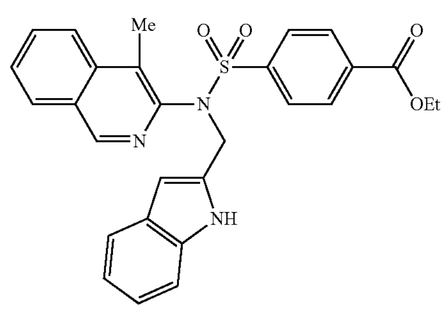 [SMILES: CCOC(=O)c1ccc(S(=O)(=O)N(Cc2cc3ccccc3[nH]2)c2ncc3ccccc3c2C)cc1] | powder<br>APCI-MS /z:<br>500[M + H]⁺ |
| 72 | 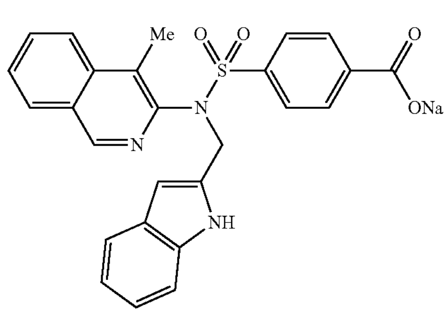 | powder<br>ESI-MS m/z:<br>470[M − Na]⁻ |

TABLE 2-continued

| Example | Structure | Physical data |
|---|---|---|
| 73 | 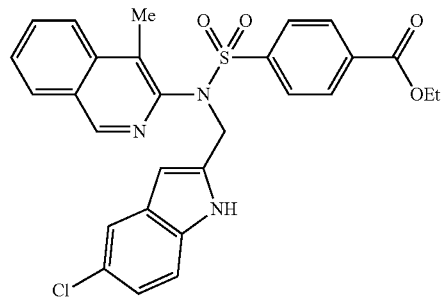 [SMILES: CCOC(=O)c1ccc(S(=O)(=O)N(Cc2cc3cc(Cl)ccc3[nH]2)c2ncc3ccccc3c2C)cc1] | powder<br>APCI-MS m/z:<br>534/536[M + H]⁺ |
| 74 | 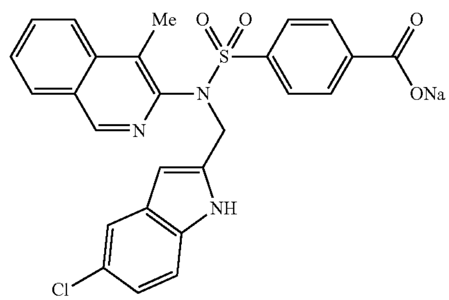 | powder<br>ESI-MS m/z:<br>504/506[M − Na]⁻ |
| 75 | 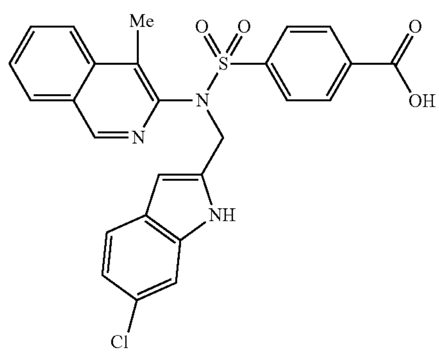 [SMILES: Cc1c(N(Cc2cc3ccc(Cl)cc3[nH]2)S(=O)(=O)c2ccc(C(=O)O)cc2)ncc2ccccc12] | powder<br>ESI-MS m/z:<br>504/506[M − Na]⁻ |
| 76 | 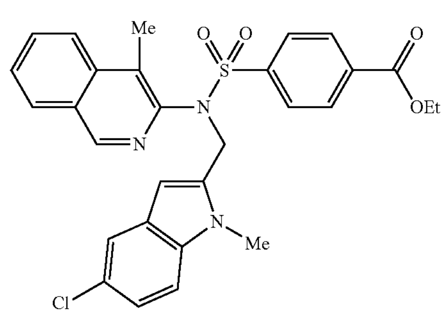 [SMILES: CCOC(=O)c1ccc(S(=O)(=O)N(Cc2cc3cc(Cl)ccc3n2C)c2ncc3ccccc3c2C)cc1] | powder<br>APCI-MS m/z:<br>549/551[M + H]⁺ |

TABLE 2-continued

| Example | Structure | Physical data |
|---|---|---|
| 77 | 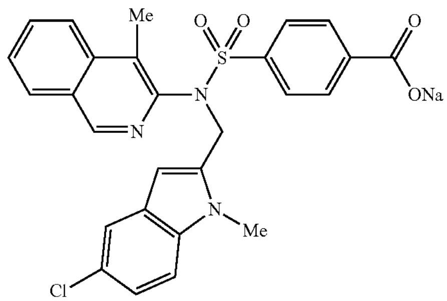 | powder<br>ESI-MS m/z:<br>518/520[M − Na]⁻ |
| 78 | 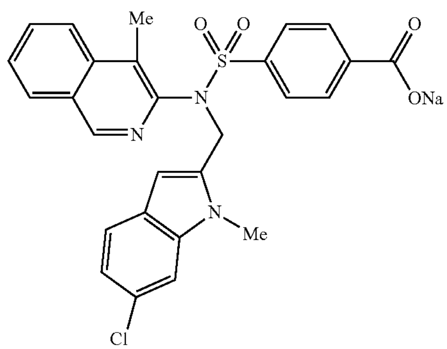 | powder<br>ESI-MS m/z:<br>518/520[M − Na]⁻ |
| 79 | 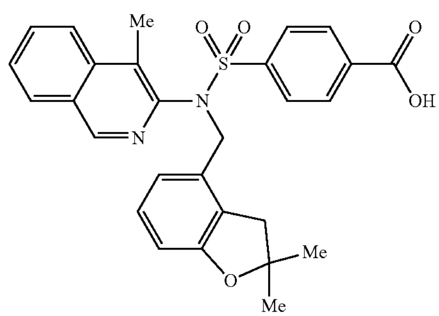 [SMILES: Cc1c(N(Cc2cccc3c2CC(C)(C)O3)S(=O)(=O)c2ccc(C(=O)O)cc2)ncc2ccccc12] | powder<br>APCI-MS m/z:<br>503[M + H]⁺ |
| 80 | 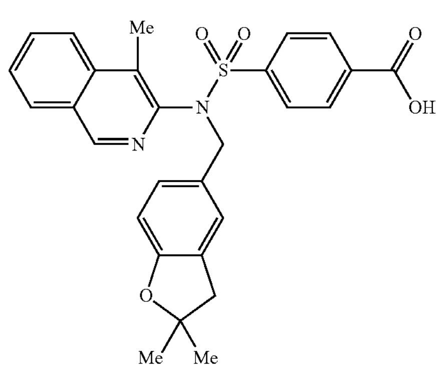 [SMILES: Cc1c(N(Cc2ccc3c(c2)CC(C)(C)O3)S(=O)(=O)c2ccc(C(=O)O)cc2)ncc2ccccc12] | powder<br>APCI-MS m/z:<br>503[M + H]⁺ |

TABLE 2-continued

| Example | Structure | Physical data |
|---|---|---|
| 81 | 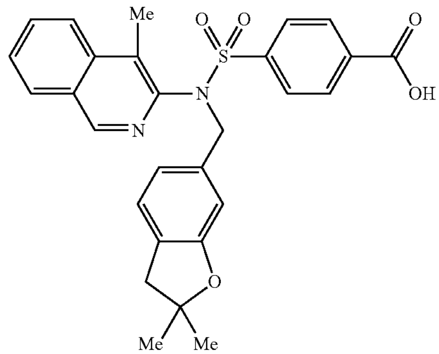 [SMILES: Cc1c(N(Cc2ccc3c(c2)OC(C)(C)C3)S(=O)(=O)c2ccc(C(=O)O)cc2)ncc2ccccc12] | powder<br>APCI-MS m/z:<br>503[M + H]+ |
| 82 | 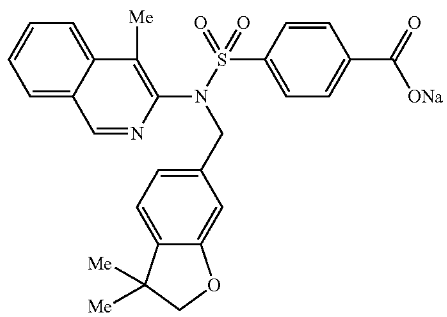 | powder<br>ESI-MS m/z:<br>501[M − Na]− |
| 83 | 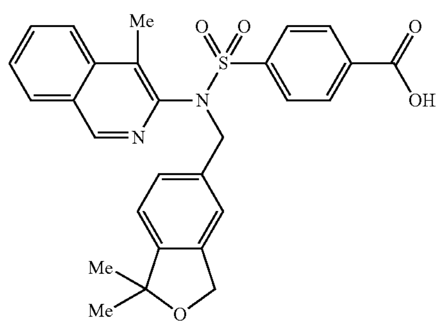 [SMILES: Cc1c(N(Cc2ccc3c(c2)COC3(C)C)S(=O)(=O)c2ccc(C(=O)O)cc2)ncc2ccccc12] | powder<br>APCI-MS m/z:<br>503[M + H]+ |
| 84 | 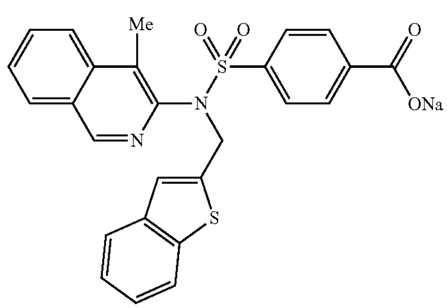 | powder<br>ESI-MS m/z:<br>487[M − Na]− |

TABLE 2-continued

| Example | Structure | Physical data |
|---------|-----------|---------------|
| 85 | 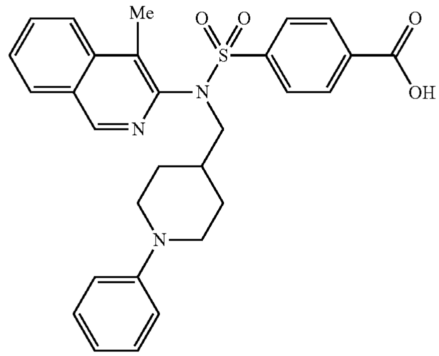 [SMILES: Cc1c(N(CC2CCN(c3ccccc3)CC2)S(=O)(=O)c2ccc(C(=O)O)cc2)ncc2ccccc12] | solid<br>APCI-MS m/z:<br>516[M + H]+ |
| 86 | 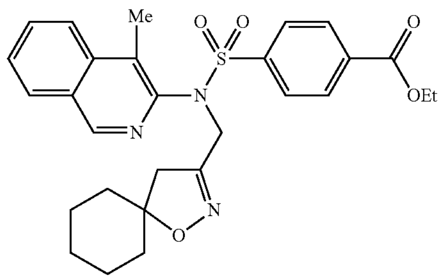 [SMILES: CCOC(=O)c1ccc(S(=O)(=O)N(CC2=NOC3(CCCCC3)C2)c2ncc3ccccc3c2C)cc1] | powder<br>APCI-MS m/z:<br>522[M + H]+ |
| 87 | 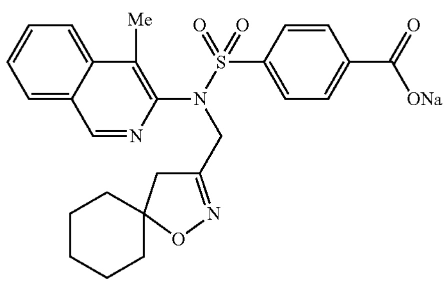 | powder<br>ESI-MS m/z:<br>492[M − Na]− |

Examples 88 to 91

The corresponding starting compounds were treated in a similar manner to Examples 7, 8 and/or 2 to give the following compounds of Table 3. Interconversions of a carboxylic acid compound and a salt thereof to each other may be carried out by a conventional salt formation and a conventional desalination, respectively.

TABLE 3

| Example | Structure | Physical data |
|---------|-----------|---------------|
| 88 | 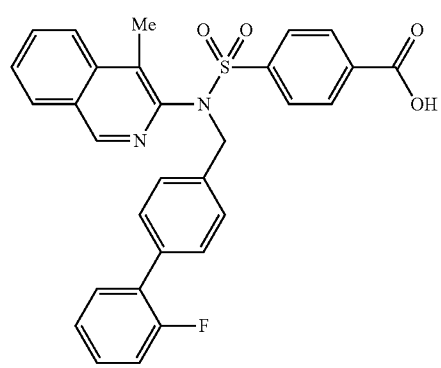 [SMILES: Cc1c(N(Cc2ccc(-c3ccccc3F)cc2)S(=O)(=O)c2ccc(C(=O)O)cc2)ncc2ccccc12] | solid<br>APCI-MS m/z:<br>527[M + H]+ |

TABLE 3-continued
| Example | Structure | Physical data |
|---|---|---|
| 89 | 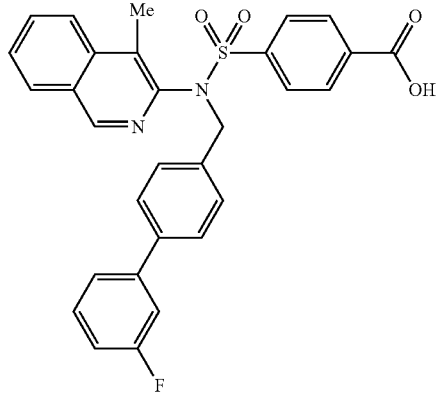 [SMILES: Cc1c(N(Cc2ccc(-c3cccc(F)c3)cc2)S(=O)(=O)c2ccc(C(=O)O)cc2)ncc2ccccc12] | solid<br>APCI-MS m/z:<br>527[M + H]⁺ |
| 90 | 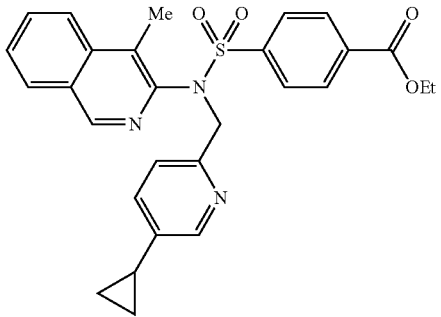 [SMILES: CCOC(=O)c1ccc(S(=O)(=O)N(Cc2ccc(C3CC3)cn2)c2ncc3ccccc3c2C)cc1] | powder<br>APCI-MS m/z:<br>502[M + H]⁺ |
| 91 | 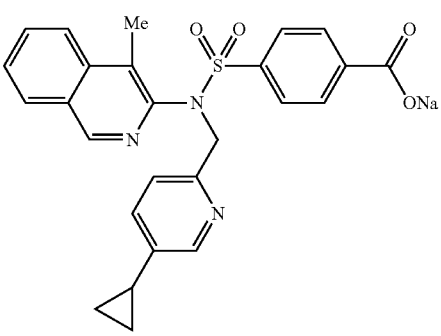 | powder<br>ESI-MS m/z:<br>472[M − Na]⁻ |

Examples 92 to 95

The corresponding starting compounds were treated in a similar manner to Examples 9 and/or 10 to give the following compounds of Table 4. Interconversions of a carboxylic acid compound and a salt thereof to each other may be carried out by a conventional salt formation and a conventional desalination, respectively.

TABLE 4

| Example | Structure | Physical data |
|---|---|---|
| 92 | (1,4-dimethylisoquinolin-3-yl)-N-(4-trifluoromethoxybenzyl) sulfonamide with 4-ethoxycarbonylphenyl | Powder APCI-MS m/z: 559[M + H]$^+$ |
| 93 | sodium salt analog of 92 | powder ESI-MS m/z: 529[M − Na]$^-$ |
| 94 | (4-methyl-1-phenylisoquinolin-3-yl)-N-(4-trifluoromethoxybenzyl) sulfonamide with 4-ethoxycarbonylphenyl | powder APCI-MS m/z: 621[M + H]$^+$ |
| 95 | sodium salt analog of 94 | powder ESI-MS m/z: 591[M − Na]$^-$ |

Example 96

The corresponding starting compound was treated in a similar manner to Examples 13 and 14 to give the following compound of Table 5. Interconversions of a carboxylic acid compound and a salt thereof to each other may be carried out by a conventional salt formation and a conventional desalination, respectively.

TABLE 5

| Example | Structure | Physical data |
|---|---|---|
| 96 | (structure shown) | solid APCI-MS m/z: 559 [M + H]⁺ |

Example 97

Preparation of 4-({(4-methyl-1-propylisoquinolin-3-yl)[4-(trifluoromethoxy)benzyl]amino}-sulfonyl)benzoic acid

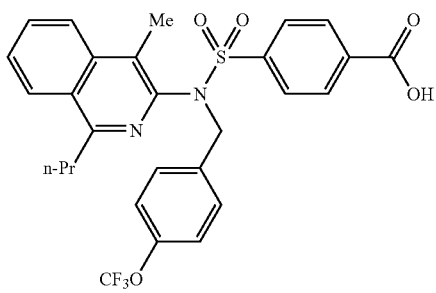

(1) Ethyl 4-({(1-bromo-4-methylisoquinolin-3-yl) [4-(trifluoromethoxy)benzyl]amino}-sulfonyl)benzoate (93.5 mg, 0.15 mmol) prepared in Example 9-(1) and 1-propenylboric acid were treated in a similar manner to Example 7-(2) to give ethyl 4-({{4-methyl-1-[(1E)-prop-1-en-1-yl]isoquinolin-3-yl}[4-(trifluoromethoxy)benzyl]amino}sulfonyl)benzoate (86.9 mg, 99%) as a pale yellow viscous material.
APCI-MS m/z:585 [M+H]⁺

(2) To a solution of the above compound (86.9 mg, 0.149 mmol) in tetrahydrofuran (5 mL) was added platinum oxide (3.4 mg, 0.0149 mmol), and the mixture was stirred under hydrogen atmosphere at room temperature for 3 hours and filtered through diatomaceous earth using ethyl acetate. The filtrate was concentrated under reduced pressure to give a crude ethyl 4-({(4-methyl-1-propylisoquinolin-3-yl)[4-(trifluoromethoxy)benzyl]amino}sulfonyl)benzoate.

(3) The crude product was treated in a similar manner to Example 14 to give 4-({(4-methyl-1-propylisoquinolin-3-yl)[4-(trifluoromethoxy)benzyl]amino}sulfonyl)benzoic acid (70.3 mg, 84%, yields for two steps) as a white powder.
APCI-MS m/z:559[M+H]⁺

Example 98

Preparation of ethyl 4-({(4-methyl-1-pyrrolidin-1-ylisoquinolin-3-yl)[4-(trifluoromethoxy)-benzyl]amino}sulfonyl)benzoate

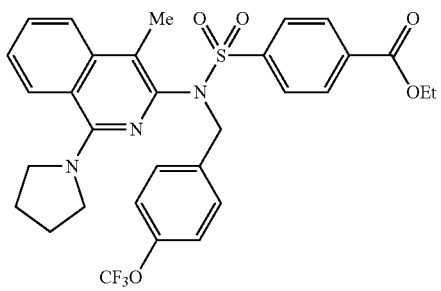

A mixture of ethyl 4-({(1-bromo-4-methylisoquinolin-3-yl)[4-(trifluoromethoxy)-benzyl]amino}sulfonyl)benzoate (93.5 mg, 0.15 mmol) prepared in Example 9-(1), pyrrolidine (0.015 mL, 0.18 mmol), 2,2'-bis(diphenylphosphino)-1,1'-binaphthyl (9.3 mg, 0.015 mmol), trisdibenzylideneacetone dipalladium (6.9 mg, 0.0075 mmol) and sodium-t-butoxide (20.2 mg, 0.21 mmol) in toluene (2 mL) was stirred at 100° C. for 4 hours under argon atmosphere. The mixture was cooled to room temperature, and then filtered, and the filtrate was concentrated under reduced pressure. The resulting residue was purified by silica gel column chromatography (ethyl acetate/hexane=10%→25%) to give ethyl 4-({(4-methyl-1-pyrrolidin-1-ylisoquinolin-3-yl) [4-(trifluoromethoxy)benzyl]amino}sulfonyl)benzoate (22.4 mg, 24%) as a yellow viscous material.
APCI-MS: m/z 614[M+H]⁺

Example 99

Preparation of 4-({(4-methyl-1-pyrrolidin-1-ylisoquinolin-3-yl) [4-(trifluoromethoxy)benzyl]-amino}sulfonyl)benzoic acid

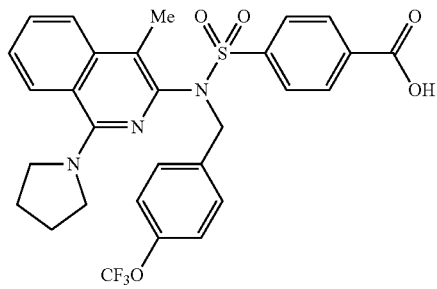

Ethyl 4-({(4-methyl-1-pyrrolidin-1-ylisoquinolin-3-yl)[4-(trifluoromethoxy)benzyl]-amino}sulfonyl)benzoate (22.4 mg, 0.0365 mmol) prepared in Example 98 was treated in a similar manner to Example 14 to give 4-({(4-methyl-1-pyrrolidin-1-ylisoquinolin-3-yl)[4-(trifluoromethoxy)benzyl]amino}sulfonyl)benzoic acid (20.8 mg, 97%) as a yellow powder.

APCI-MS: m/z 586[M+H]$^+$

Example 100

Preparation of 4-({(1-isopropoxy-4-methylisoquinolin-3-yl) [4-(trifluoromethoxy)benzyl]-amino}sulfonyl)benzoic acid

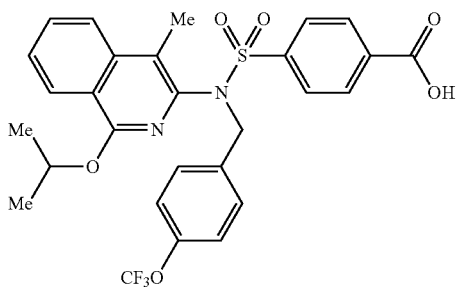

To a suspension of ethyl 4-({(1-bromo-4-methylisoquinolin-3-yl)[4-(trifluoromethoxy)-benzyl]amino}sulfonyl)benzoate (93.5 mg, 0.15 mmol) prepared in Example 9-(1) and sodium hydride (60.0 mg, 1.5 mmol) in tetrahydrofuran (2 mL) was added 2-propanol (0.115 mL, 1.5 mmol) under argon atmosphere, and the mixture was heated to reflux for 4 hours. The mixture was neutralized by 2 mol/L hydrochloric acid, and then thereto was added chloroform. The mixture was stirred, and then separated. The organic layer was concentrated under reduced pressure, and the residue was purified by silica gel column chromatography (methanol/chloroform=2%→10%) to give 4-({(1-isopropoxy-4-methylisoquinolin-3-yl) [4-(trifluoromethoxy)benzyl]amino}sulfonyl)benzoic acid (53.1 mg, 58%) as a brown powder.

APCI-MS: m/z 575 [M+H]$^+$

Example 101

Preparation of isopropyl 4-({(5-chloroisoquinolin-3-yl)[4-(trifluoromethoxy)benzyl]amino}-sulfonyl)benzoate

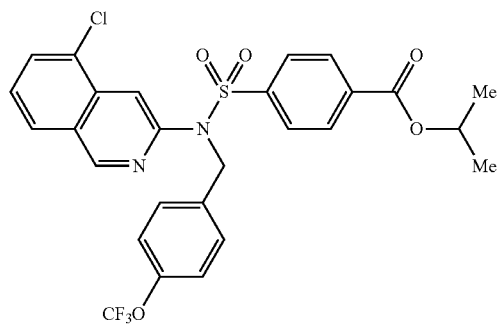

(1) 1-Bromo-5-chloroisoquinolin-3-amine (258 mg, 1 mmol) obtained in Reference example 21, ethyl 4-chlorosulfonyl-benzoate and 1-(bromomethyl)-4-(trifluoromethoxy)benzene were treated in a similar manner to Examples 1-(1) and (2) to give ethyl 4-({(1-bromo-5-chloroisoquinolin-3-yl)[4-(trifluoromethoxy)benzyl]amino}sulfonyl)-benzoate as a brown solid.

APCI-MS: m/z 643/645/647 [M+H]$^+$ (2) A mixture of the above compound (193 mg, 0.3 mmol), palladium acetate (3.4 mg, 0.015 mmol), triphenylphosphine (15.7 mg, 0.06 mmol) and potassium carbonate (82.9 mg, 0.6 mmol) in 2-propanol (2 mL) was heated to reflux for 6 hours under argon atmosphere. The reaction solution was cooled to room temperature, and thereto was added ethyl acetate. The mixture was filtered, and the insoluble was removed. The filtrate was concentrated under reduced pressure, and then purified by silica gel column chromatography (ethyl acetate/hexane=10%→30%) to give isopropyl 4-({(5-chloroisoquinolin-3-yl)[4-(trifluoromethoxy)benzyl]-amino}sulfonyl)benzoate (81.2 mg, 47%) as a pale yellow viscous material.

APCI-MS: m/z 579/581 [M+H]$^+$

Example 102

Preparation of 4-({(5-chloroisoquinolin-3-yl)[4-(trifluoromethoxy)benzyl]amino}sulfonyl)-benzoic acid

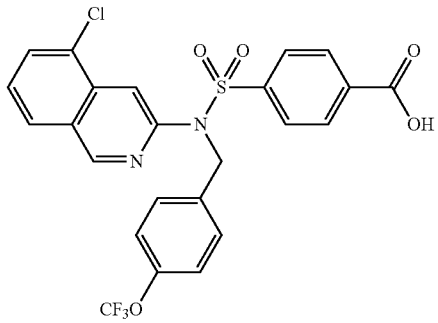

Isopropyl 4-({(5-chloroisoquinolin-3-yl) [4-(trifluoromethoxy)benzyl]amino}sulfonyl)-benzoate (42.2 mg, 0.0729 mmol) prepared in Example 101 was treated in a similar manner to Example 14 to give 4-({(5-chloroisoquinolin-3-yl)[4-(trifluoromethoxy)-benzyl]amino}sulfonyl)benzoic acid (35.8 mg, 91%) as a white powder.

APCI-MS: m/z 537/539 [M+H]$^+$

Example 103

Preparation of ethyl 4-({(4-cyclopropylisoquinolin-3-yl)[4-(trifluoromethoxy)benzyl]amino}-sulfonyl)benzoate

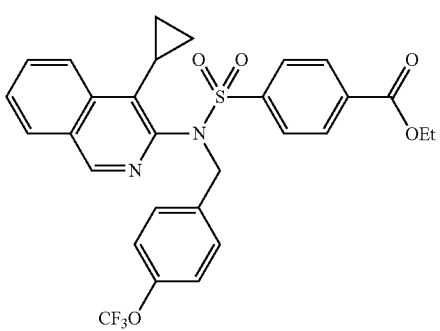

A mixture of ethyl 4-({(4-bromoisoquinolin-3-yl)[4-(trifluoromethoxy)benzyl]amino}-sulfonyl)benzoate (65.0 mg, 0.107 mmol) prepared in Example 153, cyclopropylboronic acid (27.0 mg, 0.321 mmol), palladium acetate (2.5 mg, 0.011 mmol), tricyclohexylphosphine (5.9 mg, 0.021 mmol) and tripotassium phosphate (79.0 mg, 0.375 mmol) in water (0.027 mL) and toluene (0.54 mL) was stirred under argon atmosphere at 100° C. for 5 hours. After cooling, the reaction solution was diluted with ethyl acetate, washed with water and saturated brine, dried over anhydrous sodium sulfate, and then concentrated under reduced pressure. The resulting residue was purified by silica gel column chromatography (hexane:ethyl acetate=95:5→65:35) to give ethyl 4-({(4-cyclopropylisoquinolin-3-yl)[4-(trifluoromethoxy)benzyl]amino}sulfonyl)benzoate (46.7 mg, 78%) as a white powder.

APCI-MS m/z:571[M+H]$^+$.

Example 104

Preparation of 4-({(4-cyclopropylisoquinolin-3-yl)[4-(trifluoromethoxy)benzyl]amino}-sulfonyl)benzoic acid

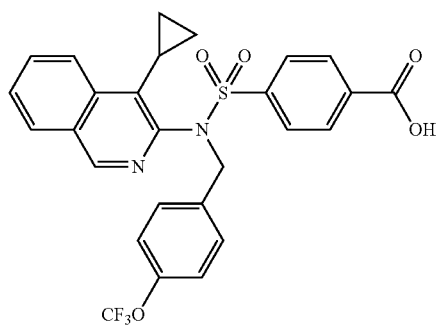

Ethyl 4-({(4-cyclopropylisoquinolin-3-yl) [4-(trifluoromethoxy)benzyl]amino}-sulfonyl)benzoate (46.0 mg, 0.081 mmol) prepared in Example 103 was treated in a similar manner to Example 14 to give 4-({(4-cyclopropylisoquinolin-3-yl) [4-(trifluoromethoxy)benzyl]amino}sulfonyl) benzoic acid (41.1 mg, 91%) as a white powder.

APCI-MS m/z:543[M+H]$^+$.

Example 105

Preparation of ethyl 4-({[4-(trifluoromethoxy)benzyl][4-(trifluoromethyl)isoquinolin-3-yl]amino}sulfonyl)benzoate

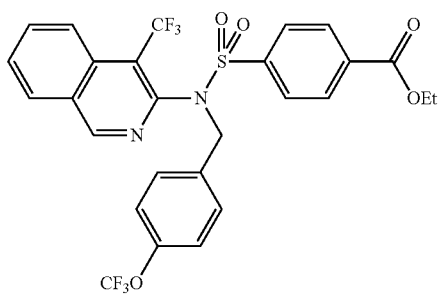

(1) Isoquinoline-3-amine and ethyl 4-chlorosulfonylbenzoate were treated in a similar manner to Example 1-(1) to give ethyl 4-[(isoquinolin-3-ylamino)sulfonyl]benzoate as a white powder.

APCI-MS m/z:357[M+H]$^+$.

(2) A mixture of the above compound (356.0 mg, 1.00 mmol) and N-iodosuccinimide (337.0 mg, 1.50 mmol) in acetic acid (5 mL) was stirred under argon atmosphere at 80° C. for 8 hours. The reaction solution was cooled, and then concentrated under reduced pressure. The residue was diluted with ethyl acetate, washed with aqueous sodium hydrogen carbonate solution and saturated brine, and then dried over anhydrous sodium sulfate, and then concentrated under reduced pressure. The resulting residue was purified by silica gel column chromatography (hexane:ethyl acetate=19:1→3:2) to give ethyl 4-{[(4-iodoisoquinolin-3-yl)amino]sulfonyl}benzoate (250.0 mg, 52%) as a pale red powder.

APCI-MS m/z:483[M+H]$^+$.

(3) The above compound (96.0 mg, 0.20 mmol) was treated in a similar manner to Example 1-(2) to give ethyl 4-({(4-iodoisoquinolin-3-yl)[4-(trifluoromethoxy)benzyl]amino}-sulfonyl)benzoate (122.0 mg, 93%) as a white powder.

APCI-MS m/z:657 [M+H]$^+$.

(4) The above compound (116.0 mg, 0.18 mmol) was treated in a similar manner to Example 11-(2) to give ethyl 4-({[4-(trifluoromethoxy)benzyl][4-(trifluoromethyl)isoquinolin-3-yl]amino}sulfonyl)benzoate (95.0 mg, 90%) as a white powder.

APCI-MS m/z:599[M+H]$^+$.

Example 106

Preparation of 4-({[4-(trifluoromethoxy)benzyl][4-(trifluoromethyl)isoquinolin-3-yl]amino}-sulfonyl)benzoic acid

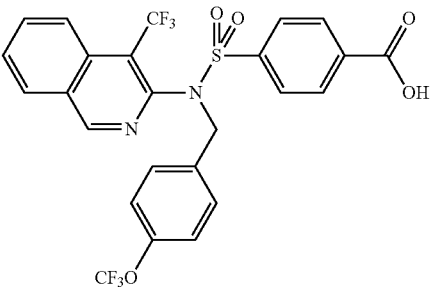

Ethyl 4-({[4-(trifluoromethoxy)benzyl][4-(trifluoromethyl)isoquinolin-3-yl]amino}-sulfonyl)benzoate (93.0 mg, 0.16 mmol) prepared in Example 105 was treated in a similar manner to Example 14 to give 4-({[4-(trifluoromethoxy)benzyl][4-(trifluoromethyl)isoquinolin-3-yl]amino}sulfonyl) benzoic acid (77.7 mg, 88%) as a white powder.

APCI-MS m/z:571[M+H]$^+$.

Example 107

Preparation of ethyl 4-({[4-methyl-1-(trifluoromethyl)isoquinolin-3-yl][4-(trifluoromethoxy)-benzyl]amino}sulfonyl)benzoate

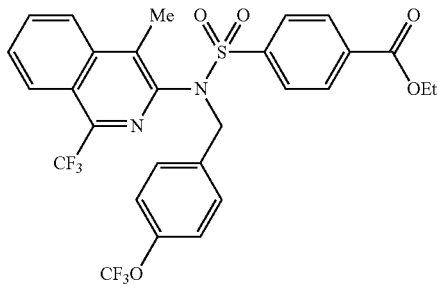

(1) Ethyl 4-({(1-bromo-4-methylisoquinolin-3-yl) [4-(trifluoromethoxy)benzyl]amino}-sulfonyl)benzoate (93.5 mg, 0.15 mmol) prepared in Example 9-(1) was treated in a similar manner to Reference example 3 to give ethyl 4-({(1-iodo-4-methylisoquinolin-3-yl)[4-(trifluoromethoxy)benzyl]amino}sulfonyl)benzoate (73.7 mg, 73%) as a white solid.
APCI-MS: m/z 671 [M+H]$^+$ (2) The above compound (73.7 mg, 0.11 mmol) was treated in a similar manner to Example 11-(2) to give ethyl 4-({[4-methyl-1-(trifluoromethyl)isoquinolin-3-yl][4-(trifluoromethoxy)benzyl]amino}sulfonyl)benzoate (52.7 mg, 78%) as a white solid.
APCI-MS: m/z 613 [M+H]$^+$

Example 108

Preparation of 4-({[4-methyl-1-(trifluoromethyl)isoquinolin-3-yl][4-(trifluoromethoxy)benzyl]-amino}sulfonyl)benzoic acid

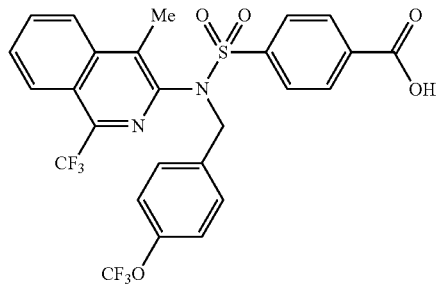

Ethyl 4-({[4-methyl-1-(trifluoromethyl)isoquinolin-3-yl][4-(trifluoromethoxy)benzyl]-amino}sulfonyl)benzoate (52.7 mg, 0.086 mmol) prepared in Example 107 was treated in a similar manner to Example 14 to give 4-({[4-methyl-1-(trifluoromethyl)isoquinolin-3-yl][4-(trifluoromethoxy)benzyl]amino}sulfonyl)benzoic acid (47.8 mg, 95%) as a white powder.
APCI-MS: m/z 585 [M+H]$^+$

Example 109

Preparation of ethyl 4-({[1-isopropyl-4-(trifluoromethyl)isoquinolin-3-yl][4-(trifluoromethoxy)benzyl]amino}sulfonyl)benzoate

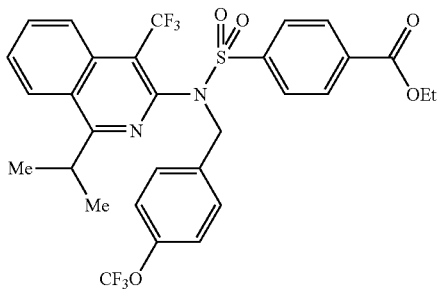

(1) 4-Iodo-1-isopropylisoquinolin-3-amine obtained in Reference example 25, ethyl 4-chlorosulfonylbenzoate and 1-(bromomethyl)-4-(trifluoromethoxy)benzene were treated in a similar manner to Examples 1-(1) and (2) to give ethyl 4-({(4-iodo-1-isopropylisoquinolin-3-yl)[4-(trifluoromethoxy)benzyl]amino}sulfonyl)benzoate as a white powder.
APCI-MS m/z:699 [M+H]$^+$.

(2) The above compound was treated in a similar manner to Example 11-(2) to give ethyl 4-({[1-isopropyl-4-(trifluoromethyl)isoquinolin-3-yl][4-(trifluoromethoxy)benzyl]amino}-sulfonyl)benzoate as a white powder.
APCI-MS m/z:641 [M+H]$^+$.

Example 110

Preparation of 4-({[1-isopropyl-4-(trifluoromethyl)isoquinolin-3-yl][4-(trifluoromethoxy)-benzyl]amino}sulfonyl)benzoic acid

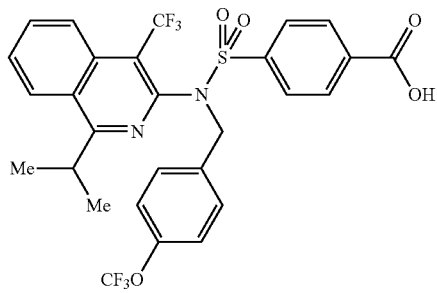

Ethyl 4-({[1-isopropyl-4-(trifluoromethyl)isoquinolin-3-yl][4-(trifluoromethoxy)-benzyl]amino}sulfonyl)benzoate prepared in Example 109 was treated in a similar manner to Example 14 to give 4-({[1-isopropyl-4-(trifluoromethyl)isoquinolin-3-yl][4-(trifluoromethoxy)benzyl]amino}sulfonyl)benzoic acid as a white powder.
APCI-MS m/z:613 [M+H]$^+$.

Example 111

Preparation of ethyl 4-({(4-acetylisoquinolin-3-yl)[4-(trifluoromethoxy)benzyl]amino}-sulfonyl)benzoate

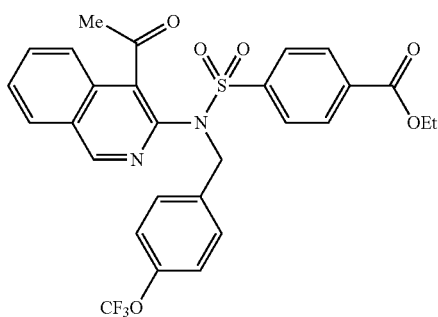

A mixture of ethyl 4-({(4-bromoisoquinolin-3-yl)[4-(trifluoromethoxy)benzyl]amino}-sulfonyl)benzoate (122.0 mg, 0.20 mmol) prepared in Example 153, tributyl(1-ethoxyvinyl)tin (94.0 mg, 0.26 mmol) and dichlorobis(triphenylphosphine)palladium (II) (14.0 mg, 0.02 mmol) in 1,4-dioxane (1 mL) was heated to reflux under argon atmosphere for 16 hours. After cooling, the reaction solution was diluted with ethyl acetate, and poured into aqueous potassium fluoride solution. The mixture was stirred for 6 hours. The insoluble was filtered off, and then the filtrate was extracted with ethyl acetate. The organic layer was washed with water. Then, thereto was added 2 mol/L hydrochloric acid, and the mixture was stirred for 3 days. Then, the organic layer was separated, washed with water and saturated brine, dried over anhydrous sodium sulfate, and then concentrated under reduced pressure. The resulting residue was purified by silica gel column chromatography (hexane:ethyl acetate=19:1→3:2) to give ethyl 4-({(4-acetylisoquinolin-3-yl) [4-(trifluoromethoxy)benzyl]amino}sulfonyl)benzoate (53.4 mg, 47%) as a white powder.

APCI-MS m/z:573[M+H]$^+$.

Example 112

Preparation of 4-({(4-acetylisoquinolin-3-yl) [4-(trifluoromethoxy)benzyl]amino}sulfonyl)-benzoic acid

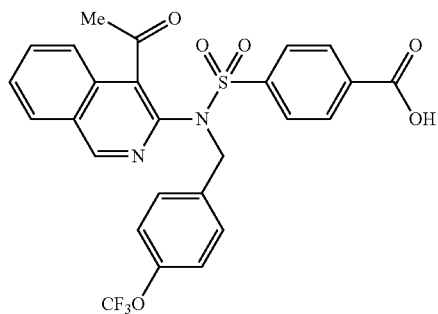

Ethyl 4-({(4-acetylisoquinolin-3-yl)[4-(trifluoromethoxy)benzyl]amino}sulfonyl)-benzoate (51.0 mg, 0.089 mmol) prepared in Example 111 was treated in a similar manner to Example 14 to give 4-({(4-acetylisoquinolin-3-yl)[4-(trifluoromethoxy)-benzyl]amino}sulfonyl)benzoic acid (36.9 mg, 76%) as a white powder.

APCI-MS m/z:545[M+H]$^+$.

Example 113

Preparation of 4-({[4-(1-hydroxyethyl)isoquinolin-3-yl][4-(trifluoromethoxy)benzyl]amino}-sulfonyl) benzoic acid

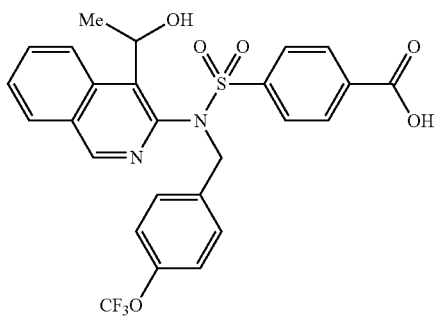

To a solution of 4-({(4-acetylisoquinolin-3-yl)[4-(trifluoromethoxy)benzyl]amino}-sulfonyl)benzoic acid (20.0 mg, 0.036 mmol) prepared in Example 112 in ethanol (1 mL) was added sodium borohydride (10.0 mg, 0.264 mmol), and the mixture was stirred at room temperature for 3 hours. To the reaction solution was added 1 mol/L hydrochloric acid. The reaction solution was concentrated under reduced pressure, and then diluted with ethyl acetate, washed with water and saturated brine, dried over anhydrous sodium sulfate, and then concentrated under reduced pressure. The resulting residue was purified by silica gel column chromatography (chloroform:methanol=10:0→9:1) to give 4-({[4-(1-hydroxyethyl)isoquinolin-3-yl][4-(trifluoromethoxy)benzyl] amino}sulfonyl)benzoic acid (17.1 mg, 87%) as a white powder.

APCI-MS m/z:547[M+H]$^+$.

Example 114

Preparation of ethyl 4-({[1-(1-hydroxyethyl)-4-methylisoquinolin-3-yl][4-(trifluoromethoxy)-benzyl] amino}sulfonyl)benzoate

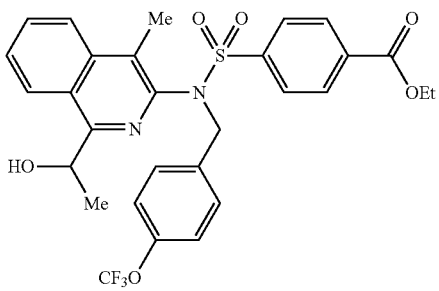

(1) A mixture of ethyl 4-({(1-bromo-4-methylisoquinolin-3-yl)[4-(trifluoromethoxy)-benzyl]amino}sulfonyl)benzoate (93.5 mg, 0.15 mmol) prepared in Example 9-(1), tributyl(1-ethoxyvinyl)tin (0.061 mL, 0.18 mmol) and dichlorobis(triphenylphosphine)palladium (II) (5.3 mg, 0.0075 mmol) in 1,4-dioxane (2 mL) was stirred at 80° C. for 4 hours under argon atmosphere. The reaction solution was concentrated under reduced pressure, and the residue was purified by silica gel chromatography (ethyl acetate: hexane=1:9→3:7) to give a crude ethyl 4-({[1-(1-ethoxyvinyl)-4-methyl isoquinolin-3-yl][4-(trifluoromethoxy)benzyl]amino}-sulfonyl)benzoate (152 mg) as a pale yellow viscous material.

(2) To a solution of the above crude product in tetrahydrofuran (5 mL) was added 6 mol/L hydrochloric acid (0.5 mL), and the mixture was stirred at room temperature for 24 hours. The reaction solution was diluted with water, and then extracted with ethyl acetate three times. The organic layer was combined, washed with saturated aqueous sodium hydrogen carbonate solution, dried over anhydrous sodium sulfate, and then concentrated under reduced pressure to give a crude ethyl 4-({(1-acetyl-4-methylisoquinolin-3-yl)[4-(trifluoromethoxy)benzyl]-amino}sulfonyl)benzoate.

(3) To a solution of the above crude product in ethanol (5 mL) was added sodium borohydride (11.3 mg, 0.3 mmol) at 0° C., and the mixture was stirred at the same temperature for 30 minutes. Then, thereto was added saturated aqueous ammonium chloride solution, and the mixture was concentrated under reduced pressure to remove ethanol, and then extracted with ethyl acetate three times. The organic layer was dried over anhydrous sodium sulfate, and then concentrated under reduced pressure. The resulting residue was purified by silica gel column chromatography (ethyl acetate:hexane=1:3→1:1) to give ethyl 4-({[1-(1-hydroxyethyl)-4-methylisoquinolin-3-yl][4-(trifluoromethoxy)benzyl]amino}sulfonyl)benzoate (83.0 mg, 94%, yields for three steps) as a colorless viscous material.

APCI-MS: m/z 589 [M+H]$^+$

Example 115

Preparation of 4-({[1-(1-hydroxyethyl)-4-methylisoquinolin-3-yl][4-(trifluoromethoxy)-benzyl]amino}sulfonyl)benzoic acid

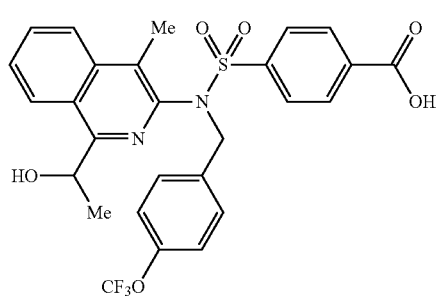

Ethyl 4-({[1-(1-hydroxyethyl)-4-methylisoquinolin-3-yl][4-(trifluoromethoxy)benzyl]-amino}sulfonyl)benzoate (83.0 mg, 0.141 mmol) prepared in Example 114 was treated in a similar manner to Example 14 to give 4-({[1-(1-hydroxyethyl)-4-methylisoquinolin-3-yl][4-(trifluoromethoxy)ben- zyl]amino}sulfonyl)benzoic acid (76.0 mg, 96%) as a white powder.

APCI-MS: m/z 561 [M+H]$^+$

Example 116

Preparation of ethyl 4-{[(1H-indol-6-ylmethyl)(4-methylisoquinolin-3-yl)amino]sulfonyl}-benzoate

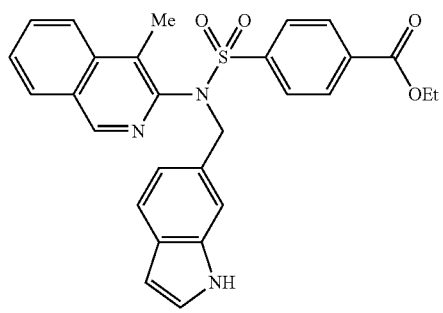 [SMILES: CCOC(=O)c1ccc(S(=O)(=O)N(Cc2ccc3cc[nH]c3c2)c2ncc3ccccc3c2C)cc1]

(1) tert-Butyl 6-(hydroxymethyl)-1H-indole-1-carboxylate (770 mg, 3.1 mmol) and ethyl 4-{[(4-methylisoquinolin-3-yl)amino]sulfonyl}benzoate (887 mg, 2.4 mmol) obtained in Example 1-(1) were treated in a similar manner to Example 3 to give tert-butyl 6-{[{[4-(ethoxycarbonyl)phenyl]sulfonyl}(4-methylisoquinolin-3-yl)amino]methyl}-1H-indole-1-carboxylate (789 mg, 55%) as a colorless oil.

APCI-MS: m/z 600 [M+H]$^+$ (2) To a solution of the above compound (789 mg, 1.32 mmol) in dimethyl sulfoxide (5.2 mL) was added water (2.6 mL) at room temperature, and the mixture was stirred at 120° C. for 5 hours. The reaction solution was cooled to room temperature, and then thereto was added water. The mixture was extracted with ethyl acetate twice. The organic layer was combined, washed with saturated brine, dried over anhydrous sodium sulfate, and then concentrated under reduced pressure. The resulting residue was purified by silica gel column chromatography (hexane:ethyl acetate=19:1→2:1) to give ethyl 4-{[(1H-indol-6-ylmethyl)(4-methylisoquinolin-3-yl)amino]sulfonyl}benzoate (535 mg, 81%) as a white solid.

APCI-MS: m/z 500 [M+H]$^+$

Example 117

Preparation of 4-{[(1H-indol-6-ylmethyl)(4-methylisoquinolin-3-yl)amino]sulfonyl}benzoic acid

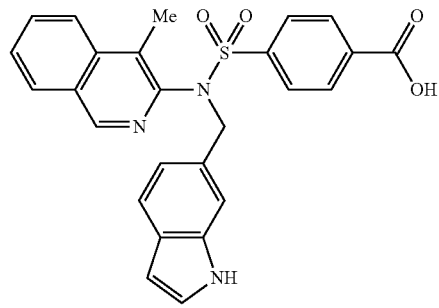 [SMILES: Cc1c(N(Cc2ccc3cc[nH]c3c2)S(=O)(=O)c2ccc(C(=O)O)cc2)ncc2ccccc12]

Ethyl 4-{[(1H-indol-6-ylmethyl)(4-methylisoquinolin-3-yl)amino]sulfonyl}benzoate (62 mg, 0.13 mmol) prepared in Example 116 was treated in a similar manner to Example 8 to give 4-{[(1H-indol-6-ylmethyl)(4-methylisoquinolin-3-yl)amino]sulfonyl}benzoic acid (28 mg, 48%) as a white solid.
APCI-MS: m/z 472 [M+H]$^+$

Example 118

Preparation of ethyl 4-{[[(1-methyl-1H-indol-6-yl)methyl](4-methylisoquinolin-3-yl)amino]-sulfonyl}benzoate

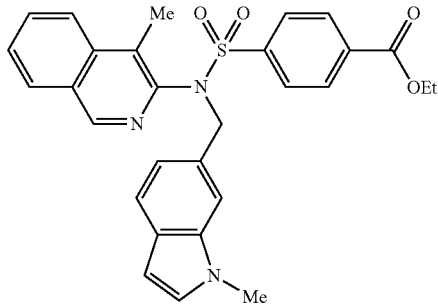 [SMILES: CCOC(=O)c1ccc(S(=O)(=O)N(Cc2ccc3ccn(C)c3c2)c2ncc3ccccc3c2C)cc1]

(1) (1-Methyl-2,3-dihydro-1H-indol-6-yl)methanol (245 mg, 1.50 mmol) obtained in Reference example 52 and ethyl 4-{[(4-methylisoquinolin-3-yl)amino]sulfonyl}benzoate (427 mg, 1.15 mmol) obtained in Example 1-(1) were treated in a similar manner to Example 3 to give ethyl 4-{[[(1-methyl-2,3-dihydro-1H-indol-6-yl)methyl](4-methylisoquinolin-3-yl)amino]sulfonyl}benzoate (127 mg, 21%) as a white solid.
APCI-MS: m/z 516 [M+H]$^+$ (2) To a solution of the above compound (125 mg, 0.24 mmol) in 1,4-dioxane (12 mL) was added 2,3-dichloro-5,6-dicyano-p-benzoquinone (61 mg, 0.26 mmol) at room temperature, and the mixture was stirred at the same temperature for 3 days. To the reaction solution was added saturated aqueous sodium bicarbonate solution, and the mixture was stirred for 3 hours, and then filtered through diatomaceous earth. The insoluble was filtered off. The filtrate was extracted with ethyl acetate twice. The organic layer was combined, washed with saturated brine, dried over anhydrous sodium sulfate, and then concentrated under reduced pressure. The resulting residue was purified by silica gel column chromatography (hexane:ethyl acetate=9:1→3:1) to give ethyl 4-{[[(1-methyl-1H-indol-6-yl)methyl](4-methylisoquinolin-3-yl)amino]sulfonyl}benzoate (87 mg, 70%) as a white solid.
APCI-MS: m/z 514 [M+H]$^+$

Example 119

Preparation of 4-{[[(1-methyl-1H-indol-6-yl)methyl](4-methylisoquinolin-3-yl)amino]-sulfonyl}benzoic acid

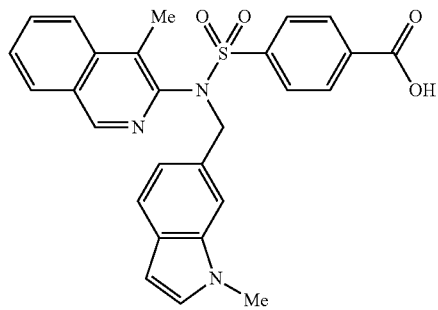 [SMILES: Cc1c(N(Cc2ccc3ccn(C)c3c2)S(=O)(=O)c2ccc(C(=O)O)cc2)ncc2ccccc12]

Ethyl 4-{[[(1-methyl-1H-indol-6-yl)methyl](4-methylisoquinolin-3-yl)amino]-sulfonyl}benzoate (83 mg, 0.16 mmol) prepared in Example 118 was treated in a similar manner to Example 8 to give 4-{[[(1-methyl-1H-indol-6-yl)methyl](4-methylisoquinolin-3-yl)amino]sulfonyl}benzoic acid (65 mg, 83%) as a white solid.
MS: 486 [M+H]$^+$, APCI

Example 120

Preparation of ethyl 4-{[[(3-chloro-1H-indol-6-yl)methyl](4-methylisoquinolin-3-yl)amino]-sulfonyl}benzoate

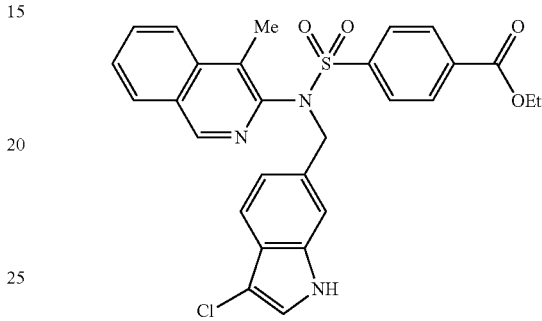

To a solution of ethyl 4-{[(1H-indol-6-ylmethyl)(4-methylisoquinolin-3-yl)amino]sulfonyl}benzoate (177 mg, 0.36 mmol) prepared in Example 116 in tetrahydrofuran (1.8 mL) was added N-chlorosuccinimide (57 mg, 0.43 mmol) at room temperature, and the mixture was stirred for 17 hours. The reaction solution was concentrated under reduced pressure, and the resulting residue was purified by silica gel column chromatography (hexane:ethyl acetate=5:1→1:1) to give ethyl 4-{[[(3-chloro-1H-indol-6-yl)methyl] (4-methylisoquinolin-3-yl)amino]sulfonyl}benzoate (124 mg, 65%) as a white solid.
APCI-MS: m/z 534/536 [M+H]$^+$

Example 121

Preparation of 4-{[[(3-chloro-1H-indol-6-yl)methyl](4-methylisoquinolin-3-yl)amino]-sulfonyl}benzoic acid

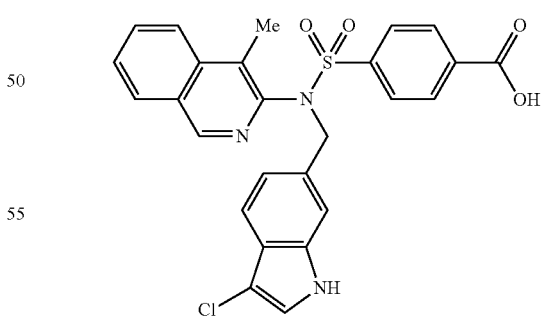

Ethyl 4-{[[(3-chloro-1H-indol-6-yl)methyl](4-methylisoquinolin-3-yl)amino]sulfonyl}-benzoate (32 mg, 0.06 mmol) prepared in Example 120 was treated in a similar manner to Example 8 to give 4-{[[(3-chloro-1H-indol-6-yl)methyl](4-methylisoquinolin-3-yl)amino]-sulfonyl}benzoic acid (8 mg, 28%) as a white solid.
APCI-MS: m/z 506/508 [M+H]$^+$

Example 122

Preparation of 4-{[[(3-chloro-1-methyl-1H-indol-6-yl)methyl] (4-methylisoquinolin-3-yl)-amino]sulfonyl}benzoic acid

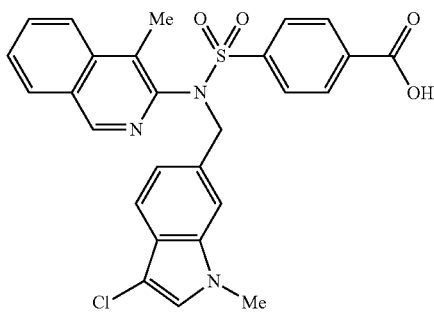 [SMILES: Cc1c(N(Cc2ccc3c(Cl)cn(C)c3c2)S(=O)(=O)c2ccc(C(=O)O)cc2)ncc2ccccc12]

(1) To a solution of ethyl 4-{[[(3-chloro-1H-indol-6-yl)methyl](4-methylisoquinolin-3-yl)amino]sulfonyl}benzoate (81 mg, 0.15 mmol) prepared in Example 120 in N,N-dimethylformamide (1 mL) was added sodium hydride (9 mg, 0.22 mmol) at 0° C., and the mixture was stirred at the same temperature for 30 minutes. To the reaction solution was added methyl iodide (29 µL, 0.46 mmol), and the mixture was stirred at room temperature for 18 hours. To the reaction solution was added water, and the mixture was extracted with ethyl acetate twice. The organic layer was combined, washed with saturated brine, dried over anhydrous sodium sulfate, and then concentrated under reduced pressure. The resulting residue was purified by silica gel column chromatography (hexane:ethyl acetate=9:1→2:1) to give a crude ethyl 4-{[[(3-chloro-1-methyl-1H-indol-6-yl)methyl] (4-methylisoquinolin-3-yl)amino]-sulfonyl}benzoate (53.0 mg) as a colorless powder.

(2) The crude product was treated in a similar manner to Example 8 to give 4-{[[(3-chloro-1-methyl-1H-indol-6-yl)methyl](4-methylisoquinolin-3-yl)amino]sulfonyl}benzoic acid (38 mg, 48%, yields for two steps) as a white solid.

APCI-MS: m/z 520/522 [M+H]$^+$

Example 123

Preparation of 4-({(4-methylisoquinolin-3-yl) [4-(trifluoromethoxy)benzyl]amino}sulfonyl)-benzamide

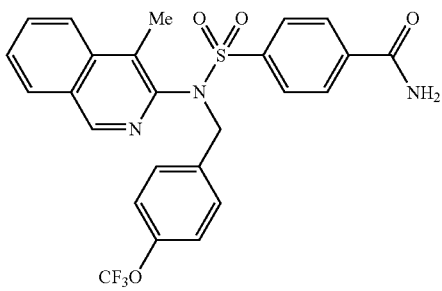

To a solution of sodium 4-({(4-methylisoquinolin-3-yl)[4-(trifluoromethoxy)-benzyl]amino}sulfonyl)benzoate (100 mg, 0.186 mmol) prepared in Example 2, ammonium chloride (50 mg, 0.929 mmol) and N,N-diisopropylethylamine (162 µL, 0.929 mmol) in N,N-dimethylacetamide (1.8 mL) was added 2-(1H-7-azabenzotriazol-1-yl)-1,1,3,3-tetramethyluronium hexafluorophosphate methanaminium (85 mg, 0.223 mmol) at 0° C., and the mixture was stirred at room temperature overnight. To the reaction solution was added saturated aqueous sodium hydrogen carbonate solution, and the mixture was extracted with ethyl acetate three times. The organic layer was combined, washed with water twice, and concentrated under reduced pressure. The resulting residue was purified by silica gel column chromatography (chloroform:methanol=100:0→91:9) to give 4-({(4-methylisoquinolin-3-yl)[4-(trifluoromethoxy)benzyl]amino}sulfonyl)benzamide (26 mg, 27%) as a colorless powder.

APCI-MS: m/z 516 [M+H]$^+$

Example 124

Preparation of N-methoxy-4-({(4-methylisoquinolin-3-yl)[4-(trifluoromethoxy)benzyl]amino}-sulfonyl)benzamide

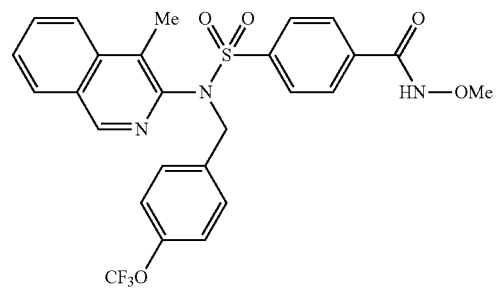

To a suspension of sodium 4-({(4-methylisoquinolin-3-yl)[4-(trifluoromethoxy)-benzyl]amino}sulfonyl)benzoate (107.7 mg, 0.200 mmol) prepared in Example 2 in chloroform (1 mL) was added oxalyl dichloride (21 µL, 0.240 mmol), and the mixture was stirred at room temperature for 2 hours. Then, thereto was added additional oxalyl dichloride (21 µL, 0.24 mmol), and the mixture was stirred at room temperature for 1 hour. The reaction solution was concentrated under reduced pressure. Then, the resulting residue was suspended in chloroform (1 mL), and added dropwise to a suspension of O-methylhydroxylamine hydrochloride (50.1 mg, 0.600 mmol) and triethylamine (139 µL, 1.00 mmol) in chloroform (1 mL), and the mixture was stirred at room temperature for 1 hour. The resulting residue was purified by silica gel column chromatography (hexane:ethyl acetate=3:1→0:10) to give N-methoxy-4-({(4-methylisoquinolin-3-yl)[4-(trifluoromethoxy)benzyl]amino}sulfonyl)-benzamide (88.1 mg, 81%) as a white powder.

APCI-MS m/z:546 [M+H]$^+$.

Example 125

Preparation of 4-(1-hydroxy-1-methylethyl)-N-(4-methylisoquinolin-3-yl)-N-[4-(trifluoromethoxy)benzyl]benzenesulfonamide

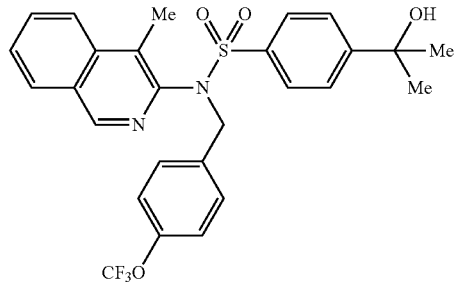

To a solution of 4-acetyl-N-(4-methylisoquinolin-3-yl)-N-[4-(trifluoromethoxy)benzyl]benzenesulfonamide (98 mg, 0.190 mmol) prepared in Example 152 in diethyl ether (2 mL) was added methylmagnesium bromide (tetrahydrofuran solution, 3 mol/L, 0.229 mmol) at 0° C., and the mixture was stirred at room temperature overnight. To the reaction solution was added 1 mol/L hydrochloric acid, and the mixture was extracted with ethyl acetate three times. The organic layer was combined, and concentrated under reduced pressure. The resulting residue was purified by silica gel column chromatography (hexane:ethyl acetate=80:20→40:60) to give (1-hydroxy-1-methylethyl)-N-(4-methylisoquinolin-3-yl)-N-[4-(trifluoromethoxy)benzyl]benzenesulfonamide (83 mg, 82%) as a colorless powder.

APCI-MS m/z:531 [M+H]$^+$.

Examples 126 to 158

The corresponding starting compounds were treated in a similar manner to Examples 1, 2 and/or 8 to give the following compounds of Table 6. Interconversions of a carboxylic acid compound and a salt thereof to each other may be carried out by a conventional salt formation and a conventional desalination, respectively.

TABLE 6

| Example | Structure | Physical data |
|---|---|---|
| 126 | 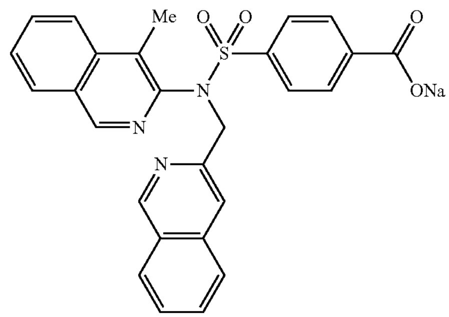 | ESI-MS m/z: 482[M − Na]$^-$ |
| 127 | 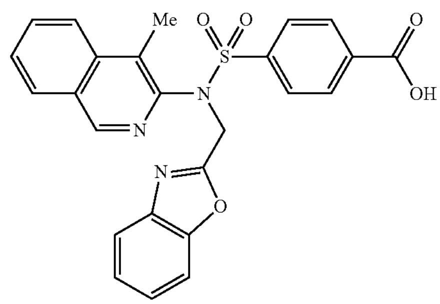 [SMILES: Cc1c(N(Cc2nc3ccccc3o2)S(=O)(=O)c2ccc(C(=O)O)cc2)ncc2ccccc12] | APCI-MS m/z: 474[M + H]$^+$ |
| 128 | 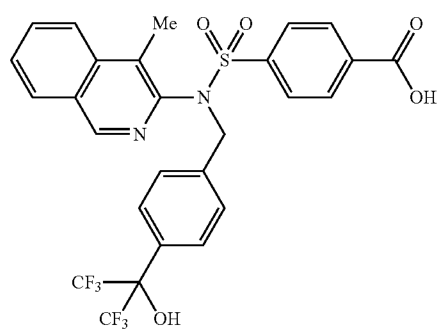 [SMILES: Cc1c(N(Cc2ccc(C(O)(C(F)(F)F)C(F)(F)F)cc2)S(=O)(=O)c2ccc(C(=O)O)cc2)ncc2ccccc12] | APCI-MS m/z: 599[M + H]$^+$ |
| 129 | 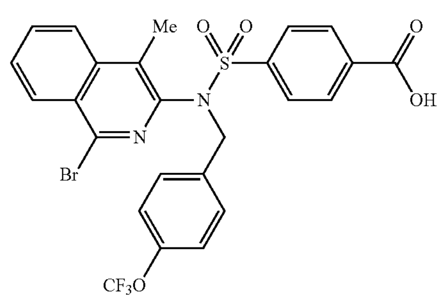 | APCI-MS m/z: 595/597[M + H]$^+$ |

TABLE 6-continued

| Example | Structure | Physical data |
|---|---|---|
| 130 | 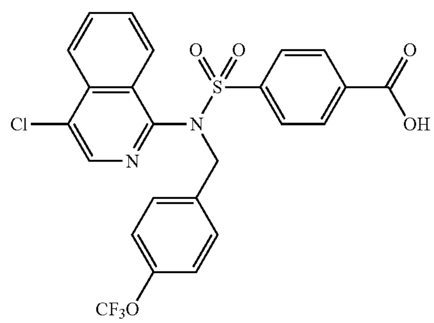 | APCI-MS m/z: 537/539[M + H]+ |
| 131 | 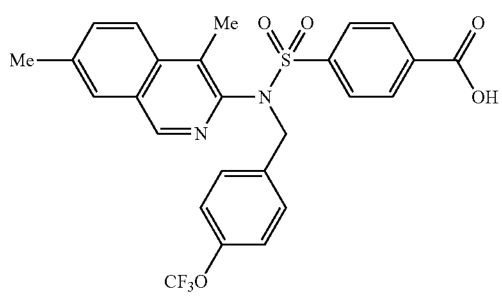 | APCI-MS m/z: 531[M + H]+ |
| 132 | 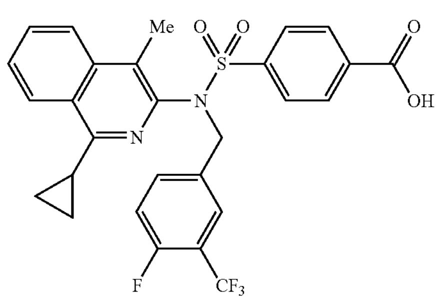 [SMILES: Cc1c(N(Cc2ccc(F)c(C(F)(F)F)c2)S(=O)(=O)c2ccc(C(=O)O)cc2)nc(C2CC2)c2ccccc12] | APCI-MS m/z: 559[M + H]+ |
| 133 | 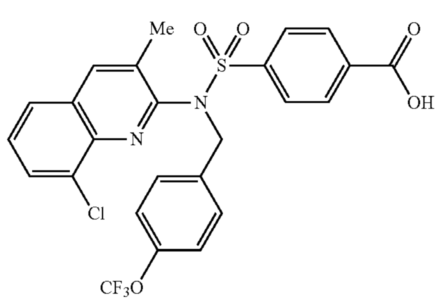 | APCI-MS m/z: 551/553[M + H]+ |
| 134 | 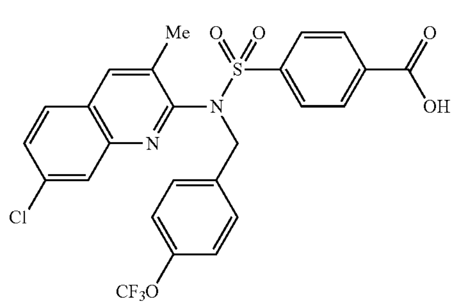 | APCI-MS m/z: 551/553[M + H]+ |

TABLE 6-continued

| Example | Structure | Physical data |
|---|---|---|
| 135 | 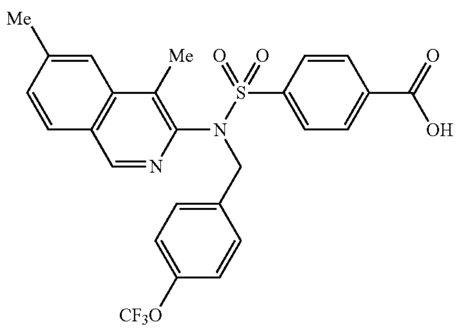 | APCI-MS m/z: 531[M + H]+ |
| 136 | 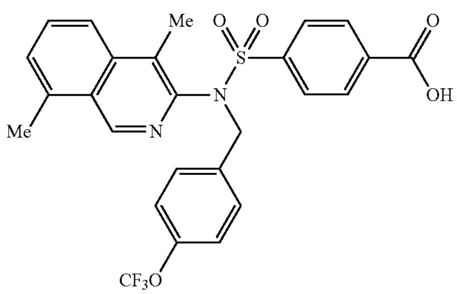 | APCI-MS m/z: 531[M + H]+ |
| 137 | 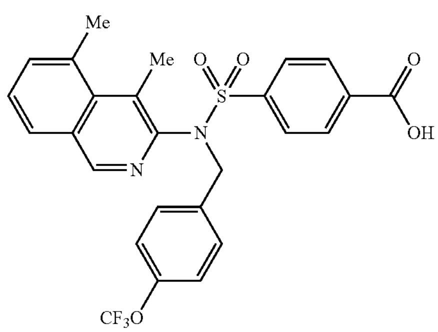 | APCI-MS m/z: 531[M + H]+ |
| 138 | 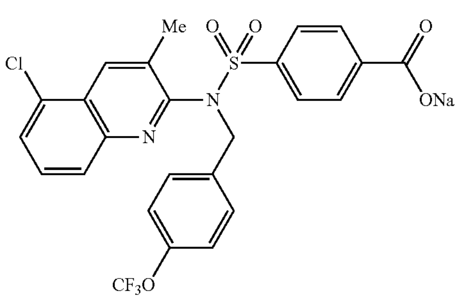 | ESI-MS m/z: 549/551[M − Na]− |
| 139 | 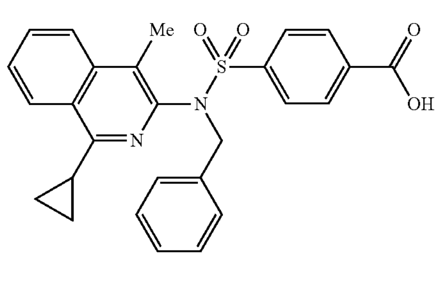 [SMILES: Cc1c(N(Cc2ccccc2)S(=O)(=O)c2ccc(C(=O)O)cc2)nc(C2CC2)c2ccccc12] | APCI-MS m/z: 473[M + H]+ |

TABLE 6-continued

| Example | Structure | Physical data |
|---|---|---|
| 140 | 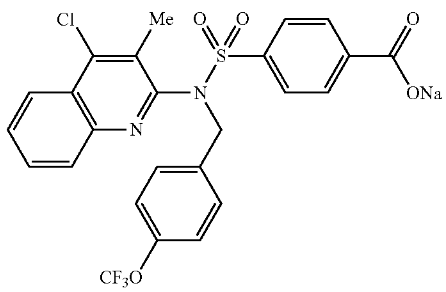 | ESI-MS m/z: 549/551[M − Na]⁻ |
| 141 | 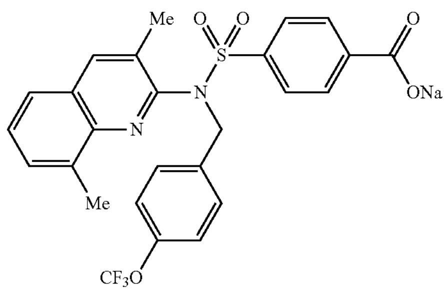 | ESI-MS m/z: 529[M − Na]⁻ |
| 142 | 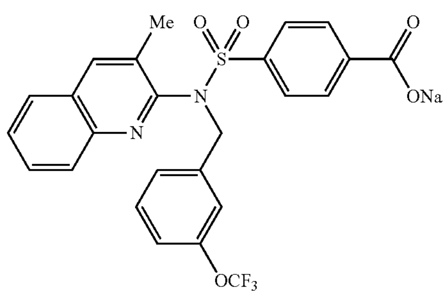 | ESI-MS m/z: 515[M − Na]⁻ |
| 143 | 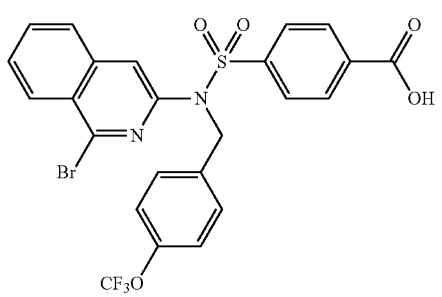 | APCI-MS m/z: 581/583[M + H]⁺ |
| 144 | 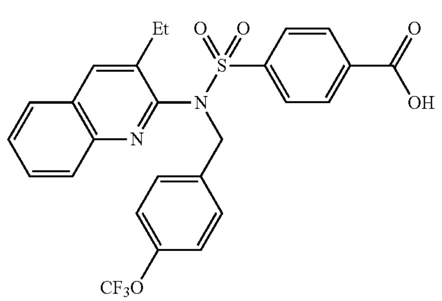 | APCI-MS m/z: 531[M + H]⁺ |

TABLE 6-continued

| Example | Structure | Physical data |
|---|---|---|
| 145 | (6-fluoro-3-methylquinolin-2-yl, N-(4-trifluoromethoxybenzyl), 4-carboxybenzenesulfonamide) | APCI-MS m/z: 535[M + H]+ |
| 146 | (7-fluoro-3-methylquinolin-2-yl, N-(4-trifluoromethoxybenzyl), 4-carboxybenzenesulfonamide) | APCI-MS m/z: 535[M + H]+ |
| 147 | (1,7-dimethyl-1H-pyrrolo[3,2-c]pyridin-6-yl, N-(4-trifluoromethoxybenzyl), sodium 4-carboxybenzenesulfonamide) | ESI-MS m/z: 518[M − Na]− |
| 148 | (1-bromo-5-chloroisoquinolin-3-yl, N-(4-trifluoromethoxybenzyl), 4-carboxybenzenesulfonamide) | APCI-MS m/z: 615/617/619[M + H]+ |
| 149 | (4-methoxyisoquinolin-3-yl, N-(4-trifluoromethoxybenzyl), 4-carboxybenzenesulfonamide) | APCI-MS m/z: 533[M + H]+ |

TABLE 6-continued

| Example | Structure | Physical data |
|---|---|---|
| 150 | 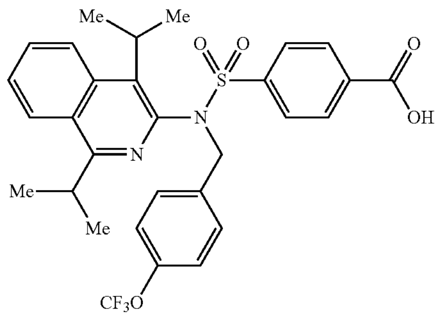 | APCI-MS m/z: 587[M + H]+ |
| 151 | 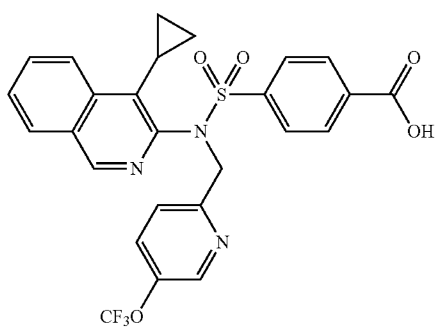 | APCI-MS m/z: 528[M + H]+ |
| 152 | 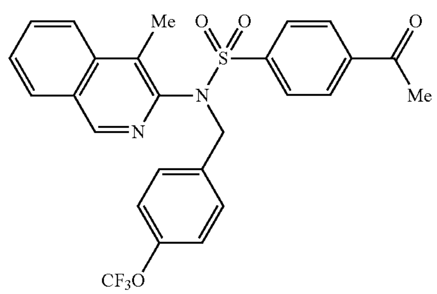 | APCI-MS m/z: 515[M + H]+ |
| 153 | 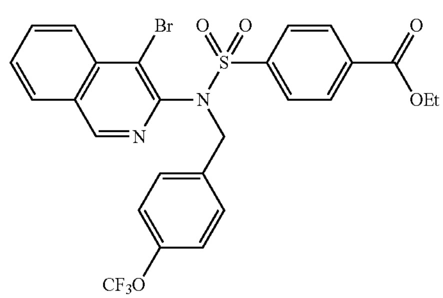 | APCI-MS m/z: 609/611[M + H]+ |
| 154 | 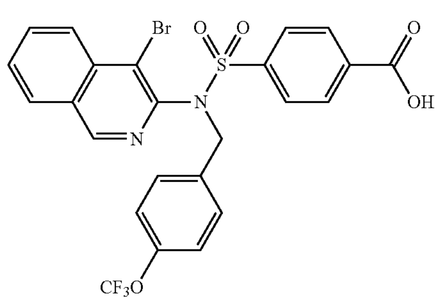 | APCI-MS m/z: 581/583[M + H]+ |

TABLE 6-continued
| Example | Structure | Physical data |
|---|---|---|
| 155 | 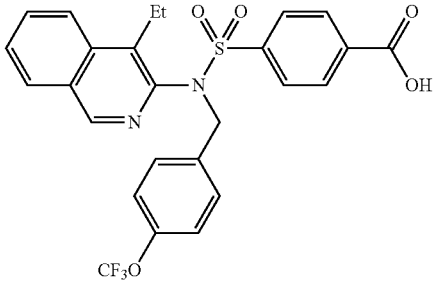 | APCI-MS m/z: 531[M + H]+ |
| 156 | 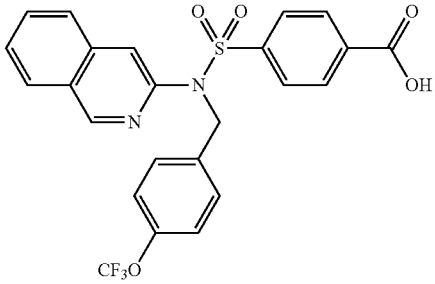 | APCI-MS m/z: 503[M + H]+ |
| 157 | 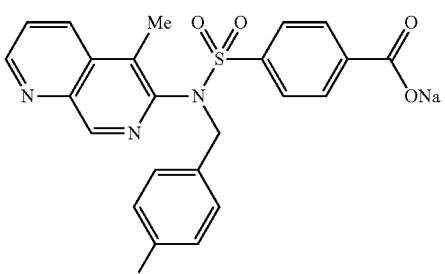 | ESI-MS m/z: 516[M − Na]− |
| 158 | 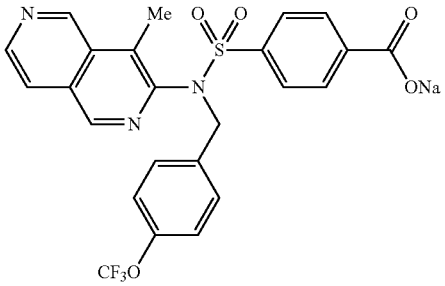 | ESI-MS m/z: 516[M − Na]− |

Examples 159 to 210

The corresponding starting compounds were treated in a similar manner to Examples 3, 4 and/or 8 to give the following compounds of Table 7. Interconversions of a carboxylic acid compound and a salt thereof to each other may be carried out by a conventional salt formation and a conventional desalination, respectively.

TABLE 7

| Example | Structure | Physical data |
|---|---|---|
| 159 | 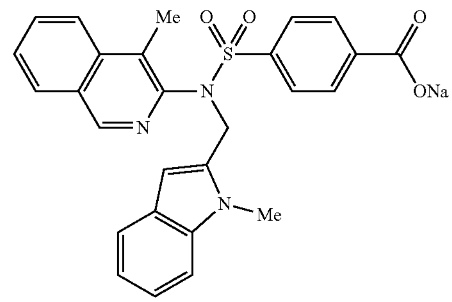 | ESI-MS m/z: 484[M − Na]⁻ |
| 160 | 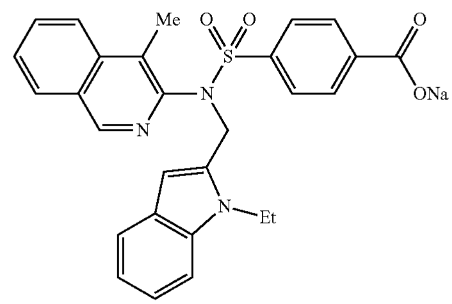 | ESI-MS m/z: 498[M − Na]⁻ |
| 161 | 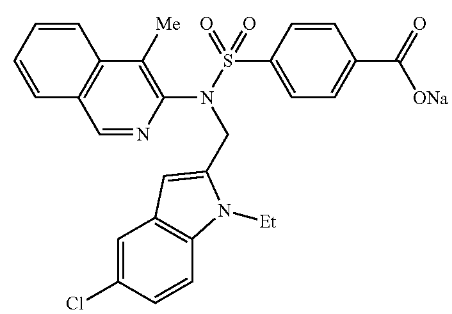 | ESI-MS m/z: 532/534[M − Na]⁻ |
| 162 | 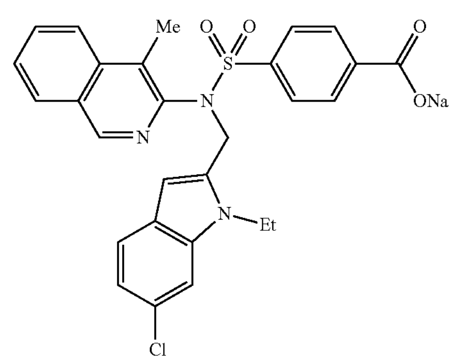 | ESI-MS m/z: 532/534[M − Na]⁻ |

TABLE 7-continued
| Example | Structure | Physical data |
|---|---|---|
| 163 | 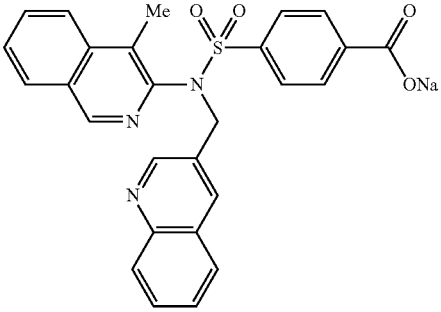 | ESI-MS m/z: 482[M − Na]⁻ |
| 164 | 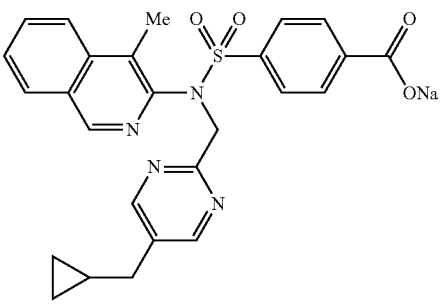 | ESI-MS m/z: 487[M − Na]⁻ |
| 165 | 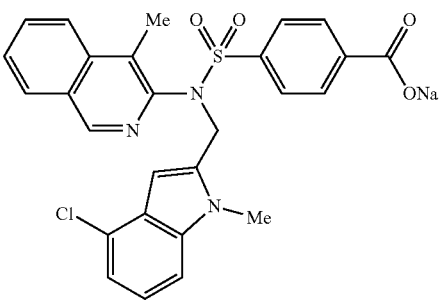 | ESI-MS m/z: 518/520[M − Na]⁻ |
| 166 | 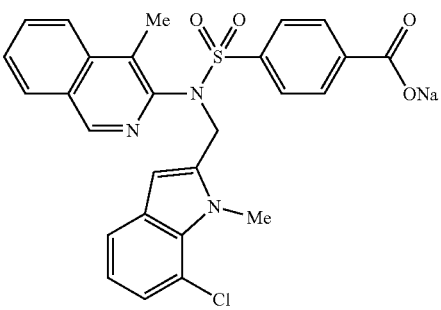 | ESI-MS m/z: 518/520[M − Na]⁻ |
| 167 | 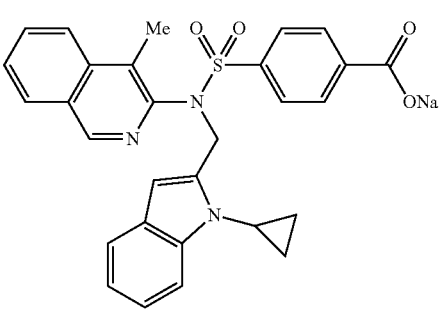 | ESI-MS m/z: 510[M − Na]⁻ |

TABLE 7-continued

| Example | Structure | Physical data |
|---|---|---|
| 168 | 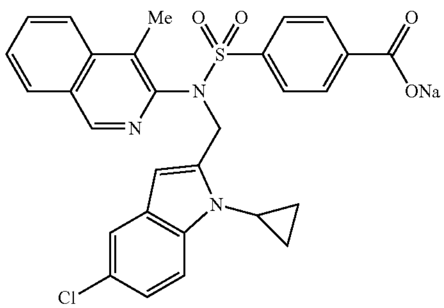 | ESI-MS m/z: 544/546[M − Na]⁻ |
| 169 | 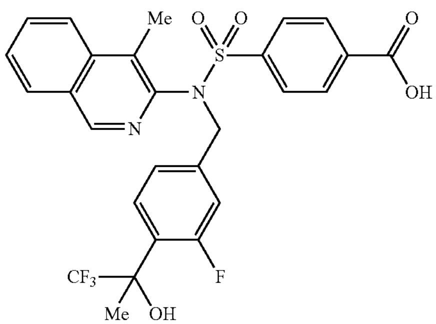 [SMILES: Cc1c(N(Cc2ccc(C(C)(O)C(F)(F)F)c(F)c2)S(=O)(=O)c2ccc(C(=O)O)cc2)ncc2ccccc12] | APCI-MS m/z: 563[M + H]⁺ |
| 170 | 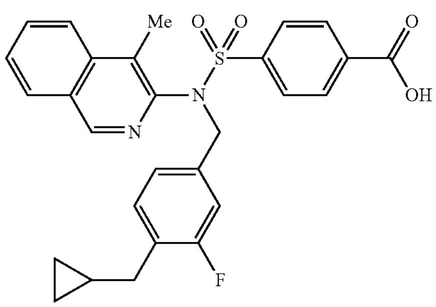 [SMILES: Cc1c(N(Cc2ccc(CC3CC3)c(F)c2)S(=O)(=O)c2ccc(C(=O)O)cc2)ncc2ccccc12] | APCI-MS m/z: 505[M + H]⁺ |
| 171 | 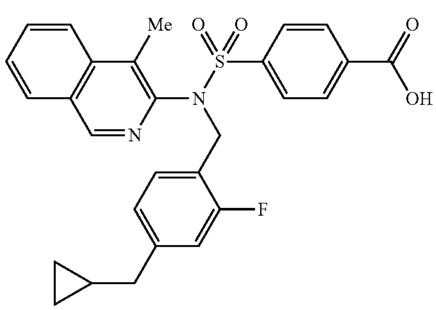 [SMILES: Cc1c(N(Cc2ccc(CC3CC3)cc2F)S(=O)(=O)c2ccc(C(=O)O)cc2)ncc2ccccc12] | APCI-MS m/z: 505[M + H]⁺ |
| 172 | 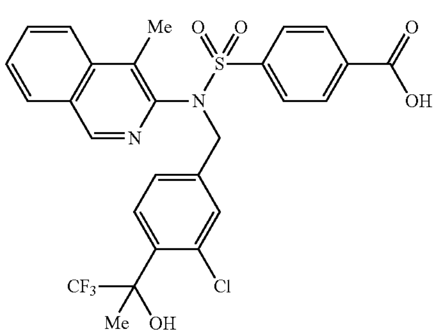 [SMILES: Cc1c(N(Cc2ccc(C(C)(O)C(F)(F)F)c(Cl)c2)S(=O)(=O)c2ccc(C(=O)O)cc2)ncc2ccccc12] | APCI-MS m/z: 579[M + H]⁺ |

TABLE 7-continued
| Example | Structure | Physical data |
|---|---|---|
| 173 | 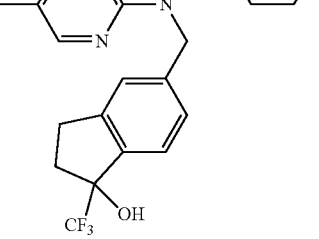 | APCI-MS m/z: 557[M + H]+ |
| 174 | 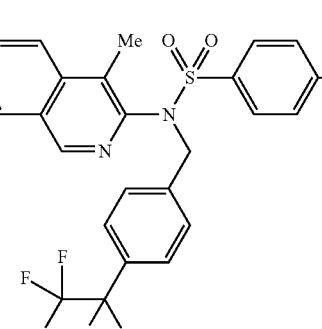 | APCI-MS m/z: 595[M + H]+ |
| 175 | 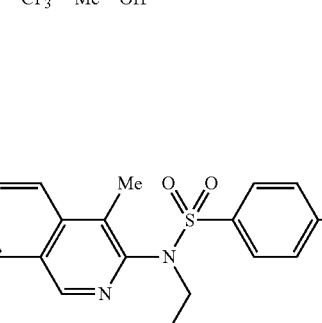 | APCI-MS m/z: 491[M + H]+ |
| 176 | 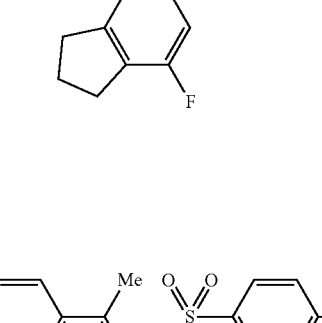 | APCI-MS m/z: 507/509[M + H]+ |

TABLE 7-continued

| Example | Structure | Physical data |
|---|---|---|
| 177 | 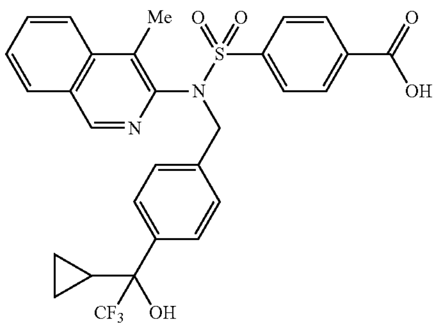 [SMILES: Cc1c(N(Cc2ccc(C(O)(C3CC3)C(F)(F)F)cc2)S(=O)(=O)c2ccc(C(=O)O)cc2)ncc2ccccc12] | APCI-MS m/z: 571[M + H]+ |
| 178 | 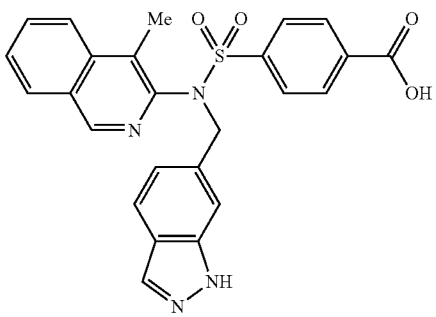 [SMILES: Cc1c(N(Cc2ccc3cn[nH]c3c2)S(=O)(=O)c2ccc(C(=O)O)cc2)ncc2ccccc12] | APCI-MS m/z: 473[M + H]+ |
| 179 | 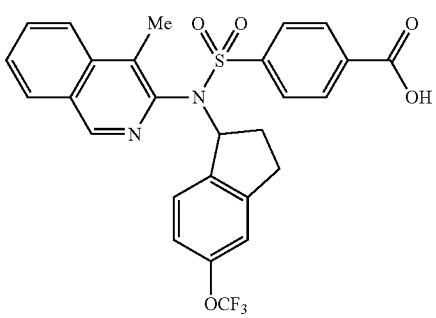 [SMILES: Cc1c(N(C2CCc3cc(OC(F)(F)F)ccc32)S(=O)(=O)c2ccc(C(=O)O)cc2)ncc2ccccc12] | APCI-MS m/z: 543[M + H]+ |
| 180 | 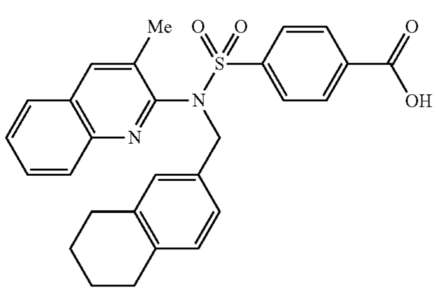 [SMILES: Cc1cc2ccccc2nc1N(Cc1ccc2c(c1)CCCC2)S(=O)(=O)c1ccc(C(=O)O)cc1] | APCI-MS m/z: 487[M + H]+ |

TABLE 7-continued

| Example | Structure | Physical data |
|---|---|---|
| 181 | 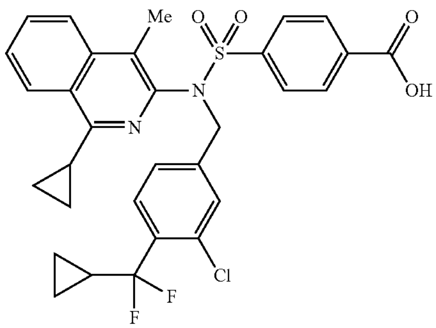 [SMILES: Cc1c(N(Cc2ccc(C(F)(F)C3CC3)c(Cl)c2)S(=O)(=O)c2ccc(C(=O)O)cc2)nc(C2CC2)c2ccccc12] | APCI-MS m/z: 597/599[M + H]+ |
| 182 | 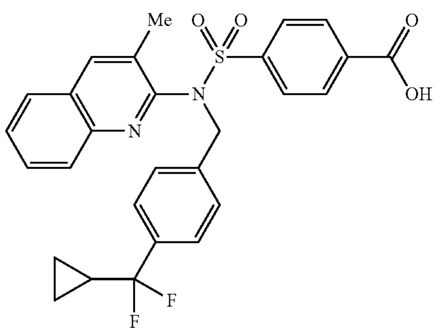 [SMILES: Cc1cc2ccccc2nc1N(Cc1ccc(C(F)(F)C2CC2)cc1)S(=O)(=O)c1ccc(C(=O)O)cc1] | APCI-MS m/z: 523[M + H]+ |
| 183 | 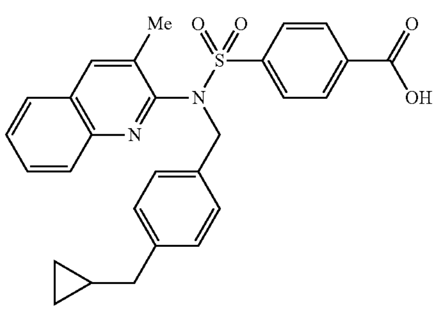 [SMILES: Cc1cc2ccccc2nc1N(Cc1ccc(CC2CC2)cc1)S(=O)(=O)c1ccc(C(=O)O)cc1] | APCI-MS m/z: 487[M + H]+ |
| 184 | 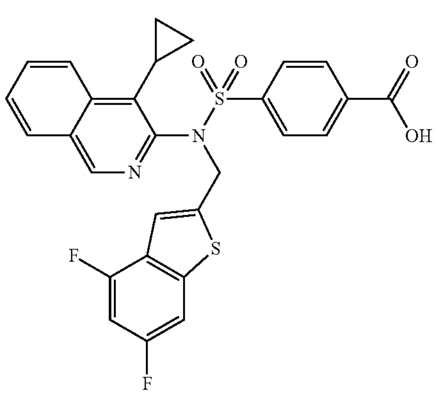 [SMILES: O=C(O)c1ccc(S(=O)(=O)N(Cc2cc3c(F)cc(F)cc3s2)c2ncc3ccccc3c2C2CC2)cc1] | ESI-MS m/z: 549[M − Na]− |

TABLE 7-continued
| Example | Structure | Physical data |
|---|---|---|
| 185 | 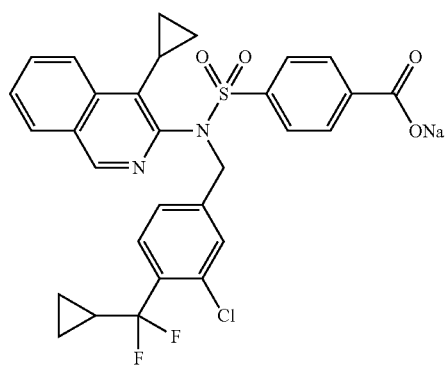 | ESI-MS m/z: 581/583[M − Na]⁻ |
| 186 | 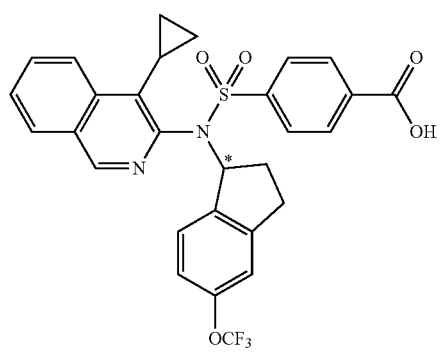<br>*Single enantiomer | APCI-MS m/z: 569[M + H]⁺ |
| 187 | 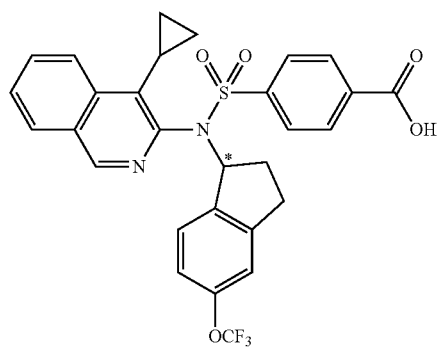<br>*the other enantiomer opposed to Example 186 | APCI-MS m/z: 569[M + H]⁺ |
| 188 | 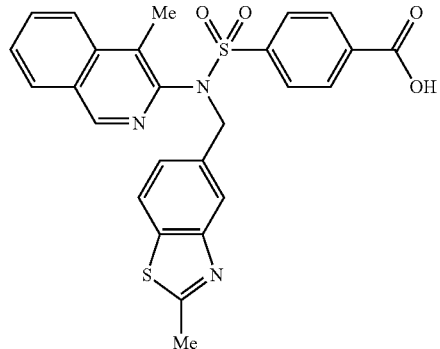 [SMILES: Cc1nc2cc(CN(c3ncc4ccccc4c3C)S(=O)(=O)c3ccc(C(=O)O)cc3)ccc2s1] | APCI-MS m/z: 504[M + H]⁺ |

TABLE 7-continued

| Example | Structure | Physical data |
|---|---|---|
| 189 | 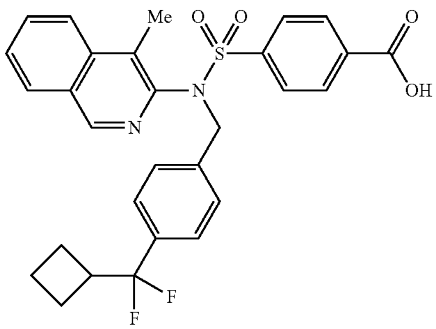 [SMILES: Cc1c(N(Cc2ccc(C(F)(F)C3CCC3)cc2)S(=O)(=O)c2ccc(C(=O)O)cc2)ncc2ccccc12] | APCI-MS m/z: 537[M + H]+ |
| 190 | 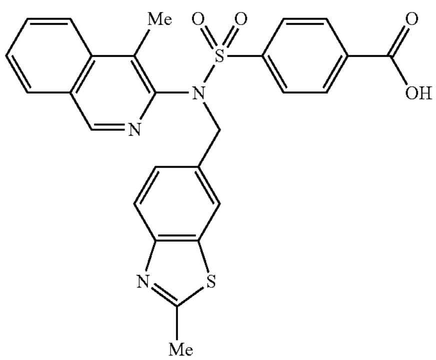 [SMILES: Cc1nc2ccc(CN(c3ncc4ccccc4c3C)S(=O)(=O)c3ccc(C(=O)O)cc3)cc2s1] | APCI-MS m/z: 504[M + H]+ |
| 191 | 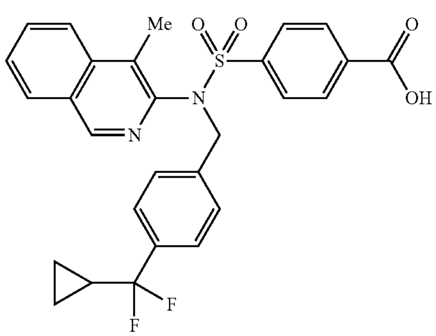 [SMILES: Cc1c(N(Cc2ccc(C(F)(F)C3CC3)cc2)S(=O)(=O)c2ccc(C(=O)O)cc2)ncc2ccccc12] | APCI-MS m/z: 523[M + H]+ |
| 192 | 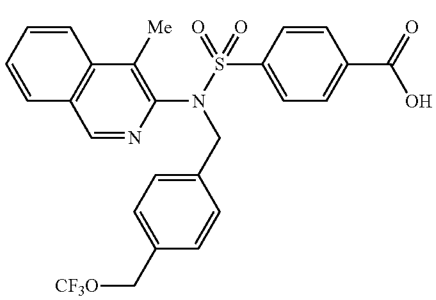 | APCI-MS m/z: 531[M + H]+ |

TABLE 7-continued

| Example | Structure | Physical data |
|---|---|---|
| 193 | 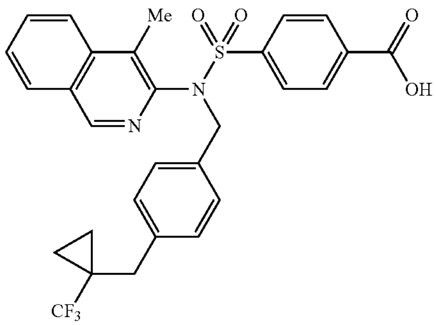 [SMILES: Cc1c(N(Cc2ccc(CC3(C(F)(F)F)CC3)cc2)S(=O)(=O)c2ccc(C(=O)O)cc2)ncc2ccccc12] | APCI-MS m/z: 555[M + H]+ |
| 194 | 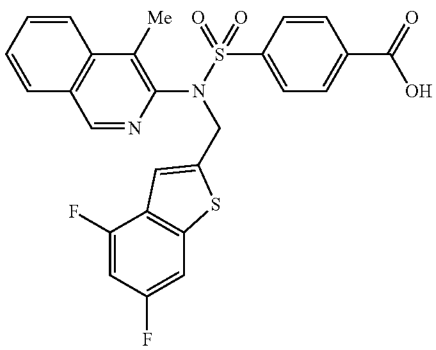 [SMILES: Cc1c(N(Cc2cc3c(F)cc(F)cc3s2)S(=O)(=O)c2ccc(C(=O)O)cc2)ncc2ccccc12] | APCI-MS m/z: 525[M + H]+ |
| 195 | 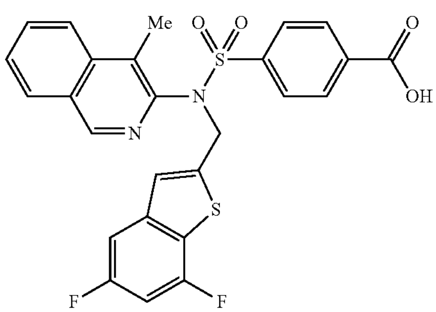 [SMILES: Cc1c(N(Cc2cc3cc(F)cc(F)c3s2)S(=O)(=O)c2ccc(C(=O)O)cc2)ncc2ccccc12] | APCI-MS m/z: 525[M + H]+ |
| 196 | 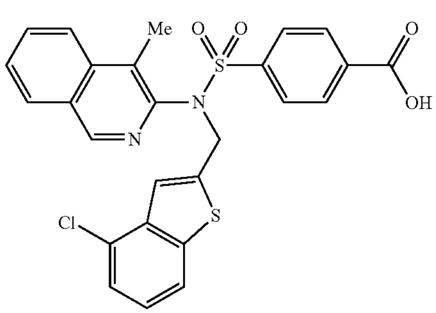 [SMILES: Cc1c(N(Cc2cc3c(Cl)cccc3s2)S(=O)(=O)c2ccc(C(=O)O)cc2)ncc2ccccc12] | APCI-MS m/z: 523/525[M + H]+ |

TABLE 7-continued

| Example | Structure | Physical data |
|---------|-----------|---------------|
| 197 | 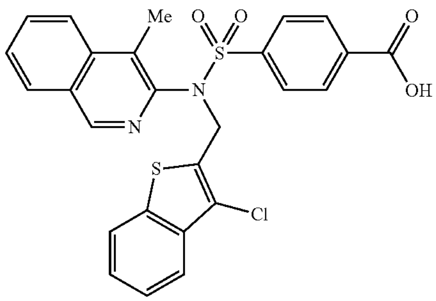 [SMILES: Cc1c(N(Cc2sc3ccccc3c2Cl)S(=O)(=O)c2ccc(C(=O)O)cc2)ncc2ccccc12] | APCI-MS m/z: 523/525[M + H]+ |
| 198 | 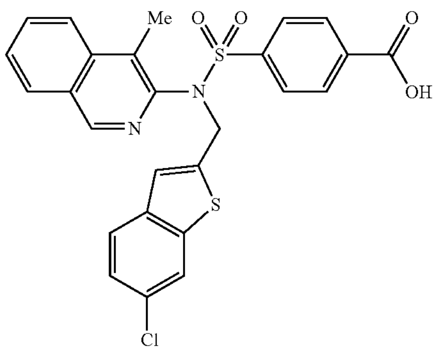 [SMILES: Cc1c(N(Cc2cc3ccc(Cl)cc3s2)S(=O)(=O)c2ccc(C(=O)O)cc2)ncc2ccccc12] | APCI-MS m/z: 523/525[M + H]+ |
| 199 | 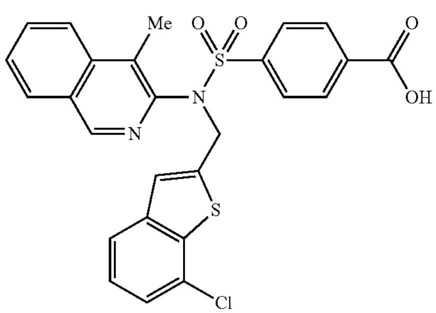 [SMILES: Cc1c(N(Cc2cc3cccc(Cl)c3s2)S(=O)(=O)c2ccc(C(=O)O)cc2)ncc2ccccc12] | APCI-MS m/z: 523/525[M + H]+ |
| 200 | 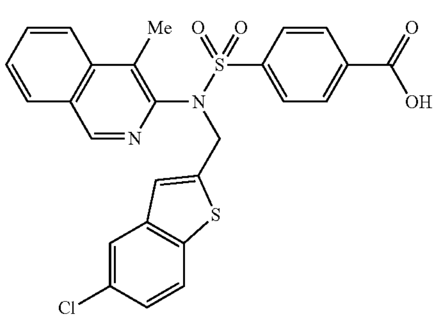 [SMILES: Cc1c(N(Cc2cc3cc(Cl)ccc3s2)S(=O)(=O)c2ccc(C(=O)O)cc2)ncc2ccccc12] | APCI-MS m/z: 523/525[M + H]+ |

TABLE 7-continued

| Example | Structure | Physical data |
|---|---|---|
| 201 | 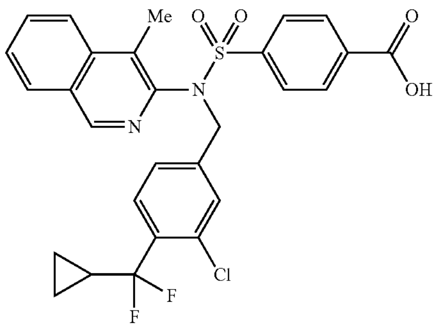 [SMILES: Cc1c(N(Cc2ccc(C(F)(F)C3CC3)c(Cl)c2)S(=O)(=O)c2ccc(C(=O)O)cc2)ncc2ccccc12] | APCI-MS m/z: 557/559[M + H]+ |
| 202 | 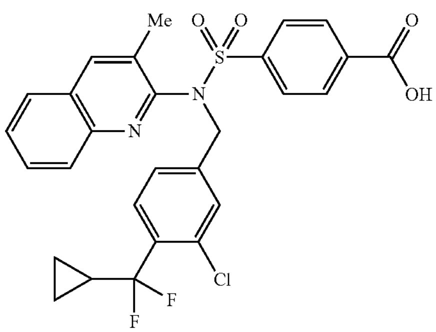 [SMILES: Cc1cc2ccccc2nc1N(Cc1ccc(C(F)(F)C2CC2)c(Cl)c1)S(=O)(=O)c1ccc(C(=O)O)cc1] | APCI-MS m/z: 557/559[M + H]+ |
| 203 | 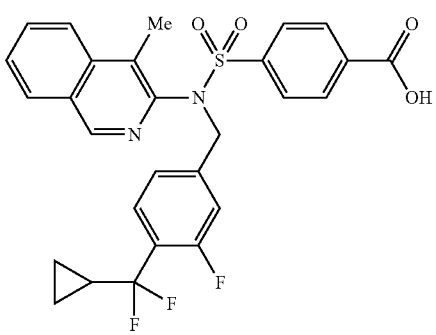 [SMILES: Cc1c(N(Cc2ccc(C(F)(F)C3CC3)c(F)c2)S(=O)(=O)c2ccc(C(=O)O)cc2)ncc2ccccc12] | APCI-MS m/z: 541[M + H]+ |
| 204 | 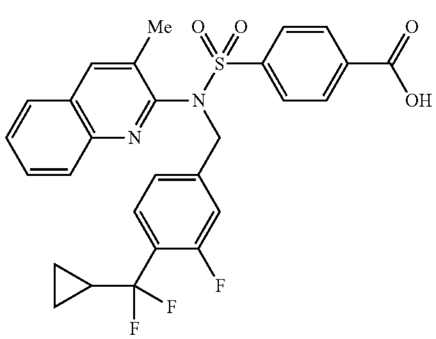 [SMILES: Cc1cc2ccccc2nc1N(Cc1ccc(C(F)(F)C2CC2)c(F)c1)S(=O)(=O)c1ccc(C(=O)O)cc1] | APCI-MS m/z: 541[M + H]+ |

TABLE 7-continued
| Example | Structure | Physical data |
|---|---|---|
| 205 | 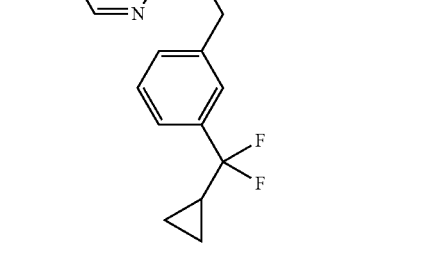 | APCI-MS m/z: 523[M + H]$^+$ |
| 206 | 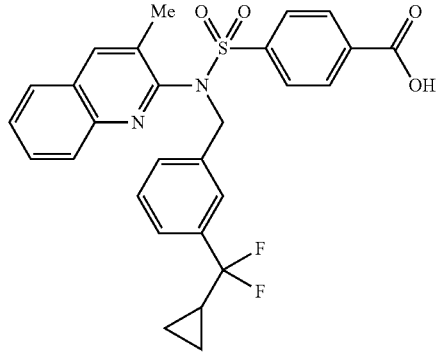 [SMILES: Cc1cc2ccccc2nc1N(Cc1cccc(C(F)(F)C2CC2)c1)S(=O)(=O)c1ccc(C(=O)O)cc1] | APCI-MS m/z: 523[M + H]$^+$ |
| 207 | 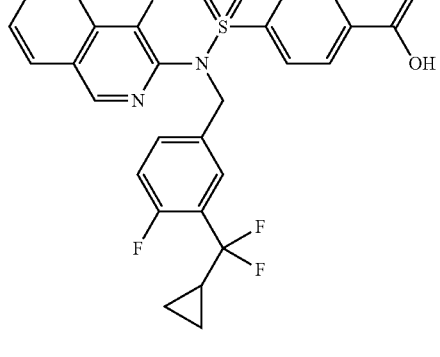 | APCI-MS m/z: 541[M + H]$^+$ |
| 208 | 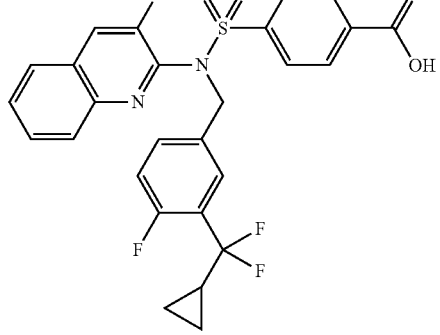 | APCI-MS m/z: 541[M + H]$^+$ |

TABLE 7-continued

| Example | Structure | Physical data |
|---|---|---|
| 209 | 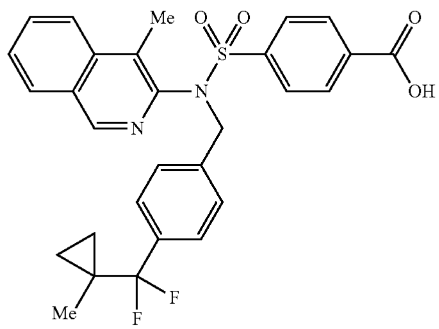 [SMILES: Cc1c(N(Cc2ccc(C(F)(F)C3(C)CC3)cc2)S(=O)(=O)c2ccc(C(=O)O)cc2)ncc2ccccc12] | APCI-MS m/z: 537[M + H]+ |
| 210 | 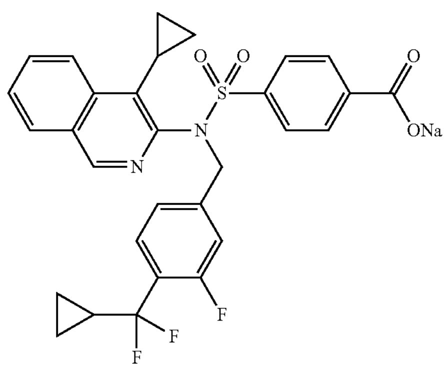 | ESI-MS m/z: 565[M − Na]− |

Examples 211 to 212

The corresponding starting compounds were treated in a similar manner to Examples 5, 6 and/or 8 to give the following compounds of Table 8. Interconversions of a carboxylic acid compound and a salt thereof to each other may be carried out by a conventional salt formation and a conventional desalination, respectively.

TABLE 8

| Example | Structure | Physical data |
|---|---|---|
| 211 | 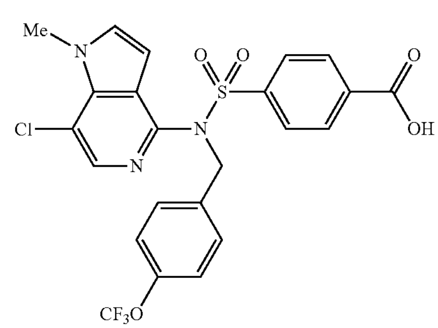 | APCI-MS m/z: 540/542[M + H]+ |

TABLE 8-continued

| Example | Structure | Physical data |
|---------|-----------|---------------|
| 212 | 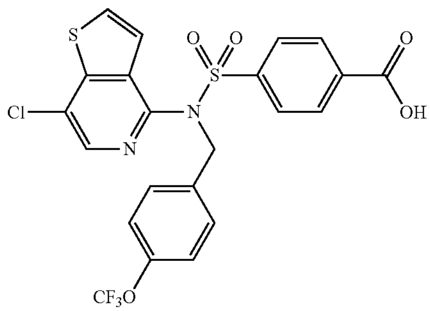 | APCI-MS m/z: 543/545[M + H]+ |

Examples 213 to 218

The corresponding starting compounds were treated in a similar manner to Examples 8, 9 and/or 10 to give the following compounds of Table 9. Interconversions of a carboxylic acid compound and a salt thereof to each other may be carried out by a conventional salt formation and a conventional desalination, respectively.

TABLE 9

| Example | Structure | Physical data |
|---------|-----------|---------------|
| 213 | 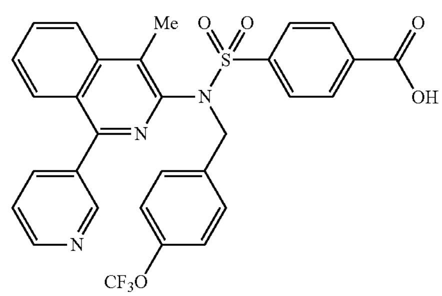 | APCI-MS m/z: 594[M + H]+ |
| 214 | 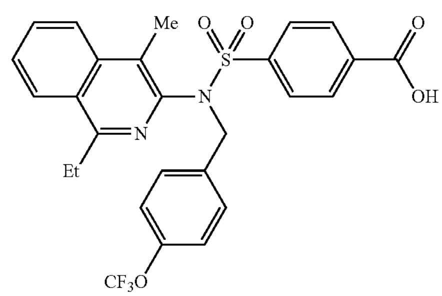 | APCI-MS m/z: 545[M + H]+ |
| 215 | 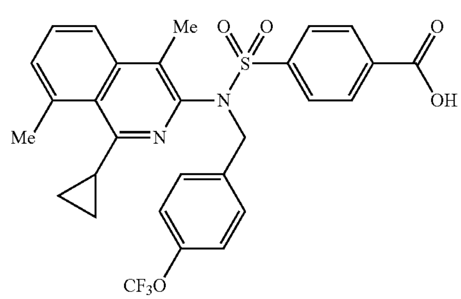 | APCI-MS m/z: 571[M + H]+ |

TABLE 9-continued

| Example | Structure | Physical data |
|---|---|---|
| 216 | 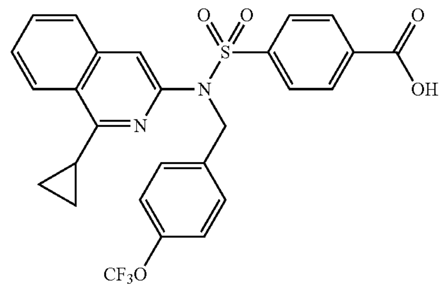 | APCI-MS m/z: 543[M + H]$^+$ |
| 217 | 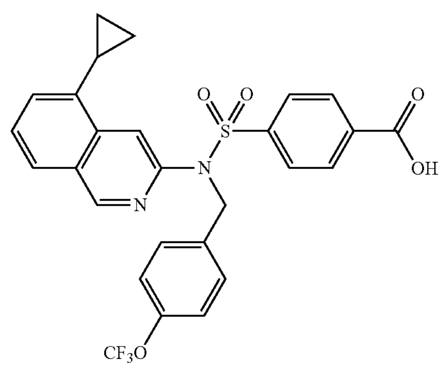 | APCI-MS m/z: 543[M + H]$^+$ |
| 218 | 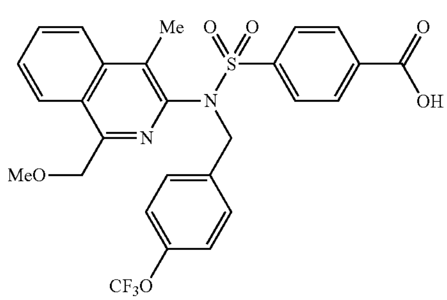 | APCI-MS m/z: 561[M + H]$^+$ |

Examples 219 to 224

The corresponding starting compounds were treated in a similar manner to Examples 8, 13 and/or 14 to give the following compounds of Table 10. Interconversions of a carboxylic acid compound and a salt thereof to each other may be carried out by a conventional salt formation and a conventional desalination, respectively.

TABLE 10
| Example | Structure | Physical data |
|---|---|---|
| 219 | 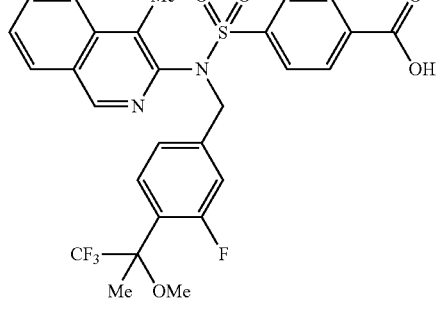 | APCI-MS m/z: 577[M + H]$^+$ |
| 220 | 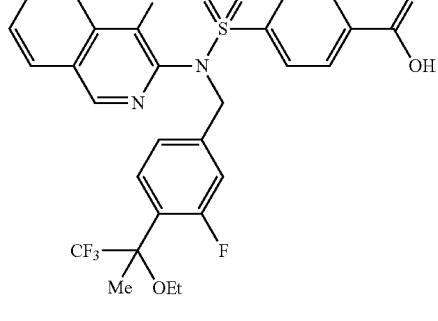 | APCI-MS m/z: 591[M + H]$^+$ |
| 221 | 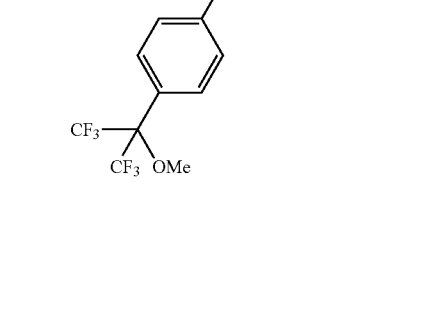 | ESI-MS m/z: 611[M − Na]$^-$ |
| 222 | 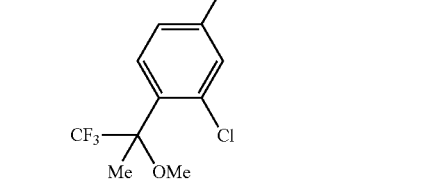 | APCI-MS m/z: 593/595[M + H]$^+$ |

TABLE 10-continued

| Example | Structure | Physical data |
|---|---|---|
| 223 | 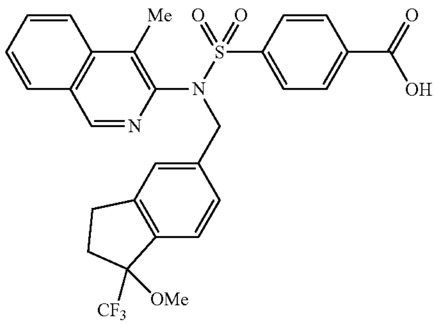 | APCI-MS m/z: 571[M + H]+ |
| 224 | 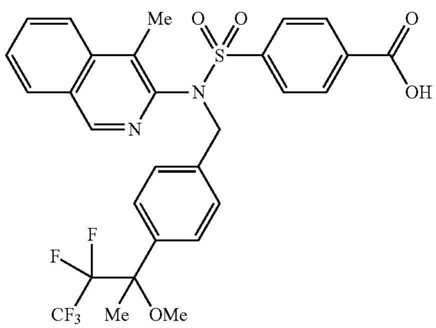 | APCI-MS m/z: 609[M + H]+ |

Examples 225 to 227

The corresponding starting compounds were treated in a similar manner to Example 97 to give the following compounds of Table 11. Interconversions of a carboxylic acid compound and a salt thereof to each other may be carried out by a conventional salt formation and a conventional desalination, respectively.

TABLE 11

| Example | Structure | Physical data |
|---|---|---|
| 225 | 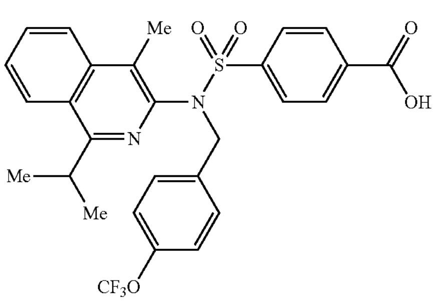 | APCI-MS m/z: 559 [M + H]+ |

TABLE 11-continued

| Example | Structure | Physical data |
|---|---|---|
| 226 | 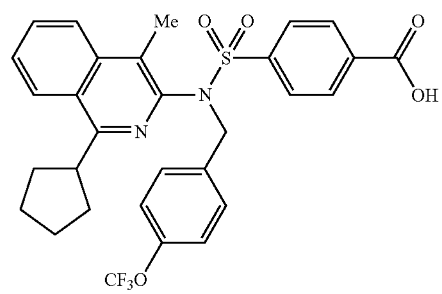 | APCI-MS m/z: 585 [M + H]+ |
| 227 | 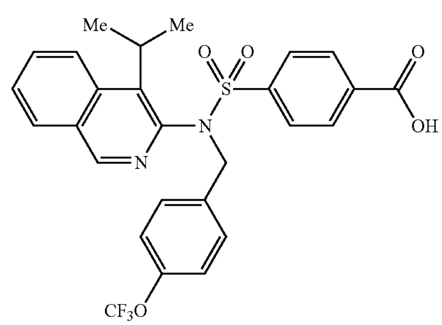 | APCI-MS m/z: 545 [M + H]+ |

Examples 228 to 229

The corresponding starting compounds were treated in a similar manner to Example 100 to give the following compounds of Table 12. Interconversions of a carboxylic acid compound and a salt thereof to each other may be carried out by a conventional salt formation and a conventional desalination, respectively.

TABLE 12

| Example | Structure | Physical data |
|---|---|---|
| 228 | 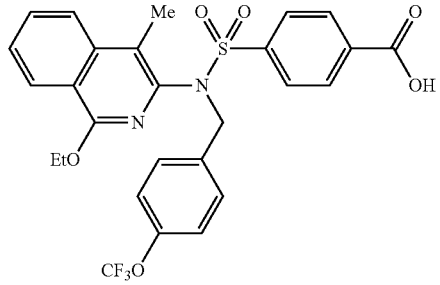 | APCI-MS m/z: 561[M + H]$^+$ |
| 229 | 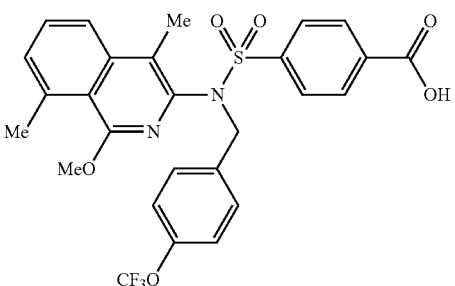 | APCI-MS m/z: 561[M + H]$^+$ |

Examples 230

The corresponding starting compound was treated in a similar manner to Examples 101 and 102 to give the following compound of Table 13. Interconversions of a carboxylic acid compound and a salt thereof to each other may be carried out by a conventional salt formation and a conventional desalination, respectively.

TABLE 13

| Example | Structure | Physical data |
|---|---|---|
| 230 | 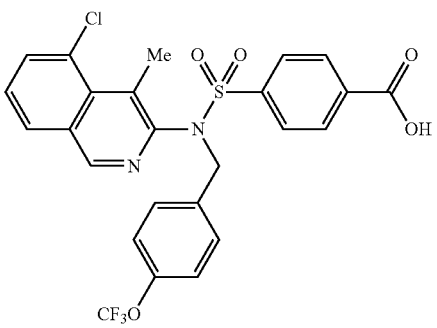 | APCI-MS m/z: 551/553[M + H]$^+$ |

Examples 231 to 232

The corresponding starting compounds were treated in a similar manner to Examples 103 and 104 to give the following compounds of Table 14. Interconversions of a carboxylic acid compound and a salt thereof to each other may be carried out by a conventional salt formation and a conventional desalination, respectively.

TABLE 14

| Example | Structure | Physical data |
|---|---|---|
| 231 | (structure) | APCI-MS m/z: 585 [M + H]+ |
| 232 | (structure) | APCI-MS m/z: 583 [M + H]+ |

Examples 233 to 235

The corresponding starting compounds were treated in a similar manner to Examples 105 and 106 to give the following compounds of Table 15. Interconversions of a carboxylic acid compound and a salt thereof to each other may be carried out by a conventional salt formation and a conventional desalination, respectively.

TABLE 15

| Example | Structure | Physical data |
|---|---|---|
| 233 | (structure) | ESI-MS m/z: 609/611[M − Na]− |
| 234 | (structure) | ESI-MS m/z: 577[M − Na]− |

TABLE 15-continued

| Example | Structure | Physical data |
|---|---|---|
| 235 | (structure) | APCI-MS m/z: 595[M − Na + 2H]⁺ |

Examples 236 to 237

The corresponding starting compounds were treated in a similar manner to Examples 120, 121 and/or 122 to give the following compounds of Table 16. Interconversions of a carboxylic acid compound and a salt thereof to each other may be carried out by a conventional salt formation and a conventional desalination, respectively.

TABLE 16

| Example | Structure | Physical data |
|---|---|---|
| 236 | (structure) | APCI-MS m/z: 506/508[M + H]⁺ |
| 237 | (structure) | APCI-MS m/z: 520/522[M + H]⁺ |

Examples 238 to 240
The corresponding starting compounds were treated in a similar manner to Example 123 to give the following compounds of Table 17.
TABLE 17
| Example | Structure | Physical data |
|---|---|---|
| 238 | 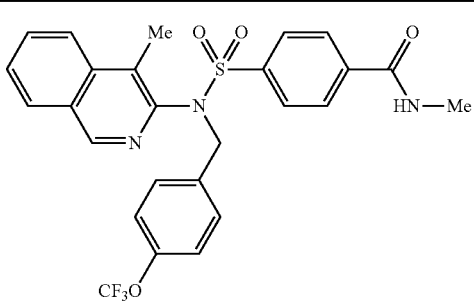 | APCI-MS m/z: 530[M + H]$^+$ |
| 239 | 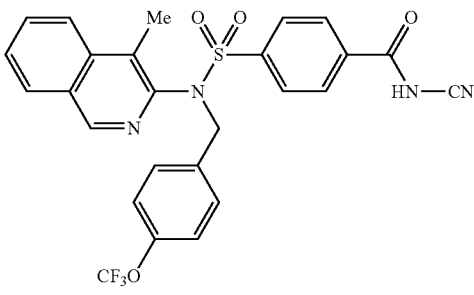 | APCI-MS m/z: 541[M + H]$^+$ |
| 240 | 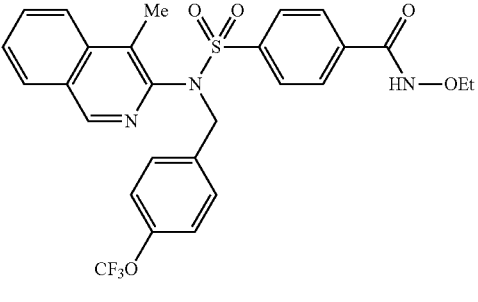 | APCI-MS m/z: 560[M + H]$^+$ |

Examples 241 to 242

The corresponding starting compounds were treated in a similar manner to Example 124 to give the following compounds of Table 18.

TABLE 18

| Example | Structure | Physical data |
|---|---|---|
| 241 | 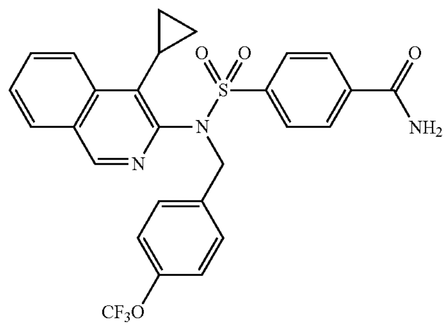 | APCI-MS m/z: 542[M + H]⁺ |
| 242 | 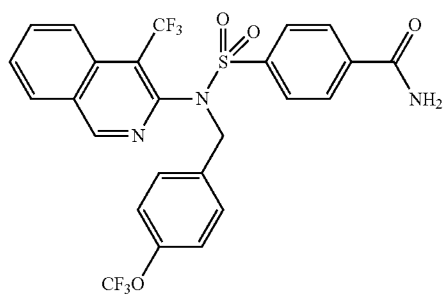 | APCI-MS m/z: 570[M + H]⁺ |

Reference Example 1

Preparation of [3-fluoro-4-(trifluoromethoxy)phenyl]methanol

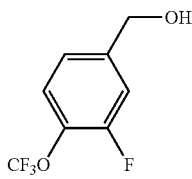

(1) To a solution of 3-fluoro-4-(trifluoromethoxy)benzoic acid (1.00 g, 4.46 mmol) in ethanol (10 ml) was added thionyl chloride (1.33 g, 11.2 mmol) at 0° C. The reaction solution was slowly warmed to room temperature, and stirred at the same temperature overnight. The reaction solution was poured into saturated aqueous sodium bicarbonate solution, and extracted with ethyl acetate twice. The organic layer was combined, washed with saturated brine, dried over anhydrous sodium sulfate, and then concentrated under reduced pressure. The resulting residue was purified by silica gel column chromatography (hexane:ethyl acetate=10:0→9:1) to give ethyl 3-fluoro-4-(trifluoromethoxy)benzoate (0.72 g, 64%) as a colorless and clear oil.

$^1$H-NMR (DMSO-d$_6$) δ 1.33 (3H, t, J=7.1 Hz), 4.35 (21-1, q, J=7.1 Hz), 7.77-7.73 (1H, m), 7.92-7.90 (1H, m), 8.00 (1H, dd, J=10.6, 1.9 Hz).

(2) To a solution of the above compound (698 mg, 2.77 mmol) in tetrahydrofuran (7 ml) was added lithium aluminum hydride (79 mg, 2.08 mmol) at 0° C. The mixture was stirred at the same temperature for 30 minutes, and stirred at room temperature for 5 hours. The reaction solution was cooled to 0° C., and then thereto were added diethyl ether and 1 mol/L aqueous sodium hydroxide solution (10 ml). The mixture was stirred at the same temperature for 15 minutes. The reaction solution was extracted with diethyl ether twice. The organic layer was combined, washed with saturated brine, dried over anhydrous sodium sulfate, and then concentrated under reduced pressure. The resulting residue was purified by silica gel column chromatography (hexane:ethyl acetate=6:1→2:1) to give the title compound, [3-fluoro-4-(trifluoromethoxy)phenyl]methanol (0.52 g, 90%) as a colorless and clear oil.

$^1$H-NMR (DMSO-d$_6$) δ 4.53 (2H, d, J=5.4 Hz), 5.44 (1H, t, J=5.7 Hz), 7.26 (1H, m), 7.40 (1H, dd, J=11.5, 1.5 Hz), 7.53-7.49 (1H, m).

Reference Example 2

Preparation of 4,7-dichloro-1-methyl-1H-pyrrolo[2,3-c]pyridine

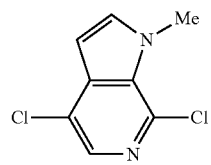 [SMILES: Cn1ccc2c(Cl)cnc(Cl)c21]

(1) To a solution of 2,5-dichloro-3-nitropyridine (5.00 g, 25.9 mmol) in tetrahydrofuran (164 ml) was added a solution of 1 mol/L vinylmagnesium bromide in tetrahydrofuran (82.9 ml, 82.9 mmol) at −78° C. The mixture was stirred at −20° C. overnight, and then to the reaction solution was added saturated aqueous ammonium chloride solution. The mixture was extracted with ethyl acetate twice. The organic layer was combined, washed with water and saturated brine, dried over anhydrous sodium sulfate, and then concentrated under reduced pressure. The resulting residue was purified by silica gel column chromatography (hexane:ethyl acetate=19:1→7:3), and then washed with diisopropyl ether to give 4,7-dichloro-1H-pyrrolo[2,3-c]pyridine (1.12 g, 23%) as a pale yellow powder.

APCI-MS m/z: 187/189[M+H]$^+$.

(2) To a solution of the above compound (150 mg, 802 μmol) in dimethyl sulfoxide (4.01 ml) were added potassium carbonate (228 mg, 1.60 mmol) and iodomethane (100 μl, 1.60 mmol) at room temperature. The mixture was stirred at the same temperature overnight, and then to the reaction solution was added water. The mixture was extracted with ethyl acetate twice. The organic layer was combined, washed with water and saturated brine, filtered through a diatomite column, and then concentrated under reduced pressure to give the title compound, 4,7-dichloro-1-methyl-1H-pyrrolo[2,3-c]pyridine (156 mg, 97%) as a yellow solid.

APCI-MS m/z: 201/203[M+H]$^+$.

Reference Example 3

Preparation of 6-(bromomethyl)-3-fluoro-2-iodopyridine

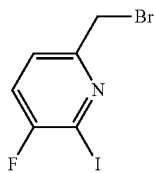

(1) To a solution of 2-bromo-3-fluoro-6-methylpyridine (1000 mg, 5.26 mmol) in 1,4-dioxane (16 mL) were added sodium iodide (1580 mg, 10.52 mmol), copper (I) iodide (150 mg, 0.26 mmol), N,N'-dimethylethylenediamine (62 μL, 0.58 mmol) under argon atmosphere. The reaction solution was heated to reflux for 4 hours, cooled to room temperature, and then to the reaction solution was added water. The mixture was extracted with ethyl acetate twice. The organic layer was combined, washed with aqueous citric acid solution and saturated brine, dried over anhydrous sodium sulfate, and then concentrated under reduced pressure to give 3-fluoro-2-iodo-6-methylpyridine (1169 mg, 94%) as a white powder.

APCI-MS m/z: 238 [M+H]$^+$.

(2) To a solution of the above compound (100 mg, 0.42 mmol) in 1,2-dichloroethane (2 mL) were added N-bromosuccinimide (86 mg, 0.49 mmol) and 2,2'-azobisisobutyronitrile (3 mg, 0.015 mmol), and the mixture was stirred at 75° C. overnight. The mixture was cooled to room temperature, and then to the reaction solution was added saturated aqueous sodium bicarbonate solution. The mixture was extracted with ethyl acetate twice. The organic layer was combined, washed with water and saturated brine, dried over anhydrous sodium sulfate, and then concentrated under reduced pressure. The resulting residue was purified by silica gel column chromatography (hexane:ethyl acetate=97:3→9:1) to give the title compound, 6-(bromomethyl)-3-fluoro-2-iodopyridine. The resulting compound was used in the next step without further purification.

Reference Example 4

Preparation of 4-(2-methoxyethoxy)benzyl 4-methylbenzenesulfonate

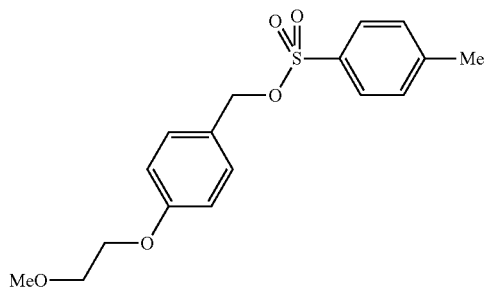 [SMILES: COCCOc1ccc(COS(=O)(=O)c2ccc(C)cc2)cc1]

(1) To a solution of 4-(2-methoxyethoxy)benzoic acid (100 mg, 0.51 mmol) in N,N-dimethylformamide (2 mL) were added potassium carbonate (282 mg, 2.04 mmol) and iodomethane (79 μL, 1.27 mmol) at room temperature. The mixture was stirred at the same temperature overnight, and then to the reaction solution was added water. The mixture was extracted with ethyl acetate twice. The organic layer was combined, washed with water and saturated brine, dried over anhydrous sodium sulfate, and then concentrated under reduced pressure. The resulting residue was dissolved in tetrahydrofuran (3 mL), and then thereto was added lithium borohydride (53 mg, 2.45 mmol) at 0° C. The reaction solution was slowly warmed to room temperature, and stirred for 3 days. To the reaction solution was added water, and the mixture was extracted with ethyl acetate twice. The organic layer was combined, washed with water and saturated brine, dried over anhydrous sodium sulfate, and then concentrated under reduced pressure to give [4-(2-methoxyethoxy)phenyl]methanol (61 mg, 68%) as a colorless and clear oil.

APCI-MS m/z: 200[M+NH$_4$]$^+$.

(2) To a solution of the above compound (58 mg, 0.32 mmol) in dichloromethane (1.5 mL) were added p-toluenesulfonyl chloride (79 mg, 0.41 mmol), N,N-diisopropylethylamine (162 μL, 0.95 mmol), and N,N-dimethyl-4-aminopyridine (8 mg, 0.064 mmol) at 0° C. The reaction solution was slowly warmed to room temperature, and stirred for 7 hours. To the reaction solution was added water, and the mixture was extracted with ethyl acetate twice. The organic layer was combined, washed with water and saturated brine, dried over anhydrous sodium sulfate, and then concentrated under reduced pressure to give the title compound, 4-(2-methoxyethoxy)benzyl 4-methylbenzenesulfonate. The resulting compound was used in the next step without further purification.

Reference Example 5

Preparation of [4-fluoro-5-(trifluoromethyl)-2-thienyl]methanol

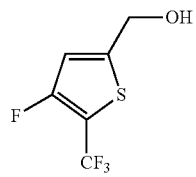 [SMILES: OCc1cc(F)c(C(F)(F)F)s1]

(1) To a solution of N,N-diisopropylamine (680 μL, 5.19 mmol) in tetrahydrofuran (5 ml) was added dropwise a solution of 1.67 mol/L n-butyllithium in hexane (3.11 ml, 5.19 mmol) at −78° C. under argon atmosphere, and the mixture was stirred at the same temperature for 15 minutes. The reaction solution was slowly warmed to 0° C., and stirred for 20 minutes, and then cooled to −40° C. Then, thereto was added dropwise a solution of 3-bromo-2-(trifluoromethyl)thiophene (1000 mg, 4.33 mmol) in tetrahydrofuran (15 ml). The mixture was stirred at the same temperature for 20 minutes, and the reaction solution was slowly warmed to −10° C., and then stirred for 5 minutes. The reaction solution was cooled to −40° C., and then thereto was added dropwise N,N-dimethylformamide (1 mL). Then, the mixture was slowly warmed to 0° C., and stirred overnight. To the reaction solution was added water, and the mixture was extracted with ethyl acetate twice. The organic layer was combined, washed with water and saturated brine, dried over anhydrous sodium sulfate, and then concentrated under reduced pressure. The resulting residue was purified by silica gel column chromatography (hexane:ethyl acetate=10:0→9:1) to give 4-bromo-5-(trifluoromethyl)thiophene-2-carbaldehyde (527 mg, 47%) as a yellow oil.

$^1$H-NMR (CDCl$_3$) δ 7.71 (1H, m), 9.93 (1H, s).

(2) To a solution of the above compound (520 mg, 2.01 mmol) in ethanol (10 mL) was added sodium borohydride (152 mg, 4.02 mmol) at 0° C. The mixture was stirred at the same temperature for 1 hour, and then to the reaction solution was added water. The mixture was extracted with ethyl acetate twice. The organic layer was combined, washed with water and saturated brine, dried over anhydrous sodium sulfate, and then concentrated under reduced pressure to give [4-bromo-5-(trifluoromethyl)-2-thienyl]methanol (432 mg, 82%) as a pale yellow oil.

$^1$H-NMR (CDCl$_3$) δ 2.01 (1H, t, J=6.0 Hz), 4.84 (2H, d, J=6.0 Hz), 6.96 (1H, s).

(3) To a solution of the above compound (427 mg, 1.64 mmol) in dichloromethane (6 mL) were added chloromethyl methyl ether (311 μL, 4.09 mmol) and N,N-diisopropylethylamine (1289 μL, 7.38 mmol) at room temperature. The mixture was stirred at the same temperature for 3 days, and then to the reaction solution was added water. The mixture was extracted with ethyl acetate twice. The organic layer was combined, washed with water and saturated brine, dried over anhydrous sodium sulfate, and then concentrated under reduced pressure. The resulting residue was purified by silica gel column chromatography (hexane:ethyl acetate=10:0→9:1) to give 3-bromo-5-[(methoxymethoxy)methyl]-2-(trifluoromethyl)thiophene (363 mg, 73%) as a colorless and clear oil.

$^1$H-NMR (CDCl$_3$) δ 3.41 (3H, s), 4.70 (2H, s), 4.72 (2H, s), 6.97 (1H, s).

(4) To a solution of the above compound (358 mg, 1.17 mmol) in tetrahydrofuran (4 mL) was added dropwise a solution of 1.67 mol/L n-butyllithium in hexane (0.84 ml, 1.41 mmol) at −78° C. under argon atmosphere. The mixture was stirred at the same temperature for 90 minutes, and then thereto was added a solution of N-fluorobenzene sulfonimide (553 mg, 1.76 mmol) in tetrahydrofuran (6 mL). The reaction solution was slowly warmed to room temperature, and stirred overnight. To the reaction solution was added water, and the mixture was extracted with ethyl acetate twice. The organic layer was combined, washed with water and saturated brine, dried over anhydrous sodium sulfate, and then concentrated under reduced pressure. The resulting residue was purified by silica gel column chromatography (hexane:ethyl acetate=10:0→19:1) to give an about 1:1 mixture of 3-fluoro-5-[(methoxymethoxy)methyl]-2-(trifluoromethyl)thiophene and 2-[(methoxymethoxy)methyl]-5-(trifluoromethyl)thiophene. The resulting mixture was dissolved in ethanol (2 mL), and then thereto was added 6 mol/L hydrochloric acid solution (1 mL) at room temperature. The mixture was stirred at the same temperature overnight, and then the reaction solution was alkalified by the addition of saturated aqueous sodium hydrogen carbonate solution, and then extracted with ethyl acetate twice. The organic layer was combined, washed with water and saturated brine, dried over anhydrous sodium sulfate, and then concentrated under reduced pressure. The resulting residue was purified by silica gel column chromatography (hexane:ethyl acetate=4:1→3:2) to give the title compound, [4-fluoro-5-(trifluoromethyl)-2-thienyl]methanol (34 mg, 15%) as a colorless and clear oil.

$^1$H-NMR (CDCl$_3$) δ 2.01 (1H, t, J=6.0 Hz), 4.81 (2H, d, J=6.0 Hz), 6.76 (1H, s).

Reference Example 6

Preparation of [4-(cyclopropoxy)phenyl]methanol

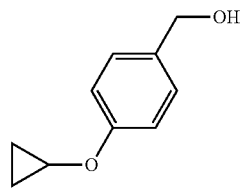 [SMILES: OCc1ccc(OC2CC2)cc1]

(1) To a solution of 1-bromo-4-(cyclopropoxy)benzene (492 mg, 2.31 mmol) in tetrahydrofuran (10 ml) was added dropwise a solution of 2.66 mol/L n-butyllithium in hexane (0.955 ml, 2.54 mmol) at −78° C. under argon atmosphere, and the mixture was stirred for 2.5 hours. Then, thereto was added dropwise N,N-dimethylformamide (0.358 ml, 4.62 mmol) at the same temperature, and the mixture was stirred for 3.5 hours with slowly warming to room temperature. To the reaction solution was added saturated aqueous ammonium chloride solution, and the mixture was stirred, and then extracted with ethyl acetate three times. The organic layer was combined, dried over anhydrous sodium sulfate, and then concentrated under reduced pressure to give a crude 4-(cyclopropoxy)benzaldehyde as a pale yellow liquid. The resulting compound was used in the next step without further purification.

(2) A solution of the above crude product in methanol (5 ml) was cooled to 0° C., and then thereto was added sodium borohydride (175 mg, 4.62 mmol), and the mixture was stirred for 1 hour. Then, thereto was added saturated brine, and then the reaction solution was concentrated under reduced pressure. The resulting residue was dissolved in ethyl acetate, washed with saturated brine, and the organic layer was dried over anhydrous sodium sulfate, and then concentrated under reduced pressure. The resulting crude product was purified by silica gel column chromatography (hexane:ethyl acetate=9:1→3:2) to give the title compound, [4-(cyclopropoxy)phenyl]methanol (216 mg, 57%, yields for 2 steps) as a white solid.
APCI-MS m/z: 182 [M+NH$_4$]$^+$.

Reference Example 7

Preparation of [4-(cyclopropylmethyl)phenyl]methanol

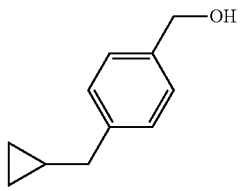 [SMILES: OCc1ccc(CC2CC2)cc1]

1-Bromo-4-(cyclopropylmethyl)benzene was treated in a similar manner to the methods of Reference examples 6-(1) and (2) to give the title compound.
APCI-MS m/z: 180[M+NH$_4$]$^+$.

Reference Example 8

Preparation of (1,1-dimethyl-2,3-dihydro-1H-inden-5-yl)methanol

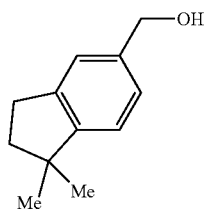 [SMILES: CC1(C)CCc2cc(CO)ccc21]

1,1-Dimethylindane-5-carbaldehyde prepared in the method of WO2006/013048A1 was treated in a similar manner to the method of Reference example 6-(2) to give the title compound.
APCI-MS m/z: 194[M+NH$_4$]$^+$.

Reference Example 9

Preparation of (3,3-dimethyl-2,3-dihydro-1-benzofuran-6-yl)methanol

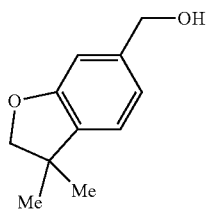 [SMILES: CC1(C)COc2cc(CO)ccc21]

To a solution of methyl 3,3-dimethyl-2,3-dihydro-1-benzofuran-6-carboxylate (44 mg, 0.21 mmol) prepared in the method of US2009/105209 in tetrahydrofuran (1.5 mL) were added lithium borohydride (23 mg, 1.07 mmol) and methanol (43 µL, 1.07 mmol) at 0° C., and the mixture was stirred at room temperature for 1 hour. To the reaction solution was added water, and the mixture was extracted with ethyl acetate twice. The organic layer was combined, washed with water and saturated brine, dried over anhydrous sodium sulfate, and then concentrated under reduced pressure to give the title compound (38 mg, 100%) as a colorless and clear oil.
APCI-MS m/z: 196 [M+NH$_4$]$^+$.

Reference Example 10

Preparation of (1,1-dimethyl-1,3-dihydro-2-benzofuran-5-yl)methanol

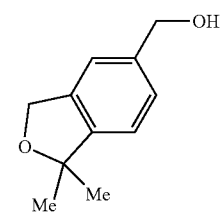 [SMILES: CC1(C)OCc2cc(CO)ccc21]

5-Bromo-1,1-dimethyl-1,3-dihydro-2-benzofuran prepared in the method of US2010/197591A1 was treated in a similar manner to the methods of Reference examples 6-(1) and (2) to give the title compound.
APCI-MS m/z: 196[M+NH$_4$]$^+$.

Reference Example 11

Preparation of (2,2-dimethyl-2,3-dihydro-1H-inden-5-yl)methanol

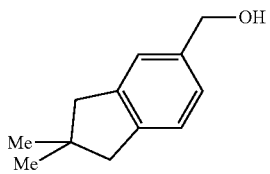 [SMILES: CC1(C)Cc2ccc(CO)cc2C1]

2,2-Dimethylindane-5-carbaldehyde prepared in the method of U.S. Pat. No. 4,952,722 was treated in a similar manner to the method of Reference example 6-(2) to give the title compound.
APCI-MS m/z: 194[M+NH$_4$]$^+$.

Reference Example 12

Preparation of 4-chloro-3-methylquinolin-2-amine

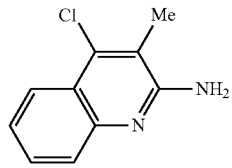 [SMILES: Cc1c(N)nc2ccccc2c1Cl]

(1) A solution of 2,4-dichloro-3-methylquinoline (1.08 g, 5.1 mmol), tris(dibenzylideneacetone)dipalladium (12 mg, 0.0025 mmol), 2,2'-bis(diphenylphosphino)-1,1'-binaphthyl (32 mg, 0.01 mmol) and sodium-t-butoxide (735 mg, 7.6 mmol) in toluene (51 mL) was stirred at room temperature for 5 minutes. To the solution was added benzophenone imine (852 μL, 5.1 mmol), and the mixture was stirred at 100° C. for 4 hours. The reaction solution was cooled to room temperature, and then thereto was added diethyl ether (10 mL). The mixture was stirred for 10 minutes. The solution was filtered through diatomaceous earth, and then concentrated under reduced pressure. The resulting residue was purified by silica gel column chromatography (hexane→hexane:ethyl acetate=10:1) to give a crude 4-chloro-N-(diphenylmethylene)-3-methylquinolin-2-amine (910 mg, 50%) as a yellow solid.

(2) The above crude compound (910 mg, 2.6 mmol) was dissolved in tetrahydrofuran (10 mL), and then thereto was added 1 mol/L hydrochloric acid solution (2 mL), and the mixture was stirred at room temperature for 1 hour. Then, thereto was added additional 1 mol/L hydrochloric acid solution (1 mL), and then the mixture was stirred for 30 minutes. To the solution was added saturated aqueous sodium bicarbonate solution, and the mixture was extracted with ethyl acetate twice. The organic layer was combined, washed with water and saturated brine, dried over anhydrous sodium sulfate, and then concentrated under reduced pressure. The resulting residue was purified by silica gel column chromatography (hexane:ethyl acetate=3:1→1:1) to give 4-chloro-3-methylquinolin-2-amine (261 mg, 53%) as a white solid.

APCI-MS m/z: 193/195 [M+H]$^+$.

Reference Example 13

Preparation of 1,7-dimethyl-1H-pyrrolo[3,2-c]pyridin-6-amine

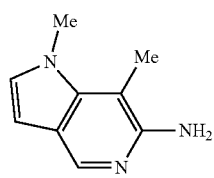 [SMILES: Cc1c(N)ncc2ccn(C)c12]

(1) To a solution of 6-chloro-7-iodo-1H-pyrrolo[3,2-c]pyridine (600 mg, 2.15 mmol) in N,N-dimethylformamide (8 mL) was added 60% sodium hydride (130 mg, 3.25 mmol) under argon atmosphere, and the mixture was stirred at room temperature for 1 hour. The reaction solution was cooled to 0° C., and then thereto was added dropwise dimethyl sulfate (250 μL, 2.64 mmol). Then, the mixture was stirred at room temperature for 3 hours. To the reaction solution was added water, and then the mixture was extracted with ethyl acetate three times. The organic layer was combined, washed with water and saturated brine, dried over anhydrous sodium sulfate, and then concentrated under reduced pressure. The resulting residue was purified by silica gel column chromatography (hexane:ethyl acetate=97:3→75:25) to give 6-chloro-7-iodo-1-methyl-1H-pyrrolo[3,2-c]pyridine (540 mg, 86%) as a colorless powder.

APCI-MS m/z: 293/295[M+H]$^+$.

(2) To a solution of the above compound (650 mg, 2.22 mmol) in tetrahydrofuran (13 mL) was added dropwise a solution of 1.65 mol/L n-butyllithium in hexane (1.75 mL, 2.89 mmol) at −78° C. under argon atmosphere. The mixture was stirred at the same temperature for 2 hours, and then thereto was added dropwise a solution of iodomethane (180 μL, 2.89 mmol) in tetrahydrofuran (4 mL), and the mixture was stirred at the same temperature for 1 hour. The reaction solution was slowly warmed to 10° C., and then to the reaction solution was added water, and the mixture was extracted with ethyl acetate three times. The organic layer was combined, washed with water and saturated brine, dried over anhydrous sodium sulfate, and then concentrated under reduced pressure. The resulting residue was purified by silica gel column chromatography (hexane:ethyl acetate=95:5→65:35) to give 6-chloro-1,7-dimethyl-1H-pyrrolo[3,2-c]pyridine (204 mg, 51%) as a colorless powder.

APCI-MS m/z: 181/183 [M+H]$^+$.

(3) A suspension of the above compound (200 mg, 1.11 mmol), benzophenone imine (560 μL, 3.35 mmol), tris(dibenzylideneacetone)dipalladium (100 mg, 0.11 mmol), 2,2'-bis(diphenylphosphino)-1,1'-binaphthyl (140 mg, 0.22 mmol) and sodium-t-butoxide (320 mg, 3.33 mmol) in toluene (10 mL) was stirred at 110° C. for 15 hours under microwave irradiation. After cooling, to the reaction solution was added water, and the mixture was extracted with ethyl acetate three times. The organic layer was combined, washed with water and saturated brine, dried over anhydrous sodium sulfate, and then concentrated under reduced pressure. The resulting residue was purified by silica gel column chromatography (hexane:ethyl acetate=98:2→40:60) to give N-(diphenylmethylene)-1,7-dimethyl-1H-pyrrolo[3,2-c]pyridin-6-amine (244 mg, 68%) as a yellow powder.

APCI-MS m/z: 326[M+H]$^+$.

(4) To a solution of the above compound (240 mg, 0.74 mmol) in tetrahydrofuran (10 mL) was added 1 mol/L hydrochloric acid solution (3.70 mL, 3.70 mmol), and the mixture was stirred at room temperature for 2 hours. The reaction solution was alkalified by the addition of saturated aqueous sodium hydrogen carbonate solution, and then thereto was added sodium chloride, and the mixture was extracted with ethyl acetate six times. The organic layer was combined, dried over anhydrous sodium sulfate, and then concentrated under reduced pressure. The resulting residue was purified by silica gel column chromatography (NH-silica gel, chloroform:methanol=100:0→95:5) to give 1,7-dimethyl-1H-pyrrolo[3,2-c]pyridin-6-amine (106 mg, 90%) as a pale yellow powder.

APCI-MS m/z: 162[M+H]$^+$.

Reference Example 14

Preparation of 4-methoxyisoquinolin-3-amine

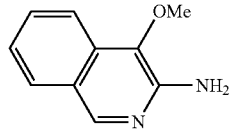 [SMILES: COc1c(N)ncc2ccccc12]

(1) To a solution of 4-methoxyisoquinoline (130 mg, 0.82 mmol) in 98% sulfuric acid (0.61 mL) was added potassium nitrate (91 mg, 0.90 mmol), and the mixture was heated to 60° C. and stirred for 2 hours. The reaction solution was cooled, and then thereto was added ice. The powders were filtered to dissolve in ethyl acetate. The solution was washed with aqueous sodium hydrogen carbonate solution and saturated brine, and then dried over anhydrous sodium sulfate, followed by concentrated under reduced pressure. The resulting residue was purified by silica gel column chromatography (hexane:ethyl acetate=9:1→2:8) to give 4-methoxy-3-nitroisoquinoline (58.3 mg, 35%) as a pale yellow powder.

APCI-MS m/z: 205[M+H]$^+$.

(2) To a mixed solution of the above compound (67.0 mg, 0.33 mmol) in acetic acid (3.3 mL) and ethanol (3.3 mL) was added reduced iron (183.0 mg, 3.28 mmol), and the mixture was heated to reflux under argon atmosphere for 2 hours. The reaction solution was cooled, and then diluted with ethyl acetate, washed with saturated aqueous sodium hydrogen carbonate solution. Then, the insoluble was filtered off. The filtrate was washed with saturated brine, and then dried over anhydrous sodium sulfate, followed by concentrated under reduced pressure. The resulting residue was purified by silica gel column chromatography (hexane:ethyl acetate=3:1→1:3) to give 4-methoxyisoquinolin-3-amine (48.1 mg, 84%) as a white powder.

APCI-MS m/z: 175[M+H]$^+$.

Reference Example 15

Preparation of 5-chloro-3-methylquinolin-2-amine

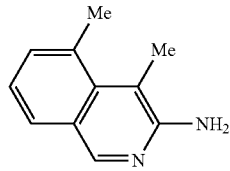 [SMILES: Cc1cccc2cnc(N)c(C)c12]

(1) A solution of diethyl(1-cyanoethyl)phosphonic acid ester (1.26 g, 8.5 mmol) in tetrahydrofuran (20 mL) was cooled to 0° C., and then thereto was added potassium-t-butoxide (744 mg, 8.5 mmol). The mixture was stirred at the same temperature for 10 minutes. Then, thereto was added 2-chloro-6-nitrobenzaldehyde (948 mg, 6.6 mmol), and then the mixture was stirred at 60° C. for 5 hours. The reaction solution was cooled to room temperature, and then to the reaction solution was added saturated aqueous sodium bicarbonate solution, and the mixture was extracted with ethyl acetate twice. The organic layer was combined, washed with water and saturated brine, dried over anhydrous sodium sulfate, and then concentrated under reduced pressure. The resulting residue was purified by silica gel column chromatography (hexane→hexane:ethyl acetate=3:1) to give 3-(2-chloro-6-nitrophenyl)-2-methylacrylonitrile (0.98 g, 86%) as a yellow oil.

APCI-MS m/z: 240/242[M+NE$_4$]$^+$ (2) To a solution of the above compound (2.0 g, 9 mmol) in ethanol (180 mL) was added tin (II) chloride dihydrate (12.2 g, 54 mmol) at room temperature, and the mixture was heated to reflux for 45 minutes. The solution was cooled to room temperature, and then thereto was added saturated aqueous hydrochloric acid solution (15 mL), and the mixture was heated to reflux for 6 hours. The solution was cooled to room temperature, and slowly added dropwise to saturated aqueous sodium bicarbonate solution. The suspension was filtered through diatomaceous earth, and the resulting solution was extracted with chloroform twice. The organic layer was combined, washed with water and saturated brine, dried over anhydrous sodium sulfate, and then concentrated under reduced pressure. To a solution of the resulting residue in ethanol (50 mL) was added sodium ethoxide (535 mg, 13.5 mmol) at room temperature, and then the mixture was heated to reflux for 4 hours. Then, thereto was added sodium ethoxide (357 mg, 9 mmol), and then the mixture was heated to reflux for 17 hours. The reaction solution was cooled to room temperature, and then to the reaction solution was added water, and the mixture was extracted with ethyl acetate twice. The organic layer was combined, washed with water and saturated brine, dried over anhydrous sodium sulfate, and then concentrated under reduced pressure. The resulting residue was purified by silica gel column chromatography (hexane:ethyl acetate=3:1→1:1) to give 5-chloro-3-methylquinolin-2-amine (457 mg, 26%) as a pale brown solid.

APCI-MS m/z: 193/195 [M+H]$^+$.

Reference Example 16

Preparation of 4,5-dimethylisoquinolin-3-amine

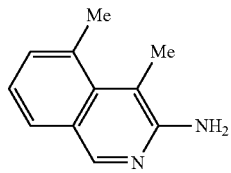 [SMILES: Cc1cccc2cnc(N)c(C)c12]

(1) A solution of sodium ethoxide (8.76 mL, 23.5 mmol, 21 wt % ethanol solution) in ethanol (10 mL) was cooled to 0° C. under argon atmosphere, and thereto was added dropwise a solution of 3-bromo-2-(cyanomethyl)benzonitrile (4.33 g, 19.6 mmol) and iodomethane (1.46 mL, 23.5 mmol) in tetrahydrofuran (10 mL) over 30 minutes, and then the mixture was stirred at room temperature for 6.5 hours. The mixture was concentrated under reduced pressure, and then the residue was neutralized by 2 mol/L hydrochloric acid, and extracted with ethyl acetate three times. The organic layer was combined, washed with saturated brine, dried over anhydrous sodium sulfate, and then concentrated under reduced pressure. The resulting residue was purified by silica gel column chromatography (ethyl acetate/hexane=10%→40%) to give 3-bromo-2-(1-cyanoethyl)benzonitrile (3.11 g, 67%) as a yellow viscous material.

APCI-MS: m/z 252/254 [M+NH$_4$]$^+$ (2) The above compound (3.11 g, 13.2 mmol), trimethylboroxine (1.85 mL, 13.2 mmol), tetrakis(triphenylphosphine)palladium (0) (306 mg, 0.265 mmol) and potassium carbonate (5.49 g, 39.7 mmol) were stirred in N,N-dimethylformamide (10 mL) at 120° C. for 6 hours under argon atmosphere. The mixture was cooled to room temperature, and then thereto was added water, and the mixture was stirred and extracted with ethyl acetate three times. The organic layer was combined, dried over anhydrous sodium sulfate, and then concentrated under reduced pressure. The resulting residue was purified by silica gel column chromatography (ethyl acetate/hexane=10%→40%) to give 2-(1-cyanoethyl)-3-methylbenzonitrile (1.99 g, 89%) as a brown solid.

APCI-MS: m/z 188 [M+NH$_4$]$^+$ (3) A suspension of the above compound (1.99 g, 11.7 mmol) in acetic acid (1 mL) was cooled to 0° C., and then thereto was added hydrogen bromide (5 mL, 25% acetic acid solution), and the mixture was stirred for 2 hours with warming to room temperature. The mixture was diluted with diisopropyl ether, and the generated solid was filtered. To the resulting solid was added saturated aqueous sodium hydrogen carbonate solution, and the mixture was stirred and the solid was filtered and dried to give a crude product. The product was suspended to wash with diisopropyl ether, and the solid was filtered, and then dried to give 1-bromo-4,5-dimethylisoquinolin-3-amine (843 mg, 29%) as a yellow powder.

APCI-MS: m/z 251/253 [M+11]$^+$ (4) To a solution of the above compound (843 mg, 3.36 mmol) in methanol-tetrahydrofuran (1:1, 10 mL) were added 10% palladium-carbon (42.2 mg) and triethylamine (0.561 mL, 4.03 mmol), and the mixture was stirred at room temperature for 2 hours under hydrogen atmosphere. The mixture was filtered through diatomaceous earth by ethyl acetate, and the filtrate was concentrated under reduced pressure. The residue was dissolved in ethyl acetate, and washed with saturated aqueous sodium hydrogen carbonate solution. The organic layer was dried over anhydrous sodium sulfate, and then concentrated under reduced pressure. The resulting residue was purified by silica gel column chromatography (ethyl acetate/hexane=25%→50%) to give 4,5-dimethylisoquinolin-3-amine (456 mg, 79%) as a yellow powder.

APCI-MS: m/z 173 [M+H]$^+$

Reference Example 17

Preparation of 4,6-dimethylisoquinolin-3-amine

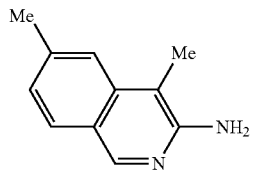

4-Bromo-2-(cyanomethyl)benzonitrile was treated in a similar manner to Reference examples 16-(1) to (4) to give 4,6-dimethylisoquinolin-3-amine as a pale yellow solid.

APCI-MS: m/z 173 [M+H]$^+$

Reference Example 18

Preparation of 4,6-dimethylisoquinolin-3-amine

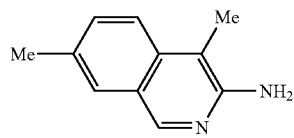

2-(cyanomethyl)-5-methylbenzonitrile was treated in a similar manner to Reference examples 16-(1), (3) and (4) to give 4,7-dimethylisoquinolin-3-amine as a yellow powder.

APCI-MS: m/z 173 [M+H]$^+$

Reference Example 19

Preparation of 4,8-dimethylisoquinolin-3-amine

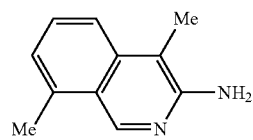

2-(Cyanomethyl)-6-methylbenzonitrile was treated in a similar manner to Reference examples 16-(1), (3) and (4) to give 4,8-dimethylisoquinolin-3-amine as a yellow powder.

APCI-MS: m/z 173 [M+H]$^+$

Reference Example 20

Preparation of 1-bromo-5-chloro-4-methylisoquinolin-3-amine

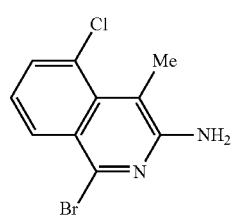 [SMILES: Cc1c(N)nc(Br)c2cccc(Cl)c12]

3-Chloro-2-(cyanomethyl)benzonitrile was treated in a similar manner to Reference examples 16-(1) and (3) to give 1-bromo-5-chloro-4-methylisoquinolin-3-amine.

APCI-MS: m/z 271/273 [M+H]$^+$

Reference Example 21

Preparation of 1-bromo-5-chloroisoquinolin-3-amine

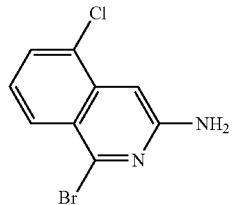

3-Chloro-2-(cyanomethyl)benzonitrile (883 g, 5 mmol) was treated in a similar manner to Reference example 16-(3) to give 1-bromo-5-chloroisoquinolin-3-amine (717 mg, 56%) as a yellow powder.
APCI-MS: m/z 257/259 [M+H]$^+$

Reference Example 22

Preparation of 5-methyl-1,7-naphthyridin-6-amine

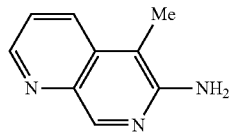 [SMILES: Cc1c(N)ncc2ncccc12]

(1) To a solution of 3-(cyanomethyl)pyridine-2-carbonitrile (synthesized by the method of *Synthesis* 1973, 47, 530 mg, 3.70 mmol) in tetrahydrofuran (14 mL) was added dropwise a solution of 1.65 mol/L n-butyllithium in hexane (2.60 mL, 4.29 mmol) at −78° C. under argon atmosphere. The mixture was stirred at the same temperature for 30 minutes, and then thereto was added dropwise iodomethane (300 µL, 4.81 mmol) in tetrahydrofuran (7 mL). The mixture was stirred at the same temperature for 1 hour. The reaction solution was slowly warmed to room temperature, and then to the reaction solution was added water, and the mixture was extracted with ethyl acetate four times. The organic layer was combined, washed with saturated brine, dried over anhydrous sodium sulfate, and then concentrated under reduced pressure. The resulting residue was purified by silica gel column chromatography (hexane:ethyl acetate=95:5→50:50) to give 3-(1-cyanoethyl)pyridine-2-carbonitrile (514 mg, 88%) as a yellow oil.
APCI-MS m/z: 175[M+NH$_4$]$^+$.
(2) The above compound was treated in a similar manner to Reference examples 16-(3) and (4) to give 5-methyl-1,7-naphthyridin-6-amine.
APCI-MS m/z: 160 [M+H]$^+$.

Reference Example 23

Preparation of 4,7-dichloro-1-methyl-1H-pyrrolo[3,2-c]pyridine

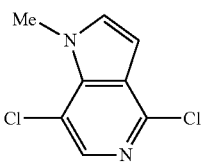 [SMILES: Cn1ccc2c(Cl)ncc(Cl)c21]

(1) To a solution of phosphorus oxychloride (6.40 µL, 73.21 mmol) in chloroform (61.2 mL) was added 2,5-dichloro-4-nitropyridine 1-oxide (3.06 g, 14.64 mmol), and the mixture was stirred under reflux overnight. The reaction solution was poured into ice, adjusted by saturated aqueous sodium hydrogen carbonate solution to pH7 to 8, and extracted with chloroform three times. The organic layer was combined, filtered through Phase-separator (Varian Inc.), and then concentrated under reduced pressure to give a crude 2,5-dichloro-4-nitropyridine (2.98 g, quant.) as a yellow oil.
(2) To a solution of vinylmagnesium bromide (54.04 mmol) in tetrahydrofuran (104 mL) was added a solution of the above crude compound (2.98 g, 15.44 mmol) in tetrahydrofuran (100 mL) at 0° C. over 40 minutes, and the mixture was stirred at room temperature for 1 hour. To the reaction solution was added saturated aqueous sodium hydrogen carbonate solution, and the mixture was extracted with ethyl acetate three times. The organic layer was combined, filtered through Phase-separator (Varian Inc.), and then concentrated under reduced pressure. The resulting residue was purified by silica gel column chromatography (hexane:ethyl acetate=80:20→50:50) to give 4,7-dichloro-1H-pyrrolo[3,2-c]pyridine (0.74 g, 27%) as a pale yellow powder.
APCI-MS m/z: 187/189[M+H]$^+$.
(3) To a solution of the above compound (300 mg, 1.60 mmol) in N,N-dimethylformamide (3 mL) were added potassium carbonate (443 mg, 3.21 mmol) and iodomethane (150 µL, 2.41 mmol), and the mixture was stirred at room temperature overnight. To the reaction solution was added water, and the mixture was extracted with ethyl acetate three times. Then, the organic layer was combined, and washed with water twice. The organic layer was filtered through Phase-separator (Varian Inc.), and then concentrated under reduced pressure. The resulting residue was purified by silica gel column chromatography (hexane:ethyl acetate=100:0→70:30) to give 4,7-dichloro-1-methyl-1H-pyrrolo[3,2-c]pyridine (240 mg, 75%) as a colorless powder.
APCI-MS m/z: 201/203 [M+H]$^+$.

Reference Example 24

Preparation of 4-bromo-1-isopropylisoquinolin-3-amine

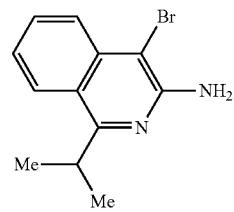 [SMILES: CC(C)c1nc(N)c(Br)c2ccccc12]

(1) 1-Bromoisoquinoline-3-amine and isopropenylboronic acid pinacol ester were treated in a similar manner to Examples 97-(1) and (2) to give 1-isopropylisoquinolin-3-amine as a white powder.
APCI-MS m/z: 187 [M+H]$^+$.
(2) A solution of the above compound (186.0 mg, 1.00 mmol) and N-bromosuccinimide (214.0 mg, 1.20 mmol) in methanol was stirred at room temperature for 1 hour. The reaction solution was concentrated under reduced pressure, and the resulting residue was purified by silica gel column chromatography (hexane:ethyl acetate=10:0→3:1) to give 4-bromo-1-isopropylisoquinolin-3-amine (155.1 mg, 58%) as a white powder.
APCI-MS m/z: 265/267[M+H]$^+$

Reference Example 25

Preparation of
4-iodo-1-isopropylisoquinolin-3-amine

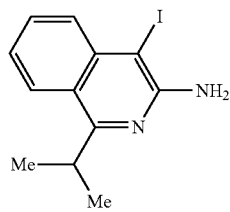 [SMILES: CC(C)c1nc(N)c(I)c2ccccc12]

(1) 1-Bromoisoquinoline-3-amine and isopropenylboronic acid pinacol ester were treated in a similar manner to Examples 97-(1) and (2) to give 1-isopropylisoquinolin-3-amine as a white powder.
APCI-MS m/z: 187 [M+H]⁺.
(2) To a solution of the above compound (146.0 mg, 0.784 mmol) in ethanol were added iodine (219.0 mg, 0.862 mmol) and silver sulfate (269.0 mg, 0.862 mmol), and the mixture was stirred at room temperature for 4 hours. The reaction solution was diluted with ethyl acetate, and the insoluble was filtered off and the filtrate was concentrated under reduced pressure. The resulting residue was purified by silica gel column chromatography (hexane:ethyl acetate=10:0→17:3) to give 4-iodo-1-isopropylisoquinolin-3-amine (78.7 mg, 32%) as a pale yellow powder.
APCI-MS m/z: 313 [M+H]⁺.

Reference Example 26

Preparation of 1,4-diisopropylisoquinolin-3-amine

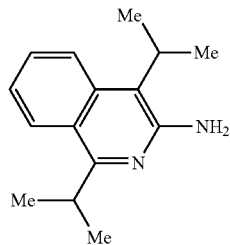 [SMILES: CC(C)c1nc(N)c(C(C)C)c2ccccc12]

4-Bromo-1-isopropylisoquinolin-3-amine obtained in Reference example 24 and isopropenylboronic acid pinacol ester were treated in a similar manner to Examples 97-(1) and (2) to give 1,4-diisopropylisoquinolin-3-amine as a white powder.
APCI-MS m/z: 229 [M+H]⁺.

Reference Example 27

Preparation of
4-bromo-1-cyclopropylisoquinolin-3-amine

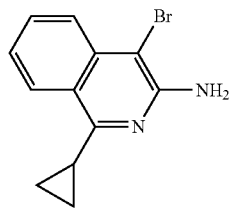 [SMILES: Nc1nc(C2CC2)c2ccccc2c1Br]

(1) 1-Bromoisoquinoline-3-amine was treated in a similar manner to Example 9-(2) to give 1-cyclopropylisoquinolin-3-amine as a white powder.
APCI-MS m/z: 185 [M+H]⁺
(2) The above compound was treated in a similar manner to Reference example 24-(2) to give 4-bromo-1-cyclopropylisoquinolin-3-amine as a white powder.
APCI-MS m/z: 263/265 [M+H]⁺.

Reference Example 28

Preparation of 4-cyclopropylisoquinolin-3-amine

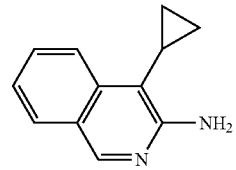 [SMILES: Nc1ncc2ccccc2c1C1CC1]

4-Bromoisoquinoline-3-amine was treated in a similar manner to Example 103 to give 4-cyclopropylisoquinolin-3-amine as a pale yellow powder.
APCI-MS m/z: 185 [M+H]⁺.

Reference Example 29

Preparation of
[4-(cyclopropylmethyl)-2-fluorophenyl]methanol

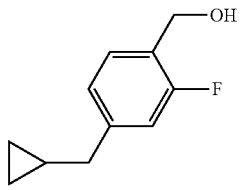 [SMILES: OCc1ccc(CC2CC2)cc1F]

(1) Methyl 4-bromo-2-fluorobenzoate (424 mg, 1.82 mmol), allyl tributyl tin (0.846 mL, 2.73 mmol), tetrakis(triphenylphosphine)palladium (0) (105 mg, 0.091 mmol) and cesium fluoride (415 mg, 2.73 mmol) were heated to reflux in 1,4-dioxane (10 mL) for 7 hours under argon atmosphere. The mixture was cooled to room temperature, and then filtered through diatomaceous earth by ethyl acetate and the filtrate was concentrated under reduced pressure. The residue was purified by silica gel column chromatography (ethyl acetate/hexane=2%→10%) to give methyl 4-allyl-2-fluorobenzoate (333 mg, 94%) as a pale yellow viscous material.
APCI-MS: m/z 195 [M+H]⁺
(2) To a solution of the above compound (333 mg, 1.71 mmol) in 1,2-dichloroethane (10 mL) was added chloroiodomethane (1.25 mL, 17.1 mmol) under argon atmosphere, and then thereto slowly added dropwise diethylzinc (8.57 mL, 8.57 mmol, hexane solution), and the mixture was stirred for 16 hours at room temperature and for 7 hours at 50° C. The mixture was cooled to room temperature, and then thereto was added saturated ammonium chloride solution, and the mixture was extracted with chloroform three times. The organic layer was dried over anhydrous sodium sulfate, and then concentrated under reduced pressure. The resulting residue was stirred in the mixture of microcapsulated osmium tetraoxide (219 mg, 0.0865 mmol), N-methylmorpholine-N-oxide (260 mg, 2.22 mmol) and acetone-acetonitrile-water (1:1:1, 6 mL) at room temperature for 21 hours. The mixture was filtered and concentrated to give a crude product, and then the product was purified by silica gel column chromatography (ethyl acetate/hexane=2%→15%) to give methyl 4-(cyclopropylmethyl)-2-fluorobenzoate (155 mg, 44%) as a colorless liquid.
APCI-MS: m/z 209 [M+H]⁺

(3) To a solution of the above compound (155 mg, 0.744 mmol) in tetrahydrofuran (5 mL) were added lithium borohydride (81.1 mg, 3.72 mmol) and methanol (0.151 mL, 3.72 mmol) at 0° C. under argon atmosphere, and the mixture was stirred at room temperature for 3 days. Then, thereto was added saturated brine, and the mixture was extracted with ethyl acetate three times, followed by dried over anhydrous sodium sulfate and concentrated under reduced pressure. The residue was purified by silica gel column chromatography (ethyl acetate/hexane=15%→40%) to give [4-(cyclopropylmethyl)-2-fluorophenyl]methanol (126 mg, 94%) as a colorless liquid.

APCI-MS: m/z 198 [M+NH$_4$]$^+$

Reference Example 30

Preparation of [4-(cyclopropylmethyl)-3-fluorophenyl]methanol

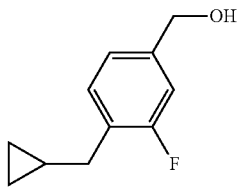 [SMILES: OCc1ccc(CC2CC2)c(F)c1]

Methyl 4-bromo-3-fluorobenzoate was treated in a similar manner to Reference examples 29-(1) to (3) to give [4-(cyclopropylmethyl)-3-fluorophenyl]methanol as a colorless liquid.

APCI-MS: m/z 198 [M+NH$_4$]$^+$

Reference Example 31

Preparation of (4-{[1-(trifluoromethyl)cyclopropyl]methyl}phenyl)methanol

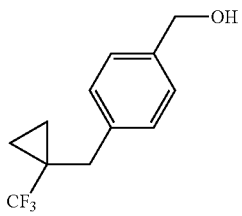 [SMILES: OCc1ccc(CC2(C(F)(F)F)CC2)cc1]

(1) To a solution of 4-bromoiodobenzene (2150 mg, 7.60 mmol) in tetrahydrofuran (20 mL) was added dropwise a solution of 1.67 mol/L n-butyllithium in hexane (4.50 mL, 7.52 mmol) at −78° C. under argon atmosphere. The mixture was stirred at the same temperature for 1 hour, and then thereto was added dropwise a solution of N-methoxy-N-methyl-1-(trifluoromethyl)cyclopropanecarboxamide (synthesized by the method of Organic Process Research and Development 2009, 13, 576, 1000 mg, 5.07 mmol) in tetrahydrofuran (10 mL), and the mixture was stirred at the same temperature for 1 hour. To the reaction solution was added saturated aqueous ammonium chloride solution at −78° C., and then the mixture was warmed to room temperature and extracted with ethyl acetate three times. The organic layer was combined, washed with water and saturated brine, dried over anhydrous sodium sulfate, and then concentrated under reduced pressure. The resulting residue was purified by silica gel column chromatography (hexane:ethyl acetate=100:0→95:5) to give (4-bromophenyl)[1-(trifluoromethyl)cyclopropyl]methanone (783 mg, 76%) as a pale brown oil.

$^1$H-NMR (CDCl$_3$) δ 1.36-1.50 (4H, m), 7.61 (2H, d, J=8.7 Hz), 7.79 (2H, d, J=8.7 Hz).

(2) To a solution of the above compound (780 mg, 3.26 mmol) in ethanol (10 mL) was added 78% hydrazine monohydrate (1000 μL, 16.1 mmol). The reaction solution was heated to reflux overnight, and cooled to room temperature, and then to the reaction solution was added water, and the mixture was extracted with ethyl acetate three times. The organic layer was combined, washed with water and saturated brine, dried over anhydrous sodium sulfate, and then concentrated under reduced pressure to give a crude (4-bromophenyl)[1-(trifluoromethyl)cyclopropyl]methanone hydrazone (784 mg) as a pale brown oil. The resultant was used in the next step without further purification.

APCI-MS m/z: 307/309[M+Na$_4$]$^+$ (3) To a solution of the above crude product (775 mg) in ethylene glycol (8 mL) was added potassium hydroxide (580 mg, 10.3 mmol), and the mixture was heated to stir at 180° C. for 2 hours. The mixture was cooled to room temperature, and then to the reaction solution was added water, and the mixture was extracted with diethyl ether three times. The organic layer was combined, washed with 2 mol/L hydrochloric acid solution, water and saturated brine, dried over anhydrous sodium sulfate, and then concentrated under reduced pressure. The resulting residue was purified by silica gel column chromatography (hexane) to give 1-bromo-4-{[1-(trifluoromethyl)cyclopropyl]methyl}benzene (148 mg, 21%, yields for two steps) as a colorless oil.

$^1$H-NMR (CDCl$_3$) δ 0.48-0.53 (2H, m), 0.92-0.97 (2H, m), 2.95 (2H, s), 7.04 (2H, d, J=8.2 Hz), 7.42 (2H, d, J=8.2 Hz).

(4) To a mixed solution of the above compound (145 mg, 0.52 mmol), palladium acetate (15 mg, 0.07 mmol), 1,1'-bis(diphenylphosphino)ferrocene (75 mg, 0.14 mmol) in N,N-dimethylformamide (5 mL) and methanol (1.1 mL) was added triethylamine (200 μL, 1.43 mmol). The reaction solution was stirred under carbon monoxide atmosphere at 90° C. overnight. The solution was cooled to room temperature, and then to the reaction solution was added water, and the mixture was extracted with ethyl acetate three times. The organic layer was combined, washed with water and saturated brine, dried over anhydrous sodium sulfate, and then concentrated under reduced pressure. The resulting residue was purified by silica gel column chromatography (hexane:ethyl acetate=98:2→90:10) to give methyl 4-{[1-(trifluoromethyl)cyclopropyl]methyl}benzoate (129 mg, 96%) as a colorless oil.

APCI-MS m/z: 259[M+H]$^+$.

(5) To a solution of the above compound (110 mg, 0.43 mmol) in tetrahydrofuran (4 mL) and methanol (110 μL, 2.71 mmol) was added lithium borohydride (60 mg, 2.75 mmol) at 0° C. The mixture was stirred at room temperature overnight, and then to the reaction solution was added water at 0° C., and the mixture was extracted with ethyl acetate three times. The organic layer was combined, washed with water and saturated brine, dried over anhydrous sodium sulfate, and then concentrated under reduced pressure to give a crude (4-{[1-(trifluoromethyl)cyclopropyl]methyl}phenyl)methanol (103 mg) as a colorless oil. The resultant was used in the next step without further purification.

APCI-MS mz: 248[M+NH$_4$]$^+$.

Reference Example 32

Preparation of {4-[cyclopropyl(difluoro)methyl]phenyl}methanol

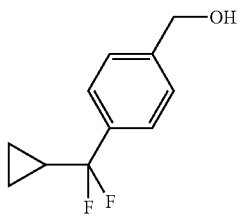 [SMILES: OCc1ccc(C(F)(F)C2CC2)cc1]

(1) To a mixed solution of (4-bromophenyl)(cyclopropyl)methanone (synthesized by the method of Pesticide Science 1980, 11, 513, 5.00 g, 22.0 mmol), palladium acetate (0.52 g, 2.3 mmol) and 1,1'-bis(diphenylphosphino)ferrocene (2.50 g, 4.5 mmol) in N,N-dimethylformamide (150 mL) and methanol (40 mL) was added triethylamine (6.7 mL, 48.1 mmol). The reaction solution was stirred under carbon monoxide atmosphere at 90° C. overnight. The solution was cooled to room temperature, and then to the reaction solution was added water, and the mixture was extracted with ethyl acetate three times. The organic layer was combined, washed with water and saturated brine, dried over anhydrous sodium sulfate, and then concentrated under reduced pressure. The resulting residue was purified by silica gel column chromatography (hexane:ethyl acetate=98:2→80:20) to give methyl 4-(cyclopropylcarbonyl)benzoate (4.28 g, 94%) as a colorless powder.

APCI-MS m/z: 205[M+H]$^+$.

(2) The above compound (1000 mg, 4.90 mmol) was dissolved in bis(2-methoxyethyl)aminosulfuric acid trifluoride (8.0 mL, 43.4 mmol) in test tubes made of fluororesin. Then, thereto was added dropwise methanol (60 μL, 1.48 mmol) at 0° C., and then the mixture was heated to stir at 80° C. for 8 days. The reaction solution was cooled, and then thereto was added dropwise saturated aqueous sodium hydrogen carbonate solution at 0° C., and the mixture was extracted with ethyl acetate three times. The organic layer was combined, washed with water and saturated brine, dried over anhydrous sodium sulfate, and then concentrated under reduced pressure. The resulting residue was purified by silica gel column chromatography (hexane:ethyl acetate=98:2→90:10) to give methyl 4-[cyclopropyl(difluoro)methyl]benzoate (924 mg, 84%) as a pale yellow oil.

$^1$H-NMR (DMSO-$d_6$) δ 0.64-0.74 (4H, m), 1.66-1.79 (1H, m), 3.88 (3H, s), 7.72 (2H, d, J=8.8 Hz), 8.07 (2H, d, J=8.8 Hz).

(3) To a solution of the above compound (920 mg, 4.07 mmol) in tetrahydrofuran (25 mL) were added lithium borohydride (340 mg, 15.6 mmol) and methanol (630 μL, 15.5 mmol) at 0° C. The mixture was stirred at room temperature overnight, and then to the reaction solution was added water at 0° C., and the mixture was extracted with ethyl acetate three times. The organic layer was combined, washed with water and saturated brine, dried over anhydrous sodium sulfate, and then concentrated under reduced pressure. The resulting residue was purified by silica gel column chromatography (hexane:ethyl acetate=95:5→65:35) to give {4-[cyclopropyl(difluoro)methyl]phenyl}methanol (905 mg, 98%) as a colorless oil.

$^1$H-NMR (DMSO-$d_6$) δ 0.58-0.71 (4H, m), 1.61-1.75 (1H, m), 4.54 (2H, d, J=5.7 Hz), 5.29 (1H, t, J=5.7 Hz), 7.42 (2H, d, J=8.8 Hz), 7.50 (2H, d, J=8.5 Hz).

Reference Example 33

Preparation of {3-[cyclopropyl(difluoro)methyl]phenyl}methanol

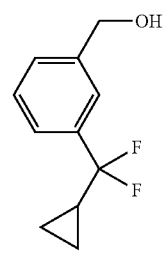 [SMILES: OCc1cccc(C(F)(F)C2CC2)c1]

Ethyl 3-(cyclopropylcarbonyl)benzoate (synthesized by the method of WO2006/067445) was treated in a similar manner to Reference examples 32-(2) and (3) to give {3-[cyclopropyl(difluoro)methyl]phenyl}methanol.

$^1$H-NMR (DMSO-$d_6$) δ 0.60-0.72 (4H, m), 1.61-1.75 (1H, m), 4.55 (2H, d, J=5.1 Hz), 5.32 (1H, t, J=5.4 Hz), 7.39-7.45 (3H, m), 7.50 (1H, s).

Reference Example 34

Preparation of {4-[difluoro(1-methylcyclopropyl)methyl]phenyl}methanol

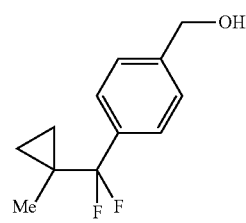 [SMILES: CC1(C(F)(F)c2ccc(CO)cc2)CC1]

(1) To a solution of methyl 4-(cyclopropylcarbonyl)benzoate (500 mg, 2.45 mmol) in tetrahydrofuran (12 mL) was added dropwise a solution of 1 mol/L lithium hexamethyldisilazane in tetrahydrofuran (3.0 mL, 3.00 mmol) at −78° C. under argon atmosphere, and the mixture was stirred for 15 minutes. To the mixture was added dropwise iodomethane (200 μL, 3.21 mmol) at the same temperature, and the reaction solution was slowly warmed to room temperature and stirred overnight. To the reaction solution was added saturated aqueous ammonium chloride solution, and the mixture was extracted with ethyl acetate three times. The organic layer was combined, washed with water and saturated brine, dried over anhydrous sodium sulfate, and then concentrated under reduced pressure. The resulting residue was purified by silica gel column chromatography (hexane:ethyl acetate=100:0→97:3) to give methyl 4-[(1-methylcyclopropyl)carbonyl]benzoate (45 mg, 8%) as a colorless oil.

APCI-MS m/z: 219[M+H]$^+$.

(2) Methyl 4-[(1-methylcyclopropyl)carbonyl]benzoate was treated in a similar manner to Reference examples 32-(2) and (3) to give {4-[difluoro(1-methylcyclopropyl)methyl]phenyl}methanol.

APCI-MS m/z: 230[M+NH$_4$]$^+$.

Reference Example 35

Preparation of {4-[cyclopropyl(difluoro)methyl]-3-fluorophenyl}methanol

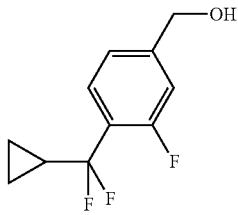 [SMILES: OCc1ccc(C(F)(F)C2CC2)c(F)c1]

(4-Bromo-2-fluorophenyl)cyclopropylketone was treated in a similar manner to Reference examples 32-(1), (2) and (3) to give {4-[cyclopropyl(difluoro)methyl]-3-fluorophenyl}methanol.

$^1$H-NMR (DMSO-$d_6$) δ 0.60-0.74 (4H, m), 1.69-1.84 (1H, m), 4.55 (2H, d, J=4.2 Hz), 5.43 (1H, t, J=5.3 Hz), 7.23 (1H, s), 7.26 (1H, d, J=6.7 Hz), 7.51 (1H, t, J=8.0 Hz).

Reference Example 36

Preparation of

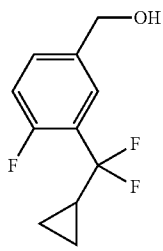 [SMILES: OCc1ccc(F)c(C(F)(F)C2CC2)c1]

(5-Bromo-2-fluorophenyl)(cyclopropyl)methanone (synthesized by the method of Bioorganic & Medicinal Chemistry Letters 2010, 20, 1652) was treated in a similar manner to Reference examples 32-(1), (2) and (3) to give {3-[cyclopropyl(difluoro)methyl]-4-fluorophenyl}methanol.

$^1$H-NMR (DMSO-$d_6$) δ 0.61-0.74 (4H, m), 1.69-1.84 (1H, m), 4.51 (2H, d, J=4.8 Hz), 5.35 (1H, t, J=5.6 Hz), 7.29 (1H, dd, J=11.2, 8.5 Hz), 7.45-7.52 (2H, m).

Reference Example 37

Preparation of {3-chloro-4-[cyclopropyl(difluoro)methyl]phenyl}methanol

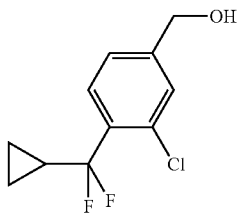 [SMILES: OCc1ccc(C(F)(F)C2CC2)c(Cl)c1]

(1) To a solution of 4-bromo-2-chloro-N-methoxy-N-methylbenzamide (synthesized by the method of Bioorganic & Medicinal Chemistry Letters 2003, 13, 3983, 5.90 g, 21.0 mmol) in tetrahydrofuran (180 mL) was added dropwise a solution of 0.7 mol/L cyclopropylmagnesium bromide in tetrahydrofuran (65.0 mL, 45.5 mmol) at 0° C. The mixture was stirred at the same temperature for 4 hours, and then to the reaction solution was added saturated aqueous ammonium chloride solution, and the mixture was extracted with ethyl acetate three times. The organic layer was combined, washed with water and saturated brine, dried over anhydrous sodium sulfate, and then concentrated under reduced pressure. The resulting residue was purified by silica gel column chromatography (hexane:ethyl acetate=100:0→93:7) to give (4-bromo-2-chlorophenyl)(cyclopropyl)methanone (3.75 g, 68%) as a pale yellow oil.

APCI-MS m/z: 259/261/263 [M+H]$^+$.

(2) (4-Bromo-2-chlorophenyl)(cyclopropyl)methanone was treated in a similar manner to Reference examples 32-(1), (2) and (3) to give {3-chloro-4-[cyclopropyl(difluoro)methyl]phenyl}methanol.

$^1$H-NMR (DMSO-$d_6$) δ 0.62-0.74 (4H, m), 1.84-1.98 (1H, m), 4.54 (2H, d, J=4.5 Hz), 5.42 (1H, t, J=5.4 Hz), 7.37 (1H, d, J=8.1 Hz), 7.50 (1H, s), 7.58 (1H, d, J=7.9 Hz).

Reference Example 38

Preparation of {4-[cyclobutyl(difluoro)methyl]phenyl}methanol

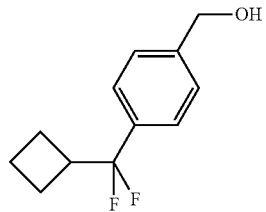 [SMILES: OCc1ccc(C(F)(F)C2CCC2)cc1]

To a solution of ethyl 4-[cyclobutyl(difluoro)methyl]benzoate (synthesized by the method of WO2005/032465, 140 mg, 0.55 mmol) in tetrahydrofuran (5 mL) and methanol (112 µL, 2.76 mmol) was added lithium borohydride (60 mg, 2.75 mmol) at 0° C. The mixture was stirred at room temperature for 3 hours, and then to the reaction solution was added water at 0° C., and the mixture was extracted with ethyl acetate three times. The organic layer was combined, washed with water and saturated brine, dried over anhydrous sodium sulfate, and then concentrated under reduced pressure to give a crude {4-[cyclobutyl(difluoro)methyl]phenyl}methanol (111 mg) as a colorless oil. The resultant was used in the next step without further purification.

APCI-MS m/z: 230[M+NH$_4$]$^+$.

Reference Example 39

Preparation of 1-cyclopropyl-2,2,2-trifluoro-1-[4-(hydroxymethyl)phenyl]ethanol

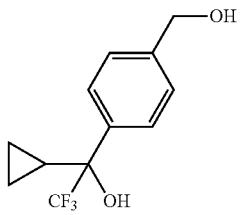 [SMILES: OCc1ccc(C(O)(C2CC2)C(F)(F)F)cc1]

(1) To a solution of (4-bromophenyl)(cyclopropyl)methanone (587 mg, 2.60 mmol) in tetrahydrofuran (5.2 mL) were added molecular sieves 4 Å (500 mg), trimethylsilyl trifluoromethane (772 μL, 5.20 mmol) and tetrabutylammonium fluoride (tetrahydrofuran solution, 1 mol/L, 3.9 mL, 3.90 mmol) at 0° C., and the mixture was stirred at room temperature for 18 hours. The solution was filtered through diatomaceous earth, and then thereto was added 1 mol/L hydrochloric acid solution (10 mL), and the mixture was extracted with ethyl acetate twice. The organic layer was combined, washed with saturated brine, dried over anhydrous sodium sulfate, and then concentrated under reduced pressure. The resulting residue was purified by silica gel column chromatography (hexane:ethyl acetate=20:1→5:1) to give 1-(4-bromophenyl)-1-cyclopropyl-2,2,2-trifluoroethanol (747 mg, 97%) as a colorless oil.

APCI-MS m/z: 353/355[M+$CH_3COO$]⁻.

(2) The above compound (747 mg, 2.53 mmol) was treated in a similar manner to Reference examples 6-(1) and (2) to give 1-cyclopropyl-2,2,2-trifluoro-1-[4-(hydroxymethyl)phenyl]ethanol (112 mg, 18%) as a colorless oil.

ESI-MS m/z: 353/355[M-H]⁻.

Reference Example 40

Preparation of {4-[(trifluoromethoxy)methyl]phenyl}methanol

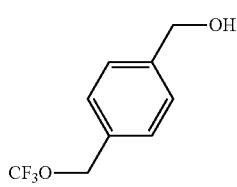

(1) To a solution of 4-[(trifluoromethoxy)methyl]benzoic acid (500 mg, 2.27 mmol) in N,N-dimethylformamide (25 mL) were added iodomethane (300 μL, 4.82 mmol) and potassium carbonate (1000 mg, 7.24 mmol). The mixture was stirred at room temperature overnight, and then to the reaction solution was added water, and the mixture was extracted with ethyl acetate three times. The organic layer was combined, washed with water and saturated brine, dried over anhydrous sodium sulfate, and then concentrated under reduced pressure. The resulting residue was purified by silica gel column chromatography (hexane:ethyl acetate=99:1→80:20) to give methyl 4-[(trifluoromethoxy)methyl]benzoate (453 mg, 85%) as a pale brown oil.

APCI-MS m/z: 235[M+H]⁺.

(2) To a solution of the above compound (450 mg, 1.92 mmol) in tetrahydrofuran (5 mL) and methanol (130 μL, 3.20 mmol) was added lithium borohydride (70 mg, 3.20 mmol) at 0° C. The mixture was stirred at room temperature overnight, and then to the reaction solution was added water at 0° C., and the mixture was extracted with ethyl acetate three times. The organic layer was combined, washed with water and saturated brine, dried over anhydrous sodium sulfate, and then concentrated under reduced pressure. The resulting residue was purified by silica gel column chromatography (hexane:ethyl acetate=85:15) to give {4-[(trifluoromethoxy)methyl]phenyl}methanol (239 mg, 60%) as a colorless solid.

APCI-MS m/z: 224 [M+$NH_4$]⁺.

Reference Example 41

Preparation of 1,1,1-trifluoro-2-[2-fluoro-4-(hydroxymethyl)phenyl]propan-2-ol

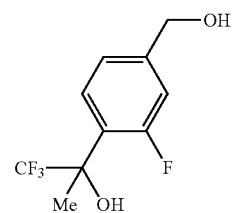 [SMILES: CC(O)(c1ccc(CO)cc1F)C(F)(F)F]

(1) To a mixed solution of 1-(4-bromo-2-fluorophenyl)ethanone (1.00 g, 4.5 mmol), palladium acetate (0.12 g, 0.54 mmol) and 1,1'-bis(diphenylphosphino)ferrocene (0.50 g, 0.90 mmol) in N,N-dimethylacetamide (22 mL) and methanol (7 mL) was added triethylamine (1.3 mL, 9.2 mmol). The reaction solution was stirred under carbon monoxide atmosphere at 90° C. overnight. The solution was cooled to room temperature, and then the reaction solution was filtered through diatomaceous earth and silica gel, and then concentrated under reduced pressure. The resulting residue was purified by silica gel column chromatography (hexane:ethyl acetate=100:0→60:40) to give methyl 4-acetyl-3-fluorobenzoate (0.83 g, 93%) as a pale yellow powder.

APCI-MS m/z: 194[M+H]⁺.

(2) To a solution of the above compound (825 mg, 4.21 mmol) in tetrahydrofuran (8.4 mL) were added trimethylsilyl trifluoromethane (1240 μL, 8.41 mmol) and tetrabutylammonium fluoride (tetrahydrofuran solution, 1 mol/L, 6.3 mL, 6.31 mmol) at 0° C., and the mixture was stirred at room temperature for 3 hours. To the solution was added 1 mol/L hydrochloric acid solution, and the mixture was extracted with ethyl acetate three times. The organic layer was combined, filtered through Phase-separator (Varian Inc.), and then concentrated under reduced pressure. The resulting residue was purified by silica gel column chromatography (hexane:ethyl acetate=100:0→60:40) to give methyl 3-fluoro-4-(2,2,2-trifluoro-1-hydroxy-1-methylethyl)benzoate (650 mg, 58%) as a pale yellow oil.

ESI-MS m/z: 324[M-H]⁻.

(3) To a solution of the above compound (648 mg, 2.43 mmol) in tetrahydrofuran (4 mL) was added lithium aluminum hydride (110 mg, 2.92 mmol) at 0° C. The mixture was stirred at room temperature for 5 hours, and then to the reaction solution were added water and 2N aqueous sodium hydroxide solution at 0° C., and the mixture was filtered through diatomaceous earth. The filtrate was extracted with ethyl acetate three times. The organic layer was combined, filtered through Phase-separator (Varian Inc.), and then concentrated under reduced pressure. The resulting residue was purified by silica gel column chromatography (hexane:ethyl acetate=80:20→40:60) to give 1,1,1-trifluoro-2-[2-fluoro-4-(hydroxymethyl)phenyl]propan-2-ol (494 mg, 85%) as a colorless powder.

APCI-MS m/z: 256[M+NH$_4$]$^+$.

Reference Example 42

Preparation of 2-[2-chloro-4-(hydroxymethyl)phenyl]-1,1,1-trifluoropropan-2-ol

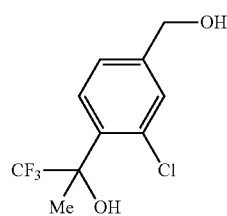 [SMILES: CC(O)(c1ccc(CO)cc1Cl)C(F)(F)F]

(1) To a solution of 4-acetyl-3-chlorobenzoic acid (synthesized by the method of Tetrahedron 1988, 44, 1631, 700 mg, 3.52 mmol) in N,N-dimethylformamide (4 mL) were added potassium carbonate (974 mg, 7.05 mmol) and iodomethane (658 µL, 10.57 mmol) at room temperature, and the mixture was stirred at room temperature for 1 hour. To the reaction solution was added water, and the mixture was extracted with ethyl acetate three times. The organic layer was combined, filtered through Phase-separator (Varian Inc.), and then concentrated under reduced pressure. The resulting residue was purified by silica gel column chromatography (hexane:ethyl acetate=100:0→75:25) to give methyl 4-acetyl-3-chlorobenzoate (707 mg, 94%) as a pale yellow powder.

APCI-MS m/z: 213/215 [M+H]$^+$.

(2) Methyl 4-acetyl-3-chlorobenzoate was treated in a similar manner to Reference examples 41-(2) and (3) to give 2-[2-chloro-4-(hydroxymethyl)phenyl]-1,1,1-trifluoropropan-2-ol.

APCI-MS m/z: 272/274[M+NH$_4$]$^+$.

Reference Example 43

Preparation of 3,3,4,4,4-pentafluoro-2-[4-(hydroxymethyl)phenyl]butan-2-ol

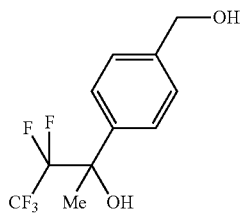 [SMILES: CC(O)(c1ccc(CO)cc1)C(F)(F)C(F)(F)F]

(1) To a solution of methyl 4-acetylbenzoate (700 mg, 3.85 mmol) in tetrahydrofuran (7.7 mL) were added (pentafluoroethyl)trimethylsilane (1370 mg, 6.93 mmol) and tetrabutylammonium fluoride (tetrahydrofuran solution, 1 mol/L, 5.7 µL, 5.78 mmol) at 0° C., and the mixture was stirred at room temperature overnight. To the solution was added 1 mol/L hydrochloric acid solution, and the mixture was extracted with ethyl acetate three times. The organic layer was combined, filtered through Phase-separator (Varian Inc.), and then concentrated under reduced pressure. The resulting residue was purified by silica gel column chromatography (hexane:ethyl acetate=100:0→70:30) to give methyl 4-(2,2,3,3,3-pentafluoro-1-hydroxy-1-methylpropyl)benzoate (765 mg, 67%) as a pale yellow viscous material.

APCI-MS m/z: 316[M+NH$_4$]$^+$.

(2) To a solution of the above compound (760 mg, 2.55 mmol) in tetrahydrofuran (13 mL) were added lithium borohydride (278 mg, 12.7 mmol) and methanol (6516 µL, 12.7 mmol) at 0° C. The mixture was stirred at room temperature overnight, and then to the reaction solution was added water at 0° C., and the mixture was extracted with ethyl acetate three times. The organic layer was combined, filtered through Phase-separator (Varian Inc.), and then concentrated under reduced pressure. The resulting residue was purified by silica gel column chromatography (hexane:ethyl acetate=100:0→60:40) to give 3,3,4,4,4-pentafluoro-2-[4-(hydroxymethyl)phenyl]butan-2-ol (580 mg, 84%) as a colorless powder.

APCI-MS m/z: 288[M+NH$_4$]$^+$.

Reference Example 44

Preparation of (7-fluoro-2,3-dihydro-1H-inden-5-yl)methanol

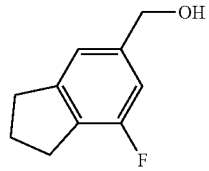 [SMILES: OCc1cc(F)c2c(c1)CCC2]

(1) To a solution of 6-bromo-4-fluoroindan-1-one (57 mg, 0.26 mmol) in trifluoroacetic acid (1.1 mL) was added triethylsilane (103 µL, 0.65 mmol), and the mixture was stirred at room temperature overnight. The reaction solution was poured into ice water, and the mixture was extracted with ethyl acetate three times. The organic layer was combined, washed with saturated aqueous sodium hydrogen carbonate solution, and the organic layer was filtered through Phase-separator (Varian Inc.), and then concentrated under reduced pressure. The resulting residue was purified by silica gel column chromatography (hexane:ethyl acetate=100:0) to give a crude 6-bromo-4-fluoroindane (61 mg) as a yellow oil. The resultant was used in the next step without further purification.

(2) The above crude product was treated in a similar manner to Reference example 41-(1) to give a crude methyl 7-fluoroindane-5-carboxylate. The resultant was used in the next step without further purification.

(3) The above crude product was treated in a similar manner to Reference example 43-(2) to give a crude (7-fluoro-2,3-dihydro-1H-inden-5-yl)methanol. The resultant was used in the next step without further purification.

Reference Example 45

Preparation of
5-(hydroxymethyl)-1-(trifluoromethyl)indan-1-ol

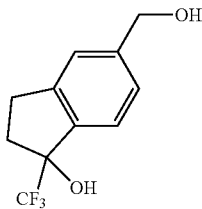 [SMILES: OCc1ccc2c(c1)CCC2(O)C(F)(F)F]

5-Bromoindan-1-one was treated in a similar manner to Reference examples 41-(1), (2) and (3) to give 5-(hydroxymethyl)-1-(trifluoromethyl)indan-1-ol.
APCI-MS m/z: 250[M+NH$_4$]$^+$.

Reference Example 46

Preparation of
[5-(cyclopropylmethyl)pyrimidin-2-yl]methanol

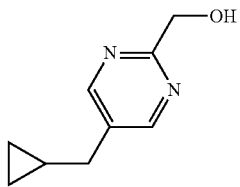 [SMILES: OCc1ncc(CC2CC2)cn1]

(1) To a solution of 2-(methylthio)pyridine-5-carbaldehyde (2000 mg, 12.97 mmol) in tetrahydrofuran (20 mL) was added a solution of 0.5 mol/L cyclopropylmagnesium bromide in tetrahydrofuran (28.6 mL) at −40° C. under argon atmosphere. The reaction solution was stirred at the same temperature for 10 minutes, and then slowly warmed to 0° C. and stirred for 1 hour. To the reaction solution was added aqueous ammonium chloride solution, and the mixture was extracted with ethyl acetate. The organic layer was washed with saturated brine, dried over anhydrous sodium sulfate, and then concentrated under reduced pressure. The resulting residue was purified by silica gel column chromatography (hexane:ethyl acetate=70:30→60:70) to give cyclopropyl[2-(methylthio)pyrimidin-5-yl]methanol (822 mg, 32%) as a colorless oil.
APCI-MS m/z: 197[M+H]$^+$ (2) To a solution of the above compound (815 mg, 4.15 mmol) in chloroform (12 mL) was added triethylsilane (1.99 mL, 12.46 mmol) at room temperature. To the reaction solution was added dropwise trifluoroacetic acid (1.54 mL, 20.15 mmol) under ice cooling, and then the mixture was slowly warmed to room temperature and stirred for 4 days. To the reaction solution was added saturated aqueous sodium bicarbonate solution, and the mixture was extracted with ethyl acetate. The organic layer was washed with saturated brine, dried over anhydrous sodium sulfate, and then concentrated under reduced pressure. The resulting residue was purified by silica gel column chromatography (hexane:ethyl acetate=95:5→75:25) to give 5-(cyclopropylmethyl)-2-(methylthio)pyrimidine (229 mg, 31%) as a colorless oil.
APCI-MS m/z: 181[M+H]$^+$ (3) To a solution of the above compound (225 mg, 1.25 mmol) in dichloromethane (5 mL) was added dropwise a solution of metachloroperoxybenzoic acid (624 mg, 2.50 mmol) in dichloromethane (5 mL) at 0° C. The reaction solution was slowly warmed to room temperature and stirred for 1 hour and 30 minutes, and then thereto was added aqueous sodium thiosulfate solution, and the mixture was stirred for additional 30 minutes. To the reaction solution was added saturated aqueous sodium bicarbonate solution, and the mixture was extracted with ethyl acetate. The organic layer was washed with saturated brine, dried over anhydrous sodium sulfate, and then concentrated under reduced pressure. The resulting residue was purified by silica gel column chromatography (hexane:ethyl acetate=70:30→65:65) to give 5-(cyclopropylmethyl)-2-(methylsulfonyl)pyrimidine (173 mg, 65%) as a colorless oil.
APCI-MS m/z: 213[M+H]$^+$ (4) To a solution of the above compound (169 mg, 0.796 mmol) in dichloromethane (4 mL) was added tetrabutylammonium cyanide (235 mg, 0.876 mmol) at room temperature, and the mixture was stirred at the same temperature overnight. To the reaction solution was added tetrabutylammonium cyanide (85 mg), and the mixture was stirred for additional 3 hours, and then thereto was added saturated aqueous sodium bicarbonate solution, and the mixture was extracted with ethyl acetate. The organic layer was washed with saturated brine, dried over anhydrous sodium sulfate, and then concentrated under reduced pressure. The resulting residue was purified by silica gel column chromatography (hexane:ethyl acetate=95:5→80:20) to give a crude 5-(cyclopropylmethyl)pyrimidine-2-carbonitrile (130 mg) as a colorless oil. The resultant was used in the next step without further purification.
APCI-MS m/z: 160[M+H]$^+$ (5) To a solution of the crude product (125 mg) in tetrahydrofuran (3 mL) was added a solution of 1.0 mol/L diisobutylaluminum hydride in toluene (0.82 mL) at −78° C. under argon atmosphere. The mixture was stirred at the same temperature for 2 hours, and then to the reaction solution was added methanol, and the mixture was slowly warmed to room temperature. To the reaction solution was added 6.0 mol/L hydrochloric acid solution, and the mixture was stirred at room temperature for 2 hours, and then thereto was added saturated aqueous sodium bicarbonate solution, and the mixture was extracted with ethyl acetate. The organic layer was washed with saturated brine, dried over anhydrous sodium sulfate, and then concentrated under reduced pressure. The resulting residue was purified by silica gel column chromatography (hexane:ethyl acetate=65:35→35:65) to give a crude 5-(cyclopropylmethyl)pyrimidine-2-carbaldehyde (94 mg) as a colorless oil. The resultant was used in the next step without further purification.
APCI-MS m/z: 163[M+H]$^+$ (6) To a mixed solution of the above crude product (88 mg) in ethanol (1 mL) and tetrahydrofuran (1 mL) was added sodium borohydride (24 mg, 0.643 mmol) at 0° C. The mixture was stirred at the same temperature for 30 minutes, and then to the reaction solution was added aqueous ammonium chloride solution, and the mixture was extracted with ethyl acetate. The organic layer was washed with saturated brine, dried over anhydrous sodium sulfate, and then concentrated under reduced pressure. The resulting residue was purified by silica gel column chromatography (hexane:ethyl acetate=50:

50→0:100) to give [5-(cyclopropylmethyl)pyrimidin-2-yl]methanol (24 mg) as a colorless oil.
APCI-MS m/z: 165 [M+H]⁺

Reference Example 47

Preparation of
(5-chloro-1-ethyl-1H-indol-2-yl)methanol

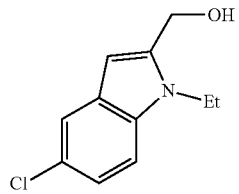 [SMILES: CCn1c(CO)cc2cc(Cl)ccc21]

(1) A mixture of ethyl 5-chloro-1H-indole-2-carboxylate (500 mg, 2.17 mmol), potassium carbonate (450 mg, 3.25 mmol), iodoethane (260 μL, 3.25 mmol) and N,N-dimethylformamide (10.8 mL) was stirred at room temperature for 3 days. To the reaction solution was added water, and the mixture was extracted with ethyl acetate twice. The organic layer was combined, washed with water three times, and the organic layer was filtered through diatomaceous earth, followed by silica gel, and then the filtrate was concentrated under reduced pressure to give ethyl 5-chloro-1-ethyl-1H-indole-2-carboxylate (566 mg, 100%) as an oil.
APCI-MS m/z: 252/254[M+H]⁺.
(2) To a solution of the above compound (561 mg, 2.23 mmol) in diethyl ether (11.1 mL) was added lithium aluminum hydride (127 mg, 3.34 mmol) in divided portions at 0° C., and the mixture was stirred at room temperature for 1.5 hours. To the reaction mixture were sequentially added water (127 μL), 15% aqueous sodium hydroxide solution (127 μL) and water (381 μL), and then the mixture was filtered through diatomaceous earth. The filtrate was concentrated under reduced pressure. The resulting residue was purified by silica gel column chromatography (hexane:ethyl acetate=9:1→3:2) to give the title compound (5-chloro-1-ethyl-1H-indol-2-yl)methanol (429 mg, 92%) as a powder.
APCI-MS mz: 210/212[M+H]⁺.

Reference Example 48

Preparation of
(6-chloro-1-ethyl-1H-indol-2-yl)methanol

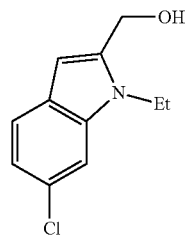 [SMILES: CCn1c(CO)cc2ccc(Cl)cc21]

Ethyl 6-chloro-1H-indole-2-carboxylate was treated in a similar manner to Reference examples 47-(1) and (2) to give the title compound (6-chloro-1-ethyl-1H-indol-2-yl)methanol.
APCI-MS m/z: 210/212[M+H]⁺.

Reference Example 49

Preparation of
(4-chloro-1-methyl-1H-indol-2-yl)methanol

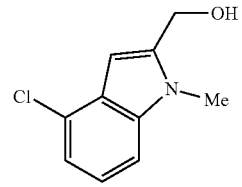 [SMILES: Cn1c(CO)cc2c(Cl)cccc21]

4-Chloro-1H-indole-2-carboxylic acid and iodomethane were treated in a similar manner to Reference examples 47-(1) and (2) to give the title compound (4-chloro-1-methyl-1H-indol-2-yl)methanol.
APCI-MS m/z: 196/198[M+H]⁺.

Reference Example 50

Preparation of
(1-cyclopropyl-1H-indol-2-yl)methanol

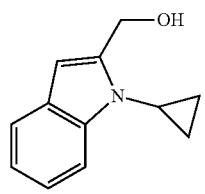 [SMILES: OCc1cc2ccccc2n1C1CC1]

(1) A mixture of methyl 1H-indole-2-carboxylate (1.00 g, 5.71 mmol), cyclopropylboronic acid (981 mg, 11.4 mmol), copper (II) acetate (1.04 g, 5.71 mmol), 2,2-bipyridyl (892 mg, 5.71 mmol), sodium carbonate (1.21 g, 11.4 mmol) and 1,2-dichloroethane (15.0 mL) was stirred at 70° C. for 19 hours. Then, thereto were added cyclopropylboronic acid (981 mg, 11.4 mmol) and sodium carbonate (1.21 g, 11.4 mmol), and the mixture was stirred at 70° C. for 8 hours, and then thereto were added cyclopropylboronic acid (981 mg, 11.4 mmol), sodium carbonate (1.21 g, 11.4 mmol), copper (II) acetate (1.04 g, 5.71 mmol) and 2,2-bipyridyl (892 mg, 5.71 mmol), and the mixture was stirred at 70° C. for 16 hours. The mixture was let stand to cool, and then to the reaction mixture was added saturated aqueous ammonium chloride solution. The mixture was filtered through diatomaceous earth, and the filtrate was extracted with ethyl acetate. The organic layer was washed with water and saturated brine, dried over sodium sulfate, and then the filtrate was concentrated under reduced pressure. The resulting residue was purified by silica gel column chromatography (hexane:ethyl acetate=19:1→17:3) to give ethyl 1-cyclopropyl-1H-indole-2-carboxylate (882 mg, 72%) as a powder.
APCI-MS m/z: 216[M+H]⁺.
(2) To a solution of the above compound (865 mg, 4.02 mmol) in toluene (20.1 mL) was added a solution of 1.01 mol/L diisobutylaluminum hydride in toluene (9.94 mL, 10.0 mmol) at −78° C., and the mixture was stirred at −78° C. for 1.5 hours. To the reaction mixture was added methanol, and the mixture was acidified by the addition of 1 mol/L hydrochloric acid, and extracted with ethyl acetate. The organic layer was washed with water and saturated brine, dried over sodium sulfate, and then the filtrate was concentrated under reduced pressure. The resulting residue was purified by silica gel column chromatography (hexane:ethyl acetate=9:1→17:3) to give (1-cyclopropyl-1H-indol-2-yl)methanol (708 mg, 94%) as a powder.

APCI-MS m/z: 188[M+H]$^+$.

Reference Example 51

Preparation of (5-chloro-1-cyclopropyl-1H-indol-2-yl)methanol

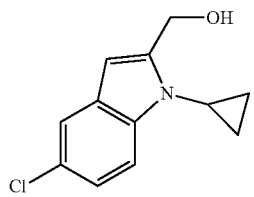 [SMILES: OCc1cc2cc(Cl)ccc2n1C1CC1]

Ethyl 5-chloro-1H-indole-2-carboxylate was treated in a similar manner to Reference examples 50-(1) and (2) to give the title compound (5-chloro-1-cyclopropyl-1H-indol-2-yl)methanol.

APCI-MS m/z: 222/224[M+H]$^+$.

Reference Example 52

Preparation of (1-methyl-2,3-dihydro-1H-indol-6-yl)methanol

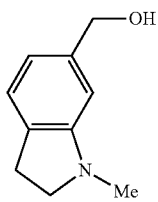 [SMILES: CN1CCc2ccc(CO)cc21]

To a solution of 1-methylindoline-6-carboxylic acid (321 mg, 1.80 mmol) in tetrahydrofuran (6 mL) was added N,N'-carbodiimidazole (309 mg, 1.89 mmol) at room temperature. The mixture was stirred at 50° C. for 15 minutes, and then cooled to 0° C. Then, thereto were added water (1 mL) and sodium hydroborate (204 mg, 5.40 mmol), and the mixture was stirred at the same temperature for 1 hour. The reaction solution was cooled to room temperature, and then thereto was added water, and the mixture was extracted with ethyl acetate twice. The organic layer was combined, washed with saturated brine, dried over anhydrous sodium sulfate, and then concentrated under reduced pressure. The resulting residue was purified by silica gel column chromatography (hex-ane:ethyl acetate=5:1→1:1) to give (1-methyl-2,3-dihydro-1H-indol-6-yl)methanol (245 mg, 83%) as a pale yellow oil.

APCI-MS m/z: 164[M+H]$^+$.

Reference Example 53

Preparation of tert-butyl 3-chloro-6-(hydroxymethyl)-1H-indazole-1-carboxylate

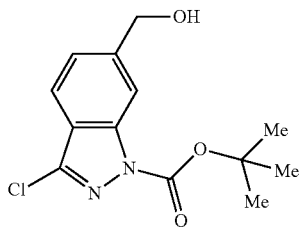 [SMILES: CC(C)(C)OC(=O)n1nc(Cl)c2ccc(CO)cc21]

(1) A solution of methyl 3-chloro-1H-indazole-6-carboxylate (891 mg, 4.2 mmol) in tetrahydrofuran (10 mL) was cooled to −78° C., and then thereto was added dropwise diisobutylaluminum hydride (tetrahydrofuran solution, 1 mol/L, 12.7 mL, 12.6 mmol) at the same temperature, and the mixture was stirred at the same temperature for 2 hours. To the reaction solution was added water, and the mixture was extracted with ethyl acetate twice. The organic layer was combined, washed with water and saturated brine, dried over anhydrous sodium sulfate, and then concentrated under reduced pressure. The resulting residue was purified by silica gel column chromatography hexane→hexane:ethyl acetate=2:1) to give (3-chloro-1H-indazol-6-yl)methanol (344 mg, 45%) as a yellow solid.

APCI-MS m/z: 183/185[M+H]$^+$.

(2) To a solution of the above compound (270 mg, 1.50 mmol) in dichloromethane (15 mL) was added di-t-butyl dicarbonate (323 mg, 1.50 mmol) at room temperature, and the mixture was stirred at the same temperature for 18 hours. To the reaction solution was added N,N-dimethyl-4-aminopyridine (5 mg, catalytic amounts), and the mixture was stirred for 1 hour. The reaction solution was concentrated under reduced pressure, and purified by silica gel column chromatography (hexane→hexane:ethyl acetate=2:1) to give tert-butyl 3-chloro-6-(hydroxymethyl)-1H-indazole-1-carboxylate (356 mg, 85%) as a pale yellow oil.

APCI-MS m/z: 283/285[M+H]$^+$.

Reference Example 54

Preparation of (4,6-difluoro-1-benzothien-2-yl)methanol

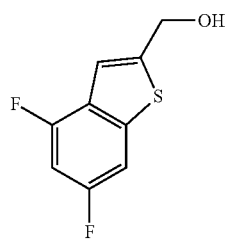 [SMILES: OCc1cc2c(F)cc(F)cc2s1]

(1) To a suspension of 2,4,6-trifluorobenzaldehyde (5.00 g, 31.2 mmol) and potassium carbonate (5.61 g, 40.6 mmol) in N,N-dimethylformamide (63 mL) was added ethyl thioglycolate (3.40 g, 28.3 mmol) at 0° C. The mixture was stirred at room temperature overnight, and then heated to stir at 60° C. for 6 hours. The mixture was cooled to room temperature, and then to the reaction solution was added water, and the mixture was extracted with ethyl acetate. The organic layer was washed with water and saturated brine, dried over anhydrous sodium sulfate, and then concentrated under reduced pressure. The resulting residue was purified by silica gel column chromatography (hexane:ethyl acetate=97:3→93:7) to give ethyl 4,6-difluoro-1-benzothiophene-2-carboxylate (1.95 g, 29%) as a pale yellow solid.

APCI-MS m/z: 243[M+H]$^+$.

(2) To a solution of the above compound (1000 mg, 4.13 mmol) in diethyl ether (21 mL) was added lithium aluminum hydride (235 mg, 6.19 mmol) in divided portions at 0° C. under argon atmosphere, and the mixture was stirred at room temperature for 40 minutes. To the reaction solution were added water (0.24 mL) and 15% aqueous sodium hydroxide solution (0.24 mL) under ice cooling, and then thereto was added additional water (0.72 mL), and then the mixture was stirred at room temperature. The insoluble was filtered off, washed with diethyl ether, and then the filtrate was combined with the washing, and concentrated under reduced pressure. The resulting residue was washed with hexane-diisopropyl ether to give (4,6-difluoro-1-benzothien-2-yl)methanol (731 mg, 88%) as a colorless powder.

$^1$H-NMR (DMSO-d$_6$) δ 4.74 (2H, d, J=5.7 Hz), 5.75 (1H, t, J=5.9 Hz), 7.26 (1H, dt, J=10.1, 2.1 Hz), 7.30 (1H, s), 7.77 (1H, dd, J=8.8, 2.1 Hz).

Reference Example 55

Preparation of (5,7-difluoro-1-benzothien-2-yl)methanol

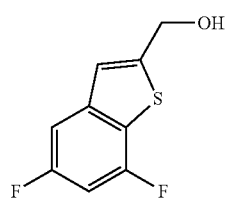 [SMILES: OCc1cc2cc(F)cc(F)c2s1]

(1) To a solution of 5,7-difluoro-1-benzothiophene-2-carboxylic acid (synthesized by the method of WO2003/055878, 1.95 g, 9.10 mmol), N,O-dimethylhydroxyamine hydrochloride (977 mg, 10.0 mmol), 1-ethyl-3-(3'-dimethylaminopropyl)carbodiimide hydrochloride (1.92 g, 10.0 mmol) and N-hydroxybenzotriazole (1.35 g, 10.0 mmol) in dichloromethane (20 mL) was added triethylamine (1.90 mL, 13.7 mmol) at room temperature. The mixture was stirred at room temperature overnight, and then to the reaction solution was added 10% hydrochloric acid solution, and the mixture was extracted with chloroform. The organic layer was washed with saturated aqueous sodium hydrogen carbonate solution, dried over anhydrous magnesium sulfate, and then concentrated under reduced pressure to give a crude 5,7-difluoro-N-methoxy-N-methyl-1-benzothiophene-2-carboxamide (2.48 g) as a colorless solid. The resultant was used in the next step without further purification.

APCI-MS m/z: 258[M+H]$^+$.

(2) To a solution of the crude product (2.45 g) in tetrahydrofuran (40 mL) was added dropwise a solution of 1 mol/L diisobutylaluminum hydride in toluene (14.3 mL, 14.3 mmol) at −70° C. under argon atmosphere. The reaction solution was slowly warmed to −40° C., and then to the reaction solution was added 10% hydrochloric acid solution (50 mL), and the mixture was extracted with diethyl ether. The organic layer was washed with saturated brine, dried over anhydrous magnesium sulfate, and then concentrated under reduced pressure to give 5,7-difluoro-1-benzothiophene-2-carbaldehyde (1.67 g, 92%, yields for two steps) as a colorless solid.

APCI-MS m/z: 213 [M+H+MeOH—H$_2$O]$^+$.

(3) To a solution of the above compound (1000 mg, 5.05 mmol) in methanol (25 mL) was added sodium borohydride (383 mg, 10.1 mmol) at 0° C. The mixture was stirred at room temperature for 40 minutes, and then to the reaction solution was added water, and the mixture was extracted with ethyl acetate twice. The organic layer was combined, washed with water and saturated brine, dried over anhydrous sodium sulfate, and then concentrated under reduced pressure. The resulting residue was purified by silica gel column chromatography (hexane:ethyl acetate=90:10→70:30) to give (5,7-difluoro-1-benzothien-2-yl)methanol (933 mg, 92%) as a colorless solid.

$^1$H-NMR (DMSO-d$_6$) δ 4.77 (2H, dd, J=5.7, 0.9 Hz), 5.84 (1H, t, J=5.7 Hz), 7.28 (1H, dt, J=9.9, 2.3 Hz), 7.35 (1H, d, J=3.6 Hz), 7.54 (1H, dd, J=9.4, 2.1 Hz).

Reference Example 56

Preparation of (7-chloro-1-benzothien-2-yl)methanol

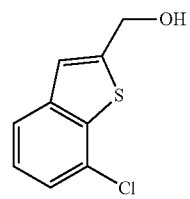 [SMILES: OCc1cc2cccc(Cl)c2s1]

To a solution of 7-chloro-1-benzothiophene-2-carboxylic acid (synthesized by the method of Journal of Chemical Society Perkin Trans. 1, 1984, 385, 1.00 g, 4.70 mmol) in tetrahydrofuran (17 mL) was added a solution of 0.95 mol/L borane-tetrahydrofuran complex in tetrahydrofuran (9.90 mL, 9.41 mmol) at 0° C. The mixture was stirred at room temperature overnight, and then to the reaction solution was added water, and the mixture was concentrated under reduced pressure to remove solvent. To the resulting residue was added saturated aqueous sodium hydrogen carbonate solution, and the mixture was extracted with ethyl acetate twice. The organic layer was combined, washed with water and saturated brine, dried over anhydrous sodium sulfate, and then concentrated under reduced pressure. The resulting residue was washed with hexane-diisopropyl ether to give (7-chloro-1-benzothien-2-yl)methanol (842 mg, 90%) as a colorless powder.

APCI-MS m/z: 216/218 [M+NH$_4$]$^+$.

Reference Example 57

Preparation of 5-(trifluoromethoxy)indan-1-ol

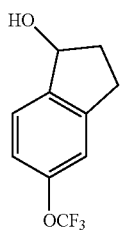

(2S)-1-(1,3,2-Dioxaborolan-2-yloxy)-3-methyl-1,1-diphenylbutan-2-amine (33 mg, 0.1 mmol) obtained in a similar manner to the method of European Journal of Organic Chemistry, 1999, p. 1775 (*Eur. J. Org. Chem.* 1999, 1775) was suspended in tetrahydrofuran (5 mL), and then thereto was added borane dimethylsulfide complex (10 mol/L, 0.1 mL, 1 mmol) at room temperature. The mixture was stirred at the same temperature for 20 minutes, and then thereto was added in divided portions 5-trifluoromethoxyindan-1-one (0.217 g, 1 mmol) obtained in a similar manner to the method of U.S. Pat. No. 6,159,996 over 1 hour, and the mixture was stirred at room temperature overnight. The mixture was cooled to 5° C., and then thereto was added methanol (2 mL). The mixture was stirred at the same temperature for 1 hour, and then the reaction solution was concentrated, and then thereto was added chloroform. The chloroform solution was poured into saturated aqueous ammonium chloride solution, and extracted with chloroform three times, and the organic layer was washed with saturated brine. The resultant was dried over magnesium sulfate, and then concentrated. To the resulting residue were added diethyl ether and hexane, and the generated white solid was filtered off. The filtrate was concentrated to give a crude 5-(trifluoromethoxy)indan-1-ol (62.5 mg). The resultant was used in the next step without further purification.

Pharmacological Experiment

1. TRPM8 Inhibition Assay

Test Compound:

The compounds of Examples were used in TRPM8 inhibition assay.

Method:

The functional activity of compounds was determined by measuring changes in intracellular calcium concentration using a $Ca^{2+}$ sensitive fluorescent dye. The changes in fluorescent signal were monitored by the cell imaging technology by Hamamatsu Photonics's Functional Drug Screening System (FDSS). Increases in intracellular $Ca^{2+}$ concentration were readily detected upon activation with menthol.

HEK293 cells stably expressing human TRPM8 were grown in flasks. On assay day, the culture medium was removed, and cells were washed with phosphate-buffered saline (PBS) and harvested with PBS containing 2 mM ethylenediaminetetraacetic acid, disodium salt (EDTA, 2Na). The cells were then incubated with assay buffer containing 3 μM Fura-2AM and 0.01% Pluronic F-127 for 60 min. Subsequently, suspended 20,000 to 50,000 cells per well were incubated with test compound (at varying concentrations) in each well for 20 min at 37° C. Changes in intracellular $Ca^{2+}$ evoked by 100 μM menthol were measured for 2 min using FDSS. $IC_{50}$ vales were determined from four-point concentration-response studies. Curves were generated using the average of quadruplicate wells for each data point.

Results:

The following Table 19 shows an $IC_{50}$ value of each test compound.

TABLE 19

| Test Compound (Example No.) | TRPM8 Blocking Test ($IC_{50}$, nM) |
|---|---|
| 2 | 2.7 |
| 4 | 3.6 |
| 6 | 22 |
| 8 | 26 |
| 10 | 1.9 |
| 12 | 43 |
| 14 | 4.7 |
| 17 | 5.0 |
| 20 | 12 |
| 22 | 93 |
| 23 | 1.8 |
| 24 | 4.6 |
| 27 | 26 |
| 28 | 16 |
| 30 | 4.9 |
| 31 | 65 |
| 32 | 8.6 |
| 34 | 2.5 |
| 35 | 3.1 |
| 41 | 12 |
| 42 | 30 |
| 43 | 37 |
| 44 | 91 |
| 45 | 35 |
| 46 | 17 |
| 51 | 26 |
| 52 | 20 |
| 56 | 4.7 |
| 60 | 8.1 |
| 61 | 1.3 |
| 62 | 8.3 |
| 64 | 11 |
| 66 | 38 |
| 67 | 67 |
| 70 | 95 |
| 77 | 44 |
| 80 | 18 |
| 81 | 58 |
| 82 | 5.3 |
| 83 | 10 |
| 84 | 3.1 |
| 85 | 79 |
| 88 | 10 |
| 89 | 15 |
| 93 | 7.6 |
| 95 | 91 |
| 96 | 4.7 |
| 97 | 11 |
| 99 | 29 |
| 100 | 21 |
| 102 | 115 |
| 104 | 0.9 |
| 106 | 2.0 |
| 108 | 21 |
| 110 | 7.4 |
| 112 | 14 |
| 113 | 25 |
| 115 | 97 |
| 117 | 54 |
| 119 | 92 |
| 121 | 15 |
| 122 | 57 |
| 123 | 21 |
| 124 | 13 |
| 125 | 62 |
| 126 | 52 |
| 127 | 195 |
| 128 | 40 |
| 129 | 15 |

TABLE 19-continued

| Test Compound (Example No.) | TRPM8 Blocking Test (IC$_{50}$, nM) |
|---|---|
| 130 | 94 |
| 131 | 109 |
| 132 | 3.8 |
| 133 | 4.3 |
| 134 | 695 |
| 135 | 136 |
| 136 | 31 |
| 137 | 3.1 |
| 138 | 11 |
| 139 | 12 |
| 140 | 81 |
| 141 | 16 |
| 142 | 17 |
| 143 | 131 |
| 144 | 54 |
| 145 | 91 |
| 146 | 70 |
| 147 | 870 |
| 148 | 287 |
| 149 | 3.9 |
| 150 | 48 |
| 151 | 2.2 |
| 152 | 95 |
| 154 | 2.3 |
| 155 | 6.2 |
| 156 | 23 |
| 157 | 339 |
| 158 | 301 |
| 159 | 32 |
| 160 | 38 |
| 161 | 105 |
| 162 | 71 |
| 163 | 166 |
| 164 | 563 |
| 165 | 21 |
| 166 | 12 |
| 167 | 83 |
| 168 | 133 |
| 169 | 55 |
| 170 | 2.9 |
| 171 | 7.1 |
| 172 | 15 |
| 173 | 78 |
| 174 | 35 |
| 175 | 4.4 |
| 176 | 21 |
| 177 | 30 |
| 178 | 601 |
| 179 | 2.1 |
| 180 | 6.9 |
| 181 | 1.0 |
| 182 | 4.0 |
| 183 | 7.7 |
| 184 | 1.1 |
| 185 | 1.2 |
| 186 | 4.3 |
| 187 | 128 |
| 188 | 155 |
| 189 | 1.7 |
| 190 | 148 |
| 191 | 4.6 |
| 192 | 8.8 |
| 193 | 3.9 |
| 194 | 1.3 |
| 195 | 6.0 |
| 196 | 2.2 |
| 197 | 4.6 |
| 198 | 11 |
| 199 | 3.9 |
| 200 | 5.4 |
| 201 | 0.6 |
| 202 | 1.4 |
| 203 | 1.5 |
| 204 | 3.1 |
| 205 | 31 |
| 206 | 21 |
| 207 | 11 |
| 208 | 9.6 |
| 209 | 1.0 |
| 210 | 0.8 |
| 211 | 987 |
| 212 | 75 |
| 213 | 116 |
| 214 | 8.1 |
| 215 | 8.2 |
| 216 | 66 |
| 217 | 239 |
| 218 | 21 |
| 219 | 2.6 |
| 220 | 5.0 |
| 221 | 1.7 |
| 222 | 1.6 |
| 223 | 3.5 |
| 224 | 5.9 |
| 225 | 2.8 |
| 226 | 9.2 |
| 227 | 5.6 |
| 228 | 7.2 |
| 229 | 44 |
| 230 | 44 |
| 231 | 6.9 |
| 232 | 10 |
| 233 | 0.9 |
| 234 | 5.0 |
| 235 | 1.6 |
| 236 | 522 |
| 237 | 12 |
| 238 | 103 |
| 239 | 14 |
| 240 | 18 |
| 241 | 8.5 |
| 242 | 10 |

2. In Vivo TRPM8 Antagonistic Assay in Rats

Test Compound:

The compounds of Examples were used in TRPM8 antagonistic assay in rats.

Method:

The antagonistic activity of compounds was assessed in the "wet-dog" shakes (WDS) model in rats. Rats exhibit shaking behavior in response to menthol, a TRPM8 agonist. Pretreatment of the rats with a TRPM8 antagonist prior to menthol administration inhibits the observed shaking behavior.

To assess the ability of a TRPM8 antagonist to prevent menthol induced shaking behavior in Sprague Dawley (SD) male rats, test compounds (3 mg/kg, po, in 0.5% methyl cellulose; N=3-4/group) were administered 1 hour prior to menthol challenge (50 mg/kg, ip, in 10% Macrogol 15 Hydroxystearate/saline). Spontaneous WDS were counted for 5 min post menthol dosing. Inhibition of the spontaneous WDS behavior relative to vehicle pretreatment is expressed as percent inhibition, calculated as follows: % Inhibition=[1−(treatment WDS count/vehicle WDS count)]×100.

Results:

The following Table 20 shows a percent inhibition at 3 mg/kg of each test compound.

TABLE 20

| Test Compound (Example No.) | TRPM8 antagonistic assay (% Inhibition @ 3 mg/kg) |
|---|---|
| 10 | 74.8% |
| 106 | 92.7% |
| 149 | 98.8% |
| 184 | 67.0% |
| 185 | 93.8% |

TABLE 20-continued

| Test Compound (Example No.) | TRPM8 antagonistic assay (% Inhibition @ 3 mg/kg) |
|---|---|
| 186 | 83.5% |
| 210 | 83.3% |
| 227 | 72.5% |

INDUSTRIAL APPLICABILITY

The compound (I) of the present invention is useful for the prevention and treatment of various diseases involving TRPM8 (e.g., chronic pain such as neuropathic pain (preferably, neuropathic pain caused by cold allodynia or diabetic neuropathy)).

The invention claimed is:

1. A compound of the general formula (I):

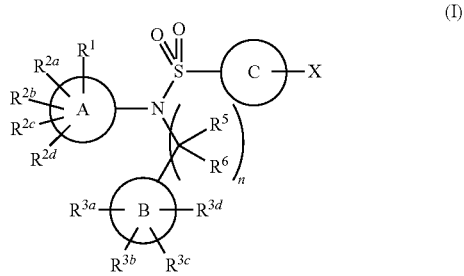

(I)

wherein
Ring A is bicyclic aromatic heterocycle comprised of (a) pyridine condensed with benzene; or (b) pyridine condensed with monocyclic aromatic heterocycle, and Ring A binds to a sulfonylamino moiety on a carbon atom adjacent to a nitrogen atom of pyridine ring constituting Ring A,
Ring B is (a) monocyclic or bicyclic aromatic hydrocarbon; (b) monocyclic or bicyclic alicyclic hydrocarbon; (c) monocyclic or bicyclic aromatic heterocycle; or (d) monocyclic or bicyclic non-aromatic heterocycle,
Ring C is (a) benzene; or (b) monocyclic aromatic heterocycle,
$R^1$ is (a) hydrogen; (b) optionally substituted alkyl; (c) optionally substituted cycloalkyl; (d) optionally substituted alkoxy; (e) optionally substituted phenyl; (f) halogen; or (g) nitrile,
$R^{2a}$, $R^{2b}$, $R^{2c}$ and $R^{2d}$ are each independently (a) hydrogen; (b) optionally substituted alkyl; (c) optionally substituted cycloalkyl; (d) optionally substituted alkoxy; (e) optionally substituted phenyl; (f) optionally substituted monocyclic aromatic heterocyclic group; (g) optionally substituted monocyclic non-aromatic heterocyclic group; (h) halogen; or (i) nitrile,
$R^{3a}$, $R^{3b}$, $R^{3c}$ and $R^{3d}$ are each independently (a) hydrogen; (b) optionally substituted alkyl; (c) optionally substituted cycloalkyl; (d) optionally substituted alkoxy; (e) optionally substituted cycloalkoxy; (f) optionally substituted phenyl; (g) optionally substituted monocyclic aromatic heterocyclic group; (h) optionally substituted monocyclic non-aromatic heterocyclic group; (i) optionally substituted phenoxy; (j) halogen; or (k) hydroxy, or
two substituent groups selected from $R^{3a}$, $R^{3b}$, $R^{3c}$ and $R^{3d}$ combine each other to form oxo,
$R^5$ and $R^6$ are each independently (a) hydrogen; (b) alkyl; (c) halogenoalkyl; (d) cycloalkyl; or (e) halogenocycloalkyl, or $R^5$ and $R^6$ combine each other at their terminals together with the adjacent carbon atom to form monocyclic alicyclic hydrocarbon,
n is 0, 1 or 2;
X is carboxy, alkoxycarbonyl, hydroxyalkyl, optionally substituted aminocarbonyl, or optionally substituted alkanoyl; or a pharmaceutically acceptable salt thereof.

2. The compound of claim 1, wherein $R^1$ is (a) hydrogen; (b) $C_1$-$C_6$ alkyl which may be optionally substituted by 1 to 7 groups selected from $C_3$-$C_7$ cycloalkyl, $C_1$-$C_6$ alkoxy, halogen, oxo and hydroxy; (c) $C_3$-$C_7$ cycloalkyl which may be optionally substituted by 1 to 7 groups selected from $C_1$-$C_6$ alkyl, $C_1$-$C_6$ alkoxy and halogen; (d) $C_1$-$C_6$ alkoxy which may be optionally substituted by 1 to 7 groups selected from $C_3$-$C_7$ cycloalkyl, $C_1$-$C_6$ alkoxy, halogen and hydroxy; (e) phenyl which may be optionally substituted by 1 to 3 groups selected from $C_1$-$C_6$ alkyl, $C_1$-$C_6$ halogenoalkyl, $C_3$-$C_7$ cycloalkyl, $C_3$-$C_7$ halogenocycloalkyl, $C_1$-$C_6$ alkoxy, $C_1$-$C_6$ halogenoalkoxy and halogen; (f) halogen; or (g) nitrile,
$R^{2a}$, $R^{2b}$, $R^{2c}$ and $R^{2d}$ are each independently (a) hydrogen; (b) $C_1$-$C_6$ alkyl which may be optionally substituted by 1 to 7 groups selected from $C_1$-$C_6$ alkoxy, $C_3$-$C_7$ cycloalkyl, halogen, oxo and hydroxy; (c) $C_3$-$C_7$ cycloalkyl which may be optionally substituted by 1 to 7 groups selected from $C_1$-$C_6$ alkyl, $C_1$-$C_6$ alkoxy and halogen; (d) $C_1$-$C_6$ alkoxy which may be optionally substituted by 1 to 7 groups selected from $C_1$-$C_6$ alkoxy, $C_3$-$C_7$ cycloalkyl and halogen; (e) phenyl which may be optionally substituted by 1 to 3 groups selected from $C_1$-$C_6$ alkyl, $C_1$-$C_6$ halogenoalkyl, $C_3$-$C_7$ cycloalkyl, $C_3$-$C_7$ halogenocycloalkyl, $C_1$-$C_6$ alkoxy, $C_1$-$C_6$ halogenoalkoxy and halogen; (f) 5 to 6-membered monocyclic aromatic heterocyclic group which may be optionally substituted by 1 to 3 groups selected from $C_1$-$C_6$ alkyl. $C_1$-$C_6$ halogenoalkyl, $C_3$-$C_7$ cycloalkyl, $C_3$-$C_7$ halogenocycloalkyl, $C_1$-$C_6$ alkoxy, $C_1$-$C_6$ halogenoalkoxy and halogen; (g) 4 to 7-membered monocyclic non-aromatic heterocyclic group which may be optionally substituted by 1 to 3 groups selected from $C_1$-$C_6$ alkyl, $C_1$-$C_6$ halogenoalkyl, $C_3$-$C_7$ cycloalkyl, $C_3$-$C_7$ halogenocycloalkyl, $C_1$-$C_6$ alkoxy, $C_1$-$C_6$ halogenoalkoxy and halogen; (h) halogen; or (i) nitrile,
$R^{3a}$, $R^{3b}$, $R^{3c}$ and $R^{3d}$ are each independently (a) hydrogen; (b) $C_1$-$C_6$ alkyl which may be optionally substituted by 1 to 7 groups selected from $C_3$-$C_7$ cycloalkyl, $C_3$-$C_7$ halogenocycloalkyl (in which the cycloalkyl and halogenocycloalkyl may be each independently optionally substituted by 1 to 3 groups selected from $C_1$-$C_6$ alkyl and $C_1$-$C_6$ halogenoalkyl), $C_1$-$C_6$ alkoxy, $C_1$-$C_6$ halogenoalkoxy, phenyl, 5 to 6-membered monocyclic aromatic heterocyclic group, 4 to 7-membered monocyclic non-aromatic heterocyclic group (in which the phenyl, aromatic heterocyclic group and non-aromatic heterocyclic group may be each independently optionally substituted by 1 to 3 groups selected from $C_1$-$C_6$ alkyl, $C_1$-$C_6$ halogenoalkyl, $C_3$-$C_7$ cycloalkyl, $C_3$-$C_7$ halogenocycloalkyl, $C_1$-$C_6$ alkoxy, $C_1$-$C_6$ halogenoalkoxy and halogen), halogen, oxo and hydroxy; (c) $C_3$-$C_7$ cycloalkyl which may be optionally substituted by 1 to 7 groups selected from $C_1$-$C_6$ alkyl, $C_1$-$C_6$ halogenoalkyl, $C_1$-$C_6$ alkoxy, $C_1$-$C_6$ halogenoalkoxy, halogen and hydroxy; (d) $C_1$-$C_6$ alkoxy which may be optionally substituted by 1 to 7 groups selected from $C_3$-$C_7$ cycloalkyl, $C_3$-$C_7$ halogenocycloalkyl (in which the cycloalkyl and halogenocycloalkyl may be each independently optionally substituted by 1 to 3 groups selected from $C_1$-$C_6$ alkyl and $C_1$-$C_6$ halogenoalkyl), $C_1$-$C_6$ alkoxy, $C_1$-$C_6$ halogenoalkoxy, phenyl, 5 to 6-membered monocyclic aromatic heterocyclic group, 4 to 7-membered monocyclic non-aromatic heterocyclic group (in which the phenyl, aromatic heterocyclic group and non-aromatic heterocyclic group may be each independently optionally substituted by 1 to 3 groups selected from $C_1$-$C_6$ alkyl, $C_1$-$C_6$ halogenoalkyl, $C_3$-$C_7$ cycloalkyl, $C_3$-$C_7$ halogenocycloalkyl, $C_1$-$C_6$ alkoxy, $C_1$-$C_6$ halogenoalkoxy and halogen), halogen and hydroxy; (e) $C_3$-$C_7$ cycloalkoxy which may be optionally substituted by 1 to 7 groups selected from $C_1$-$C_6$ alkyl, $C_1$-$C_6$ halogenoalkyl, $C_1$-$C_6$ alkoxy, $C_1$-$C_6$ halogenoalkoxy, halogen and hydroxy; (f) phenyl which may be optionally substituted by 1 to 3 groups selected from $C_1$-$C_6$ alkyl, $C_1$-$C_6$ halogenoalkyl, $C_3$-$C_7$ cycloalkyl, $C_3$-$C_7$ halogenocycloalkyl, $C_1$-$C_6$ alkoxy, $C_1$-$C_6$ halogenoalkoxy and halogen; (g) 5 to 6-membered monocyclic aromatic heterocyclic group which may be optionally substituted by 1 to 3 groups selected from $C_1$-$C_6$ alkyl, $C_1$-$C_6$ halogenoalkyl, $C_3$-$C_7$ cycloalkyl, $C_3$-$C_7$ halogenocycloalkyl, $C_1$-$C_6$ alkoxy, $C_1$-$C_6$ halogenoalkoxy and halogen; (h) 4 to 7-membered monocyclic non-aromatic heterocyclic group which may be optionally substituted by 1 to 3 groups selected from $C_1$-$C_6$ alkyl, $C_1$-$C_6$ halogenoalkyl, $C_3$-$C_7$ cycloalkyl, $C_3$-$C_7$ halogenocycloalkyl, $C_1$-$C_6$ alkoxy, $C_1$-$C_6$ halogenoalkoxy and halogen; (i) phenoxy which may be optionally substituted by 1 to 3 groups selected from $C_1$-$C_6$ alkyl, $C_1$-$C_6$ halogenoalkyl, $C_3$-$C_7$ cycloalkyl, $C_3$-$C_7$ halogenocycloalkyl, $C_1$-$C_6$ alkoxy, $C_1$-$C_6$ halogenoalkoxy and halogen; (j) halogen; or (k) hydroxy, or two substituent groups selected from $R^{3a}$, $R^{3b}$, $R^{3c}$ and $R^{3d}$ combine each other to form oxo, $R^5$ and $R^6$ are each independently (a) hydrogen; (b) $C_1$-$C_6$ alkyl; (c) $C_1$-$C_6$ halogenoalkyl; (d) $C_3$-$C_7$ cycloalkyl; or (e) $C_3$-$C_7$ halogenocycloalkyl, or $R^5$ and $R^5$ combine each other at their terminals together with the adjacent carbon atom to form 3 to 7-membered monocyclic alicyclic hydrocarbon, X is (a) carboxy; (b) $C_1$-$C_6$ alkoxycarbonyl; (c) hydroxy-$C_1$-$C_6$ alkyl; (d) aminocarbonyl wherein a nitrogen atom may be optionally substituted by one group selected from $C_1$-$C_6$ alkyl, $C_1$-$C_6$ alkoxy and nitrite; or (e) $C_2$-$C_7$ alkanoyl which may be optionally substituted by 1 to 3 halogens, or a pharmaceutically acceptable salt thereof.

3. The compound of claim 2, wherein Ring A is quinoline, isoquinoline or pyrrolopyridine, or a pharmaceutically acceptable salt thereof.

4. The compound of claim 2, wherein Ring A, $R^1$, $R^{2a}$, $R^{2b}$, $R^{2c}$ and $R^{2d}$ combine each other to form a group of the following formula:

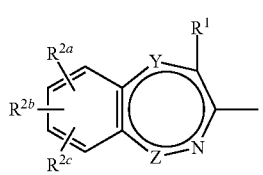

wherein one of Y and Z is $CR^{2d}$, and the other is a chemical bond, or a pharmaceutically acceptable salt thereof.

5. The compound of claim 4, wherein Ring C is benzene, and X is carboxy and binds to Ring C at 4-position to the aminosulfonyl moiety, or a pharmaceutically acceptable salt thereof.

6. The compound of claim 5, wherein Ring B is (a) monocyclic or bicyclic aromatic hydrocarbon; or (b) monocyclic or bicyclic aromatic heterocycle, and n is 0 or 1, or a pharmaceutically acceptable salt thereof.

7. The compound of claim 6, wherein a partial structure:

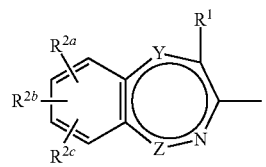

is a group of the following formula (A):

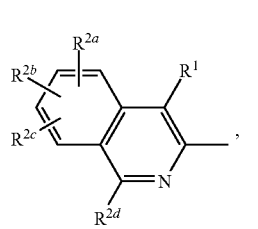

or a pharmaceutically acceptable salt thereof.

8. The compound of claim 6, wherein a partial structure:

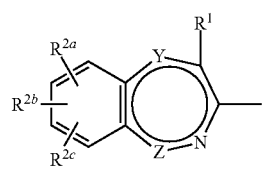

is a group of the following formula (B):

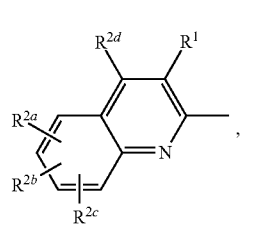

or a pharmaceutically acceptable salt thereof.

9. The compound of claim 7 wherein $R^1$ is (a) $C_1$-$C_6$ alkyl which may be optionally substituted by 1 to 7 halogens; (b) $C_3$-$C_7$ cycloalkyl; (c) alkoxy; or (d) halogen, $R^{2b}$ and $R^{2b}$ are hydrogen, $R^{2b}$ is (a) hydrogen; (b) $C_1$-$C_6$ alkyl which may be optionally substituted by 1 to 7 halogens; (c) $C_3$-$C_7$ cycloalkyl; or (d) $C_1$-$C_6$ alkoxy, $R^{3a}$ and $R^{3b}$ are each independently (a) hydrogen; (b) $C_1$-$C_6$ alkyl which may be optionally substituted by 1 to 7 groups selected from $C_3$-$C_7$ cycloalkyl (in which the cycloalkyl may be optionally substituted by 1 to 3 groups selected from $C_1$-$C_6$ alkyl and $C_1$-$C_6$ halogenoalkyl), $C_1$-$C_6$ alkoxy, $C_1$-$C_6$ halogenoalkoxy, and halogen; (c) $C_3$-$C_7$ cycloalkyl which may be optionally substituted by 1 to 7 groups selected from $C_1$-$C_6$ alkyl, $C_1$-$C_6$ halogenoalkyl, and halogen; (d) $C_1$-$C_6$ alkoxy which may be optionally substituted by 1 to 7 groups selected from $C_3$-$C_7$ cycloalkyl, $C_1$-$C_6$ alkoxy, $C_1$-$C_6$ halogenoalkoxy, and halogen; or (e) halogen, $R^{3c}$ and $R^{3d}$ are hydrogen, $R^5$ and $R^6$ are hydrogen, n is 1, or a pharmaceutically acceptable salt thereof.

10. The compound of claim 1, which is selected from he group consisting of 4-({(4-methylisoquinolin-3-yl)[4-(trifluoromethoxy)benzyl]amino}sulfonyl)benzoic acid;

4-{[[3-fluoro-4-(trifluoromethoxy)benzyl](4-methylisoquinolin-3-yDamino]sulfonyl}benzoic acid;

4-({(1-cyclopropyl-4-methylisoquinolin-3-yl)[4-(trifluoromethoxy)benzyl]amino}sulfonyl)-benzoic acid;

4-{[[4-(1-ethoxy-2,2,2-trifluoro-1-methylethyl)benzyl](4-methylisoquinolin-3-yl)amino]-sulfonyl}benzoic acid;

4-(3-methylquinolin-2-yl)[4-(trifluoromethoxy)benzyl]amino}sulfonyl)benzoic acid;

4-{[[4-fluoro-3-(trifluoromethyl)benzyl](3-methylisoquinolin-2-amino]sulfonyl}benzoic acid;

4-{[(4-t-butylbenzyl)(4-methylisoquinolin-3-amino]sulfony}benzoic acid;

4-{[[4-(cyclopropylmethyl)benzyl](4-methylisoquinolin-3-amino}sulfonyl}benzoic acid;

4-{[[R4-fluoro-3-(trifluoromethyl)benzyly]4-methylisoquinolin-3-y0amino]sulfonyl}benzoic acid;

4-{[(4-methylisoquinolin-3-yl))2-naphthylmethy)amino]sulfony}benzoic acid;

4-({(1-methoxy-4-methylisoquinolin-3-yl)[4-(trifluoromethoxy)benzya]amino}sulfony)-benzoic acid:

4-({(4-chloroisoquinolin-3-yl)[4-(trifluoromethoxy)benzyl]amino}sulfonyl)benzoic acid;

4-([(4-methylisoquinolin-3-yl)(5,6,7,8-tetrahydronaphthalen-2-ylmethy) amino]sulfonyl}-benzoic acid;

4-{[(2,3-dihydro-1H-inden-5-yl)methyl)(4-methylisoquinolin-3-yl)amino]sulfony}benzoic acid:

4-{[[(1,1-dimethyl-2,3-dihydro-1H-inden-5-yl)methyl](4-methylisoquinolin-3-yl)amino]-sulfonyl}benzoic acid;

4-{[[(2,2-dimethyl-2,3-dihydro-1H-inden-5-yl)mthyl]4-methylisoquinolin-3-yl)amino]-sulfonyl}benzoic acid;

4-{[[(3,3-dimethyl-2,3-dihydro-1-benzofuran-6-yl)methyl](4-methylisoquinolin-3-yl)amino]sulfonyl}benzoic acid;

4-{[[(1-benzothiophen-2-yl)methyl](4-methylisoquinolin-3-yl)amino]sulfonyl}benzoic acid;

4-({(1,4-dimethylisoquinolin-3-yl)[4-(trifluoromethoxy)benzyl]amino}sulfonyl)benzoic acid; and 4-({(4-methylisoquinolin-3-yl)[4-(2,2,2-trifluoro-1-methoxy-1-methylethyl)benzyl]amino}-sulfonyl benzoic acid; or a pharmaceutically acceptable salt thereof.

11. The compound of claim 1, which is selected from the group consisting of 4-({(1-cyclopropyl-4-methylisoquino-y)[4-(trifluoromethoxy)benzyl]amino}sulfonyl)-benzoic acid;

4-({(1-methoxy-4-methylisoquinolin-3-yl)[4-(trifluoromethoxy)benzyl]amino}sulfonyl)-benzoic acid;

4-({(1-isopropyl-4-methylisoquinolin-3-yl)[4-(trifluoromethoxy)benzyl]amino}sulfonyl)-benzoic acid;

4-{[{3-chloro-44cyclopropyl(difluoro)methyl]benzyl}(4-methylisoquinolin-3-yl)amino]-sulfonyl}benzoic acid;

4-({(4-cyclopropylisoquinolin-3-yl)[4-(trifluoromethoxy)benzyl]amino}sulfonyl) benzoic acid;

4-{[{3-chloro-4-[cyclopropyl(difluoro)methyl]benzyl}(1-cyclopropyl-4-methylisoquinolin-3-yl)amino]sulfonyl}benzoic acid;

4-{[{44cyclopropyl(difluoro)methyl]-3-fluorobenzyl}(4-methylisoquinolin-3-yl)amino]-sulfonyl}benzoic acid;

4-({[4-(trifluoromethoxy)benzyl][4-(trifluoromethyl)isoquinolin-3-yl]amino}sulfonyl)benzoic acid;

4-R(4-cyclopropylisoquinolin-3-yl){[5-(trifluoromethyl)pyridin-2-yl]methyl}amino)sulfonyl]-benzoic acid;

4-{[{3-chloro-4-[cyclopropyl(difluoro)methyl]benzyl}(4-cyclopropylisoquinolin-3-yl)amino]-sulfonyl}benzoic acid;

4-{[{4-[cyclopropyl(difluoro)methyl]-3-fluorobenzyl}(4-cyclopropylisoquinolin-3-yl)amino]-sulfonyl}benzoic acid;

4-({(4-cyclopropylisoquinolin-3-yl)[5-(trifluoromethoxy)-2, 3-dihydro-1 H-inden-1-yl]amino}sulfonyl)benzoic acid;

4-({{3-chloro-4-[cyclopropyl(difluoro)methypenzyl][4-(trifluoromethyl)isoquinolin-3-yl]-amino}sulfonyl) benzoic acid; and 4-({{4-[cyclopropyl(difluoro)methyl]-3-fluorobenzyl}[4-(trifluoromethyl)isoquinolin-3-yl]-amino}sulfonyl) benzoic acid; or a pharmaceutically acceptable salt thereof.

12. A pharmaceutical composition, comprising as the active ingredient the compound of claim 1 or a pharmaceutically acceptable salt thereof.

13. The compound of claim 9, wherein Ring B is benzene or pyridine, $R^1$ is methyl, trifluoromethyl, isopropyl, cyclopropyl, or methoxy, $R^{3a}$ and $R^{3b}$ are each independently (a) hydrogen; (b) $C_1$-$C_6$ alkyl which may be optionally substituted by 1 to 7 groups selected from $C_3$-$C_7$ cycloalkyl (in which the cycloalkyl may be optionally substituted by 1 to 3 groups selected from $C_1$-$C_6$ alkyl and $C_1$-$C_6$ halogenoalkyl), $C_1$-$C_6$alkoxy, $C_1$-$C_6$ halogenoalkoxy, and halogen; (c) $C_3$-$C_7$ cycloalkyl; (d) $C_1$-$C_6$alkoxy which may be optionally substituted by 1 to 7 halogens; or (e) halogen, or a pharmaceutically acceptable salt thereof.

14. The compound of claim 1, which is 4-({(1-cyclopropyl-4-methylisoquinolin-3-yl)[4-(trifluoromethoxy)benzy]amino}sulfonyl)benzoic acid or a pharmaceutically acceptable salt thereof.

15. The compound of claim 1, which is 4-({(1-isopropyl-4-methylisoquinolin-3-yl)[4-(trifluoromethoxy)benzyl]amino}sulfonyl)benzoic acid or a pharmaceutically acceptable salt thereof.

16. The compound of claim 1, which is 4-{[{3-chloro-4-[cyclopropyl(difluoro)methyl]benzyl}(4-methylisoquinolin-3-yl)amino]sulfonyl}benzoic acid or a pharmaceutically acceptable salt thereof.

17. The compound of claim 1, which is 4-({(4-cyclopropylisoquinolin-3-yl)[4-(trifluoromethoxy)benzyl]amino}sulfonyl) benzoic acid or a pharmaceutically acceptable salt thereof.

18. The compound of claim 1, which is 4-{[{3-chloro-4-[cyclopropyl(difluoro)methyl]benzyl}(1-cyclopropyl-4-methylisoquinolin-3-yl)amino}-sulfonyl}benzoic acid or a pharmaceutically acceptable salt thereof.

19. The compound of claim 1, which is 4-{[{4-[cyclopropyl(difluoro)methyl]-3-fluorobenzyl}(4-methylisoquinolin-3-yl)amino]sulfonyl}benzoic acid or a pharmaceutically acceptable salt thereof.

20. The compound of claim 1, which is 4-({[4-(trifluoromethoxy)benzyl][4-(trifluoromethyl)isoquinolin-3-yl]amino}sulfonyl)benzoic acid or a pharmaceutically acceptable salt thereof.

21. The compound of claim 1, which is 4-[((4-cyclopropylisoquinolin-3-yl){[5-(trifluoromethyl)pyridin-2-yl]methyl}amino)sulfonyl]benzoic acid or a pharmaceutically acceptable salt thereof.

22. The compound of claim 1, which is 4-{[{4-[cyclopropyl(difluoro)methyl]-3-fluorobenzyl}(4-cyclopropylisoquinolin-3-yl)amino]sulfonyl}benzoic acid or a pharmaceutically acceptable salt thereof.

23. A method for treating a disease or condition selected from chronic pain, cephalalgia, urologic disease, carcinoma, respiratory disease, gastrointestinal disease, psychiatric disease, neurological disease, and dermatosis, the method comprising administering to a subject an effective amount of a compound of claim 1 or a pharmaceutically acceptable salt thereof.

24. The method of claim 23, wherein the disease or condition is selected from chronic pain and urologic disease.

25. The method of claim 24, wherein the disease or condition is selected from neuropathic pain, nociceptive pain, and mixed pain.

\* \* \* \* \*

UNITED STATES PATENT AND TRADEMARK OFFICE
CERTIFICATE OF CORRECTION

PATENT NO. : 8,987,445 B2
APPLICATION NO. : 14/004911
DATED : March 24, 2015
INVENTOR(S) : Yasuyuki Tsuzuki et al.

It is certified that error appears in the above-identified patent and that said Letters Patent is hereby corrected as shown below:

Claims

In claim 11, column 207, lines 60-61, "methylisoquino-quinolin" should read --methylisoquinolin--.

In claim 11, column 208, lines 6-7, "3--yl" should read as --3-yl--.

In claim 11, column 208, lines 10-11, "4({(4-cyclopropylisoquinolin" should read as --4[(4-cyclopropylisoquinolin--.

In claim 11, column 208, lines 21-23, "iso-quinolin" should read as --isoquinolin--.

Signed and Sealed this
Thirteenth Day of October, 2015

Michelle K. Lee
*Director of the United States Patent and Trademark Office*

UNITED STATES PATENT AND TRADEMARK OFFICE
CERTIFICATE OF CORRECTION

PATENT NO. : 8,987,445 B2
APPLICATION NO. : 14/004911
DATED : March 24, 2015
INVENTOR(S) : Yasuyuki Tsuzuki et al.

It is certified that error appears in the above-identified patent and that said Letters Patent is hereby corrected as shown below:

Claims

Claim 1, Col. 203, Line 67, "combine each other" should read as --combine with each other--.

Claim 1, Col. 204, Line 3, "combine each other" should read as --combine with each other--.

Claim 2, Col. 204, Line 37, "alkyl." should read as --alkyl,--.

Claim 2, Col. 205, Line 37, "combine each other" should read as --combine with each other--.

Claim 2, Col. 205, Lines 40-41, "combine each other" should read as --combine with each other--.

Claim 4, Col. 205, Line 55, "combine each other" should read as --combine with each other--.

Claim 9, Col. 206, Line 60, "alkoxy" should read as --$C_1$-$C_6$ alkoxy--.

Claim 9, Col. 206, Line 61, "$R^{2b}$ and $R^{2b}$" should read as --$R^{2a}$, $R^{2b}$, and $R^{2c}$--.

Claim 9, Col. 206, Line 62, "$R^{2b}$" should read as --"$R^{2d}$"--.

Claim 10, Col. 207, Lines 17-18, "4-{[[3-fluoro-4-(trifluoromethoxy)benzyl](4-methylisoquinolin-3-yDamino]sulfonyl}benzoic acid;" should read as --4-{[[3-fluoro-4-(trifluoromethoxy)benzyl](4-methylisoquinolin-3-yl)amino]sulfonyl}benzoic acid;--.

Claim 10, Col. 207, Lines 32-33, "4-{[[R4-fluoro-3-(trifluoromethyl)benzyly]4-methylisoquinolin-3-y0amino]sulfonyl}benzoic acid;" should read as --4-{[[4-fluoro-3-(trifluoromethyl)benzyl]4-methylisoquinolin-3-yl)amino]sulfonyl}benzoic acid;--.

Signed and Sealed this
Nineteenth Day of January, 2016

Michelle K. Lee
*Director of the United States Patent and Trademark Office*

Claims

Claim 10, Col. 207, Lines 34-35, "4-{[(4-methylisoquinolin-3-yl))2-naphthylmethy)amino]sulfony}benzoic acid;" should read as --4-{[(4-methylisoquinolin-3-yl))2-naphthylmethyl)amino]sulfonyl}benzoic acid;--.

Claim 10, Col. 207, Lines 36-37, "4-({(1-methoxy-4-methylisoquinolin-3-yl)[4-(trifluoromethoxy)benzy]- amino}sulfony)-benzoic acid:" should read as --4-({(1-methoxy-4-methylisoquinolin-3-yl)[4-(trifluoromethoxy)benzyl]- amino}sulfonyl)-benzoic acid;--.

Claim 10, Col. 207, Lines 40-41, "4-([(4-methylisoquinolin-3-yl)(5,6,7,8-tetrahydronaphthalen-2-ylmethy)amino]sulfonyl}-benzoic acid;" should read as --4-([(4-methylisoquinolin-3-yl)(5,6,7,8-tetrahydronaphthalen-2-ylmethyl)amino]sulfonyl}-benzoic acid;--.

Claim 10, Col. 207, Lines 42-43, "4-{[(2,3-dihydro-1H-inden-5-yl)methyl)(4-methylisoquinolin-3-yl)amino]sulfony}benzoic acid:" should read as --4-{[(2,3-dihydro-1H-inden-5-ylmethyl)(4-methylisoquinolin-3-yl)amino]sulfonyl}benzoic acid;--.

Claim 10, Col. 207, Line 47-48, "4-{[[(2,2-dimethyl-2,3-dihydro-1H-inden-5-yl)mthyl]4-methylisoquinolin-3-yl)amino]-sulfonyl}benzoic acid;" should read as --4-{[[(2,2-dimethyl-2,3-dihydro-1H-inden-5-yl)methyl](4-methylisoquinolin-3-yl)amino]-sulfonyl}benzoic acid;--.

Claim 10, Col. 207, Lines 56-58, "4-({(4-methylisoquinolin-3-yl)[4-(2,2,2-trifluoro-1-methoxy-1-methylethyl- )benzyl]amino}-sulfonyl benzoic acid;" should read as --4-({(4-methylisoquinolin-3-yl)[4-(2,2,2-trifluoro-1-methoxy-1-methylethyl- )benzyl]amino}-sulfonyl)benzoic acid;--.

Claim 11, Col. 207, Lines 60-61, "4-({(1-cyclopropyl-4-methylisoquino -y)[4-(trifluoromethoxy)benzyl]amino}sulfonyl)-benzoic acid;" should read as --4-({(1-cyclopropyl-4-methylisoquino -quinolin-3-yl)[4-(trifluoromethoxy)benzyl]amino}sulfonyl)-benzoic acid;--.

Claim 11, Col. 207, Lines 66-67, "4-{[{3-chloro-44cyclopropyl(difluoro)methyl]benzyl}(4-methylisoquinolin-3-yl)amino]-sulfonyl}benzoic acid;" should read as --4-{[{3-chloro-4-[cyclopropyl(difluoro)methyl]benzyl}(4-methylisoquinolin-3-yl)amino]-sulfonyl}benzoic acid;--.

Claim 11, Col. 208, Lines 6-7, "4-{[{44cyclopropyl(difluoro)methyl]-3-fluorobenzyl}(4-methylisoquinolin-3- -yl)amino]-sulfonyl}benzoic acid;" should read as --4-{[{4-[cyclopropyl(difluoro)methyl]-3-fluorobenzyl}(4-methylisoquinolin-3- -yl)amino]-sulfonyl}benzoic acid;--.

Claim 11, Col. 208, Lines 10-11, "4-R(4-cyclopropylisoquinolin-3-yl){5-(trifluoromethyl)pyridin-2-yl]methyl}amino)sulfonyl]-benzoic acid;" should read as --4-({(4-cyclopropylisoquinolin-3-yl){5-(trifluoromethyl)pyridin-2-yl]methyl}amino)sulfonyl]-benzoic acid;--.

CERTIFICATE OF CORRECTION (continued)
U.S. Pat. No. 8,987,445 B2

Claims

Claim 11, Col. 208, Lines 18-20, "4-({(4-cyclopropylisoquinolin-3-yl)[5-(trifluoromethoxy)-2,3-dihydro-1    H-inden-1-yl]amino}sulfonyl)benzoic acid;" should read as --4-({(4-cyclopropylisoquinolin-3-yl)[5-(trifluoromethoxy)-2,3-dihydro-1H-inden-1-yl]amino}sulfonyl)benzoic acid;--.

Claim 11, Col. 208, Lines 21-23, "4-({{3-chloro-4-[cyclopropyl(difluoro)methypenzyl}[4-(trifluoromethyl)iso-quinolin-3-yl]-amino}sulfonyl)benzoic acid" should read as --4-({{3-chloro-4-[cyclopropyl(difluoro)methyl]benzyl}[4-(trifluoromethyl)iso- quinolin-3-yl]-amino}sulfonyl)benzoic acid--.

Claim 13, Col. 208, Line 40, "$C_i$-$C_6$" should read as --$C_1$-$C_6$.--.

Claim 14, Col. 208, Lines 45-46, "4-({(1-cyclopropyl-4-methylisoquinolin-3-yl)[4-(trifluoromethoxy)benzy]amino}sulfonyl)benzoic acid" should read as --4-({(1-cyclopropyl-4-methylisoquinolin-3-yl)[4-(trifluoromethoxy)benzyl]amino}sulfonyl)benzoic acid--.